US007226951B2

(12) United States Patent
Vasudevan et al.

(10) Patent No.: US 7,226,951 B2
(45) Date of Patent: Jun. 5, 2007

(54) COMPOUNDS HAVING SELECTIVE CYTOCHROME P450RAI-1 OR SELECTIVE CYTOCHROME P450RAI-2 INHIBITORY ACTIVITY AND METHODS OF OBTAINING THE SAME

(75) Inventors: Jayasree Vasudevan, Anaheim, CA (US); Liming Wang, Irvine, CA (US); Xiaoxia Liu, Tustin, CA (US); Kwok Yin Tsang, Irvine, CA (US); Ling Li, Irvine, CA (US); Janet A. Takeuchi, Anaheim, CA (US); Thong Vu, Garden Grove, CA (US); Richard Beard, Newport Beach, CA (US); Smita Bhat, Irvine, CA (US); Vidyasagar Vuligonda, Irvine, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 135 days.

(21) Appl. No.: 11/014,460

(22) Filed: Dec. 16, 2004

(65) Prior Publication Data
US 2005/0176689 A1 Aug. 11, 2005

Related U.S. Application Data

(60) Provisional application No. 60/530,462, filed on Dec. 17, 2003.

(51) Int. Cl.
*A61K 31/135* (2006.01)
*C07C 62/00* (2006.01)
*C07C 69/52* (2006.01)
*C07C 211/16* (2006.01)
(52) U.S. Cl. ........................ 514/654; 562/500; 564/384
(58) Field of Classification Search ................ 514/654; 562/500; 564/384
See application file for complete search history.

(56) References Cited

U.S. PATENT DOCUMENTS

| 4,326,055 | A |  | 4/1982 | Loeliger |
|---|---|---|---|---|
| 5,349,105 | A |  | 9/1994 | Chandraratna |
| 5,648,503 | A |  | 7/1997 | Vuligonda et al. |
| 5,723,666 | A |  | 3/1998 | Vuligonda et al. |
| 5,952,345 | A |  | 9/1999 | Klein et al. |
| 6,252,090 | B1 | * | 6/2001 | Vasudevan et al. ............ 549/23 |
| 6,291,677 | B1 | * | 9/2001 | Vasudevan et al. ......... 546/165 |
| 6,303,785 | B1 | * | 10/2001 | Vasudevan et al. ......... 546/144 |
| 6,313,107 | B1 |  | 11/2001 | Vasudevan et al. |
| 6,369,225 | B1 | * | 4/2002 | Vasudevan et al. ......... 544/238 |
| 6,369,261 | B1 | * | 4/2002 | Johnson et al. ................ 560/59 |
| 6,380,256 | B1 | * | 4/2002 | Vasudevan et al. ......... 514/567 |
| 2002/0160986 | A1 | * | 10/2002 | Vasudevan et al. ......... 514/150 |
| 2002/0183285 | A1 | * | 12/2002 | Vasudevan et al. ......... 514/150 |

FOREIGN PATENT DOCUMENTS

GB 1 277 227 A 6/1972
WO WO 200218361 A2 * 3/2002

OTHER PUBLICATIONS

Sengupta S et al: "Indoarenediazonium salts: a new class of aromatic substrates for differential palladium catalyzed reations" Tetrahedron Letters, vol. 39, No. 7, Feb. 12, 1998, pp. 715-718, XP004106780 the whole document, particularly compound 8.
Castro C E et al: "Copper(I) substitutions. Scope and mechanism of cuprous acetylide substitutions" Journal of the American Chemical Society, vol. 91, No. 23, Nov. 5, 1969, pp. 6464-6470, XP002326252 the whole document, particularly table VI, 5$^{th}$ entry.
Asao N et al: "Pi-pi chelation controlled chemoselective conjugate addition of lithium dimethylcuprate" Tetrahedron Letters, vol. 44, No. 9, Feb. 24, 2002, pp. 1803-1805, XP004408806 the whole document, particularly compounds 1a and 2a.
Costa A et al: "P2-Et-mediated deprotonation of ortho-halobenzyl sulfones: synthetic applications as zwitterionic synthons" SYNLETT, vol. 12, 2001, pp. 1881-1884, XP001084388 the whole document, particularly compound 13.
Hamon D P G et al: "Enantioselective syntheses of 2-arylpropanoic acid non-steroidal anti-inflammatory drugs and related compounds" TETRAHEDRON, vol. 51, No. 46, Nov. 13, 1995, pp. 12645-12660, XP004104649 the whole document, particularly compounds 35a and 35b.
Bouchain G et al: "Development of potential antitumor agents. Synthesis and biological evaluation of a new set of sulfonamide derivatives as histone deacetylase inhibitors" Journal of Medicinal Chemistry, vol. 46, No. 5, Feb. 27, 2003, pp. 820-830, XP002292252 the whole document, particularly pp. 827 and 828, compounds 20 and 21.
Xin Z et al: "A practical and efficient intramolecular Michael addition of ureas to alpha, beta-unsaturated esters" Tetrahedron Letters, vol. 41, No. 8, Feb. 2000, pp. 1147-1150, XP004188577 the whole document, particularly compounds 2a, 2b, 2e, 2f and 2g.
Nakao K et al: "Qualitative structure-activity analyses of novel hydroxyphenylurea derivatives as antioxidants" Bioorganic & Medicinal Chemistry, vo. 6, No. 6, 1998, pp. 849-868, XP002309788 the whole document, particularly compound 22.
Kwon B-M et al: "Synthesis and biological activity of cinnamaldehydes as angiogenesis inhibitors" Bioorganic & Medicinal Chemistry Letters, vol. 7, No. 19, Oct. 7, 1997, pp. 2473-2476, XP004136467 the whole document, particularly compound 2k.
Konek F Von et al: "Uber einige neue Derivate de Paracumar- und Vanillinsaure" Chemische Berichte, vol. 51, 1918, pp. 855-865, XP002326243 the whole document, particularly paragraph bridging pp. 857 and 858.
White et al. Identification of the human cytochrome P450, P450RAI-2, which is predominantly expressed in the adult cerebellum and is responsible for all *trans* retinoic acid metabolism, Prac. Natl. Acad. Sci. USA vol. 97 No. 12 pp. 6403-6408 (2000).

(Continued)

*Primary Examiner*—Kamal A. Saeed
*Assistant Examiner*—Nyeemah Grazier
(74) *Attorney, Agent, or Firm*—Hamilton, Brook, Smith & Reynolds, P.C.

(57) ABSTRACT

Compounds of formulas 1 through 17 provided in the specification specifically or selectively inhibit either the cytochrome P450RAI-1 enzyme or the cytochrome P450RAI-2 enzyme.

4 Claims, 1 Drawing Sheet

OTHER PUBLICATIONS

Figure 1:
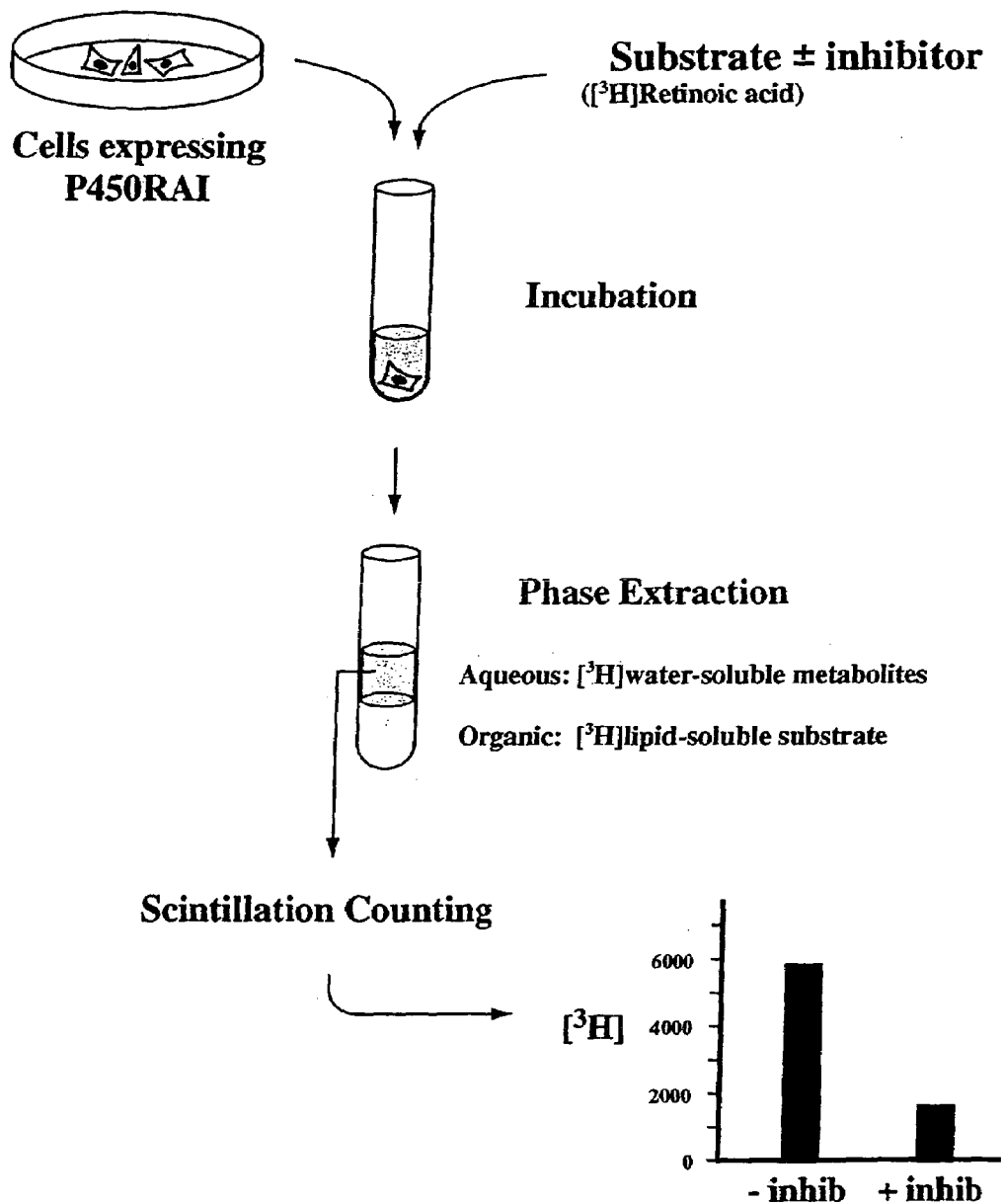

Kuijpers, et al., "The effects of oral liarozole on epidermal proliferation and differentiation in severe plaque psoriasis are comparable with those of acitretin," *British Journal of Dermatology*, (1998) 139: pp. 380-389.

Kang, et al., "Liarozole Inhibits Human Epidermal Retinoid Acid 4-Hydroxylase Activity and Differentially Augments Human Skin Responses to Retinoic Acid and Retinol In Vivo," *The Journal of Investigative Dermatology*, (Aug. 1996) vol. 107, No. 2: pp. 183-187.

Van Wauwe, et al., "Liarzole, an Inhibitor of Retinoic Acid Metabolism, Exerts Retinoid-Mimetic Effects in Vivo," *The Journal of Pharmacology and Experimental Therapeutics*, (1992) vol. 261, No. 2: pp. 773-779.

De Porre, et al., "Second Generation Retinoic Acid Metabolism Blocking Agent (Ramba) R116010: Dose Finding in Healthy Male Volunteers," University of Leuven, Belgium, p. 30.

Wauwe, et al., "Ketoconazole Inhibits the in Vitro and in Vivo Metabolism of All-Trans-Retinoic Acid," *The Journal of Pharmacology and Experimental Therapeutics*, (1998) vol. 245, No. 2: pp. 718-722.

White, et al., cDNA Cloning of Human Retinoic Acid-metabolizing Enzyme (hP450RAI) Identifies a Novel Family of Cytochromes P450, *The Journal of Biological Chemistry*, (1997) vol. 272, No. 30, Issue of Jul. 25 pp. 18538-18541.

Hanzlik, et al., "Cyclopropylamines as Suicide Substrates for Cytochromes P450RAI," *Journal of Medicinal Chemistry*, (1997), vol. 22, No. 7, pp. 759-761.

Ortiz de Montellano, "Topics in Biology—The Inactivation of Cytochrome P450RAI," *Annual Reports in Medicinal Chemistry*, (1984), Chapter 20, pp. 201-210.

Hanzlik, et al. "Suicidal Inactivation of Cytochrome P450RAI by Cyclopropylamines-Evidence for Cation-Radical Intermediates," *J. Am. Chem. Soc.*, (1982), vol. 104, No. 107, pp. 2048-2052.

Bligh et al. (1959) Canadian Journal of Biochemistry 37, 911-917.

Lopez, et al. in Tet Lett., 1999, 40, 11, p. 2071-2074.

Barlaam et al. J. Med. Chem., 1999, 42, 23, 4890-4908.

Floyd et al., Journal of Pharmaceutical Sciences, 1970, 59 (6), p. 869-870.

Teng, et al, Journal of Medicinal Chemistry, 1996, 39, p. 3035-3038.

\* cited by examiner

COMPOUNDS HAVING SELECTIVE CYTOCHROME P450RAI-1 OR SELECTIVE CYTOCHROME P450RAI-2 INHIBITORY ACTIVITY AND METHODS OF OBTAINING THE SAME

CROSS-REFERENCE TO PRIORITY APPLICATION

The present application claims priority of provisional application Ser. No. 60/530,462, filed on Dec. 17, 2003.

BACKGROUND OF THE INVENTION

1. Field of the Invention

The present invention is directed to compounds having selective cytochrome P450RAI-1 or selective cytochrome P450RAI-2 inhibitory activity and to methods of obtaining these compounds.

2. Background Art

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis. Retinoid compounds have relatively recently been also discovered to be useful for treating type II non-insulin dependent diabetes mellitus (NIDDM).

Several compounds having retinoid-like activity are actually marketed under appropriate regulatory approvals in the United States of America and elsewhere as medicaments for the treatment of several diseases responsive to treatment with retinoids. Retinoic acid (RA) itself is a natural product, biosynthesized and present in a multitude of human and mammalian tissues and is known to play an important rule in the regulation of gene expression, tissue differentiation and other important biological processes in mammals including humans. Relatively recently it has been discovered that a catabolic pathway in mammals, including humans, of natural retinoic acid includes a step of hydroxylation of RA catalyzed by the enzyme Cytochrome P450RAI (retinoic acid inducible). In fact, in the present state of the art it is known that at least three sub-species of cytochrome P450RAI enzymes exist, and these are termed P450RAI1, P450RAI2 and P450RAI3. White et al. Identification of the human cytochrome P450, P450RAI-2, which is predominantly expressed in the adult cerebellum and is responsible for all trans retinoic acid metabolism, *Proc. Natl. Acad. Sci. USA* Volume 97 No. 12 pp 6403 6408 (Jun. 6, 2000).

Several inhibitors of cytochrome P450RAI have been synthesized or discovered in the prior art, including the well known ketoconazole, liarozole and R116010 compounds. The chemical structures of these prior art compounds are provided below. U.S. Pat. No. 6,313,107 describes a number of compounds having cytochrome P450RAI inhibitory activity.

It has also been noted in the prior art, that administration to mammals, including humans, of certain inhibitors of CP-450RAI results in significant increase in endogeneous RA levels, and further that treatment with CP450RAI inhibitors, for example with liarozole, gives rise to effects similar to treatment by retinoids, for example amelioration of psoriasis.

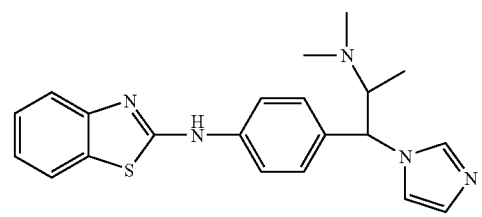

R116010

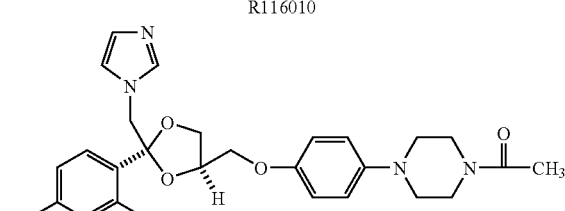

KETOCONAZOLE

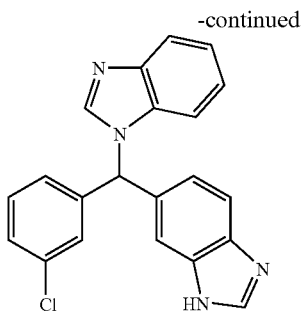

LIAROZOLE

The following publications describe or relate to the above-summarized role of CP450RAI in the natural catabolism of RA, to inhibitors of CP-450RAI and to in vitro and in vivo experiments which demonstrate that inhibition of CP450RAI activity results in increased endogenous RA levels and potential therapeutic benefits:

Kuijpers, et al, "The effects of oral liarozole on epidermal proliferation and differentiation in severe plaque psoriasis are comparable with those of acitretin", *British Journal of Dermatology*, (1998) 139: pp 380–389.

Kang, et al., "Liarozole Inhibits Human Epidermal Retinoid Acid 4-Hydroxylase Activity and Differentially Augments Human Skin Responses to Retinoic Acid and Retinol In Vivo", *The Journal of Investigative Dermatology*, (August 1996) Vol. 107, No. 2: pp 183–187.

Van Wauwe, et al., "Liarozole, an Inhibitor of Retinoic Acid Metabolism, Exerts Retinoid-Mimetic Effects in Vivo", *The Journal of Pharmacology and Experimental Therapeutics*, (1992) Vol. 261, No 2: pp 773–779.

De Porre, et al., "Second Generation Retinoic Acid Metabolism Blocking Agent (Ramba) R116010: Dose Finding in Healthy Male Volunteers", University of Leuven, Belgium, pp 30.

Wauwe, et al., "Ketoconazole Inhibits the in Vitro and in Vivo Metabolism of All-Trans-Retinoic Acid", *The Journal of Pharmacology and Experimental Therapeutics*, (1988) Vol. 245, No. 2: pp 718–722.

White, et al., "cDNA Cloning of Human Retinoic Acid-metabolizing Enzyme (hP450RAI) Identifies a Novel Family of Cytochromes P450, *The Journal of Biological Chemistry*, (1997) Vol. 272, No. 30, Issue of July 25 pp 18538–18541.

Hanzlik, et al., "Cyclopropylamines as Suicide Substrates for Cytochromes P450RAI", *Journal of Medicinal Chemistry* (1979), Vol. 22, No. 7, pp 759–761.

Ortiz de Montellano, "Topics in Biology—The Inactivation of Cytochrome P450RAI", *Annual Reports in Medicinal Chemistry*, (1984), Chapter 20, pp 201–210.

Hanzlik, et al. "Suicidal Inactivation of Cytochrome P450RAI by Cyclopropylamines—Evidence for Cation-Radical Intermediates", 3. *J. Am. Chem. Soc.*, (1982), Vol. 104, No. 107, pp. 2048–2052. White et al. *Proc. Natl. Acad. Sci. USA* supra.

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$, and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated bygone or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

Similar to the desirability of providing compounds that are selective or specific to one or more retinoid receptor subtypes, it is also desirable to provide compounds that specifically or selectively inhibit either the cytochrome P450RAI-1 enzyme or the cytochrome P450RAI-2 enzyme. The present invention provides such compounds and methods in the form of synthetic guidelines how to obtain them.

SUMMARY OF THE INVENTION

The present invention relates to compounds of Formula 1

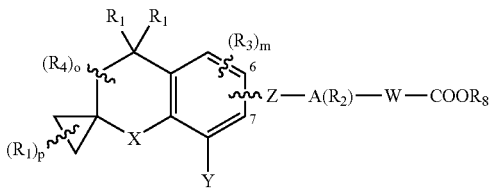

Formula 1 wherein

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O, S or NR where R is H, alkyl of 1 to 6 carbons or benzyl;

Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, or I or alkoxy of 1 to 6 carbons;

Z is —C≡C—,

—(CR$_1$=CR$_1$)$_{n'}$ where n' is an integer having the value 1–5,

—CO—NR$_1$—,

NR$_1$—CO—;

—CO—O—,

—O—CO—,

—CS—NR$_1$—,

NR$_1$—CS—,

—CO—S—,

—S—CO—,

—N=N—;

—NR$_1$—CO—NR$_1$—;

$R_1$ is independently H or alkyl of 1 to 6 carbons;

p is an integer having the values of 0 to 4;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 2;

$R_4$ is independently H, alkyl of 1 to 6 carbons, or F, fluorosubstituted alkyl of 1 to 6 carbons, or halogen;

o is an integer having the values of 0 to 2;

W is $-C(R_5)_2-$ or $-CR_5=CR_5-$;

$R_5$ is independently H, halogen, or alkyl of 1 to 3 carbons with the proviso that when W is $-C(R_5)_2-$ then at least one $R_5$ is alkyl of 1 to 3 carbons, and $R_8$ is H, alkyl of 1 to 6 carbons, $-CH_2O(C_{1-6}$-alkyl), $CH_2OCO(C_{1-6}$-alkyl) or a cation of a pharmaceutically acceptable base.

The present invention also relates to compounds of Formula 2

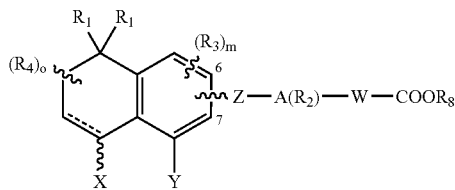

Formula 2 wherein the dashed line represents a bond or absence of a bond;

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is alkyl of 1 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, or I, OR, SR, $NRR_7$, $-CO-OR$ where R is H, alkyl of 1 to 6 carbons or benzyl;

Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, $COOR_8$ or alkoxy of 1 to 6 carbons;

Z is $-C\equiv C-$, $-(CR_1=CR_1)_{n'}-$ where n' is an integer having the value 1–5, $-CO-NR_1-$, $NR_1-CO-$;

$-CO-O-$, $-O-CO-$, $-CS-NR_1-$, $NR_1-CS-$, $-CO-S-$, $-S-CO-$, $-N=N-$;

$-NR_1-CO-NR_1-$;

$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 2;

$R_4$ is independently H, alkyl of 1 to 6 carbons, or fluorosubstituted alkyl of 1 to 6 carbons, or halogen;

o is an integer having the values of 0 to 4;

W is $-C(R_5)_2-$ or $-CR_5=CR_5-$;

$R_5$ is independently H, halogen, or alkyl of 1 to 3 carbons with the proviso that when W is $-C(R_5)_2-$ then at least one $R_5$ is alkyl of 1 to 3 carbons;

$R_7$ is H, lower alkyl, cycloalkyl of 3 to 6 carbons, lower alkyl substituted cycloalkyl of 3 to 6 carbons, and $R_8$ is H, alkyl of 1 to 6 carbons, $-CH_2O(C_{1-6}$-alkyl), $CH_2OCO(C_{1-6}$-alkyl) or a cation of a pharmaceutically acceptable base.

The present invention also relates to compounds of Formula 3

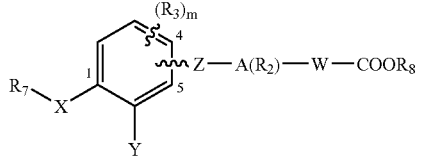

Formula 3 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O, S or NR where R is H, alkyl of 1 to 6 carbons, $C_{1-6}$-trialkylsilyl or benzyl;

Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, or I;

Z is $-C\equiv C-$, $-(CR_1=CR_1)_{n'}-$ where n' is an integer having the value 1–5, $-CO-NR_1-$,

NR, $-CO-$;

$-CO-O-$, $-O-CO-$, $-CS-NR_1-$, $NR_1-CS-$, $-CO-S-$, $-S-CO-$, $-N=N-$;

$-NR_1-CO-NR_1-$;

$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

W is $-C(R_5)_2-$ or $-CR_5=CR_5-$;

$R_5$ is independently H, halogen, or alkyl of 1 to 3 carbons with the proviso that when W is —C($R_5$)$_2$— then at least one $R_5$ is alkyl of 1 to 3 carbons;

$R_7$ is H, alkyl of 1 to 6 carbons, cycloalkyl of 3 to 6 carbons or $C_{1-6}$ alkyl substituted cycloalkyl of 1 to 6 carbons, and $R_8$ is H, alkyl of 1 to 6 carbons, —CH$_2$O($C_{1-6}$-alkyl), CH$_2$OCO($C_{1-6}$-alkyl) or a cation of a pharmaceutically acceptable base.

The present invention also relates to compounds of Formula 4

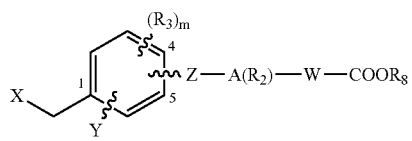

Formula 4 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is $OR_7$, $SR_7$ or $NRR_7$ where R is H, alkyl of 1 to 6 carbons or benzyl;

Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, or —COOR$_1$;

Z is —C≡C—,

—(CR$_1$=CR$_1$)$_{n'}$ where n' is an integer having the value 1–5,

—CO—NR$_1$—,

NR$_1$—CO—;

—CO—O—,

—O—CO—,

—CS—NR$_1$—,

NR$_1$—CS—,

—CO—S—,

—S—CO—,

—N=N—;

—NR$_1$—CO—NR$_1$—;

$R_1$ is independently H or alkyl of 1 to 6 carbons;

$R_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

W is —C($R_5$)$_2$— or —CR$_5$=CR$_5$—;

$R_5$ is independently H, halogen, or alkyl of 1 to 3 carbons with the proviso that when W is —C($R_5$)$_2$— then at least one $R_5$ is alkyl of 1 to 3 carbons;

$R_7$ is H, alkyl of 1 to 6 carbons, cycloalkyl of 3 to 6 carbons or $C_{1-6}$ alkyl substituted cycloalkyl of 1 to 6 carbons, and $R_8$ is H, alkyl of 1 to 6 carbons, —CH$_2$O($C_{1-6}$-alkyl), CH$_2$OCO($C_{1-6}$-alkyl) or a cation of a pharmaceutically acceptable base.

The present invention also relates to compounds of Formula 5

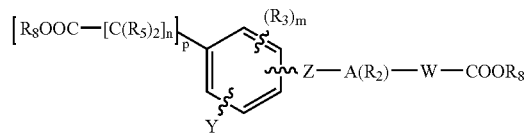

Formula 5 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, or —COOR$_1$;

Z is —C≡C—,

—(CR$_1$=CR$_1$)$_{n'}$ where n' is an integer having the value 1–5,

—CO—NR$_1$—,

NR —CO—;

—O—CO—,

—CS—NR$_1$—,

NR$_1$—CS—,

—CO—S—,

—S—CO—,

—N=N—;

—NR$_1$—CO—NR$_1$—;

$R_1$ is independently H or alkyl of 1 to 6 carbons;

$R_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

n is an integer having the values of 0 or 1;

p is an integer having the values of 0 or 1;

W is —C($R_5$)$_2$— or —CR$_5$=CR$_5$—;

$R_5$ is independently H, halogen, or alkyl of 1 to 3 carbons with the proviso that when W is —C($R_5$)$_2$— then at least one $R_5$ is alkyl of 1 to 3 carbons, and $R_8$ independently is H, alkyl of 1 to 6 carbons, —CH$_2$O ($C_{1-6}$-alkyl), CH$_2$OCO($C_{1-6}$-alkyl) or a cation of a pharmaceutically acceptable base.

The present invention also relates to compounds of Formula 6

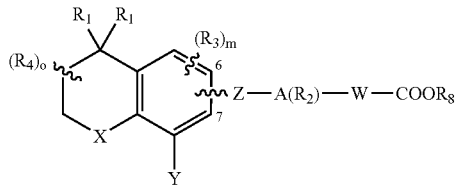

Formula 6 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O, S, NR or CO where R is H or alkyl of 1 to 6 carbons;

Y is H, alkyl of 1 to 10 carbons, benzyl, $C_{1-6}$ alkyl or halogen substituted benzyl, fluoro-substituted alkyl of 1 to 10 carbons, cycloalkyl of 3- to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, $OR_7$, $CH_2$—$NRR_7$ or —$COOR_1$;

Z is —C≡C—,
—$(CR_1$=$CR_1)_{n'}$ where n' is an integer having the value 1–5,
—CO—$NR_1$—,
$NR$, —CO—;
—CO—O—,
—O—CO—,
—CS—$NR_1$—,
$NR_1$—CS—,
—CO—S—,
—S—CO—,
—N=N—;
—$NR_1$—CO—$NR_1$—;

$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_4$ is independently H, alkyl of 1 to 6 carbons, or F; fluorosubstituted alkyl of 1 to 6 carbons, or halogen;

o is an integer having the values of 0 to 4;

W is —$C(R_5)_2$— or —$CR_5$=$CR_5$—;

$R_5$ is independently H, halogen, or alkyl of 1 to 3 carbons with the proviso that when W is $C(R_5)_2$— then at least one $R_5$ is alkyl of 1 to 3 carbons, and $R_7$ is H, alkyl of 1 to 6 carbons, cycloalkyl of 3 to 6 carbons or $C_{1-6}$ alkyl substituted cycloalkyl of 1 to 6 carbons, and $R_8$ is H, alkyl of 1 to 6 carbons, —$CH_2O(C_{1-6}$-alkyl), $CH_2OCO(C_{1-6}$-alkyl) or a cation of a pharmaceutically acceptable base.

The present invention also relates to compounds of Formula 7

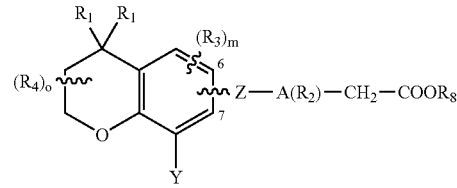

Formula 7 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Y is alkenyl-alkynyl of 4 to 6 carbons, alkynyl-alkenyl of 4 to 6 carbons, $OR_7$, $CH_2$—$NRR_7$ or —$COOR_1$;

Z is —C≡C—,
—CO—O—,
—$NR_1$—CO—$NR_1$—;

R is independently H or alkyl of 1 to 6 carbons;

$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_4$ is independently H, alkyl of 1 to 6 carbons, or F; fluorosubstituted alkyl of 1 to 6 carbons, or halogen;

o is an integer having the values of 0 to 4;

$R_7$ is H, alkyl of 1 to 6 carbons, cycloalkyl of 3 to 6 carbons or $C_{1-6}$-alkyl substituted cycloalkyl of 1 to 6 carbons, and $R_8$ is H, alkyl of 1 to 6 carbons, —$CH_2O(C_{1-6}$-alkyl), $CH_2OCO(C_{1-6}$-alkyl) or a cation of a pharmaceutically acceptable base.

The present invention also relates to compounds of Formula 8

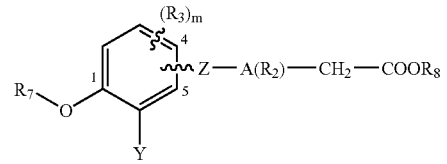

Formula 8 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Y is alkenyl of 2 to 6 carbons, alkynyl of 2 to 6 carbons, alkenyl-alkynyl of 4 to 6 carbons, alkynyl-alkenyl of 4 to 6 carbons;

Z is —C≡C—,
—CO—O—,
—$NR_1$—CO—$NR_1$—;

$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_7$ is H, alkyl of 1 to 6 carbons, cycloalkyl of 3 to 6 carbons or $C_{1-6}$ alkyl substituted cycloalkyl of 1 to 6 carbons, and $R_8$ is H, alkyl of 1 to 6 carbons, —$CH_2O(C_{1-6}$-alkyl), $CH_2OCO(C_{1-6}$-alkyl) or a cation of a pharmaceutically acceptable base.

The present invention also relates to compounds of Formula 9

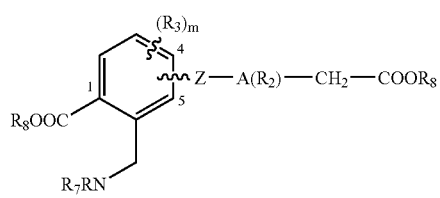

Formula 9 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Z is —C≡C—,
—CO—O—,
—$NR_1$—CO—$NR_1$—;

R is H or alkyl of 1 to 6 carbons;

$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_7$ is H, alkyl of 1 to 6 carbons, cycloalkyl of 3 to 6 carbons or $C_{1-6}$ alkyl substituted cycloalkyl of 1 to 6 carbons, and $R_8$ independently is H, alkyl of 1 to 6 carbons, —$CH_2O$ ($C_1$-alkyl), $CH_2OCO(C_{1-6}$-alkyl) or a cation of a pharmaceutically acceptable base.

The present invention also relates to compounds of Formula 10

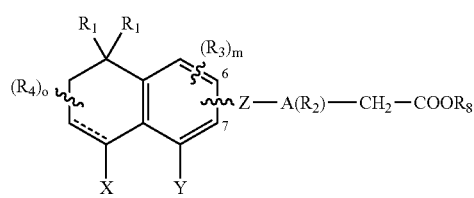

Formula 10 wherein the dashed line represents a bond or absence of a bond;

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is $NRR_7$, or $COOR_8$;

Y is H, alkenyl of 2 to 6 carbons, alkenyl-alkynyl of 4 to 6 carbons, alkynyl-alkenyl of 4 to 6 carbons, $OR_7$ or —$COOR_1$;

Z is —C≡C—,
—CO—O—,
—$NR_1$—CO—$NR_1$—;

R is independently H or alkyl of 1 to 6 carbons;

$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_4$ is independently H, alkyl of 1 to 6 carbons, or F; fluorosubstituted alkyl of 1 to 6 carbons, or halogen;

o is an integer having the values of 0 to 4;

$R_7$ is H, alkyl of 1 to 6 carbons, cycloalkyl of 3 to 6 carbons or $C_{1-6}$ alkyl substituted cycloalkyl of 1 to 6 carbons, and $R_8$ independently is H, alkyl of 1 to 6-carbons, —$CH_2O$ ($C_{1-6}$-alkyl), $CH_2OCO(C_{1-6}$-alkyl) or a cation of a pharmaceutically acceptable base.

The present invention also relates to compounds of Formula 11

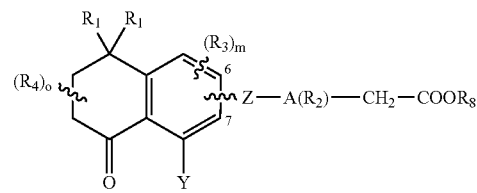

Formula 11 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Y is, alkenyl of 2 to 6 carbons, alkenyl-alkynyl of 4 to 6 carbons, or alkynyl-alkenyl of 4 to 6 carbons;

Z is —C≡C—,
—CO—O—,
—$NR_1$—CO—$NR_1$—;

$R_1$ is independently H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_4$ is independently H, alkyl of 1 to 6 carbons, or F; fluorosubstituted alkyl of 1 to 6 carbons, or halogen;

o is an integer having the values of 0 to 4, and $R_8$ is H, alkyl of 1 to 6 carbons, —$CH_2O(C_{1-6}$-alkyl), $CH_2OCO(C_{1-6}$-alkyl) or a cation of a pharmaceutically acceptable base.

The present invention also relates to compounds of Formula 12

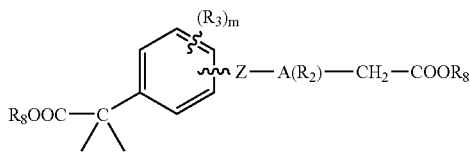

Formula 12 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Z is —C≡C—,
—CO—O—,
—NR, —CO—$NR_1$—;
$R_1$ is independently H or alkyl of 1 to 6 carbons;
$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
m is an integer having the values 0 to 3, and
$R_8$ independently is H, is alkyl of 1 to 6 carbons, —$CH_2O$ ($C_{1-6}$-alkyl), $CH_2OCO(C_{1-6}$-alkyl) or a cation of a pharmaceutically acceptable base.

The present invention also relates to compounds of Formula 13

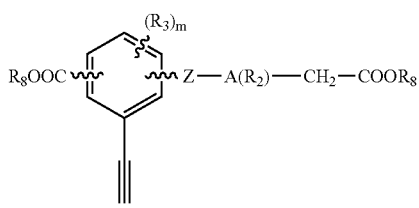

Formula 13 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Z is —C≡C—,
—CO—O—,
—$NR_1$—CO—$NR_1$—;
$R_1$ is independently H or alkyl of 1 to 6 carbons;
$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
m is an integer having the values 0 to 3, and
$R_8$ independently is H, alkyl of 1 to 6 carbons, —$CH_2O$ ($C_{1-6}$-alkyl), $CH_2OCO(C_{1-6}$-alkyl) or a cation of a pharmaceutically acceptable base.

The present invention also relates to compounds of Formula 14

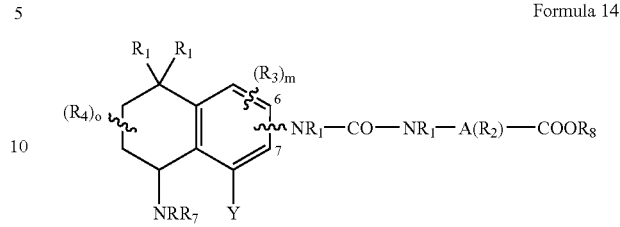

Formula 14 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, $OR_7$, $CH_2$—$NRR_7$ or —$COOR_1$;
R is independently H or alkyl of 1 to 6 carbons;
$R_1$ is independently H or alkyl of 1 to 6 carbons;
$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;
$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
m is an integer having the values 0 to 3;
$R_4$ is independently H, alkyl of 1 to 6 carbons, or F; fluorosubstituted alkyl of 1 to 6 carbons, or halogen;
o is an integer having the values of 0 to 4;
$R_7$ is H, alkyl of 1 to 6 carbons, cycloalkyl of 3 to 6 carbons or $C_{1-6}$ alkyl substituted cycloalkyl of 1 to 6 carbons, and
$R_8$ is H, alkyl of 1 to 6 carbons, —$CH_2O(C_{1-6}$-alkyl), $CH_2OCO(C_{1-6}$-alkyl) or a cation of a pharmaceutically acceptable base.

The present invention also relates to compounds of Formula 15

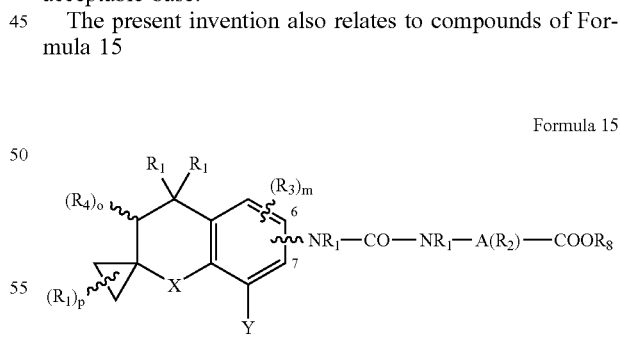

Formula 15 wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O or S;
Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, OR$_7$, CH$_2$—NRR$_7$ or —COOR$_1$;

$R_1$ is independently H or alkyl of 1 to 6 carbons;

p is an integer having the values of 0 to 4;

$R_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_4$ is independently H, alkyl of 1 to 6 carbons, or F; fluorosubstituted alkyl of 1 to 6 carbons, or halogen;

o is an integer having the values of 0 to 4;

$R_7$ is H, alkyl of 1 to 6 carbons, cycloalkyl of 3 to 6 carbons or $C_{1-6}$ alkyl substituted cycloalkyl of 1 to 6 carbons, and $R_8$ is H, alkyl of 1 to 6 carbons, —CH$_2$O($C_{1-6}$-alkyl), CH$_2$OCO($C_{1-6}$-alkyl) or a cation of a pharmaceutically acceptable base.

The present invention also relates to compounds of Formula 16

Formula 16

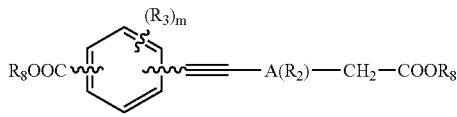

wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

$R_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3, and $R_8$ independently is H, alkyl of 1 to 6 carbons, —CH$_2$O ($C_{1-6}$-alkyl), CH$_2$OCO($C_{1-6}$-alkyl) or a cation of a pharmaceutically acceptable base.

The present invention also relates to compounds of Formula 17

Formula 17

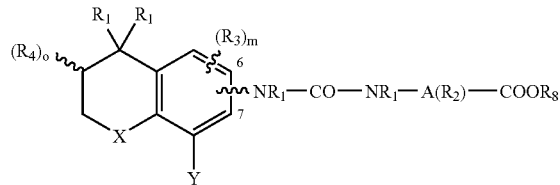

wherein A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O or S;

Y is H, alkyl of 1 to 10 carbons, benzyl, $C_{1-6}$ alkyl or halogen substituted benzyl, fluoro-substituted alkyl of 1 to 10 carbons, cycloalkyl of 3 to 6 carbons, $C_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, OR$_7$, CH$_2$—NRR$_7$ or —COOR$_1$;

$R_1$ is independently H or alkyl of 1 to 6 carbons;

$R_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_4$ is independently H, alkyl of 1 to 6 carbons, or F; fluorosubstituted alkyl of 1 to 6 carbons, or halogen;

o is an integer having the values of 0 to 4;

$R_7$ is H, alkyl of 1 to 6 carbons, cycloalkyl of 3 to 6 carbons or $C_{1-6}$ alkyl substituted cycloalkyl of 1 to 6 carbons, and $R_8$ is H, alkyl of 1 to 6 carbons, —CH$_2$O($C_{1-6}$-alkyl), CH$_2$OCO($C_{1-6}$-alkyl) or a cation of a pharmaceutically acceptable base.

The present invention also relates to pharmaceutical compositions comprising one or more of the compounds of Formulas 1 through 17 and to methods of using such pharmaceutical compositions to treat the diseases conditions which are normally treatable with retinoids. The invention still more advantageously relates to using the pharmaceutical compositions containing one or more compounds of Formulas 1 through 17 for treatment of diseases or conditions where treatment with an cytochrome P450RAI1 or with a cytochrome P450RAI2 sspecific or selective inhibitor provides a therapeutic advantage.

BRIEF DESCRIPTION OF THE DRAWING FIGURE

FIG. 1 is a schematic representation of the P450RAI cell based assay utilized to evaluate the ability of a compound of to inhibit the Cytochrome P450RAI enzyme.

BIOLOGICAL ACTIVITY, MODES OF ADMINISTRATION

P450RAI-1 and P450RAI-2 Cell-Based Inhibitor Assay:

FIG. 1 shows a schematic diagram of the P450RAI-1 and P450RAI-2 cell based assay. P450RAI-1 stably transfected HeLa cells, or P450RAI-2 stably transfected HeLa cells, as applicable, are maintained in 100 millimolar tissue culture dishes in Modified Eagle's Medium (MEM) containing 10% Fetal Bovine Serum (FBS) and 100 µg/ml hygromycin. Exponentially growing cells are harvested by incubating in trypsin. Cells are then washed with 1× Phosphate Buffered Saline (PBS) and plated in a 48-well plate at $5 \times 10^5$ cells in 0.2 ml MEM medium containing 10% FBS and 0.05 µCi [$^3$H]-RA in the presence or absence of increasing concentrations of the test compounds. The compounds are diluted in 100% DMSO and then added in triplicate wells at either 10, 1 or 0.1 µM final concentration. As a positive control for RA metabolism inhibition, cells are also incubated with ketoconazole at 100, 10 and 1 µM. Cells are incubated for 3 hours at 37° C. The retinoids are then extracted using the-procedure of Bligh et al. (1959) Canadian Journal of Biochemistry 37, 911–917, modified by using methylenechloride instead of chloroform. The publication Bligh et al. (1959) Canadian Journal of Biochemistry 37, 911–917 is specifically incorporated herein by reference. The water soluble radioactivity is quantified using a β-scintillation counter. $IC_{50}$ values represent the concentration of inhibitor required to inhibit all-trans-RA metabolism by 50 percent and are derived manually from log-transformed data. The $IC_{50}$ values obtained in this assay with both the RAI-1 and RAI-2 enzymes for several compounds which are preferred for use in the co-administration methods and formulations of the present invention are disclosed in Table 1 below. The data demonstrate that the tested compounds have specific or selective inhibitory activity for either of the CP450RAI1 or of the CP450RAI2 enzyme.

TABLE 1

| Compound # | Structures | RAR $EC_{50}$/(EFFICACY)/$K_d$ nM  | | | P450RAI-2 Whole cell $IC_{50}$ μM | P450RAI-2 Whole cell $IC_{50}$ μM |
|---|---|---|---|---|---|---|
| | | α | β | γ | | |
| 2 | 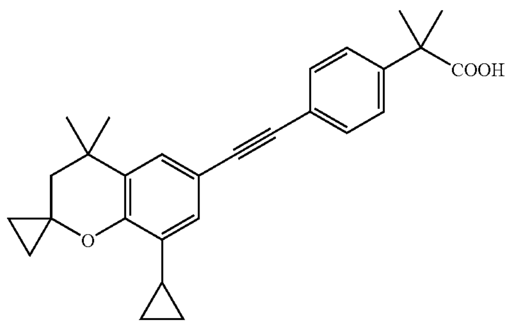 | $NA^1$ 558 | NA 3439 | NA 5577 | 0.03 | >10 |
| 1 | 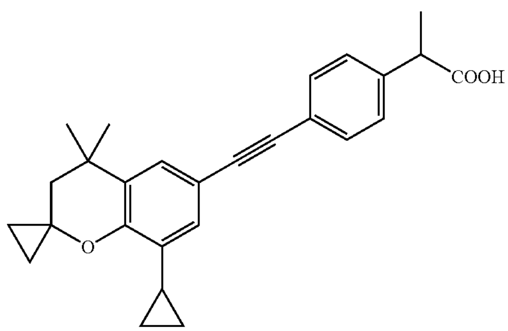 | NA 2090 | NA 3016 | NA 3486 | 0.009 | 8 |
| 3 | 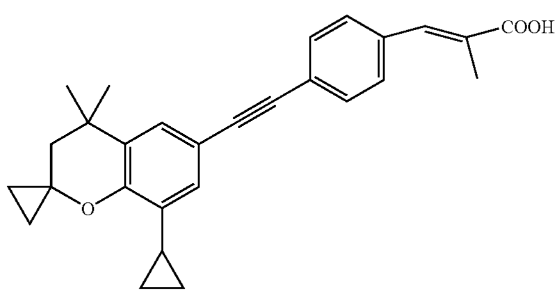 | NA >10K | $WA^2$ (15) 520 | NA (10) 6040 | 0.25 | >10 |
| 4 | 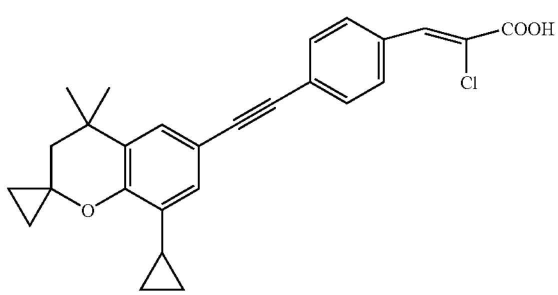 | NA >10K | WA (20) >10K | WA (15) >10K | 0.12 | >10 |

TABLE 1-continued

| Compound # | Structures | RAR EC$_{50}$/(EFFICACY)/K$_d$ nM α | β | γ | P450RAI-2 Whole cell IC$_{50}$ μM | P450RAI-2 Whole cell IC$_{50}$ μM |
|---|---|---|---|---|---|---|
| 13 | (structure) | NA 397 | NA >10K | NA >10K | 0.06 | 8 |
| 12 | (structure) | NA >10K | NA >10K | NA >10K | 0.16 | >10 |
| 11 | (structure) | NA >10K | NA >10K | NA >10K | 0.07 | 3 |
| 10 | (structure) | NA >10K | WA (15) >10K | NA >10K | 0.07 | 0.7 |

TABLE 1-continued

| Compound # | Structures | RAR EC$_{50}$/(EFFICACY)/K$_d$ nM | | | P450RAI-2 Whole cell IC$_{50}$ μM | P450RAI-2 Whole cell IC$_{50}$ μM |
|---|---|---|---|---|---|---|
| | | α | β | γ | | |
| 14 | 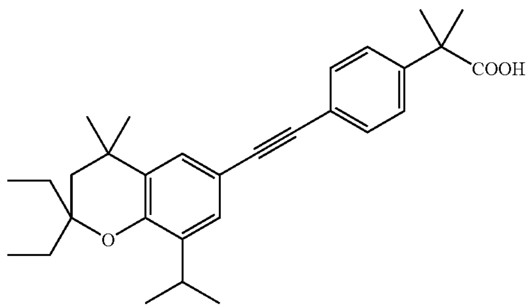 | NA 5170 | WA (10) 7400 | WA (25) >10K | 0.7 | >10 |
| 15 | 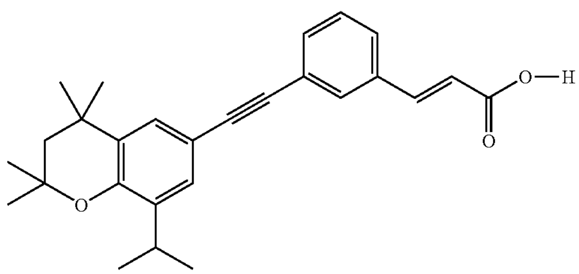 | NA 8896 | NA >10K | NA >10K | 0.6 | >10 |
| 9 | 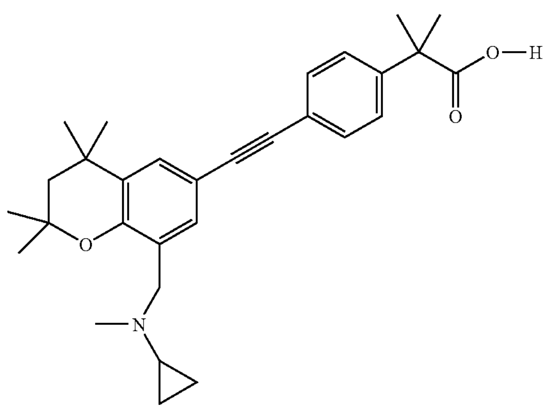 | NA >10K | NA >10K | NA >10K | 0.12 | >10 |
| 8 | 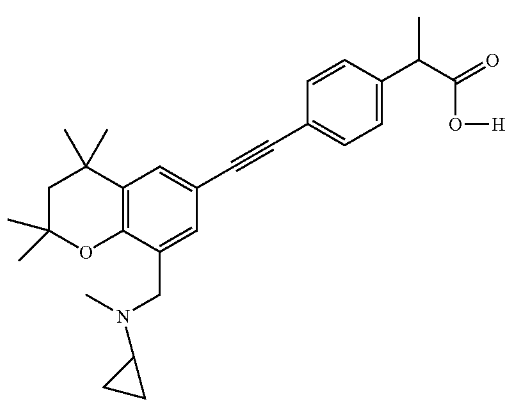 | NA 957 | WA (15) 4805 | NA >10K | 0.05 | >10 |

TABLE 1-continued
| Compound # | Structures | RAR EC₅₀/(EFFICACY)/K_d nM | | | P450RAI-2 Whole cell IC₅₀ μM | P450RAI-2 Whole cell IC₅₀ μM |
|---|---|---|---|---|---|---|
| | | α | β | γ | | |
| 6 | 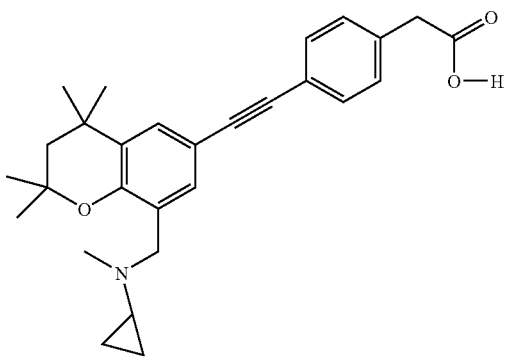 | NA 3412 | NA >10K | NA >10K | 0.06 | 4 |
| 7 | 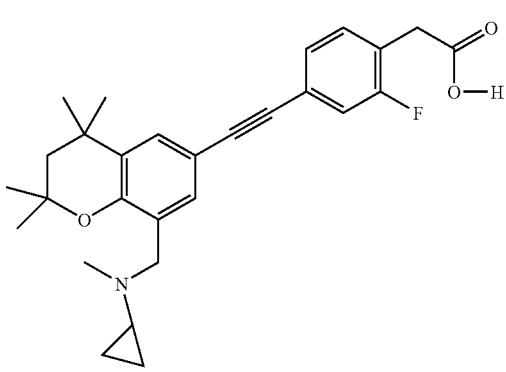 | NA >10K | NA >10K | NA >10K | 0.04 | 2 |
| 18 | 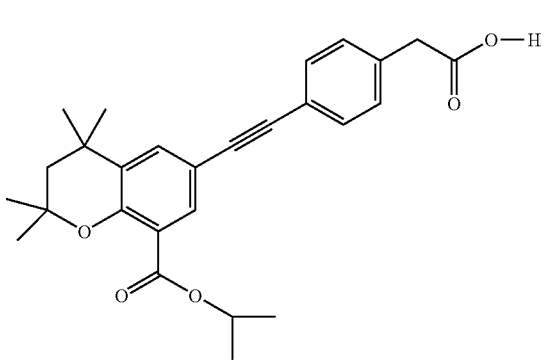 | | | | 0.4 | >10 |
| 20 | 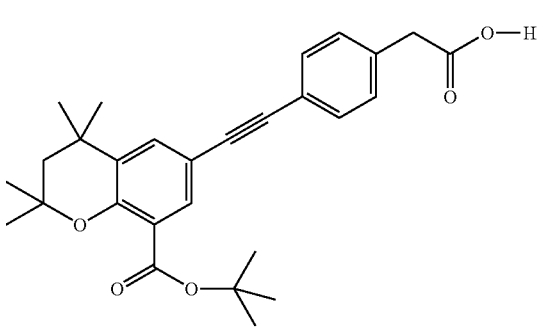 | | | | 2.9 | >10 |

TABLE 1-continued
| Compound # | Structures | RAR EC$_{50}$/(EFFICACY)/K$_d$ nM | | | P450RAI-2 Whole cell IC$_{50}$ μM | P450RAI-2 Whole cell IC$_{50}$ μM |
|---|---|---|---|---|---|---|
| | | α | β | γ | | |
| 19 | 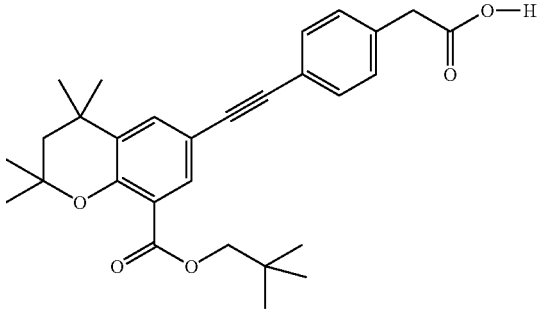 | | | | 7 | >10 |
| 45 | 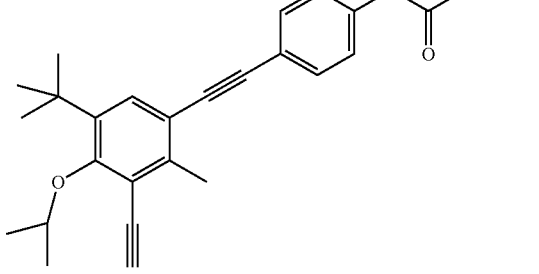 | 118 (52) 9.9 | 18 (55) 76 | 31 (68) 255 | 0.7 | >10 |
| 46 | 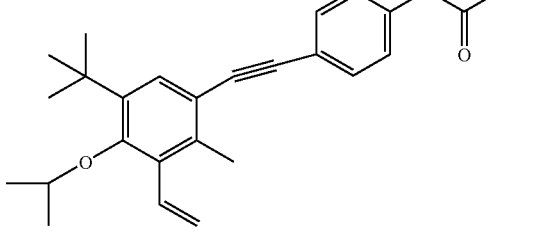 | 65 (67) 85 | 10 (75) 45 | 7 (65) 215 | 0.7 | >10 |
| 47 | 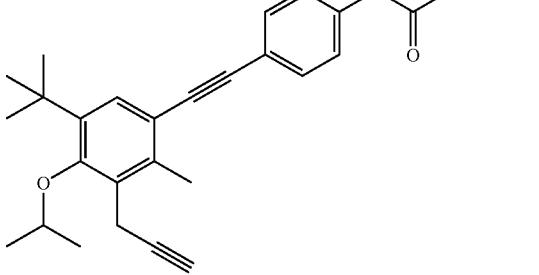 | WA (10) 2242 | 38 (59) 4473 | 125 (66) 1954 | 0.1 | 8.8 |
| 16 | 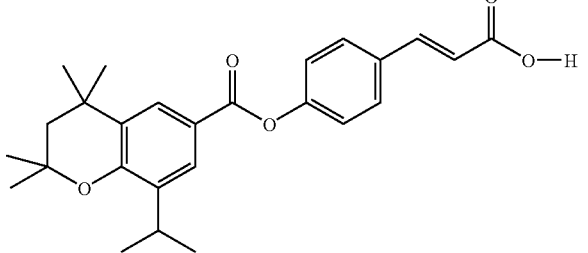 | WA (~5) 3083 | WA (35) 810 | WA (~5) >10K | 1.3 | >10 |

TABLE 1-continued

| Compound # | Structures | RAR EC₅₀/(EFFICACY)/K_d nM | | | P450RAI-2 Whole cell IC₅₀ μM | P450RAI-2 Whole cell IC₅₀ μM |
|---|---|---|---|---|---|---|
| | | α | β | γ | | |
| 17 | 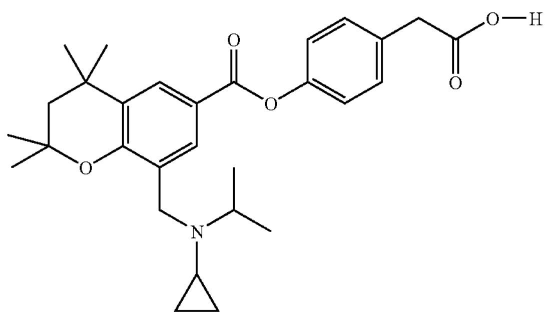 | NA | NA | NA | 2.5 | >10 |
| 23 | 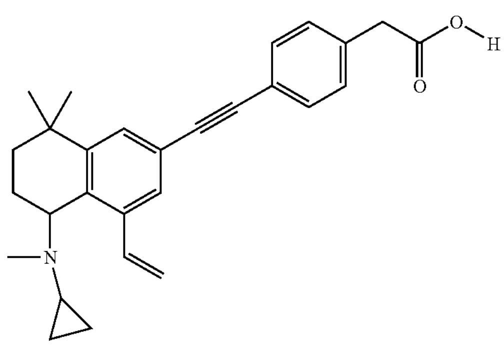 | NA >10K | WA (40) >10K | WA (35) >10K | 0.008 | 0.5 |
| 49 | 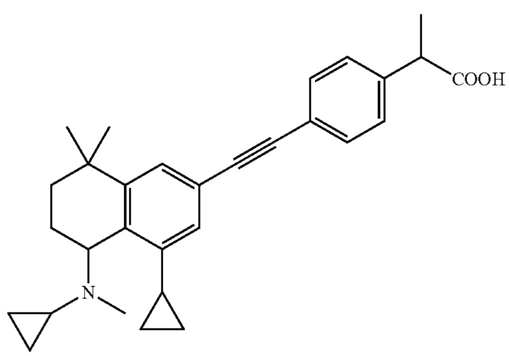 | 5282 | >10K | >10K | 0.05 | >10 |
| 50 | 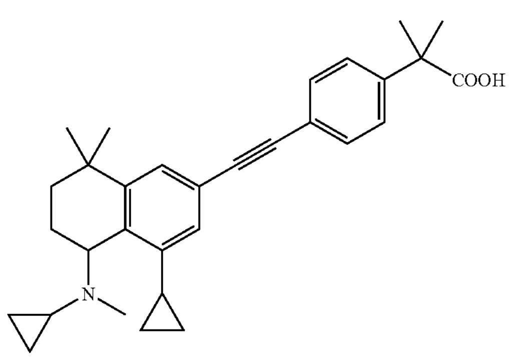 | >10K | >10K | >10K | 0.1 | >10 |

TABLE 1-continued
| Compound # | Structures | RAR EC$_{50}$/(EFFICACY)/K$_d$ nM α | β | γ | P450RAI-2 Whole cell IC$_{50}$ μM | P450RAI-2 Whole cell IC$_{50}$ μM |
|---|---|---|---|---|---|---|
| 48 | 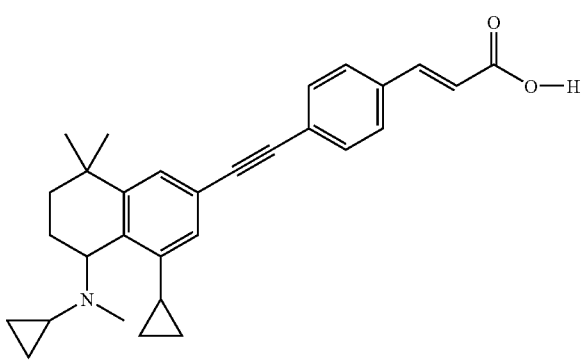 | NA >10K | WA (40) >10K | WA (25) >10K | 0.7 | 10 |
| 52 | 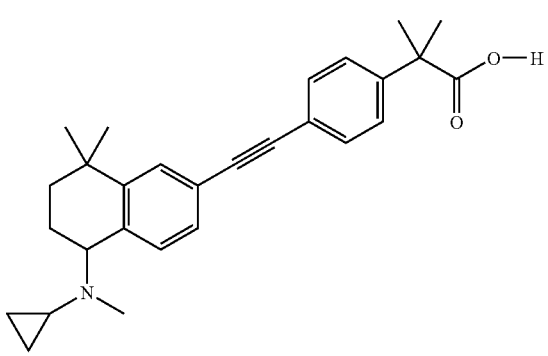 | NA >10K | WA (<5) >10K | NA >10K | 0.4 | >10 |
| 51 | 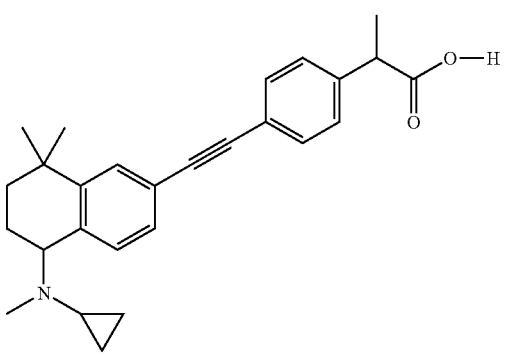 | NA >10K | WA (5) >10K | NA >10K | 0.2 | >10 |
| 53 | 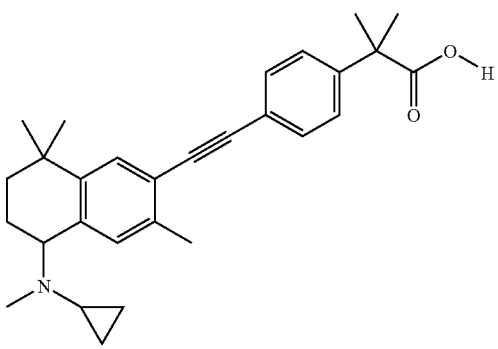 | NA >10K | NA 3906 | NA >10K | 0.5 | 5 |

TABLE 1-continued
| Compound # | Structures | RAR EC$_{50}$/(EFFICACY)/K$_d$ nM | | | P450RAI-2 Whole cell IC$_{50}$ μM | P450RAI-2 Whole cell IC$_{50}$ μM |
|---|---|---|---|---|---|---|
| | | α | β | γ | | |
| 54 | 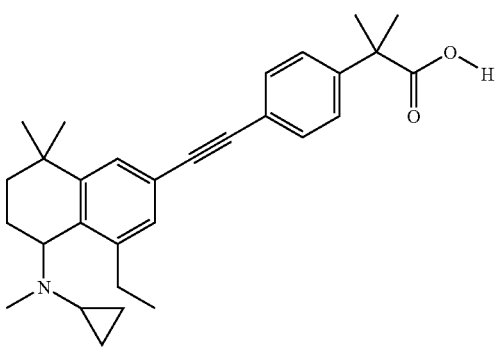 | NA 1808 | NA 5088 | NA >10K | 0.2 | >10 |
| 28 | 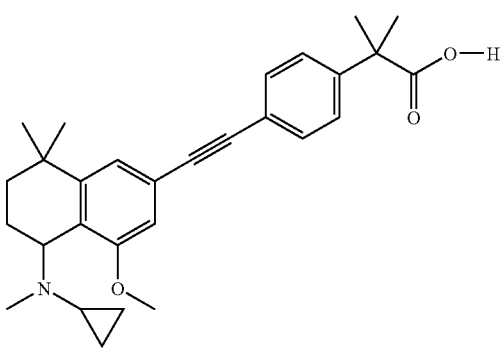 | NA >10K | NA >10K | NA 4200 | 0.25 | >10 |
| 25 | 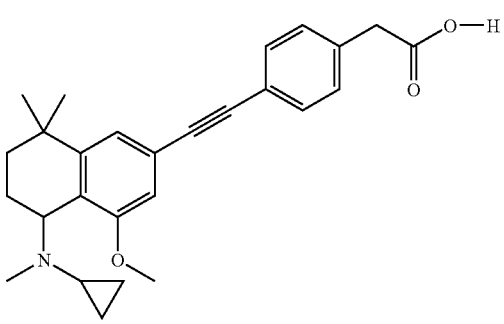 | NA >10K | NA >10K | NA 317 | 0.1 | >10 |
| 26 | 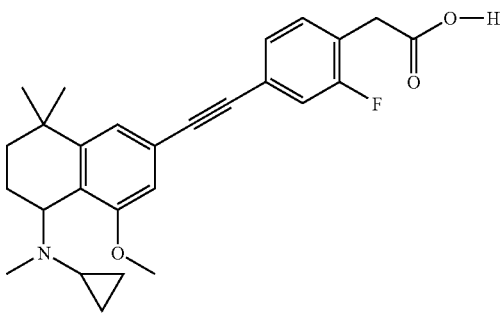 | NA >10K | WA (25) >10K | NA 1123 | 0.018 | 5 |

TABLE 1-continued
| Compound # | Structures | RAR EC$_{50}$/(EFFICACY)/K$_d$ nM | | | P450RAI-2 Whole cell IC$_{50}$ μM | P450RAI-2 Whole cell IC$_{50}$ μM |
|---|---|---|---|---|---|---|
| | | α | β | γ | | |
| 29 | 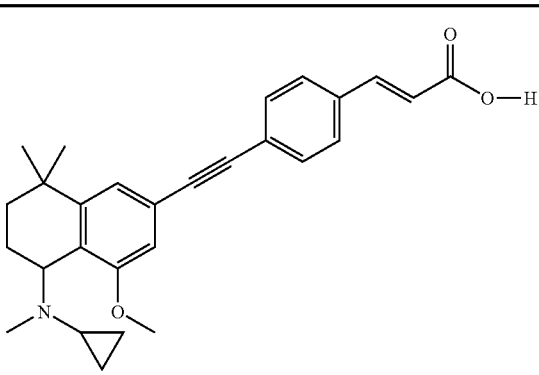 | NA >10K | NA >10K | NA >10K | 0.6 | >10 |
| 27 | 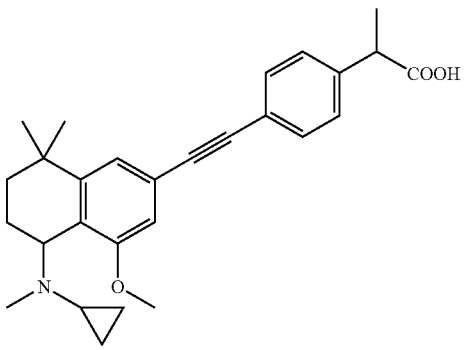 | NA 118 | NA 1275 | NA >10K | 0.028 | >10 |
| 30 | 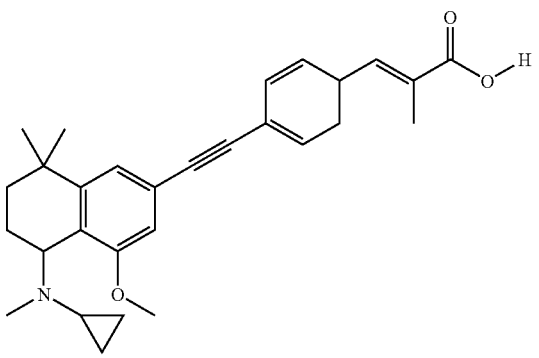 | NA >10K | NA (15) >10K | NA >10K | 0.18 | >10 |
| 41 | 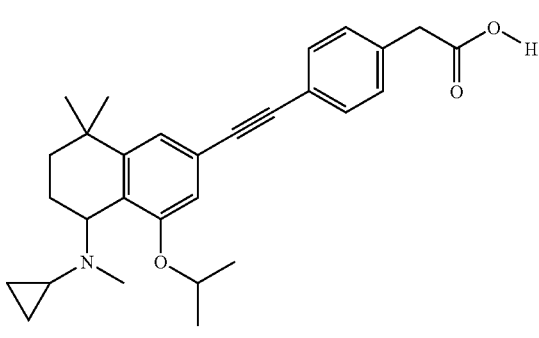 | NA >10K | NA >10K | WA (30) >10K | 0.016 | >10 |

TABLE 1-continued

| Compound # | Structures | RAR EC$_{50}$/(EFFICACY)/K$_d$ nM | | | P450RAI-2 Whole cell IC$_{50}$ μM | P450RAI-2 Whole cell IC$_{50}$ μM |
|---|---|---|---|---|---|---|
| | | α | β | γ | | |
| 22 | 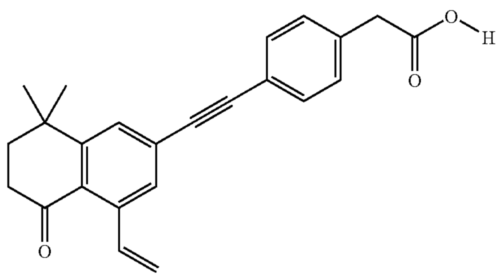 | NA >10K | WA (15) >10K | NA 10K | 0.007 | 0.2 |
| 24 | 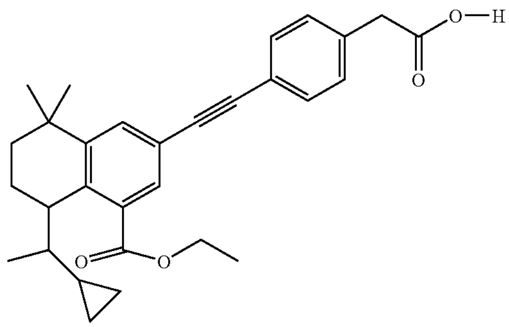 | NA 8570 | WA (30) 7188 | NA 7747 | 0.035 | 5 |
| 32 | 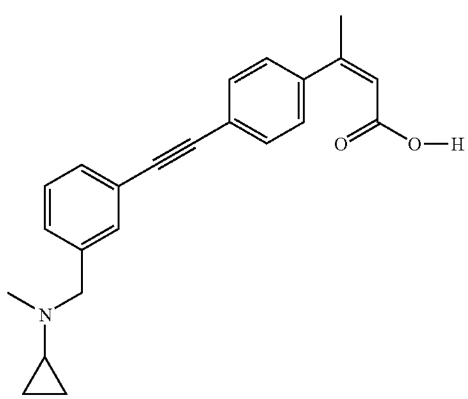 | NA >10 | NA >10K | NA >10K | 0.44 | >10 |
| 33 | 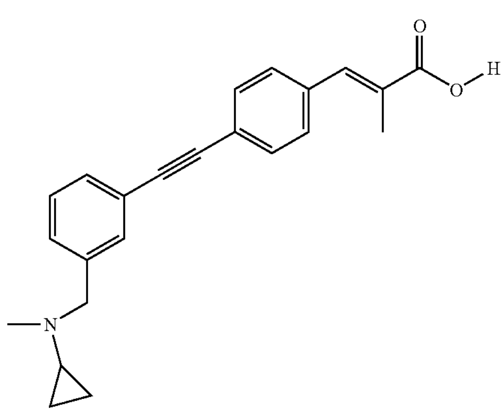 | NA 3252 | WA (30) | WA (10) >10K | >10 | 1 |

TABLE 1-continued
| Compound # | Structures | RAR EC$_{50}$/(EFFICACY)/K$_d$ nM | | | P450RAI-2 Whole cell IC$_{50}$ μM | P450RAI-2 Whole cell IC$_{50}$ μM |
|---|---|---|---|---|---|---|
| | | α | β | γ | | |
| 55 | 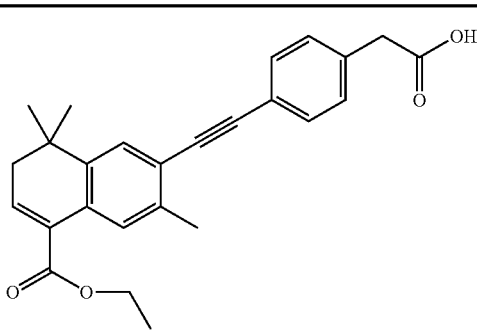 | NA >10K | WA (35) >10K | WA (30) >10K | 1.4 | >10 |
| 56 | 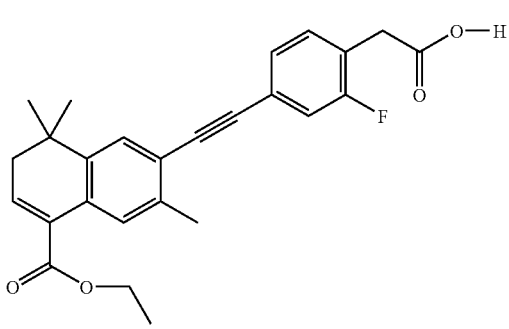 | NA >10K | WA (50) >10K | NA >10K | 0.5 | 10 |
| 57 | 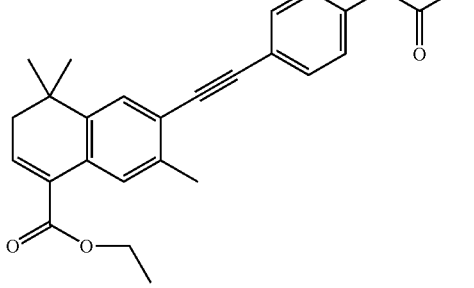 | NA 6028 | WA (50) 4979 | WA (35) 7738 | 0.4 | 10 |
| 60 | 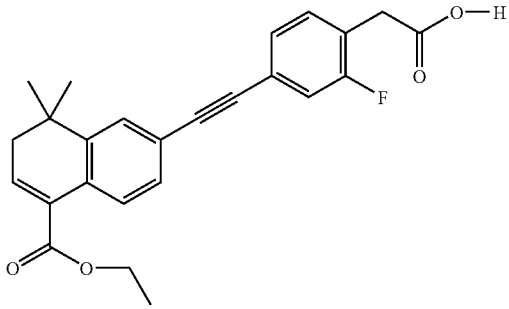 | NA 6315 | WA (60) 3957 | WA (15) 8992 | 0.06 | 2.6 |

TABLE 1-continued

| Compound # | Structures | RAR EC$_{50}$/(EFFICACY)/K$_d$ nM | | | P450RAI-2 Whole cell IC$_{50}$ μM | P450RAI-2 Whole cell IC$_{50}$ μM |
|---|---|---|---|---|---|---|
| | | α | β | γ | | |
| 58 | 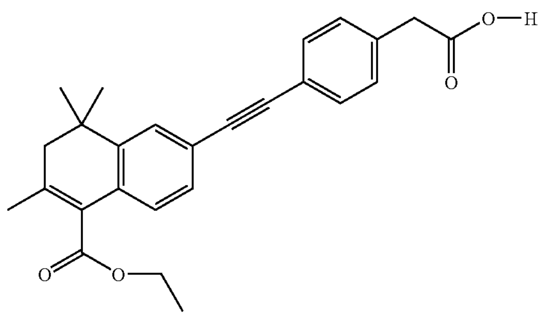 | NA >10K | WA (25) 4614 | NA >10K | 3.5 | >10 |
| 59 | 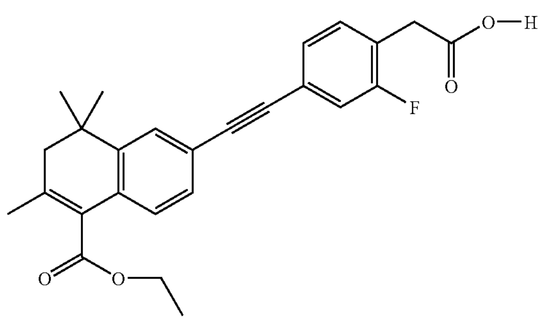 | NA >10K | WA (35) 2862 | NA >10K | 1.2 | >10 |
| 38 | 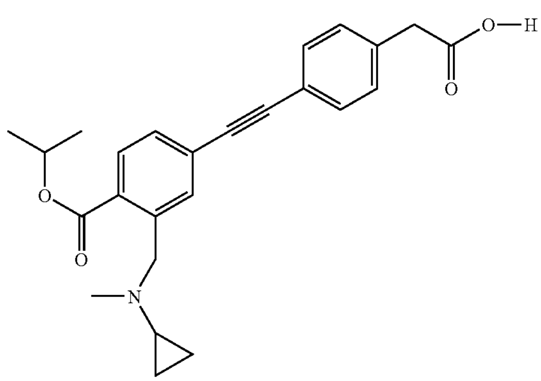 | WA (10) >10K | NA >10K | NA >10K | 4 | >10 |
| 39 | 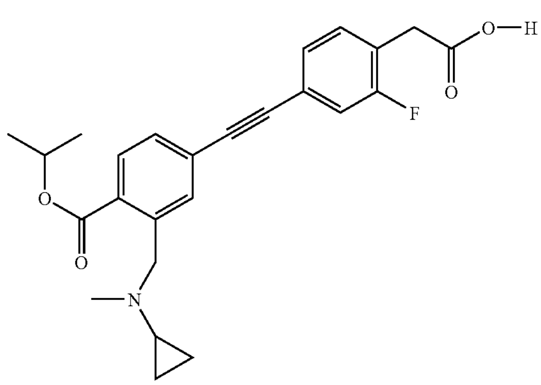 | NA >10K | NA >10K | NA >10K | 2.5 | >10 |

TABLE 1-continued

| Compound # | Structures | RAR EC$_{50}$/(EFFICACY)/K$_d$ nM | | | P450RAI-2 Whole cell IC$_{50}$ μM | P450RAI-2 Whole cell IC$_{50}$ μM |
|---|---|---|---|---|---|---|
| | | α | β | γ | | |
| 40 | 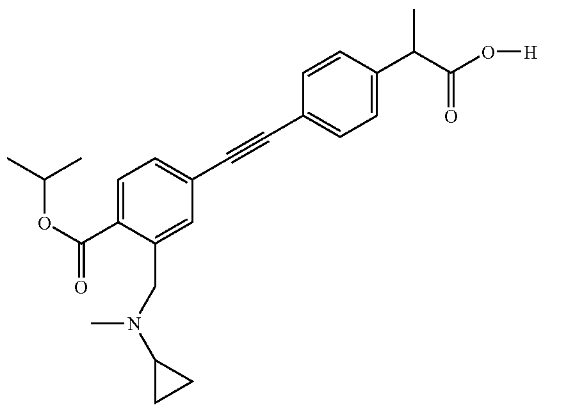 | NA >10K | NA >10K | NA >10K | 1.3 | >10 |
| 42 | 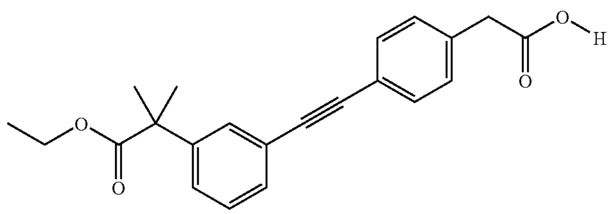 | NA >10K | WA (10) 2765 | NA >10K | 0.06 | 2 |
| 43 | 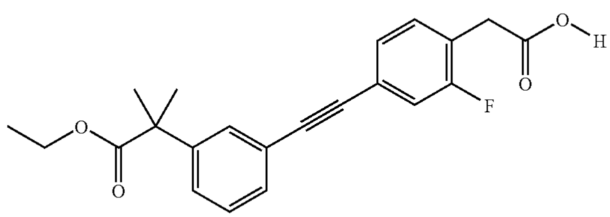 | WA (10) 2661* | WA (60) 1158 | WA (20) 3348* | 0.01 | 0.7 |
| 44 | 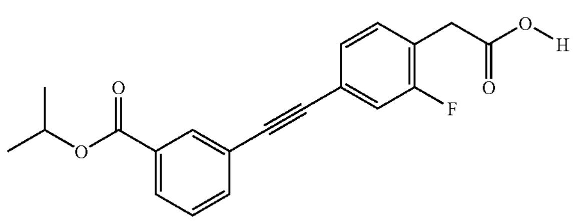 | NA >10K | 8169 | NA >10K | 0.7 | 7.5 |
| 61 | 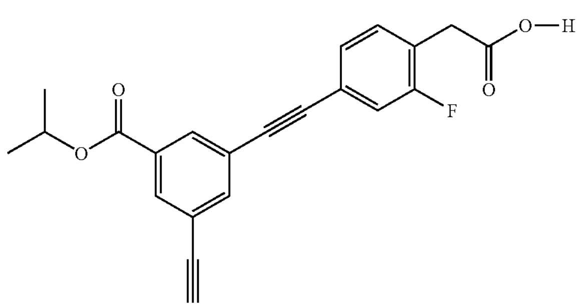 | NA >10K | NA >10K | NA >10K | 0.22 | 8.1 |

TABLE 1-continued

| Compound # | Structures | RAR EC₅₀/(EFFICACY)/K_d nM | | | P450RAI-2 Whole cell IC₅₀ μM | P450RAI-2 Whole cell IC₅₀ μM |
|---|---|---|---|---|---|---|
| | | α | β | γ | | |
| 62 | 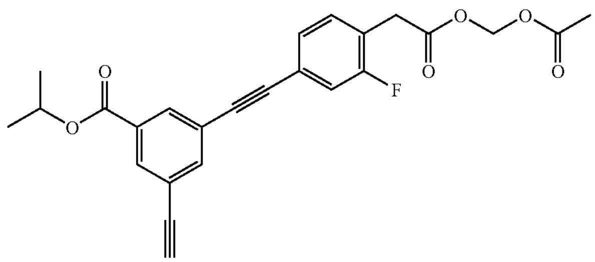 | NA >10K | NA >10K | NA >10K | 0.4 | 6.1 |
| 35 | 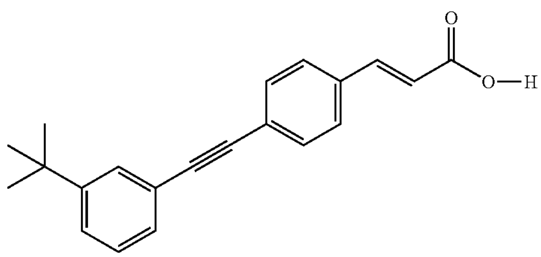 | NA 1931 | 16 (80) 2089 | 126 (48) 2888 | >10 | 0.5 |
| 36 | 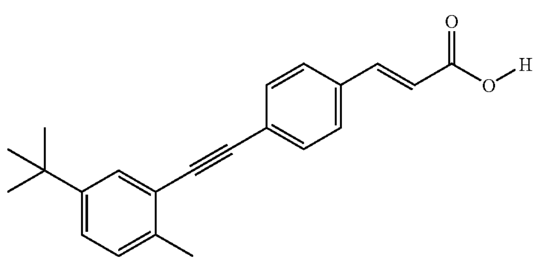 | NA >10K | WA (40) 3518 | WA (15) 2084 | >10 | 0.4 |
| 21 | 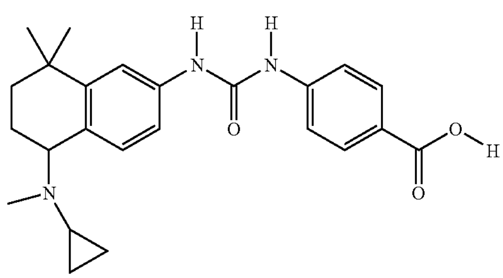 | NA >10K | NA >10K | NA >10K | >10 | 0.7 |
| 5 | 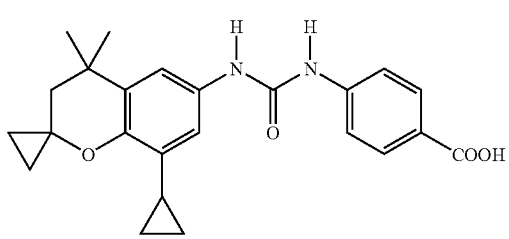 | NA >10K | 320 (55) 4536 | WA (15) >10K | >10 | 0.45 |

TABLE 1-continued

| Compound # | Structures | RAR EC$_{50}$/(EFFICACY)/K$_d$ nM | | | P450RAI-2 Whole cell IC$_{50}$ µM | P450RAI-2 Whole cell IC$_{50}$ µM |
|---|---|---|---|---|---|---|
| | | α | β | γ | | |
| 31 | 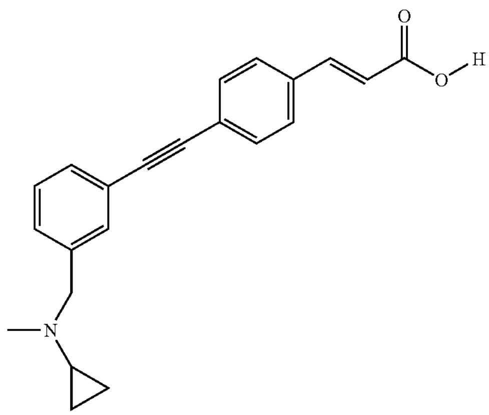 | NA >10K | WA (25) >10K | NA >10K | >10 | 0.6 |
| 34 | 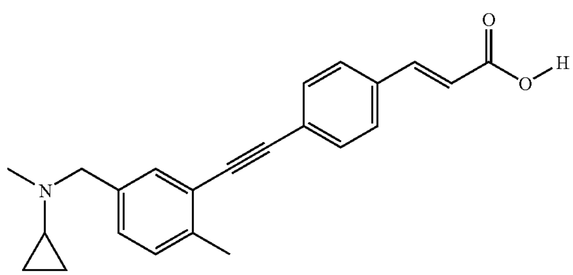 | NA 5648 | WA (20) 3492 | NA 8528 | >10 | 0.12 |
| 37 | 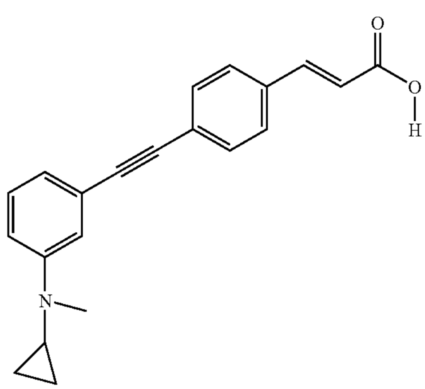 | WA (10) >10K | WA (70) 7015 | WA (15) >10K | >10 | 0.5 |
| 63 | 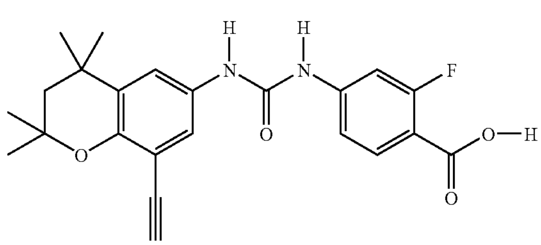 | NA >100K | 853 (37) 11K | NA >100K | >10 | 0.68 |

NA[1] = Not Active;
WA[2] = Weakly Active

Modes of Administration

The compounds of the invention are useful for curing or alleviating the symptoms and conditions of the diseases and conditions which are responsive to treatment by retinoids and/or to the organism's endogenous retinoic acid. Specifically by way of example and without limitation the compounds of the invention are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds of the invention are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the compounds of the invention can be used as agents to treat diseases of the eye, including, without limitation, proliferative vitreoretinopathy (PVR), retinal detachment, dry eye and other corneopathies, as well as for the treatment and prevention of various cardiovascular diseases, including, without limitation, diseases associated with lipid metabolism such as dyslipidemias, prevention of post-angioplasty restenosis and as agents to increase the level of circulating tissue plasminogen activator (TPA). Other uses for the compounds of the invention include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis. The compounds of the invention may also have use for treating type II non-insulin dependent diabetes mellitus (NIDDM).

The compounds of this invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, the compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds, or to control by naturally occurring retinoic acid will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation with constitute a therapeutically effective concentration for total application. If administered systemically, an amount between 0.01 and 5 mg per kg of body weight per day would be expected to effect a therapeutic result in the treatment of many diseases for which these compounds are useful.

In some applications pharmaceutical formulations containing the CP-450RAI inhibitory compounds may be co-administered with formulations containing retinoids. In such cases the dose of the cytochrome P450RAI inhibitory compounds is in the range of 0.01 and 5 mg per kg body weight per day.

GENERAL EMBODIMENTS AND SYNTHETIC METHODOLOGY

Definitions

The term alkyl refers to and covers any and all groups which are known as normal alkyl and branched-chain alkyl. Unless specified otherwise, lower alkyl means the above-defined broad definition of alkyl groups having 1 to 6 carbons in case of normal lower alkyl, and 3 to 6 carbons for lower branch chained alkyl groups. A pharmaceutically acceptable salt may be prepared for any compound used in accordance with the invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Some compounds used in accordance with the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds used in accordance with the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

General Synthetic Methodology

The novel compounds used in accordance with the invention are encompassed by the general Formulas 1 through 17 provided above. In each of these formulas a linker or tethering group designated Z covalently connects an aromatic or heteroaromatic moiety designated $A(R_2)$-W-$COOR_8$, $A(R_2)$—$CH_2$—$COOR_8$ or $A(R_2)$—$COOR_8$ and another cyclic moiety which in accordance with these formulas is a substituted phenyl, substituted tetrahydronaphthalene, substituted dihydronaphthalene, substituted chroman, substituted thiochroman or substituted tetrahydroquinoline moiety.

Generally speaking compounds such as $X_4A(R_2)$-W-$COOR_8$, $X_4$-$A(R_2)$—$CH_2$—$COOR_8$ and $X_4$-$A(R_2)$—$COOR_8$ are commercially available, or can be made in accordance with the chemical literature, or with such modification of known chemical processes, or of chemical processes disclosed herein which are within the skill of the practicing organic chemist. The group $X_4$ represents a reactive group, which is suitable for coupling the $X_4$-$A(R_2)$-W-$COOR_8$, $X_4$-$A(R_2)$—$CH_2$—$COOR_8$ and $X_4$-$A(R_2)$—$COOR_8$ compounds to a derivative of the substituted phenyl, substituted tetrahydronaphthalene, substituted dihydronaphthalene, substituted chroman, substituted thiochroman, or substituted tetrahydroquinoline moiety so that as a result of the coupling the linker or tether moiety Z is formed. In many instances the group $X_4$ is a leaving group such as halogen, or trifluoromethanesulfonyloxy, or a group capable of participating in a Wittig or Horner Emmons reaction. In some instances the group $X_4$ is an ethynyl group capable of undergoing a coupling reaction with a leaving group (such as a halogen or a trifluoromethanesulfonyloxy group) attached to the substituted phenyl, substituted tetrahydronaphthalene, substituted dehydronaphthalene, substituted chroman, substituted thiochroman or substituted tetrahydroquinoline moiety. The group $X_4$ can also represent an OH or an $NH_2$ group that forms an ester (COO) or amide (CONH) linker, respectively, when reacted with an activated carboxyl derivative of the substituted phenyl, substituted tetrahydronaphthalene, substituted dihydronaphthalene, substituted chroman, substituted thiochroman, or substituted tetrahydroquinoline moiety. The compounds of the formulas $X_4$-$A(R_2)$-W-$COOR_8$, $X_4$-$A(R_2)$—$CH_2$—$COOR_8$ and $X_4$-A $(R_2)$—$COOR_8$ are generally referred to in this description as "coupling reagents" or just "reagents" and the preparation of several examples of these coupling reagents is described in the specific examples below. Further examples are the pyridyl, thienyl, furyl, pyridazine, pyrazine and other heteroaryl analogs of the coupling reagents described in the specific examples. These reagents can be obtained in accordance with the chemical literature, or with such modification of known chemical processes, or of chemical processes disclosed herein which are within the skill of the practicing organic chemist.

Still further in accordance with the general synthetic methodology to provide the compounds of Formulas 1 through 17 a derivative of the substituted phenyl, substituted tetrahydronaphthalene, substituted dihydronaphthalene, substituted chroman, substituted thiochroman, or substituted tetrahydroquinoline moiety is synthesized first, having a covalently attached $X_5$ group. The $X_5$ group reacts with the $X_4$ group of the reagents $X_4$-$A(R_2)$-W-$COOR_8$, $X_4$-$A(R_2)$—$CH_2$—$COOR_8$— and $X_4$-$A(R_2)$—$COOR_8$ to form the linker designated Z in Formulas 1 through 17. The $X_5$ group is one that is capable of participating in a catalyzed coupling reaction, (such as an ethynyl group when $X_4$ is a leaving group), or a leaving group (such as halogen or trifluoromethanesulfonyloxy when $X_4$ is an ethynyl group), or an activated carboxylic acid function (when $X_4$ is OH or $NH_2$). The $X_5$ group can also be an OH, SH or $NH_2$ group when the $X_4$ group is an activated carboxylic acid function. Specific examples for substituted phenyl, substituted tetrahydronaphthalene, substituted dihydronaphthalene, substituted chroman, substituted thiochroman, or substituted tetrahydroquinoline intermediates having an $X_5$ functionality are provided below, and are also available in the chemical scientific and patent literature.

Generally speaking, for reagents and reactions covalently joining a substituted tetrahydronaphthalene, substituted dihydronaphthalene, substituted chroman, substituted thiochroman, or substituted tetrahydroquinoline intermediate with a substituted aryl or heteroaryl group, of the formulas $A(R_2)$-W-$COOR_8$, $A(R_2)$—$CH_2$—$COOR_8$ and $A(R_2)$—$COOR_8$ to form a compound including the linker designated Z, reference is made to U.S. Pat. Nos. 5,648,503; 5,723,666, 5,952,345, 6,252,090 and 6,313,107 the specification of each of which are expressly incorporated herein by reference.

The substituted phenyl, substituted tetrahydronaphthalene, substituted dihydronaphthalene, substituted chroman, substituted thiochroman or substituted tetrahydroquinoline moiety of the novel compounds used in accordance with the invention are derivatized in a manner to include the specific substituents (such as for example the cycloalkyl substituents) encompassed within the scope of the invention, either before or after the $A(R_2)$-W-$COOR_8$, $A(R_2)$—$CH_2$—$COOR_8$ or $A(R_2)$—$COOR_8$ moiety has been attached and the linker Z has formed, as illustrated by the below described specific examples.

The W-$COOR_8$, $CH_2$—$COOR_8$ or $COOR_8$ moiety of the compounds of Formulas 1 through 17 can be modified in order to obtain still further novel compounds. One such modification is saponification of compounds where the $R_8$ group is an alkyl, $CH_2O(C_{1-6}$-alkyl) or $CH_2OCO(C_{1-6}$-alkyl) group. Another modification is esterification of the carboxylic acid function when the $R_8$ group is H or a cation. Such saponification and esterification reactions are well known in the art and within the skill of the practicing organic chemist.

SPECIFIC EMBODIMENTS

With reference to the symbol A in Formulas 1 through 17, the preferred novel compounds used in accordance with the present invention are those where A is phenyl, naphthyl, pyridyl, thienyl or furyl. Even more preferred are compounds where A is phenyl. As far as substitutions on the A (phenyl) and A (pyridyl) groups are concerned, compounds are usually preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred novel compounds used in accordance with the invention either there is no $R_2$ substituent on the A group, or the $R_2$ substituent is preferably a fluoro group that is preferably located on the aromatic carbon adjacent (ortho) to the carbon bearing the W—$COOR_8$, $CH_2$—$COOR_8$ or $COOR_8$ group.

As far as the W-$COOR_8$ moiety is concerned, the variable W preferably represents —CH=CH—, —$CR_5$CH—, CH=$CR_5$— (cinnamic acid derivatives) $C(R_5)_2$ or $CHR_5$ where $R_5$ is preferably methyl. For the $R_8$ group H, lower alkyl of 1 to 3 carbons, —$CH_2O(C_{1-3}$-alkyl) and —$CH_2OCO(C_{1-3}$-alkyl) groups are preferred, as well as the pharmaceutically acceptable salts of the free acids when $R_8$ is H. Among the lower alkyl, —$CH_2O(C_{1-3}$-alkyl) and —$CH_2OCO(C_{1-3}$-alkyl) groups methyl, ethyl, $CH_2OCH_3$ and $CH_2OCOCH_3$ respectively, are presently most preferred.

The linker group Z in all of the novel compounds used in accordance with the invention is preferably ethynyl, (—C≡C—), ester (CO—O), or ureido (NHCONH). Moreover for chroman, thichroman and tetrahydroquinoline derivatives the linker Z is preferably attached to the 6 position (e.g. see Formula 1). For tetrahydronaphthalene and dihydronaphthalene derivatives the linker Z is preferably attached to the to the 6 position as such positions are numbered in Formulas 2 and 11.

The $R_1$ group is preferably methyl when it serves as a substituent attached to a carbon of the chroman, thiochroman, tetrahydroquinoline, tetrahydronaphthalene or dihydronaphthalene nucleus and is preferably hydrogen when it forms part of a linker Z.

The aromatic portion of the chroman, thiochroman, tetrahydroquinoline, tetrahydronaphthalene or dihydronaphthalene nuclei of the compounds of the present invention is either preferably not substituted with an $R_3$ group (the variable m is zero (0)), or $R_3$ is alkyl or halogen. The non-aromatic portion of the chroman, thiochroman, tetrahydroquinoline, tetrahydronaphthalene or dihydronaphthalene nuclei of the compounds of the present invention is either preferably not substituted with an $R_4$ group (the variable o is zero (0)), or $(R_4)_o$ represents methyl groups, still more prefreably geminal dimethyl or geminal diethyl groups attached to the 2-position of the chroman nucleus.

Structures of the most preferred compounds of the invention are shown in Table 1. Whereas most of the compounds shown in Table 1 are carboxylic acids, it should be understood that the $C_{1-3}$ alkyl esters, $CH_2OCH_3$ and $CH_2OCOCH_3$ esters and the pharmaceutically acceptable salts of these compounds are also preferred.

The compounds of the invention can be synthesized by applying the general synthetic methodology described above, and by such modifications of the hereinafter described specific synthetic routes which will become readily apparent to the practicing synthetic organic chemist in light of this disclosure and in view of general knowledge available in the art. The hereinafter disclosed specific reaction schemes are directed to the synthesis of exemplary and preferred compounds of the invention. Whereas each of the specific and exemplary synthetic routes shown in these schemes may describe specific compounds of the invention only within the scope of one or two of the general Formulas 1 through 17, the synthetic processes and methods used therein are adaptable within the skill of the practicing organic chemist and can be used with such adaptation for the synthesis of compounds of the invention which are not specifically described herein as examples.

SPECIFIC EXAMPLES

The reactions schemes provided below together with the applicable experimental descriptions disclose the presently preferred synthetic routes for preparing the preferred compounds of the invention.

Synthetic Procedures for Preparing Coupling Reagents

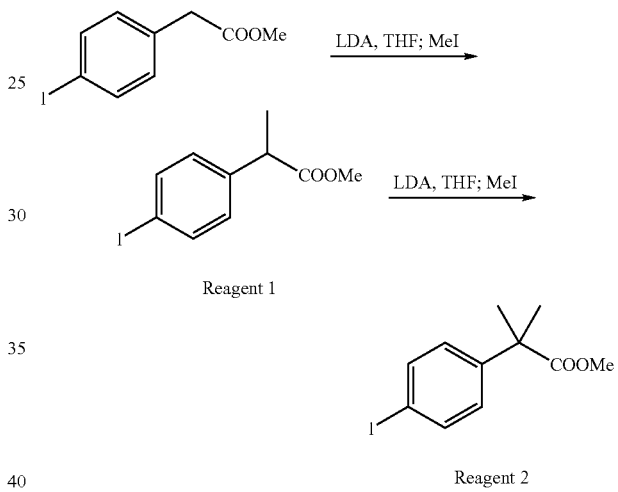

Reagent 1

Reagent 2

General Procedure A: Methyl-2-(4-iodophenyl)propionate (Reagent 1)

A stirred, cooled (−78° C.) solution of methyl-4-iodophenyl acetate (described in U.S. Pat. No. 6,252,090, incorporated herein by reference; 2.77 g, 10 mmol) in anhydrous tetrahydrofaran (20 mL) was treated with a 1.5M solution of lithium diisopropyl amide in tetrahydrofuran and cyclohexane (8 mL, 12 mmol). The reaction mixture was allowed to warm to 0° C. over 40 minutes, cooled again to −78° C. and treated with methyl iodide (0.75 mL, 12 mmol). The reaction mixture was allowed to warm to room temperature over 1 h. It was then quenched with saturated aqueous ammonium chloride solution, diluted with water and extracted with diethyl ether. The combined organic phase was washed with brine (×1), dried over anhydrous magnesium sulfate, filtered and evaporated in vacuo to afford the title product as a yellow oil (2.7 g, 92.7%).

$^1$H NMR (300 MHz, CDCl$_3$): δ 7.66 (d, 2H, J=8.5 Hz), 7.06 (d, 2H, J=8.5 Hz), 3.70–3.66 (m, 1H), 3.67 (s, 3H), 1.49 (d, 3H, J=7.0 Hz).

Methyl-2-(4-idophenyl)-2-methyl propionate (Reagent 2)

Following General Procedure A and using methyl-2-(4-iodophenyl)propionate (1.45 g, 5 mmol), lithium diisopropyl amide (1.5 M in tetrahydrofuran and cyclohexane, 4 mL, 6 mmol), tetrahydrofuran (15 mL) and methyl iodide (0.5 mL, 8 mmol), the title compound was obtained as an oil (1.5 g, 98%).

¹H NMR (300 MHz, CDCl₃): δ 7.66 (d, 2H, J=8.7 Hz), 7.11 (d, 2H, J=8.7 Hz), 3.66 (s, 3H), 1.58 (s, 6H).

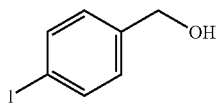

4-Iodo-benzyl alcohol

A stirred, cooled (−78° C.) solution of ethyl-4-iodo-benzoate (available from Lancaster, 12.9 g, 45 mmol) in anhydrous dichloromethane (100 mL) under argon was treated with a 1M solution of di-isobutyl aluminum hydride in dichloromethane (100 mL, 100 mmol). The reaction mixture was allowed to warm to 0° C. in 1.5 h, quenched with saturated aqueous ammonium chloride solution and the resulting emulsion was filtered over a bed of celite. The phases in the filtrate were-separated and the aqueous phase was extracted with dichloromethane (×1). The combined organic phase was dried over anhydrous sodium sulfate, filtered and evaporated in vacuo to afford the title product as a white solid (9 g, 85%).

¹H NMR (300 MHz, CDCl₃): δ 7.65 (d, 2H, J=7.6 Hz), 7.05 (d, 2H, J=7.6 Hz), 4.57 (s, 2H), 2.40 (br s, 1H).

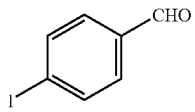

4-Iodo-benzaldehyde

A solution of 4-iodobenzyl alcohol (9 g, 38.29 mmol) in dichloromethane (90 mL) and acetonitrile (10 mL) was treated sequentially with 4 A molecular sieves powder (9 g), tetra-n-propyl ammoniumperruthenate (0.13 g) and N-methyl morpholine-N-oxide (9 g, 76.6 mmol). After stirring at ambient temperature for 2 h, the reaction mixture was diluted with hexane and subjected to flash column chromatography over-silica-gel-(230–400 mesh) using-6–1% ethyl acetate in hexane as the eluent to afford the title compound (2.5 g pure and 4 g~95% pure, 73%).

¹H NMR (300 MHz, CDCl₃): δ 9.96 (s, 1H), 7.92 (d, 2H, J=8.5 Hz), 7.59 (d, 2H, J=8.5 Hz).

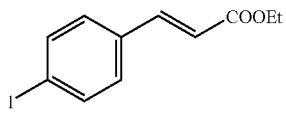

Ethyl-4-iodo-cinnamate (Reagent 3)

A stirred, cooled (−78° C.) solution of triethylphosphonoacetate (11.1 mL, 56 mmol) in anhydrous tetrahydrofuran (100 mL) was treated with a 1.6M solution of n-butyl lithium in hexanes (27 mL, 43.75 mmol). After 10 min, the reaction mixture was cannulated into a cooled (−78° C.) solution of 4-iodo-benzaldehyde (6.5 g, 28 mmol) in tetrahydrofuran (20 mL). The reaction mixture was allowed to warm to 0° C. over 1 h. It was quenched with saturated aqueous ammonium chloride solution and extracted with diethyl ether (×2). The combined organic phase was dried over anhydrous magnesium sulfate, filtered and evaporated in vacuo to afford an oil that was subjected to flash column chromatography over silica gel (230–400 mesh) using 6–8% ethyl acetate in hexane as the eluent to afford the title compound (2.7 g pure, 3.2 g~95% pure, 69%).

¹H NMR (300 MHz, CDCl₃): δ 7.70 (d, 2H, J=8.5 Hz), 7.57 (d, 1H, J=15.8 Hz), 7.21 (d, 2H, J=8.5 Hz), 6.43 (d, 1H, J=15.8 Hz), 4.25 (q, 2H, J=7.1 Hz), 1.33 (t, 3H, J=7.1 Hz).

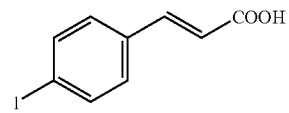

4-Iodo-cinnamic acid

A solution of ethyl-4-iodo-cinnamate (3.2 g, 10.5 mmol) in methanol (25 mL), tetrahydrofuran (25 ml) and water (15 mL) was treated with lithium hydroxide monohydrate (4.2 g, 100 mmol) and the resulting reaction mixture was stirred at ambient temperature over 2 days. The volatiles were evaporated in vacuo and the residue was neutralized with saturated aqueous ammonium chloride solution. The precipitated solid was filtered, washed with water and hexane and dried to afford the title product as a white solid (2.9 g, 91%). It was used as such for the next step.

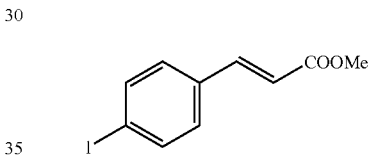

Methyl-4-iodo-cinnamate (Reagent 4)

A stirred, cooled (ice bath) solution of 4-iodo-cinnamic Acid in methanol was treated with a solution of diazomethane in diethyl ether. The reaction mixture was allowed to warm to ambient temperature, the volatiles were-evaporated in vacuo to afford the title compound.

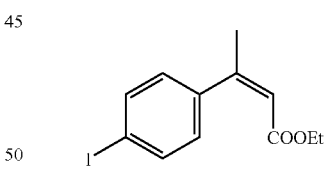

3-(4-Iodo-phenyl)-but-2Z-enoic acid ethyl ester (Reagent 5)

A stirred, cooled (−78° C.) solution of triethyl-2-phosphonoacetate (4.55 g, 20 mmol) in anhydrous tetrahydrofuran (10 mL) was treated with a 1.6M solution of n-butyl lithium in hexanes (12.8 mL, 20.5 mmol). After 30 min, a solution of 4-iodo-acetophenone (2.5 g, 10 mmol) in tetrahydrofuran (5 mL) was cannulated into the reaction mixture. After 4 h, it was quenched with saturated aqueous ammonium chloride solution and extracted with diethyl ether (×2). The combined organic phase was dried over anhydrous magnesium sulfate, filtered and evaporated in vacuo to afford an oil that was subjected to flash column chromatography over silica gel (230–400 mesh) using 5–10% ethyl acetate in hexane as the eluent, followed by preparative normal phase HPLC to afford the title compound (0.53 g, 15%).

¹H NMR (300 MHz, CDCl₃): δ 7.67 (d, J=8.2 Hz, 2H), 6.94 (d, J=8.2 Hz, 2H), 5.91 (s, 1H), 4.01 (q, J=7.1 Hz, 2H), 2.14 (s, 6H), 1.12 (t, J=7.1 Hz, 3H).

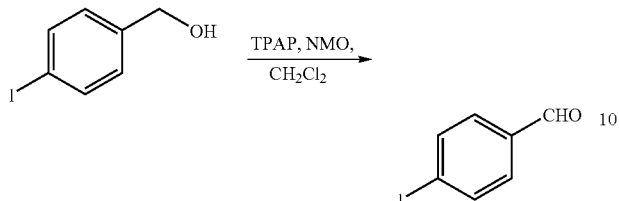

3-Iodo-benzaldehyde

A solution of 3-iodobenzyl alcohol (Aldrich, 4.72 g, 20 mmol) in dichloromethane (50 mL) and acetonitrile (5 mL) was treated sequentially with 4 A molecular sieves powder (5 g), tetra-n-propyl ammoniumperruthenate (0.1 g) and N-methyl morpholine-N-oxide (2.34 g, 40 mmol). After stirring at ambient temperature for 3 h, the reaction mixture was diluted with hexane and subjected to flash column chromatography over silica gel (230–400 mesh) using 6–10% ethyl acetate in hexane as the eluent to afford the title compound (3.7 g, 80%). It was used as such for the next step.

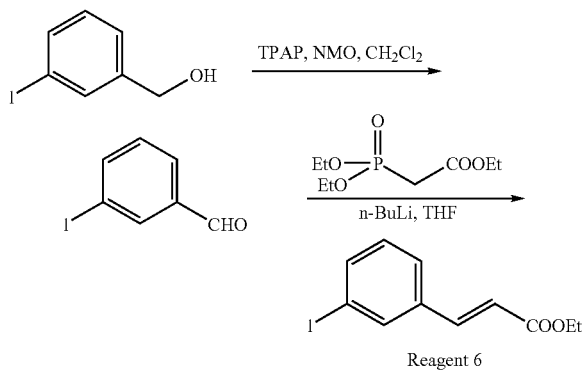

Ethyl-3-iodo-cinnamate (Reagent 6)

A stirred, cooled (−78° C.) solution of triethylphosphonoacetate (11.44 g, 51 mmol) in anhydrous tetrahydrofuran (100 mL) was treated with a 1.6M solution of n-butyl lithium in hexanes (30 mL, 48 mmol). After 10 min, the reaction mixture was cannulated into a cooled (−78° C.) solution of 4-iodo-benzaldehyde (3.7 g, 16 mmol) in tetrahydrofuran (20 mL). The reaction mixture was allowed to warm to 0° C. over 1 h. It was quenched with saturated aqueous ammonium chloride solution and extracted with diethyl ether (×2). The combined organic phase was dried over anhydrous magnesium sulfate, filtered and evaporated in vacuo to afford an oil that was subjected to flash column chromatography over silica gel (230–400 mesh) using 8–10% ethyl acetate in hexane as the eluent to afford the title compound (4.6 g, 95%).

¹H NMR (300 MHz, CDCl₃): δ 7.83 (s, 1H), 7.65 (dd, 1H, J=7.9, 2 Hz), 7.53 (d, 1H, J=15.8 Hz), 7.43 (dd, 1H, J=7.6, 2 Hz), 7.07 (dd, 1H, J=7.6, 7.9 Hz), 6.38 (d, 1H, J=15.8 Hz), 4.24 (q, 2H, J=6.9 Hz), 1.34 (t, 3H, J=6.9 Hz).

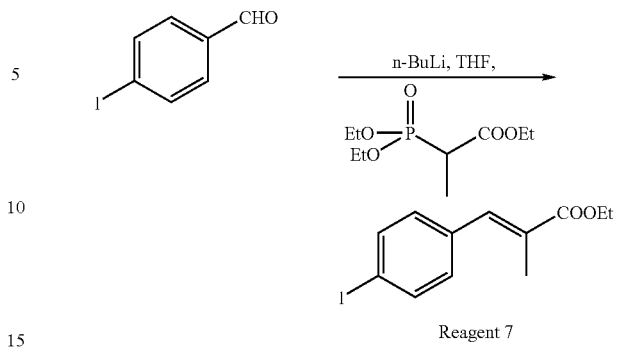

(E)-3-(4-Iodo-phenyl)-2-methyl-acrylic acid ethyl ester (Reagent 7)

A stirred, cooled (−78° C.) solution of triethyl-2-phosphonopropionate (10 g, 41.9 mmol) in anhydrous tetrahydrofuran (100 mL) was treated with a 1.6M solution of n-butyl lithium in hexanes (25 mL, 40 mmol). After 10 min, the reaction mixture was cannulated into a cooled (−78° C.) solution of 4-iodo-benzaldehyde (4.66 g, 20 mmol) in tetrahydrofuran (25 mL). After 30 minutes, it was quenched with saturated aqueous ammonium chloride solution and extracted with diethyl ether (×2). The combined organic phase was dried over anhydrous magnesium sulfate, filtered and evaporated in vacuo to afford an oil that was subjected to flash column chromatography over silica gel (230–400 mesh) using 9–10% ethyl acetate in hexane as the eluent to afford the title compound (6.3 g, 99%).

¹H NMR (300 MHz, CDCl₃): δ 7.71 (d, 2H, J=8.4 Hz), 7.58 (s, 1H), 7.12 (d, 2H, J=8.4 Hz), 4.27 (q, 2H, J=7.2 Hz), 2.08 (d, 3H, J=1.5 Hz), 1.35 (t, 3H, J=7.2 Hz).

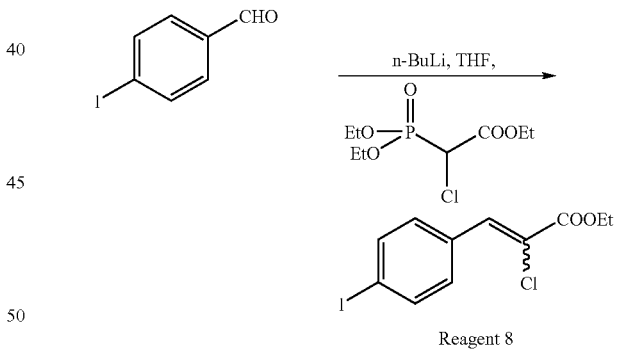

2-Chloro-3-(4-iodo-phenyl)-acrylic acid ethyl ester (Reagent 8)

A stirred, cooled (−78° C.) solution of chloro-(dipropylphosphinoyl)-acetic acid ethyl ester (6.1 g, 23.5 mmol) in anhydrous tetrahydrofuran (700 mL) was treated with a 1.6M solution of n-butyl lithium in hexanes (14 mL, 22 mmol). After 10 min, the reaction mixture was cannulated into a cooled (−78° C.) solution of 4-iodo-benzaldehyde (2.61 g, 11.2 mmol) in tetrahydrofuran (25 mL). After 30 minutes, it was quenched with saturated aqueous ammonium chloride solution and extracted with diethyl ether (×2). The combined organic phase was dried over anhydrous magnesium sulfate, filtered and evaporated in vacuo to afford an oil that was subjected to flash column, chromatography over

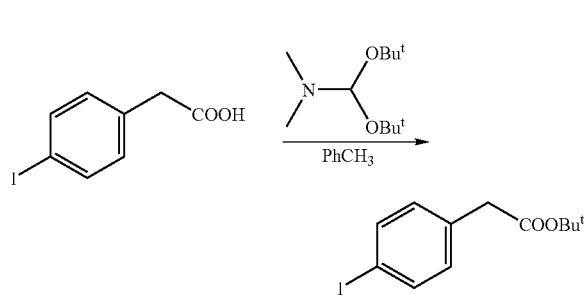

4-Iodo-tert-butyl phenyl acetate (Reagent 10)

A solution of 4-iodo phenyl acetic acid (Lancaster, 1.31 g, 5 mmol) in anhydrous toluene (10 mL) was heated to 80° C. and treated with a solution of N,N-dimethyl formamide di-t-butyl acetal. After 2 h the reaction mixture was cooled to ambient temperature and subjected to flash column chromatography on silica gel (23–400 mesh) using 10% ethyl acetate in hexane as the eluent to afford the title compound (0.7 g, 44%).

$^1$H NMR (300 MHz, CDCl$_3$): δ 7.62 (d, 2H, J=8.2 Hz), 7.01 (d, 2H, J=8.2 Hz), 3.45 (s, 2H), 1.43 (s, 9H).

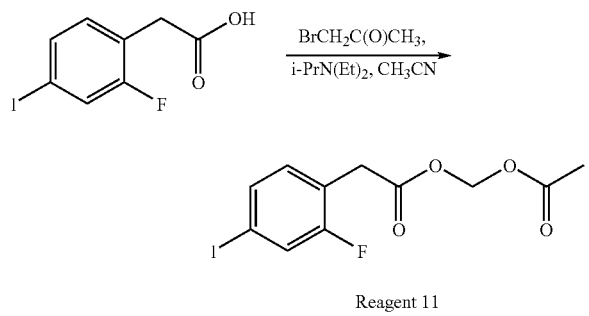

Reagent 11

(2-Fluoro-4-iodo-phenyl)-acetic acid acetoxymethyl ester (reagent 11)

A solution of 2-fluoro-4-iodo phenyl acetic acid (described in U.S. Pat. No. 6,252,090, incorporated herein by reference; 0.82 g, 2.93 mmol) in anhydrous acetonitrile (10 mL) was treated with N,N-diisopropyl ethyl amine (1.27 mL, 7.32 mmol) followed by acetoxy methyl bromide/bromo methylacetate (0.896 g, 5.86 mmol) and the resulting reaction mixture was stirred overnight at ambient temperature. The volatiles were evaporated in vacuo and the residue was diluted with water and extracted with diethyl ether (×2). The combined organic phase was dried over anhydrous magnesium sulfate, filtered and evaporated in vacuo to an oil that was subjected to flash column chromatography over silica gel (230–400 mesh) using 10–20% ethyl acetate in hexane as the eluent to afford the title compound as an oil (0.75 g, 72%). $^1$H NMR (300 MHz, CDCl$_3$): 7.42 (m, 2H), 6.97 (dd, J=8.0 & 8.0 Hz, 1H), 5.73 (s, 2H), 3.65 (s, 2H), 2.08 (s, 3H).

(2-Fluoro-4-iodo-phenyl)-acetic acid 2-trimethylsilanyl-ethyl ester

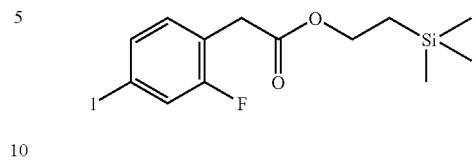

A solution of 2-fluoro-4-iodo phenyl acetic acid (0.3 g, 1.07 mmol) and 2-(trimethylsilyl)ethanol (0.28 mL, 1.951 mmol) in anhydrous dichloromethane (5 mL) was treated with 4-(dimethylamino)pyridine (0.275 g, 2.3 mmol) and 1-(3-dimethylaminopropyl)-3-ethylcarbodiimide hydrochloride (0.37 g, 1.95 mmol) and the resulting reaction mixture was stirred at ambient temperature overnight. The reaction mixture was then subjected to flash column chromatography using 5% ethyl acetate in hexane as the eluent to afford the title compound as a white solid (0.37 g, 91%).

$^1$H NMR (300 MHz, CDCl$_3$): 7.44 (m, 2H), 7.02 (dd, J=8.0, 8.0 Hz, 1H), 4.20 (t, J=8.5 Hz, 2H), 3.59 (s, 2H), 0.98 (t, J=8.5 Hz, 2H), 0.02 (s, 9H).

Synthesis of Preferred Embodiments

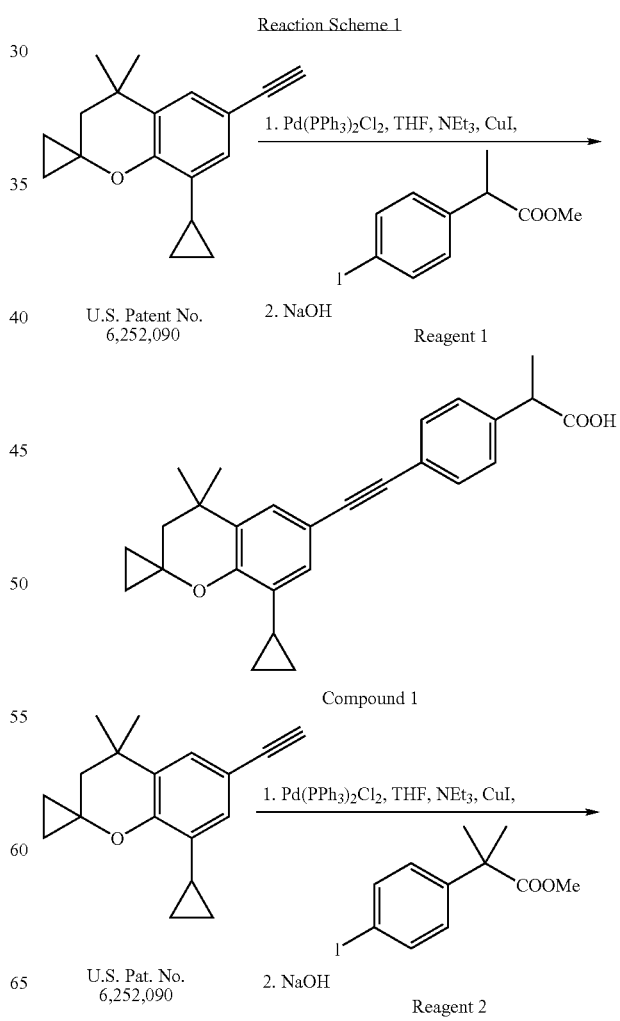

Reaction Scheme 1

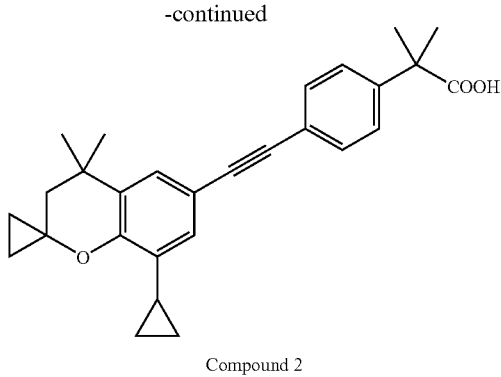

Compound 2

General Procedure B: 2-{4-[(8-Cyclopropyl-3,4-dihydro-4,4-dimethylspiro[2H-1-benzopyran-2,1'-cyclopropane]-6-yl)ethynyl]-phenyl}-propionic acid methyl ester (Intermediate 1)

A solution of 8-cyclopropyl-6-ethynyl-3,4-dihydro-4,4-dimethylspiro[2H-1-benzopyran-2,1'-cyclopropane] (described in U.S. Pat. No. 6,252,090; 0.068 g, 0.27 mmol), and methyl-2-(4-iodo phenyl)propionate (Reagent 1, 0.086 g, 0.3 mmol) in triethyl amine (3 mL), was treated with copper(I)iodide (0.028 g, 0.15 mmol) and sparged with argon for 5 minutes. Dichlorobis(triphenylphosphine)palladium(II) (0.057 g, 0.08 mmol) was added and the reaction mixture was stirred overnight at room temperature. It was diluted with diethyl ether and filtered over a bed of celite. The filtrate was evaporated in vacuo to brown oil that was subjected to flash column chromatography over silica gel (230–400 mesh) to afford the title compound as an oil (0.072 g, 56%).

$^1$H NMR (300 MHz, CDCl$_3$): δ 7.46 (d, 2H, J=8.4 Hz), 7.29 (d, 1H, J=2.1 Hz), 7.25 (d, 2H, J=8.4 Hz), 6.80 (d, 1H, J=2.1 Hz), 3.68 (q, 1H, J=7.2 Hz), 3.66 (s, 3H), 2.02–1.90 (m, 1H), 1.90 (s, 2H), 1.49 (d, 3H, J=7.2 Hz), 1.39 (s, 6H), 1.03–0.99 (m, 2H), 0.90–0.83 (m, 2H), 0.68–0.59 (m, 4H).

2-{4-[(8-Cyclopropyl-3,4-dihydro-4,4-dimethylspiro[2H-1-benzopyran-21'-cyclopropane]-6-yl)ethynyl]-phenyl}-propionic acid (Compound 1)

A solution of 2-{4-[(8-cyclopropyl-3,4-dihydro-4,4-dimethylspiro[2H-1-benzopyran-2,1-cyclopropane]-6-yl)ethynyl]-phenyl}-propionic acid methyl ester (Intermediate 1, 0.072 g, 0.174 mmol) in methanol (5 mL) was treated with a 1M solution of sodium hydroxide (1 mL, 1 mmol) and the resulting reaction mixture was heated at 55° C. for 4 h. The reaction mixture was cooled to ambient temperature and the volatiles were evaporated in vacuo to a residue that was diluted with 10% hydrochloric acid till neutral and extracted with ethyl acetate. The organic phase was washed with water and brine, dried over anhydrous magnesium-sulfate, filtered and evaporated in vacuo to afford the title product as a white solid after flash column chromatography over silica gel (230–400 mesh) (0.04 g, 57%).

$^1$H NMR (300 MHz, CDCl$_3$): δ 7.46 (d, 2H, J=8.1 Hz), 7.30–7.25 (m, 3H), 6.80 (d, 1H, J=1.8 Hz), 3.74 (q, 1H, J=7.2 Hz), 1.99–1.96 (m, 1H), 1.91 (s, 2H), 1.51 (d, 3H, J=7.2 Hz), 1.39 (s, 6H), 1.04–0.99 (m, 2H), 0.90–0.83 (m, 2H), 0.68–0.59 (m, 4H).

2-{4-[(8-Cyclopropyl-3,4-dihydro-4,4-dimethylspiro[2H-1-benzopyran-2,1'-cyclopropane]-6-yl)ethynyl]-phenyl}-2-methyl-propionic acid methyl ester (Intermediate 2)

Following General Procedure B and using 8-cyclopropyl-6-ethynyl-3,4-dihydro-4,4-dimethylspiro[2H-1-benzopyran-2,1'-cyclopropane] (0.096 g, 0.38 mmol), methyl-2-(4-iodo phenyl)-2-methyl-propionate (Reagent 2, 0.127 g, 0.41 mmol), triethyl amine (3 mL), copper(I)iodide (0.040 g, 0.21 mmol) and dichlorobis(triphenylphosphine)palladium(II) (0.080 g, 0.11 mmol) followed by flash column chromatography over silica gel (230–400 mesh), the title compound was obtained as an oil (0.046 g, 47%).

$^1$H NMR (300 MHz, CDCl$_3$): δ 7.39 (d, 2H, J=8.4 Hz), 7.23–7.20 (m, 3H), 6.72 (d, 1H, J=2.1 Hz), 3.58 (s, 3H), 1.92–1.84 (m, 1H), 1.84 (s, 2H), 1.51 (s, 6H), 1.33 (s, 6H), 0.97–0.92 (m, 2H), 0.83–0.76 (m, 2H), 0.59–0.52 (m, 4H).

2-{4-[(8-Cyclopropyl-3,4-dihydro-4,4-dimethylspiro[2H-1-benzopyran-2,1'-cyclopropane]-6-yl)ethynyl]-phenyl}-2-methyl-propionic acid (Compound 2)

A solution of 2-{4-[(8-cyclopropyl-3,4-dihydro-4,4-dimethylspiro[2H-1-benzopyran-2,1'-cyclopropane]-6-yl)ethynyl]-phenyl}2-methyl-propionic acid methyl ester (Intermediate 2, 0.046 g, 0.107 mmol) in methanol (5 mL) was treated with a 1M solution of sodium hydroxide (1.2 mL, 1.2 mmol) and the resulting reaction mixture was heated at 55° C. for 4 h. The reaction mixture was cooled to ambient temperature and the volatiles were evaporated in vacuo to a residue that was neutralized with 10% hydrochloric acid and extracted with ethyl acetate. The organic phase was washed with water and brine, dried over anhydrous magnesium sulfate, filtered and evaporated in vacuo to afford the title product as a white solid after flash column chromatography over silica gel (230–400 mesh) (0.067 g, 89%).

$^1$H NMR (300 MHz, CDCl$_3$): δ 7.47 (d, 2H, J=8.1 Hz), 7.36 (d, 2H, J=8.1 Hz), 7.30 (d, 1H, J=2.1 Hz), 6.80 (d, 1H, J=2.1 Hz), 1.99–1.91 (m, 1H), 1.91 (s, 2H), 1.60 (s, 6H), 1.40 (s, 6H), 1.04–0.99 (m, 2H), 0.90–0.84 (m, 2H), 0.69–0.59 (m, 4H).

Reaction Scheme 2

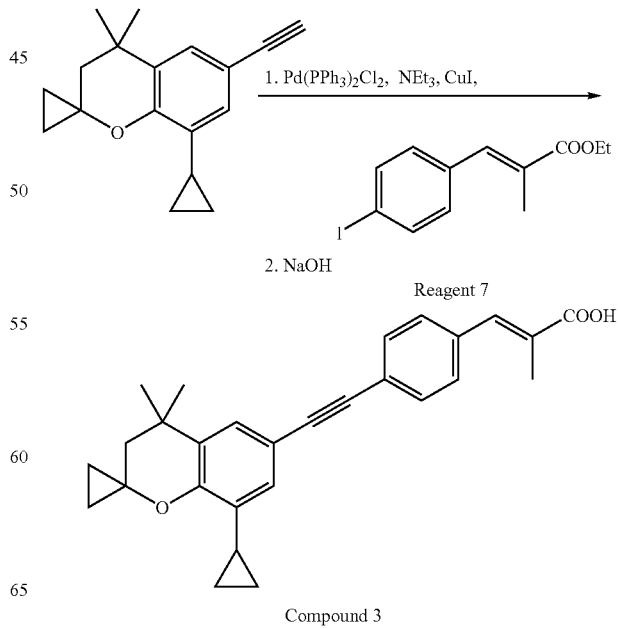

Compound 3

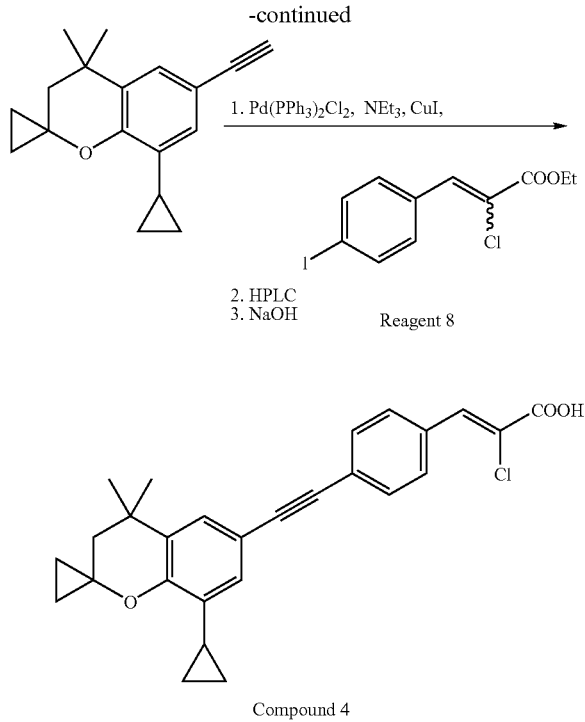

Compound 4

(E)-3-{4-[8-Cyclopropyl-3,4-dimethylspiro[2H-1-benzopyran-2,1'-cyclopropane]-6-yl]ethynyl-phenyl}-2-methylacrylic acid ethyl ester (Intermediate 3)

Following General Procedure B and using 8-cyclopropyl-6-ethynyl-3,4-dihydro-4,4-dimethylspiro[2H-1-benzopyran-2,1'-cyclopropane] (0.077 g, 0.3 mmol), (E)-3-(4-iodophenyl)-2-methyl-acrylic acid ethyl ester (Reagent 7, 0.106 g, 0.23 mmol), triethyl amine (3 mL), copper(I)iodide (0.029 g, 0.15 mmol) and dichlorobis(triphenylphosphine)palladium(II) (0.064 g, 0.09 mmol) followed by flash column chromatography over silica gel (230–400 mesh), the title compound was obtained (0.06 g, 45%).

$^1$H NMR (300 MHz, CDCl$_3$): δ 7.65 (d, 1H, J=1.5 Hz), 7.52 (d, 2H, J=8.7 Hz), 7.37 (d, 2H, J=8.7 Hz), 7.32 (d, 1H, J=1.8 Hz), 6.82 (d, 1H, J=1.8 Hz), 4.27 (q, 2H, J=7.2 Hz), 2.14 (d, 3H, J=1.5 Hz), 1.99 (m, 1H), 1.91 (s, 2H), 1.40 (s, 12H), 1.35 (t, 3H, J=7.2 Hz), 1.04–1.00 (m, 2H), 0.91–0.84 (m, 2H), 0.69–0.59 (m, 4H).

(E)-3-{4-[8-Cyclopropyl-3,4-dimethylspiro[2H-1-benzopyran-2,1'-cyclopropane]-6-yl]ethynyl-phenyl}-2-methylacrylic acid (Compound 3)

A solution of (E)-3-{4-[8-cyclopropyl-3,4-dimethylspiro[2H-1-benzopyran-2,1'-cyclopropane]-6-yl]ethynyl-phenyl}-2-methyl-acrylic acid ethyl ester (Intermediate 3, 0.06 g, 0.13 mmol) in ethanol (2 mL) was treated with a 1M solution of sodium hydroxide (0.5 mL, 0.5 mmol) and the resulting reaction mixture was heated at 55° C. for 4 h. The reaction mixture was cooled to ambient temperature and the volatiles were evaporated in vacuo to a residue that was neutralized with 5% hydrochloric acid and extracted with ethyl acetate. The organic phase was washed with water and brine, dried over anhydrous magnesium sulfate; filtered and evaporated in vacuo to afford the title product as a yellow solid after flash column chromatography over silica gel (230–400 mesh) (0.044 g, 82%).

$^1$H NMR (300 MHz, CDCl$_3$): δ 7.81 (d, 1H, J=1.5 Hz), 7.54 (d, 2H, J=8.4 Hz), 7.41 (d, 2H, J=8.4 Hz), 7.33 (d, 1H, J=2.1 Hz), 6.83 (d, 1H, J=2.1 Hz), 2.17 (d, 3H, J=1.5 Hz), 2.00 (m, 1H), 1.92 (s, 2H), 1.41 (s, 12H), 1.05–1.00 (m, 2H), 0.91–0.84 (m, 2H), 0.69–0.60 (m, 4H).

(Z)-2-Chloro-3-{4-[8-cyclopropyl-3,4-dimethylspiro[2H-1-benzopyran-2,1'-cyclopropane]-6-yl]ethynyl}-acrylic acid ethyl ester (Intermediate 4)

Following General Procedure B and using 8-cyclopropyl-6-ethynyl-3,4-dihydro-4,4-dimethylspiro[2H-1-benzopyran-2,1'-cyclopropane] (0.11 g, 0.436 mmol), (E,Z)-2-chloro-3-(4-iodo-phenyl)-acrylic acid ethyl ester (Reagent 8, 0.162 g, 0.48 mmol), triethyl amine (3 mL), copper(I) iodide (0.041 g, 0.21 mmol) and dichlorobis(triphenylphosphine)palladium(II) (0.092 g, 0.13 mmol) followed by flash column chromatography over silica gel (230–400 mesh), and preparative normal phase HPLC using 5% ethyl acetate in hexane as the mobile phase, the title compound was obtained (0.09 g, 45%).

$^1$H NMR (300 MHz, CDCl$_3$): δ 7.88 (s, 1H), 7.83 (d, 2H, J=8.1 Hz), 7.55 (d, 2H, J=8.1 Hz), 7.33 (d, 1H, J=2.1 Hz), 6.82 (d, 1H, J=2.1 Hz), 4.36 (q, 2H, J=6.9 Hz), 1.99 (m, 1H), 1.92 (s, 2H), 1.41 (s, 12H), 1.39 (t, 3H, J=6.9 Hz), 1.05–1.00 (m, 2H), 0.91–0.84 (m, 2H), 0.70–0.60 (m, 4H).

(Z)-2-Chloro-3-{4-[8-cyclopropyl-3,4-dimethylspiro[2H-1-benzopyran-2,1-cyclopropane]-6-yl]ethynyl}-acrylic acid (Compound 4)

A solution of (Z)-2-chloro-3-{4-[8-cyclopropyl-3,4-dimethylspiro[2H-1-benzopyran-2,1'-cyclopropane]-6-yl]ethynyl}-acrylic acid ethyl ester (Intermediate 4, 0.09 g, 0.19 mmol) in ethanol (1 mL) and tetrahydrofuran (3 ml) was treated with a 1M solution of sodium hydroxide (0.7 mL, 0.7 mmol) and the resulting reaction mixture was heated at 55° C. overnight. The reaction mixture was cooled to ambient temperature and the volatiles were evaporated in vacuo to a residue that was neutralized with 10% hydrochloric acid and extracted with ethyl acetate. The organic phase was washed with water and brine, dried over anhydrous magnesium sulfate, filtered and evaporated in vacuo to afford the title product as a yellow solid after flash column chromatography over silica gel (230–400 mesh) (0.08 g, 95%).

$^1$H NMR (300 MHz, CDCl$_3$): δ 7.74 (s, 1H), 7.55 (d, 2H, J=8.11 Hz), 7.31 (d, 2H, J=8.11 Hz), 7.20 (d, 1H, J=1.8 Hz), 6.70 (d, 1H, J=1.8 Hz), 1.86 (m, 1H), 1.79 (s, 2H), 1.27 (s, 12H), 0.94–0.81 (m, 2H), 0.77–0.71 (m, 2H), 0.59–0.47 (m, 4H).

Reaction Scheme 3

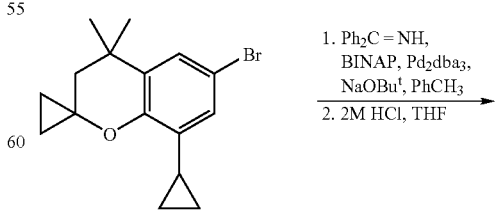

U.S. Pat. No. 6,252,090

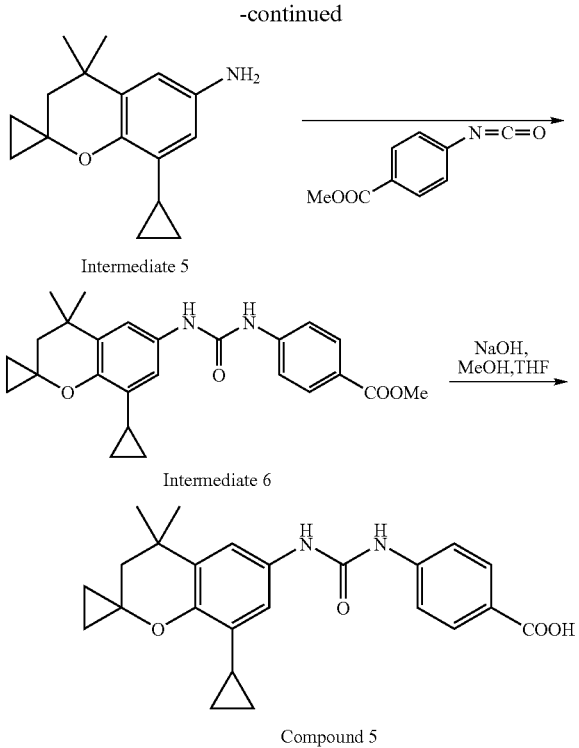

Intermediate 5

Intermediate 6

Compound 5

6-Amino-8-cyclopropyl-3,4-dihydro-4,4-dimethylspiro[2H-1-benzopyran-21'-cyclopropane] (Intermediate 5)

A solution of 6-bromo-8-cyclopropyl-3,4-dihydro-4,4-dimethylspiro[2H-1-benzopyran-2,1'-cyclopropane] (described in U.S. Pat. No. 6,252,090; 0.322 g, 1.049 mmol), benzophenone imine (Fluka 0.093 mL, 1.15 mmol), sodium-tert-butoxide (0.142 g, 1.47 mmol), tris(dibenzylideneacetone)dipalladium(0) (0.023 g, 0.025 mmol) and (S)-(−)-2,2'-bis(diphenylphosphino)-1,1'-binaphthyl (Aldrich, 0.047 g, 0.075 mmol) in 7 mL of anhydrous toluene was sparged with argon and heated at 95° C. for 36 h. The reaction mixture was cooled to ambient temperature, quenched with water and extracted with ethyl acetate. The combined organic phase was washed with water and brine, dried over anhydrous magnesium sulfate, filtered and evaporated in vacuo to afford a thick brown oil (0.73 g). The oil was dissolved in tetrahydrofuran (3.5 mL) and treated with 2M hydrochloric acid (1.7 mL). After stirring at ambient temperature for 20 minutes, 0.5 mL of 2M hydrochloric acid and 40 mL of water were added and the reaction mixture was extracted with hexane:ethyl acetate (2:1, 3×60 mL). The aqueous phase was neutralized with potassium hydroxide and extracted with dichloromethane (3×50 mL). The combined organic phase was dried over anhydrous magnesium sulfate, filtered and evaporated in vacuo to afford an oil that on flash column chromatography over silica gel (230–400 mesh) afforded the title product as a brown solid (0.15 g, 58%).

$^1$H NMR (300 MHz, CDCl$_3$): δ 6.46 (d, 1H, J=2.7 Hz), 6.01 (d, 1H, J=2.7 Hz), 3.28 (br s, 2H), 2.02–1.93 (m, 1H), 1.87 (s, 2H), 1.34 (s, 6H), 0.97–0.93 (m, 2H), 0.85–0.78 (m, 2H), 0.61–0.59 (m, 4H).

4-{3-[8-Cyclopropyl-3,3-dihydro-4,4-dimethylspiro(2H-1-benzopyran-2,2'-cyclopropane)-6-yl]-ureido}-benzoic acid methyl ester (Intermediate 6)

A solution of 4-isocyanato-benzoic acid methyl ester (Aldrich, 0.17 g, 0.97 mmol) in anhydrous toluene (5 mL) was treated with a solution of 6-amino-8-cyclopropyl-3,4-dihydro-4,4-dimethylspiro[2H-1-benzopyran-2,1'-cyclopropane] (Intermediate 5, 0.07 g, 0.28 mmol) in toluene (1 mL). The resulting reaction mixture was stirred at ambient temperature overnight and at 50–60° C. for 5 h. The volatiles were evaporated in vacuo and the residue was subjected to flash column chromatography over silica gel (230–400 mesh) to afford the title compound as a white solid (0.073 g, 62%).

$^1$H NMR (300 MHz, CDCl$_3$): δ 7.93 (d, 2H, J=9.0 Hz), 7.39 (d, 2H, J=9.0 Hz), 7.06 (d, 1H, J=2.4 Hz), 6.62 (br s, 1H), 6.53 (d, 1H, J=2.4 Hz), 3.88 (s, 3H), 2.05–1.97 (m, 1H), 1.89 (s, 2H), 1.35 (s, 6H), 1.01–0.97 (m, 2H), 0.90–0.83 (m, 2H), 0.67–0.54 (m, 4H).

4-{3-[8-Cyclopropyl-3,3-dihydro-4,4-dimethylspiro(2H-1-benzopyran-2,2'-cyclopropane)-6-yl]-ureido}-benzoic acid (Compound 5)

A solution of 4-{3-[8-cyclopropyl-3,3-dihydro-4,4-dimethylspiro(2H-1-benzopyran-2,2'-cyclopropane)-6-yl]-ureido}-benzoic acid methyl ester (Intermediate 6, 0.072 g, 0.17 mmol) in methanol (3.4 mL) and tetrahydrofuran (7 mL) was treated with a 0.5M solution of sodium hydroxide (3.4 mL, 1.7 mmol) and the resulting reaction mixture was stirred at ambient temperature overnight. The volatiles were evaporated in vacuo to a residue that was diluted with water, neutralized with 10% hydrochloric acid and extracted with ethyl acetate. The organic phase was dried over anhydrous magnesium sulfate, filtered and evaporated in vacuo to afford the title product as a white solid (0.066 g, 95%).

$^1$H NMR (300 MHz, CD$_3$COCD$_3$): δ 8.27 (br s, 1H), 7.82 (d, 2H, J=9.0 Hz), 7.52 (d, 2H, J=9.0 Hz), 7.20 (d, 1H, J=2.4 Hz), 6.66 (d, 1H, J=2.4 Hz), 1.93–1.90 (m, 1H), 1.80 (s, 2H), 1.24 (s, 6H), 0.80–0.73 (m, 2H), 0.72–0.67 (m, 2H), 0.57–0.41 (m, 4H).

Reaction Scheme 4

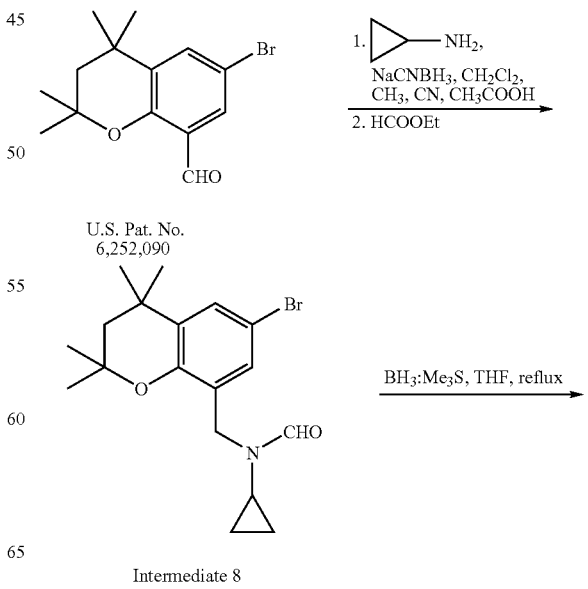

Intermediate 8

-continued

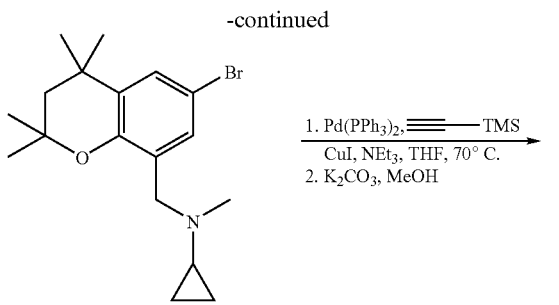

Intermediate 9

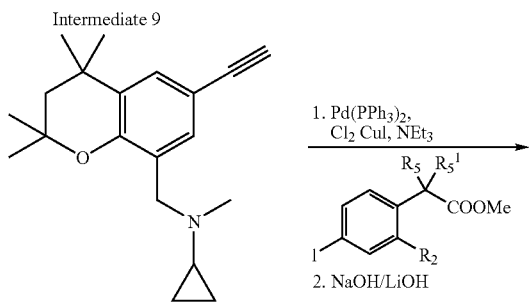

Intermediate 11

(U.S. Pat. No. 6,252,090) $R_2$ = H, $R_5$ = $R_5^1$ = H
(U.S. Pat. No. 6,252,090) $R_2$ = F, $R_5$ = $R_5^1$ = H
Reagent 1 $R_2$ = H, $R_5$ = H, $R_5^1$ = Me
Reagent 2 $R_2$ = H, $R_5$ = $R_5^1$ = Me

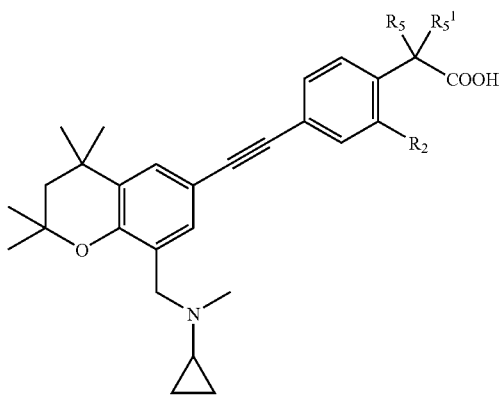

Compound 6 $R_2$ = H, $R_5$ = $R_5^1$ = H
Compound 7 $R_2$ = F, $R_5$ = $R_5^1$ = H
Compound 8 $R_2$ = H, $R_5$ = H, $R_5^1$ = Me
Compound 9 $R_2$ = H, $R_5$ = $R_5^1$ = Me General Procedure C: 6-Bromo-8-[(cyclopropyl-amino)-methyl]-2,2,4,4-tetramethyl-chroman (Intermediate 7)

A stirred, cooled (ice bath) solution of 6-bromo-2,2,4,4-tetramethyl chroman-8-carbaldehyde (U.S. Pat. No. 6,252,090, 2.4 g, 8.4 mmol) in dichloromethane (10 mL) and acetonitrile (9 mL) was treated with cyclopropyl amine (1.45 mL, 21 mmol). After 5 minutes, acetic acid (1 mL) was added followed by sodium cyanoborohydride (1.33 g, 21 mmol). The reaction mixture was stirred at ambient temperature for 2 h. The volatiles were distilled off in vacuo, the residue was diluted with water and extracted with ethyl acetate (×2). The combined organic extract was washed with water, saturated aqueous sodium bicarbonate and brine, dried over anhydrous sodium sulfate, filtered and evaporated in vacuo to an oil. Flash column chromatography over silica gel (230–400 mesh) afforded the title compound (1.4 g, 50%) as a clear oil.

$^1$H NMR (300 MHz, CDCl$_3$): δ 7.27 (d, 1H, J=2.1 Hz), 7.16 (d, 1H, J=2.1 Hz), 3.73 (s, 2H), 2.19 (br s, 1H), 2.09–2.04 (m, 1H), 1.82 (s, 2H), 1.35 (s, 6H), 1.32 (s, 6H), 0.43–0.36 (m, 4H).

6-Bromo-8-[(cyclopropyl-formyl-amino)-methyl]-2,2,4,4-tetramethyl-chroman (Intermediate 8)

A solution of 6-bromo-8-[(cyclopropyl-amino)-methyl]-2,2,4,4-tetramethyl-chroman (Intermediate 7, 1.4 g, 4.14 mmol) in ethyl formate was refluxed for 6 h. The solvent was distilled off in vacuo to afford the title compound as a clear oil (1.56 g, 100%).

$^1$H NMR (300 MHz, CDCl$_3$): δ 8.37, 8.27 (2s, 1H), 7.35, 7.29 (2d, 1H, J=2.1 Hz), 7.13, 7.11 (2d, 1H, J=2.1 Hz), 4.48 (s, 2H), 2.60–2.50 (m, 1H), 1.81 (s, 2H), 1.34 (s, 6H), 1.32 (s, 6H), 0.74–0.70 (m, 4H).

6-Bromo-8-[(cyclopropyl-methyl-amino)-methyl]-2,2,4,4-tetramethyl-chroman (Intermediate 9)

A solution of 6-bromo-8-[(cyclopropyl-formyl-amino)-methyl]-2,2,4,4-tetramethyl-chroman (Intermediate 8, 1.46 g, 4.0 mmol) in anhydrous tetrahydrofuran (30 mL) was treated with a 2M solution of borane:methylsulfide complex in tetrahydrofuran (5 mL, 10 mmol) and the resulting reaction mixture was refluxed for 2 h. It was then cooled in an ice bath, quenched cautiously with saturated aqueous sodium carbonate solution and extracted with diethyl ether. The organic phase was washed with water and brine, dried over anhydrous magnesium sulfate, filtered and evaporated in vacuo to afford the title product as a white solid (1.55 g, 100%).

$^1$H NMR (300 MHz, CDCl$_3$): δ 7.26 (d, 1H, J=2.1 Hz), 7.20 (d, 1H, J=2.1 Hz), 3.64 (s, 2H), 2.27 (s, 3H), 1.83 (s, 2H), 1.83–1.78 (m, 1H), 1.34 (s, 6H), 1.33 (s, 6H), 0.48–0.47 (m, 4H).

General Procedure D: 8-[(Cyclopropyl-methyl-amino)-methyl]-2,2,4,4-tetramethyl-6-trimethylsilanylethynyl chroman (Intermediate 10)

A solution of 6-bromo-8-[(cyclopropyl-formyl-amino)-methyl]-2,2,4,4-tetramethyl-chroman (Intermediate 9, 1.5 g, 4.2 mmol) in triethyl amine (5 mL) and anhydrous tetrahydrofuran (10 mL) was treated with copper(I)iodide (0.32 g, 1.68 mmol) and sparged with argon for 5 minutes. Trimethylsilyl acetylene (2.5 mL, 17.6 mmol) was then added followed by dichlorobis(triphenylphosphine)palladium(II) (0.737 g, 1.05 mmol). The resulting reaction mixture was heated at 70° C. for 17 h. It was then cooled to ambient temperature, diluted with diethyl ether and filtered over a bed of celite. The filtrate was evaporated vacuo to an oil which was subjected to flash column chromatography over silica gel (230–400 mesh) to afford the title compound as a brown oil.

$^1$H NMR (300 MHz, CDCl$_3$): δ 7.08@(d, 1H, J=2.1 Hz), 6.97 (d, 1H, J=2.1 Hz), 3.40 (s, 2H), 2.03 (s, 3H), 1.57 (s, 2H), 1.57–1.53 (m, 1H), 1.09 (2s, 12H), 0.25–0.22 (m, 4H), 0.012 (s, 9H).

General Procedure F: 8-[(Cyclopropyl-methyl-amino)-methyl]-6-ethynyl-2,2,4,4-tetramethyl-chroman (Intermediate 11)

A solution of 8-[(cyclopropyl-methyl-amino)-methyl]-2,2,4,4-tetramethyl-6-trimethylsilanylethynyl chroman (Intermediate 10, 0.729 g, 1.97 mmol) in methanol (30 mL) was treated with potassium carbonate (1.4 g, 10.2 mmol) and the resulting reaction mixture was stirred at ambient temperature overnight. The solvent was evaporated in vacuo, the residue was diluted with water and extracted with ethyl acetate. The organic phase dried over anhydrous magnesium sulfate, filtered and evaporated in vacuo to afford the title compound as a brown oil (0.571 g, 98%).

$^1$H NMR (300 MHz, CDCl$_3$): δ 7.35 (d, 1H, J=2.1 Hz), 7.25 (d, 1H, J=2.1 Hz), 3.66 (s, 2H), 2.98 (s, 1H), 2.28 (s, 3H), 1.83 (s, 2H), 1.83–1.77 (m, 1H), 1.35 (s, 6H), 1.34 (s, 6H), 0.50–0.47 (m, 4H).

(4-{8-[(Cyclopropyl-methyl-amino)-methyl]-2,2,4,4-tetramethyl-chroman-6-ylethynyl}phenyl)-acetic acid methyl ester (Intermediate 12)

Following General Procedure B and using 8-[(cyclopropyl-methyl-amino)-methyl]-6-ethynyl-2,2,4,4-tetramethyl-chroman (Intermediate 11, 0.09 g, 0.3 mmol), 4-iodo phenyl acetic acid methyl ester (U.S. Pat. No. 6,252,090, 0.092 g, 0.33 mmol), triethyl amine (3 mL), copper(I)iodide (0.029 g, 0.15 mmol) and dichlorobis(triphenylphosphine)palladium (II) (0.064 g, 0.09 mmol) followed by flash column chromatography over silica gel (230–400 mesh), the title compound was obtained as a yellow oil (0.085 g, 65%).

$^1$H NMR (300 MHz, CDCl$_3$): δ 7.46 (d, 2H, J=8.4 Hz), 7.37 (d, 1H, J=2.1 Hz), 7.27–7.22 (m, 3H), 3.70 (s, 3H), 3.67 (s, 2H), 3.63 (s, 2H), 2.29 (s, 3H), 1.83 (s, 2H), 1.83–1.81 (m, 1H), 1.35 (2s, 12H), 0.50–0.47 (m, 4H).

(4-{8-[(Cyclopropyl-methyl-amino)-methyl]-2,2,4,4-tetramethyl-chroman-6-ylethynyl}phenyl)-acetic acid (Compound 6)

A solution of (4-{8-[(cyclopropyl-methyl-amino)-methyl]-2,2,4,4-tetramethyl-chroman-6-ylethynyl}phenyl)-acetic acid methyl ester (Intermediate 12, 0.057 g, 0.13 mmol) in methanol (1 mL) and tetrahydrofuran (3 mL) was treated with a 1M solution of sodium hydroxide (0.4 mL, 0.4 mmol) and the resulting reaction mixture was stirred at ambient temperature overnight. The volatiles were evaporated in vacuo to a residue that was washed with hexane, neutralized with saturated aqueous ammonium chloride solution and extracted with ethyl acetate. The organic phase was washed with water and brine, and dried over anhydrous magnesium sulfate, filtered and evaporated in vacuo to afford the title product as a yellow oil (0.046 g, 84%).

$^1$H NMR (300 MHz, CDCl$_3$): δ 7.42–7.26 (m, 6H), 3.94 (s, 2H), 3.57 (s, 2H), 2.48 (s, 3H), 2.04 (m, 1H), 1.82 (s, 2H), 1.35 (s, 6H), 1.33 (s, 6H), 0.55–0.50 (m, 4H).

(4-{8-[(Cyclopropyl-methyl-amino)-methyl]-2,2,4,4-tetramethyl-chroman-6-ylethynyl}-2-fluoro-phenyl)-acetic acid methyl ester (Intermediate 13)

Following General Procedure B and using 8-[(cyclopropyl-methyl-amino)-methyl]-6-ethynyl-2,2,4,4-tetramethyl-chroman (Intermediate 11, 0.084 g, 0.28 mmol), 2-fluoro-4-iodo phenyl acetic acid methyl ester (U.S. Pat. No. 6,252,090, 0.091 g, 0.3 mmol), triethyl amine (3 mL), copper(I)iodide (0.027 g, 0.14 mmol) and dichlorobis(triphenylphosphine)palladium(II) (0.060 g, 0.085 mmol) followed by flash column chromatography over silica gel (230–400 mesh), the title compound was obtained as a yellow oil (0.083 g, 64%).

$^1$H NMR (300 MHz, CDCl$_3$): δ 7.37 (d, 1H, J=2.1 Hz), 7.27–7.24 (m, 4H), 3.72 (s, 3H), 3.67 (s, 4H), 2.29 (s, 3H), 1.83 (s, 2H), 1.83–1.81 (m, 1H), 1.35 (s, 12H), 0.50–0.47 (m, 4H).

(4-{8-[(Cyclopropyl-methyl-amino)-methyl]-2,2,4,4-tetramethyl-chroman-6-ylethynyl}-2-fluoro-phenyl)-acetic acid (Compound 7)

A solution of (4-{8-[(cyclopropyl-methyl-amino)-methyl]-2,2,4,4-tetramethyl-chroman-6-ylethynyl}-2-fluoro-phenyl)-acetic acid methyl ester (Intermediate 13, 0.060 g, 0.13 mmol) in methanol (1 mL) and tetrahydrofuran (3 mL) was treated with a 1M solution of sodium hydroxide (0.4 mL, 0.4 mmol) and the resulting reaction mixture was stirred at ambient temperature overnight. The volatiles were evaporated in vacuo to a residue that was washed with hexane, neutralized with saturated aqueous ammonium chloride solution and extracted with ethyl acetate. The organic phase was washed with water and brine, and dried over anhydrous magnesium sulfate, filtered and evaporated in vacuo to afford the title product as a yellow oil (0.056 g, 95%).

$^1$H NMR (300 MHz, CDCl$_3$): δ 7.43 (d, 1H, J=2.1 Hz), 7.37–7.13 (m, 4H), 3.99 (s, 2H), 3.61 (s, 2H), 2.52 (s, 3H), 2.10–2.04 (m, 1H), 1.83 (s, 2H), 1.83–1.81 (m, 1H), 1.36 (s, 6H), 1.35 (s, 6H), 0.90–0.82 (m, 2H), 0.59–0.57 (m, 2H).

2-(4-{8-[(Cyclopropyl-methyl-amino)-methyl]-2,2,4,4-tetramethyl-chroman-6-ylethynyl}-phenyl)-propionic acid methyl ester (Intermediate 14)

Following General Procedure B and using 8-[(cyclopropyl-methyl-amino)-methyl]-6-ethynyl-2,2,4,4-tetramethyl-chroman (Intermediate 11, 0.08 g, 0.27 mmol), methyl-2-(4-iodophenyl)propionate (Reagent 1, 0.086 g, 0.29 mmol), triethyl amine (3 mL), copper(I)iodide (0.026 g, 0.14 mmol) and dichlorobis(triphenylphosphine)palladium(II) (0.057 g, 0.08 mmol) followed by flash column chromatography over silica gel (230–400 mesh), the title compound was obtained as a brown oil (0.067 g, 54%).

$^1$H NMR (300 MHz, CDCl$_3$): δ 7.46 (d, 2H, J=8.4 Hz), 7.37 (d, 1H, J=2.1 Hz), 7.27–7.22 (m, 3H), 3.72 (q, 1H, J=7.2 Hz), 3.67 (s, 5H), 2.29 (s, 3H), 1.83 (s, 2H), 1.83–1.79 (m, 1H), 1.50 (d, 3H, J=7.2 Hz), 1.35 (s, 12H), 0.50–0.47 (m, 4H).

2-(4-{8-[(Cyclopropyl-methyl-amino)-methyl]-2,2,4,4-tetramethyl-chroman-6-ylethynyl}-phenyl)-propionic acid (Compound 8)

A solution of 2-(4-{8-[(cyclopropyl-methyl-amino)-methyl]-2,2,4,4-tetramethyl-chroman-6-ylethynyl}-phenyl)-propionic acid methyl ester (Intermediate 14, 0.057 g, 0.12 mmol) in methanol (1 mL) and tetrahydrofuran (3 mL) was treated with a 1M solution of sodium hydroxide (0.3 mL, 0.3 mmol) and the resulting reaction mixture was stirred at ambient temperature overnight. The volatiles were evaporated in vacuo to a residue that was washed with hexane, neutralized with saturated aqueous ammonium chloride solution and extracted with ethyl acetate. The organic phase was washed with water and brine, and dried over anhydrous magnesium sulfate, filtered and evaporated in vacuo to afford the title product as a yellow solid (0.024 g, 45%).

$^1$H NMR (300 MHz, CDCl$_3$): δ 7.38–7.23 (2m, 6H), 3.85–3.82 (m, 1H), 3.82 (s, 2H), 2.39 (s, 3H), 1.94–1.85 (m, 1H), 1.80 (s, 2H), 1.41 (d, 3H, J=7.2 Hz), 1.33 (s, 12H), 0.70–0.60 (m, 2H), 0.50–0.48 (m, 2H).

2-(4-{8-[(Cyclopropyl-methyl-amino)-methyl]-2,2,4,4-tetramethyl-chroman-6-ylethynyl}-phenyl)-2-methyl-propionic acid methyl ester (Intermediate 15)

Following General Procedure B and using 8-[(cyclopropyl-methyl-amino)-methyl]-6-ethynyl-2,2,4,4-tetramethyl-chroman (Intermediate 11, 0.08 g, 0.27 mmol), methyl-2-(4-iodophenyl)-2-methyl-propionate (Reagent 2, 0.082 g, 0.27 mmol), triethyl amine (2 mL), copper(I)iodide (0.020 g, 0.1 mmol) and dichlorobis(triphenylphosphine)palladium (II) (0.07 g, 0.1 mmol) followed by flash column chromatography over silica gel (230–400 mesh) using 10% ethyl acetate in hexane as the eluent, the title compound was obtained as a brown oil (0.040 g, 31%).

$^1$H NMR (300 MHz, CDCl$_3$): δ 7.50–7.28 (m, 6H), 3.68 (s, 3H), 3.66 (s, 2H), 2.30 (s, 3H), 1.85 (s, 2H), 1.85–1.81 (m, 1H), 1.60 (s, 3H), 1.59 (s, 3H), 1.37 (s, 6H), 1.36 (s, 6H), 0.50–0.47 (m, 4H).

2-(4-{8-[(Cyclopropyl-methyl-amino)-methyl]-2,2,4,4-tetramethyl-chroman-6-ylethynyl}-phenyl)-2-methyl-propionic acid (Compound 9)

A solution of 2-(4-{8-[(cyclopropyl-methyl-amino)-methyl]-2,2,4,4-tetramethyl-chroman-6-ylethynyl}-phenyl)-2-methyl-propionic acid methyl ester (Intermediate 15, 0.040 g, 0.084 mmol) in methanol (2.5 mL) and tetrahydrofuran (2.5 mL) was treated with a 2M solution of sodium hydroxide (1 mL, 2 mmol) and the resulting reaction mixture was refluxed overnight. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to an oil. Preparative reverse phase HPLC on a partisil 10 ODS-3 column using 10% water in acetonitrile as the mobile phase afforded the title compound (0.008 g, 27%).

$^1$H NMR (300 MHz, CDCl$_3$): δ 7.46–7.32 (m, 6H), 6.90–6.50 (br s, 1H), 3.84 (s, 2H), 2.41 (s, 3H), 1.97–1.92 (m, 1H), 1.83 (s, 2H), 1.55 (s, 6H), 1.36 (2s, 12H), 0.73–0.68 (m, 2H), 0.52–0.46 (m, 2H).

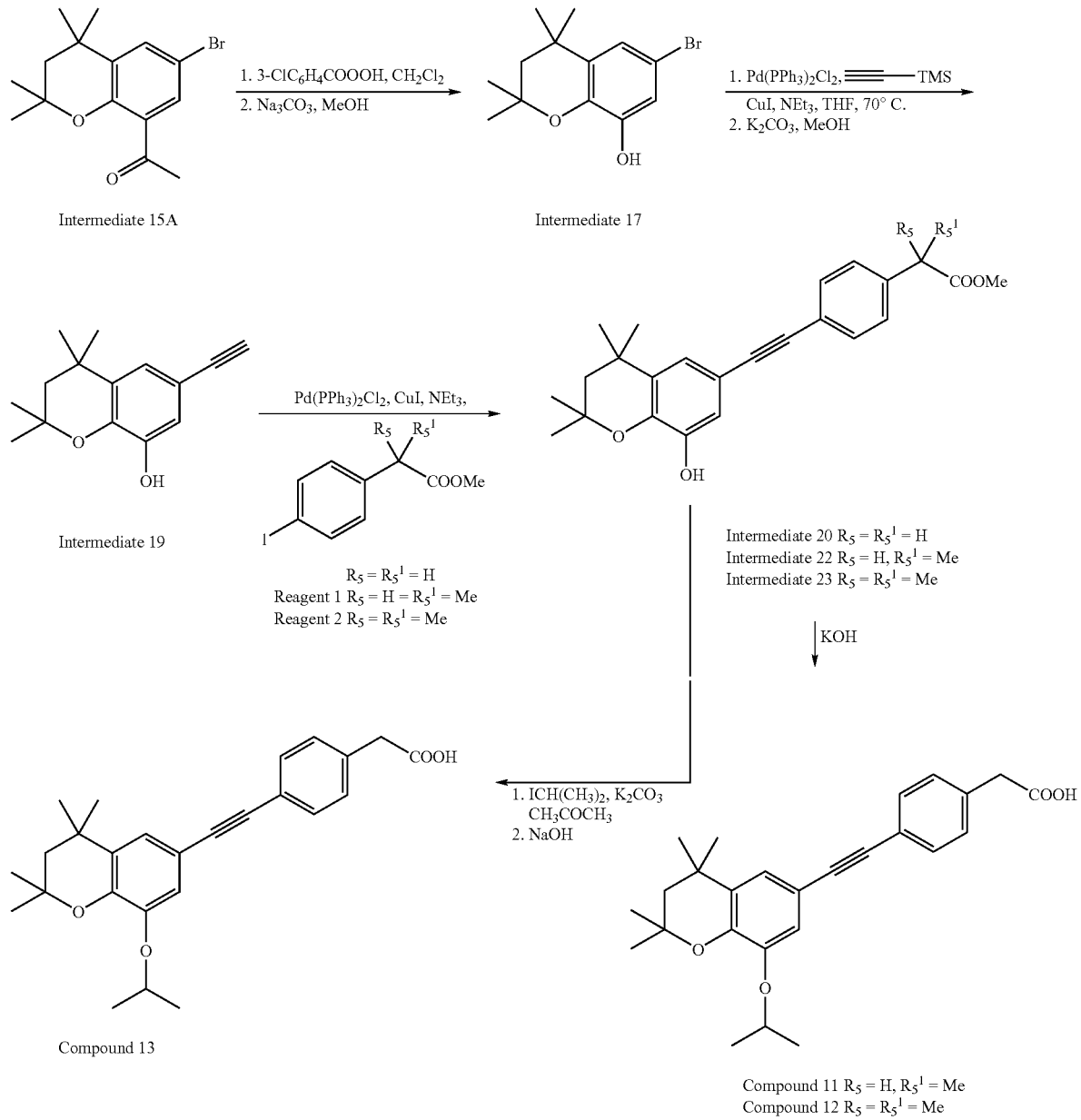

Reaction Scheme 5

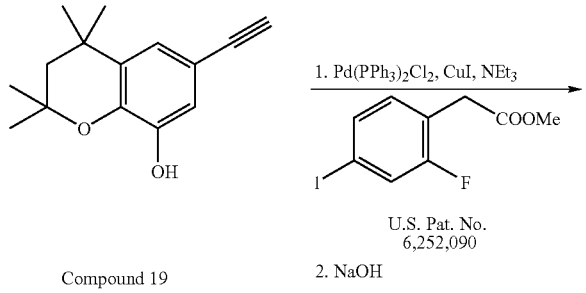

Compound 19

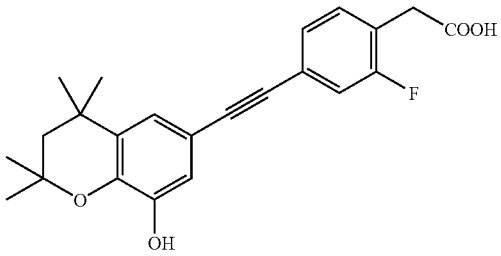

Compound 10

8-acetyl-6-bromo-2,24,4-tetramethyl chroman (Intermediate 15A)

A stirred, cooled (−78° C.) solution of 6-bromo-2,2,4,4-tetramethyl chroman (1 g, 3.72 mmol) in anhydrous dichloromethane (10 mL) was treated with aluminum chloride (0.8 g, 6.8 mmol) followed by acetyl chloride (0.4 mL, 6.08 mmol). After 10 minutes, the reaction mixture was diluted with water and extracted with diethyl ether. The organic phase was washed with water, and dried over anhydrous sodium sulfate, filtered and evaporated to a residue that was subjected to flash column chromatography on silica gel (230–400 mesh) using 10% ethyl acetate in hexane as the eluent to afford the title compound as a solid (0.78 g, 67%).

$^1$H NMR (300 MHz, CDCl$_3$): δ 7.64 (d, 1H, J=2.6 Hz), 7.49 (d, 1H, J=2.6 Hz), 2.60 (s, 3H), 1.87 (s, 2H), 1.41 (s, 6H), 1.36 (s, 6H).

8-Acetoxy-6-bromo-2,2,44-tetramethyl chroman (Intermediate 16)

A solution of 8-acetyl-6-bromo-2,2,4,4-tetramethyl chroman (Intermediate 15A, 1.3 g, 4.18 mmol) in anhydrous dichloromethane (30 mL) was treated with a 77% aqueous solution of 3-chloroperoxybenzoic acid (5.75 g, 33.44 mmol) and the resulting reaction mixture was stirred at ambient temperature for 24 h. The reaction mixture was then cooled in an ice bath and cautiously quenched with saturated sodium thiosulfate solution. The phases were separated and the organic phase was washed with saturated, aqueous sodium bicarbonate solution, water and brine, dried over anhydrous sodium sulfate, filtered and evaporated in vacuo to afford a residue that on flash column chromatography over silica gel (230–400 mesh) using 10% ethyl acetate in hexane as the eluent afforded the title compound as an oil (1.3 g, 92%).

$^1$H NMR (300 MHz, CDCl$_3$): δ 7.27 (s, 1H), 7.00 (s, 1H), 2.29 (s, 3H), 1.83 (s, 2H), 1.34 (s, 6H), 1.32 (s, 6H).

6-Bromo-8-hydroxy-2,2,4,4-tetramethyl chroman (Intermediate 17)

A solution of 8-acetoxy-6-bromo-2,2,4,4-tetramethyl chroman (Intermediate 16, 1.3 g, 3.98 mmol) in methanol was treated with sodium carbonate (0.8 g, 7.95 mmol) and the resulting reaction mixture was stirred at ambient temperature overnight. The volatiles were evaporated in vacuo, the residue was diluted with water and extracted with ethyl acetate. The organic phase was dried over anhydrous magnesium sulfate and evaporated in vacuo to afford a residue that on flash column chromatography over silica gel (230–400 mesh) using 10% ethyl acetate in hexane as the eluent afforded the title product as an oil (0.95 g, 84%).

$^1$H NMR (300 MHz, CDCl$_3$): δ 6.91 (d, 1H), 6.88 (d, 1H), 5.67 (s, 1H), 1.84 (s, 2H), 1.37 (s, 6H), 1.32 (s, 6H).

6-Bromo-8-trimethylsilanylethynyl-2,2,4,4-tetramethyl chroman (Intermediate 18)

Following General Procedure D and using 6-bromo-8-hydroxy-2,2,24,4-tetramethyl chroman (Intermediate 17, 1.0 g, 3.51 mmol), triethyl amine (5 mL), copper(I)iodide (0.066 g, 0.351 mmol), trimethylsilyl acetylene (2.5 mL, 17.6 mmol) and dichlorobis(triphenylphosphine)palladium(II) (0.246 g, 0.351 mmol) followed by flash column chromatography over silica gel (230–400 mesh) using 0.5% ethyl acetate in hexane as the eluent, the title compound (1.08 g,~100%) was obtained as a brown oil.

$^1$H NMR (300 MHz, CDCl$_3$): δ 6.97 (d, 1H), 6.86 (d, 1H), 5.61 (s, 1H), 1.84 (s, 2H), 1.37 (s, 6H), 1.33 (s, 6H), 0.24 (s, 9H).

6-Ethynyl-8-hydroxy-2,2,4,4-tetramethyl-chroman (Intermediate 19)

A solution of 6-bromo-8-trimethylsilanylethynyl-2,2,4,4-tetramethyl chroman (Intermediate 18, 0.47 g, 1.56 mmol) in methanol (5 mL) was treated with potassium carbonate (0.2 g, 1.45 mmol) and the resulting reaction mixture was heated at 80° C. for 3 h. The solvent was evaporated in vacuo, the residue was diluted with water and extracted with ethyl acetate.

The organic phase dried over anhydrous magnesium sulfate, filtered and evaporated in vacuo to afford the title compound as a brown oil (0.35 g, 99%).

$^1$H NMR (300 MHz, CDCl$_3$): δ 6.97 (d, 1H), 6.86 (d, 1H), 5.70 (br s, 1H), 2.92 (s, 1H), 1.84 (s, 2H), 1.37 (s, 6H), 1.33 (s, 6H).

[4-(8-Hydroxy-2,2,4,4-tetramethyl-chroman-6-ylethynyl)-phenyl]-acetic acid methyl ester (Intermediate 20)

Following General Procedure B and using 6-ethynyl-8-hydroxy-2,2,4,4-tetramethyl-chroman (Intermediate 19, 0.035 g, 0.15 mmol), 4-iodo phenyl acetic acid methyl ester (0.060 g, 0.23 mmol), triethyl amine (3 mL), copper(I)iodide (0.020 g, 0.11 mmol) and dichlorobis(triphenylphosphine) palladium(II) (0.07 g, 0.1 mmol) followed by flash column chromatography over silica gel (230–400 mesh), and preparative normal phase HPLC using 10% ethyl acetate in hexane as the mobile phase, the title compound was obtained (0.015 g, 25%).

$^1$H NMR (300 MHz, CDCl$_3$): δ 7.46 (d, 2H, J=8.1 Hz), 7.24 (d, 2H, J=8.1 Hz), 7.03 (d, 1H, J=2.1 Hz), 6.91 (d, 1H, J=2.1 Hz), 5.72 (s, 1H), 3.69 (s, 3H), 3.63 (s, 2H), 1.86 (s, 2H), 1.38 (s, 6H), 1.35 (s, 6H).

[2-Fluoro-4-(8-hydroxy-2,2,4,4-tetramethyl-chroman-6-yl-ethynyl-phenyl]-acetic acid methyl ester (Intermediate 21)

Following General Procedure B and using 6-ethynyl-8-hydroxy-2,2,4,4-tetramethyl-chroman (Intermediate 19, 0.05 g, 0.22 mmol), 2-fluoro-4-iodo phenyl acetic acid methyl ester (0.096 g, 0.33 mmol), triethyl amine (3 mL), copper(I)iodide (0.020 g, 0.1 mmol) and dichlorobis(triphenylphosphine)palladium(II) (0.07 g, 0.1 mmol) followed by flash column chromatography over silica gel (230–400 mesh), and preparative normal phase HPLC using 10% ethyl acetate in hexane as the mobile phase, the title compound was obtained (0.037 g, 43%).

$^1$H NMR (300 MHz, CDCl$_3$): δ 7.27–7.18 (m, 3H), 7.03 (d, 1H, J=1.8 Hz), 6.90 (d, 1H, J=1.8 Hz), 5.68 (s, 1H), 3.72 (s, 3H), 3.67 (s, 2H), 1.87 (s, 2H), 1.39 (s, 6H), 1.36 (s, 6H).

[2-Fluoro-4-(8-hydroxy-2,2,4,4-tetramethyl-chroman-6-yl-ethynyl)-phenyl]-acetic acid (Compound 10)

A solution of [2-fluoro-4-(8-hydroxy-2,2,4,4-tetramethyl-chroman-6-ylethynyl)-phenyl]-acetic acid methyl ester. (Intermediate 21, 0.037 g, 0.0493 mmol) in methanol (2 mL) and tetrahydrofuran (1 mL) was treated with a 2M solution of potassium hydroxide (2 mL, 4 mmol) and the resulting reaction mixture was stirred at ambient temperature for 2 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.024 g, 69%).

$^1$H NMR (300 MHz, CDCl$_3$): δ 7.26–7.24 (m, 3H), 7.03 (d, 1H, J=1.8 Hz), 6.90 (d, 1H, J=1.8 Hz), 3.71 (s, 2H), 1.87 (s, 2H), 1.39 (s, 6H), 1.36 (s, 6H).

2-[4-(8-Hydroxy-2,2,4,4-tetramethyl-chroman-6-ylethynyl)-phenyl]-propionic acid methyl ester (Intermediate 22)

Following general procedure B and using 6-ethynyl-8-hydroxy-2,2,4,4-tetramethyl-chroman (Intermediate 19, 0.04 g, 0.17 mmol), methyl-2-(4-iodophenyl)propionate (Reagent 1, 0.075 g, 0.26 mmol), triethyl amine (3 mL), copper(I)iodide (0.020 g, 0.1 mmol) and dichlorobis(triphenylphosphine)palladium(II) (0.07 g, 0.1 mmol) followed by flash column chromatography over silica gel 230–400 mesh) and preparative normal phase HPLC using 5% ethyl acetate in hexane as the mobile phase, the title compound was obtained as a brown oil (0.018 g, 26%).

$^1$H NMR (300 MHz, CDCl$_3$): δ 7.46 (d, 2H, J=8.5 Hz), 7.26 (d, 2H, J=8.5 Hz), 7.03 (d, 1H, J=1.8 Hz), 6.91 (d, 1H, J=1.8 Hz), 5.66 (s, 1H), 3.67 (q, 1H, J=7.5 Hz), 1.87 (s, 2H), 1.50 (d, 3H, J=7.5 Hz), 1.39 (s, 6H), 1.36 (s, 6H).

2-[4-(8-Hydroxy-2,2,4,4-tetramethyl-chroman-6-ylethynyl)-phenyl]-propionic acid (Compound 11)

A solution of 2-[4-(8-hydroxy-2,2,4,4-tetramethyl-chroman-6-ylethynyl)-phenyl]-propionic acid methyl ester (Intermediate 22, 0.018 g, 0.046 mmol) in methanol (1 mL) and tetrahydrofuran (0.5 mL) was treated with a 2M solution of potassium hydroxide (1 mL, 2 mmol) and the resulting reaction mixture was stirred at 80° C. for 2 h. The volatiles were evaporated in vacuo to a residue that was neutralized with saturated aqueous ammonium chloride solution and extracted with ethyl acetate. The organic phase was washed with water and brine, and dried over-anhydrous magnesium sulfate, filtered and evaporated in vacuo to afford the title product as a yellow solid (0.017 g, 100%).

$^1$H NMR (300 MHz, CDCl$_3$): δ 7.50–7.30 (m, 4H), 7.02 (s, 1H), 6.91 (s, 1H), 3.80–3.70 (m, 1H), 1.86 (s, 2H), 1.52 (d, 3H, J=7.2 Hz), 1.39 (s, 6H), 1.36 (s, 6H).

2-[4-(8-Hydroxy-2,2,4,4-tetramethyl-chroman-6-ylethynyl)-phenyl]-2-methyl-propionic acid methyl ester (Intermediate 23)

Following General Procedure B and using 6-ethynyl-8-hydroxy-2,2,4,4-tetramethyl-chroman (Intermediate 19, 0.057 g, 0.25 mmol), methyl-2-(4-iodophenyl)-2-methyl-propionate (Reagent-2, 0.112 g, 0.37 mmol), triethyl amine (3 mL), copper(I)iodide (0.020 g, 0.1 mmol) and dichlorobis (triphenylphosphine)palladium(II) (0.07 g, 0.1 mmol) followed by flash column chromatography over silica gel (230–400 mesh) and preparative normal phase HPLC using 5% ethyl acetate in hexane as the mobile phase, the title compound was obtained as a brown oil (0.035 g, 35%).

$^1$H NMR (300 MHz, CDCl$_3$): δ 7.46 (d, 2H, J=8.5 Hz), 7.29 (d, 2H, J=8.5 Hz), 7.03 (d, 1H, J=1.8 Hz), 6.91 (d, 1H, J=1.8 Hz), 5.67 (s, 1H), 3.66 (s, 3H), 1.86 (s, 2H), 1.58 (s, 6H), 1.39 (s, 6H), 1.36 (s, 6H).

2-[4-(8-Hydroxy-2,2,4,4-tetramethyl-chroman-6-ylethynyl)-phenyl]-2-methyl-propionic acid (Compound 12)

A solution of 2-[4-(8-hydroxy-2,2,4,4-tetramethyl-chroman-6-ylethynyl)-phenyl]-2-methyl-propionic acid methyl ester (Intermediate 23, 0.035 g, 0.087 mmol) in methanol (2 mL) and tetrahydrofuran (1 mL) was treated with a 1M solution of potassium hydroxide (2 mL, 4 mmol) and the resulting reaction mixture was stirred at 80° C. for 2 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product as a yellow solid (0.034 g, 100%).

$^1$H NMR (300 MHz, CDCl$_3$): δ 7.47 (d, 2H, J=8.7 Hz), 7.35 (d, 2H, J=8.7 Hz), 7.03 (d, 1H, J=1.8 Hz), 6.91 (d, 1H, J=1.8 Hz), 1.86 (s, 2H), 1.60 (s, 6H), 1.39 (s, 6H), 1.36 (s, 6H).

[4 (8-Isopropoxy-2,2,4,4-tetramethyl-chroman-6-ylethynyl)-phenyl]-acetic acid methyl ester (Intermediate 24)

A solution of [4-(8-hydroxy-2,2,4,4-tetramethyl-chroman-6-ylethynyl)-phenyl]-acetic acid methyl ester (Intermediate 20, 0.02 g, 0.076 mmol) in acetone (2 mL) was treated with potassium carbonate (0.026 g, 0.19 mmol) and 2-iodopropane (5 mL, large excess) and the resulting reaction mixture was refluxed for 30 h. The volatiles were evaporated in vacuo, the residue was diluted with water and extracted with ethyl acetate. The organic phase was dried over anhydrous magnesium sulfate, filtered and evaporated in vacuo to afford the title product as an oil (0.02 g, 91%).

$^1$H NMR (300 MHz, CDCl$_3$): δ 7.47 (d, 2H, J=8.4 Hz), 7.24 (d, 2H, J=8.4 Hz), 7.14 (d, 1H, J=2.1 Hz), 6.93 (d, 1H, J=2.1 Hz), 4.40 (heptet, 1H, J=6.3 Hz), 3.70 (s, 3H), 3.63 (s, 2H), 1.83 (s, 2H), 1.38 (s, 6H), 1.35 (s, 6H), 1.33 (d, 3H, J=6.3 Hz).

[4-(8-Isopropoxy-2,2,4,4-tetramethyl-chroman-6-ylethynyl)-phenyl]-acetic acid (Compound 13)

A solution of [4-(8-isopropoxy-2,2,4,4-tetramethyl-chroman-6-ylethynyl)-phenyl]-acetic acid methyl ester (Intermediate 24, 0.02 g, 0.05 mmol) in methanol (1 mL) was treated with a 2M solution of sodium hydroxide (1 mL, 2 mmol) and the resulting reaction mixture was stirred at ambient temperature for 3 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to an oil. Flash column chromatography over silica gel (230–400 mesh) using 5% methanol in ethyl acetate as the eluent followed by preparative reverse phase HPLC using 10% water in acetonitrile as the mobile phase afforded the title product (0.015 g, 78%).

$^1$H NMR (300 MHz, CDCl$_3$): δ 7.47 (d, 2H, J=8.4 Hz), 7.24 (d, 2H, J=8.4 Hz), 7.14 (d, 1H, J=2.1 Hz), 6.92 (d, 1H, J=2.1 Hz), 4.40 (heptet, 1H, J=7.5 Hz), 3.65 (s, 2H), 1.83 (s, 2H), 1.37 (s, 6H), 1.35 (s, 6H), 1.33 (d, 3H, J=7.5 Hz).

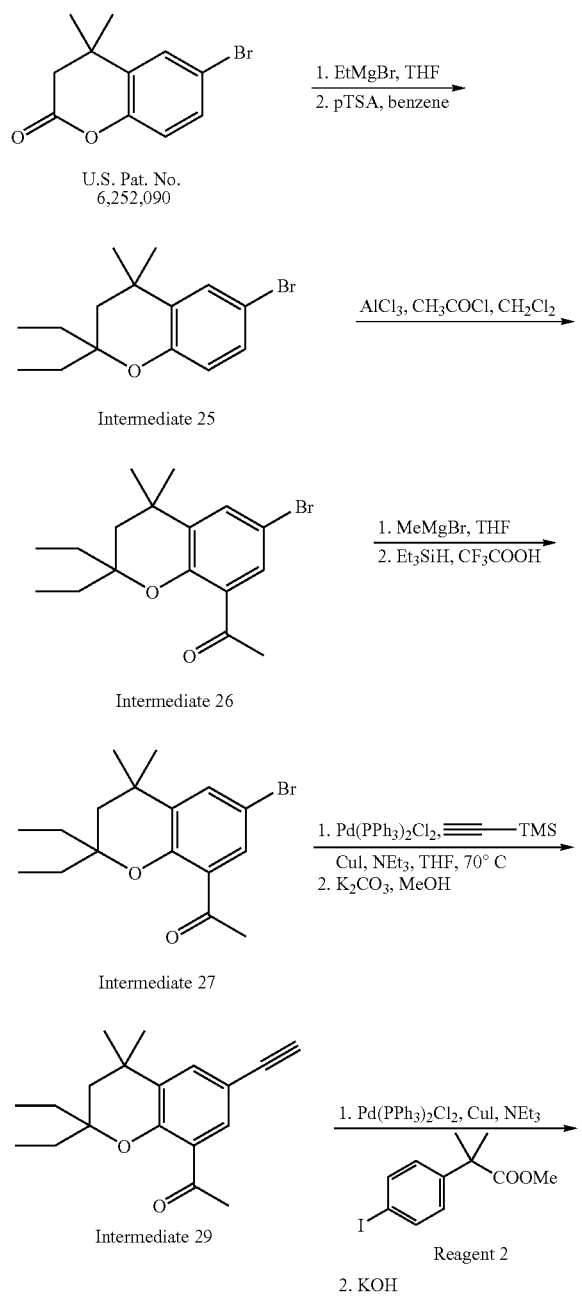

Reasction Scheme 6

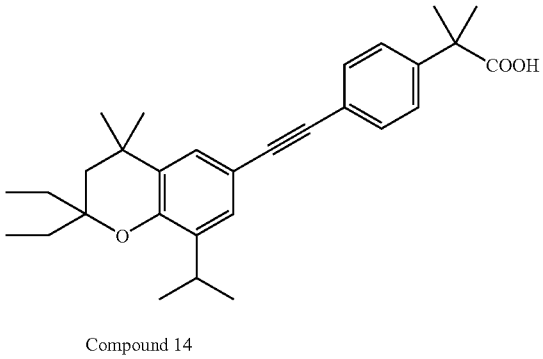

Compound 14

6-Bromo-2,2-diethyl-4,4-dimethylchroman (Intermediate 25)

A solution of 6-bromo-4,4-dimethyl-chroman-2-one (U.S. Pat. No. 6,252,090, 4 g, 15.7 mmol) in anhydrous tetrahydrofuran (20 mL) was treated with a 3M solution of ethyl magnesium bromide (10.5 mL, 31.5 mmol) and stirred at ambient temperature for 2 h. The reaction mixture was poured into cold dilute hydrochloric acid and extracted with ethyl acetate (×2). The combined organic extract was dried over anhydrous sodium sulfate, filtered and evaporated in vacuo to afford a residue which was dissolved in 50 mL of benzene, treated with p-toluene sulfonic acid (1 g, 3.92 mmol) and the resulting reaction mixture was refluxed overnight. The reaction mixture cooled to ambient temperature, filtered on silica gel and washed with 10% ethyl acetate in hexane. The filtrate and washings were evaporated in vacuo to an oil which was subjected to flash column chromatography over silica gel (230–400 mesh) using 5% ethyl acetate in hexane as the eluent to afford the title compound as a pale yellow oil (3.9 g, 84%).

$^1$H NMR (300 MHz, CDCl$_3$): δ 7.36 (d, 1H, J=2.4 Hz), 7.35 (dd, 1H, J=2.4, 8.4 Hz), 6.70 (d, 1H, J=8.4 Hz), 1.79 (s, 2H), 1.73–1.55 (m, 4H), 1.34 (s, 6H), 0.90 (t, 6H, J=7.5 Hz).

8-Acetyl-6-bromo-2,2-diethyl-4,4-dimethyl chroman (Intermediate 26)

A stirred, cooled (ice bath) suspension of aluminum chloride (1.1 g, 8.38 mmol) in anhydrous dichloromethane (20 mL) was treated with acetyl chloride (0.6 mL, 8.38 mmol). After 5 minutes, a solution of 6-bromo-2,2-diethyl-4,4-dimethyl chroman (Intermediate 25, 1.66 g, 5.59 mmol) in dichloromethane was added. The reaction mixture was stirred for 1 h. The reaction mixture was then poured into water and extracted with diethyl ether (×2). The combined organic phase was washed with saturated aqueous sodium bicarbonate solution, dried over anhydrous sodium sulfate, filtered and evaporated in vacuo to a residue which was subjected to flash column chromatography over silica gel (230–400 mesh) using 10% ethyl acetate in hexane as the eluent to afford the title compound as an oil (1.6 g, 84%).

$^1$H NMR (300 MHz, CDCl$_3$): δ 7.64 (d, 1H, J=2.1 Hz), 7.48 (d, 1H, J=2.1 Hz), 2.62 (s, 3H), 1.84 (s, 2H), 1.75–1.59 (m, 4H), 1.36 (s, 6H), 0.93 (t, 6H, J=7.5 Hz).

6-Bromo-2,2-diethyl-8-isopropyl-4,4-dimethyl chroman (Intermediate 27)

A stirred, cooled (ice bath) solution of 8-acetyl-6-bromo-2,2-diethyl-4,4-dimethyl chroman (Intermediate 26, 1.57 g, 4.62 mmol) in anhydrous tetrahydrofuran (10 mL) was treated with a 3M solution of methyl magnesium bromide in diethyl ether (3.1 mL, 9.24 mmol). The reaction mixture was allowed to warm to ambient temperature over 2 h. The reaction mixture was poured into cold, dilute aqueous hydrochloric acid and extracted with ethyl acetate. The organic phase was dried over anhydrous magnesium sulfate, filtered and evaporated in vacuo to a residue which on flash column chromatography over silica gel (230–400 mesh) using 5–10% ethyl acetate in hexane as the eluent afforded an oil (1.41 g, 86%). A stirred, cooled (ice bath) solution of the oil (1.4 g, 3.93 mmol) in dichloromethane (10 mL) was treated with triethylsilane (5 mL, 31.46 mmol) followed after 30 minutes by trifluoroacetic acid (2.4 mL, 31.46 mmol) and the resulting reaction mixture was allowed to warm to ambient temperature and stirred for 3 h. The volatiles were distilled off in vacuo and the residue was diluted with water and extracted with ethyl acetate. The combined organic phase was dried over anhydrous sodium sulfate, filtered and evaporated in vacuo to an oil which was subjected to flash column chromatography over silica gel (230–400 mesh) to afford the title compound as a clear oil (0.89 g, 66%) and some recovered starting material (0.23 g, 16.4%).

$^1$H NMR (300 MHz, CDCl$_3$): δ 7.21 (d, 1H, J=2.1 Hz), 7.11 (d, 1H, J=2.1 Hz), 3.40–3.30 (m, 1H), 1.78 (s, 2H), 1.68–1.58 (m, 4H), 1.33 (s, 6H), 1.90 (d, 6H, J=6.6 Hz), 0.92 (t, 6H, J=7.5 Hz).

2,2-Diethyl-8-isopropyl-6-trimethylsilanylethynyl-4,4-dimethyl chroman (Intermediate 28)

Following General Procedure D and using 6-bromo-2,2-diethyl-8-isopropyl-4,4-dimethyl chroman (Intermediate 27, 0.89 g, 2.62 mmol), triethyl amine (5 mL), tetrahydrofuran (10 mL), copper(I)iodide (0.050 g, 0.26 mmol), trimethylsilyl acetylene (2.5 mL, 17.6 mmol) and dichlorobis(triphenylphosphine)palladium(11) (0.184 g, 0.26 mmol) followed by flash column chromatography over silica gel (230–400 mesh) using hexane to 2% ethyl acetate in hexane as the eluent, the title compound (0.73 g, 79%) was obtained as a brown oil.

$^1$H NMR (300 MHz, CDCl$_3$): δ 7.31 (d, 1H), 7.12 (d, 1H), 3.20–3.10 (m, 1H), 1.70 (s, 2H), 1.70–1.45 (m, 4H), 1.34 (s, 6H), 0.95 (d, 6H), 0.68 (t, 6H), 0.00 (s, 9H).

2,2-Diethyl-6-ethynyl-8-isopropyl-4,4-dimethyl chroman (Intermediate 29)

A solution of 2,2-diethyl-8-isopropyl-6-trimethylsilanylethynyl-4,4-dimethyl chroman (Intermediate 28, 0.73 g, 2.04 mmol) in methanol (40 mL) was treated with potassium carbonate (0.15 g, 1.08 mmol) and the resulting reaction mixture was heated at 80° C. for 3 h. The solvent was evaporated in vacuo, the residue was diluted with water and extracted with ethyl acetate. The organic phase was dried over anhydrous magnesium sulfate, filtered and evaporated in vacuo to afford the title compound as a brown oil (0.56 g, 96%).

$^1$H NMR (300 MHz, CDCl$_3$): δ 7.27 (d, 1H), 7.16 (d, 1H), 3.31–3.06 (m, 1H), 2.96 (s, 1H), 1.81 (s, 2H), 1.81–1.56 (m, 4H), 1.31 (s, 6H), 1.17 (d, 6H), 0.91 (t, 6H).

2-[4-(2,2-Diethyl-8-isopropyl-4,4-dimethyl-chroman-6-ylethynyl)-phenyl]-2-methyl-propionic acid methyl ester (Intermediate 30)

Following General Procedure B and using 2,2-diethyl-6-ethynyl-8-isopropyl-4,4-dimethyl chroman (Intermediate 29, 0.069 g, 0.24 mmol), methyl-2-(4-iodophenyl)-2-methyl-propionate (Reagent 2, 0.146 g, 0.48 mmol), triethyl amine (3 mL), copper(I)iodide (0.025 g, 0.13 mmol) and dichlorobis(triphenylphosphine)palladium(II) (0.075 g, 0.107 mmol) followed by flash column chromatography over silica gel (230–400 mesh) using 5% ethyl acetate in hexane as the eluent, the title compound was obtained as a yellow oil (0.070 g, 62%).

$^1$H NMR (300 MHz, CDCl$_3$): δ 7.47 (d, 2H, J=8.2 Hz), 7.31 (d, 2H, J=8.2 Hz), 7.30 (d, 1H, J=2.1 Hz), 7.20 (d, 1H, J=2.1 Hz), 3.65 (s, 3H), 3.40–3.20 (m, 1H), 1.78 (s, 2H), 1.68–1.57 (m, 4H), 1.58 (s, 6H), 1.34 (s, 6H), 1.21 (d, 6H, J=7.0 Hz), 0.91 (t, 6H, J=7.3 Hz).

2-[4-(2,2-Diethyl-8-isopropyl-4,4-dimethyl-chroman-6-ylethynyl)-phenyl]-2-methyl-propionic acid (Compound 14)

A solution of 2-[4 (2,2-diethyl-8-isopropyl-4,4-dimethyl-chroman-6-ylethynyl)-phenyl]-2-methyl-propionic acid methyl ester (Intermediate 30, 0.070 g, 0.15 mmol) in methanol (3 mL) and tetrahydrofuran (0.5 mL) was treated with a 5M solution of potassium hydroxide (2 mL, 10 mmol) and the resulting reaction mixture was stirred at ambient temperature for 2 days. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford a residue that on preparative reverse phase HPLC using 110% water in acetonitrile as the mobile phase afforded the title product as a yellow solid (0.035 g, 51%).

$^1$H NMR (300 MHz, CDCl$_3$): δ 7.48 (d, 2H, J=8.1 Hz), 7.36 (d, 2H, J=8.2 Hz), 7.31 (d, 1H, J=2.1 Hz), 7.20 (d, 1H, J=2.1 Hz), 3.40–3.20 (m, 1H), 1.79 (s, 2H), 1.69–1.60 (m, 4H), 1.61 (s, 6H), 1.35 (s, 6H), 1.21 (d, 6H, J=7.2 Hz), 0.92 (t, 6H, J=7.5 Hz).

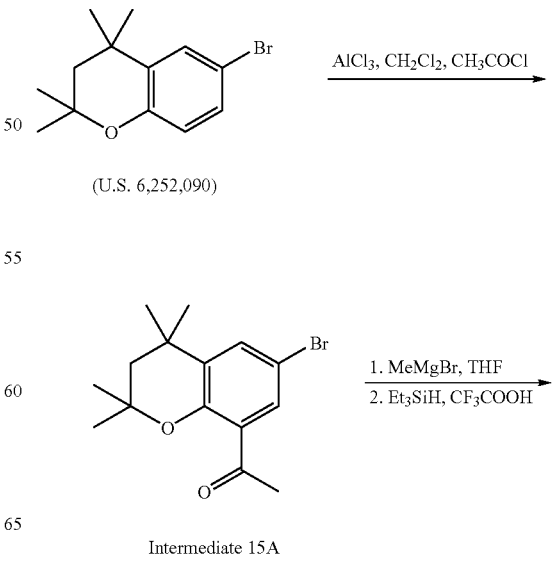

Reaction Scheme 7

-continued

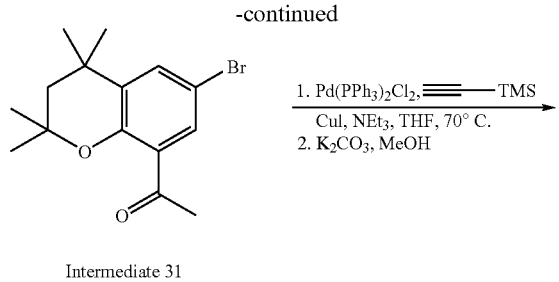

Intermediate 31

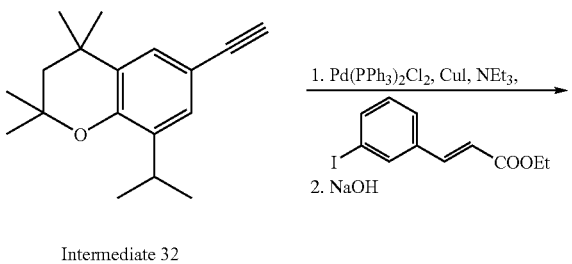

Intermediate 32

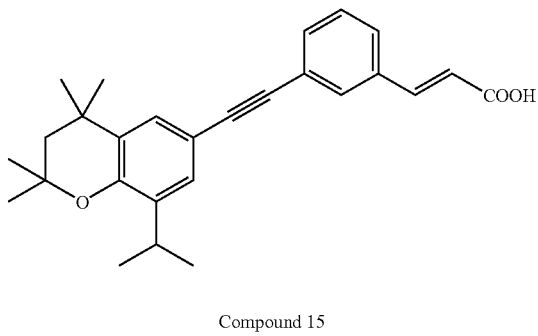

Compound 15

6-Bromo-8-isopropyl-2,2,4,4-tetramethyl-chroman (Intermediate 31)

A stirred, cooled (ice bath) solution of 8-acetyl-6-bromo-2,2,4,4-tetramethylchroman (Intermediate 15A, 3.1 g, 10 mmol) in anhydrous tetrahydrofuran (4 mL) was treated with a 3M solution of methyl magnesium bromide in diethyl ether (11 mL, 44 mmol). The reaction mixture was allowed to warm to ambient temperature overnight. The reaction mixture was poured into cold, dilute aqueous hydrochloric acid and extracted with ethyl acetate. The organic phase was dried over anhydrous magnesium sulfate, filtered and evaporated in vacuo to a residue which on flash column chromatography over silica gel (230–400 mesh) using 10% ethyl acetate in hexane as the eluent afforded an oil (2.85 g, 87%). The oil (1.67 g, 5.122 mmol) was cooled (ice bath) and treated with triethylsilane (10 mL, 62 mmol) followed after 30 minutes by trifluoroacetic acid (5 mL, 65 mmol) and the resulting reaction mixture was allowed to warm to ambient temperature overnight. The reaction mixture was diluted with water and extracted with ethyl acetate. The combined organic phase was dried over anhydrous sodium sulfate, filtered and evaporated in vacuo to an oil which was subjected to flash column chromatography over silica gel (230–400 mesh) to afford the title compound as a clear oil (1 g, 63%).

$^1$H NMR (300 MHz, CDCl$_3$): δ 7.20 (d, 1H, J=2.3 Hz), 7.09 (d, 1H, J=2.3 Hz), 3.25 (heptet, 1H, J=7.1 Hz), 1.79 (s, 2H), 1.33 (s, 6H), 1.31 (s, 6H), 1.15 (d, 6H, J=7.1 Hz).

6-Ethynyl-8-isopropyl-2,2,4,4-tetramethyl-chroman (Intermediate 32)

Following General Procedure D and using 6-bromo-8-isopropyl-2,2,4,4-tetramethyl chroman (Intermediate 31, 1 g, 3.2 mmol), triethyl amine (10 mL), copper(I)iodide (0.04 g, 0.21 mmol), trimethylsilyl acetylene (5 mL, 35 mmol) and dichlorobis(triphenylphosphine)palladium(II) (0.12 g, 0.17 mmol) followed by flash column chromatography over silica gel (230–400 mesh), the intermediate trimethylsilylacetylene was obtained, which was dissolved in methanol and treated with potassium carbonate and the resulting reaction mixture was stirred at ambient temperature overnight.

The solvent was evaporated in vacuo, the residue was diluted with water and extracted with ethyl acetate. The organic phase was dried over anhydrous magnesium sulfate, filtered and evaporated in vacuo to afford the title compound as a brown oil (0.6 g, 73%). %).

$^1$H NMR (300 MHz, CDCl$_3$): δ 7.34 (d, 1H, J=2.1 Hz), 7.21 (d, 1H, J=2.1 Hz), 3.50 (heptet, 1H, J=6.8 Hz), 3.00 (s, 1H), 1.85 (s, 2H), 1.38 (s, 6H), 1.37 (s, 6H), 1.22 (d, 6H, J=6.8 Hz).

3-[3-(8-Isopropyl-2,2,4,4-tetramethyl-chroman-6-ylethynyl)-phenyl]-acrylic acid ethyl ester (Intermediate 33)

Following General Procedure B and using 6-ethynyl-8-isopropyl-2,2,4,4-tetramethylchroman (Intermediate 32, 0.05 g, 0.2 mmol), ethyl-3-iodo cinnamate (Reagent 6, 0.118 g, 0.39 mmol), triethyl amine (2 mL), copper(I)iodide (0.025 g, 0.13 mmol) and dichlorobis(triphenylphosphine)palladium(II) (0.075 g, 0.107 mmol) followed by flash column chromatography over silica gel (230–400 mesh), the title compound was obtained (0.058 g, 69%).

$^1$H NMR (300 MHz, CDCl$_3$): δ 7.62–7.22 (m, 6H), 7.14 (d, 1H, J=1.8 Hz), 6.39 (d, 1H, J=16.1 Hz), 4.19 (q, 2H, J=7.0 Hz), 3.21 (heptet, 1H, J=6.7 Hz), 1.76 (s, 2H), 1.29 (s, 12H), 1.27 (t, 3H, J=7.0 Hz). 1.13 (d, 6H, J=6.7 Hz).

3-[3-(8-Isopropyl-2,2,4,4-tetramethyl-chroman-6-ylethynyl)-phenyl]-acrylic acid (Compound 15)

A solution of 3-[3-(8-isopropyl-2,2,4,4-tetramethyl-chroman-6-ylethynyl)-phenyl]-acrylic acid ethyl ester (Intermediate 33, 0.058 g, 0.13 mmol) in ethanol (2 mL) and tetrahydrofuran (2 mL) was treated with a 5N solution of potassium hydroxide (2 mL, 10 mmol) and the reaction mixture was stirred at ambient temperature overnight. The Volatiles were evaporated in vacuo, the residue was neutralized with dilute hydrochloric acid and extracted with ethyl acetate. The organic phase was washed with water and brine, dried over anhydrous magnesium sulfate and evaporated to afford the title compound (0.036 g, 66%).

$^1$H NMR (300 MHz, CDCl$_3$): δ 7.69 (d, 1H, J=15.8 Hz), 7.65 (s, 1H), 7.47 (d, 1H, J=7.6 Hz), 7.39 (d, 1H, J=7.9 Hz), 7.32–7.17 (m, 2H), 7.14 (d, 1H, J=1.8 Hz), 6.41 (d, 1H, J=15.8 Hz), 3.21 (heptet, 1H, J=6.7 Hz), 1.76 (s, 2H), 1.29 (s, 12H), 1.13 (d, 6H, J=6.7 Hz).

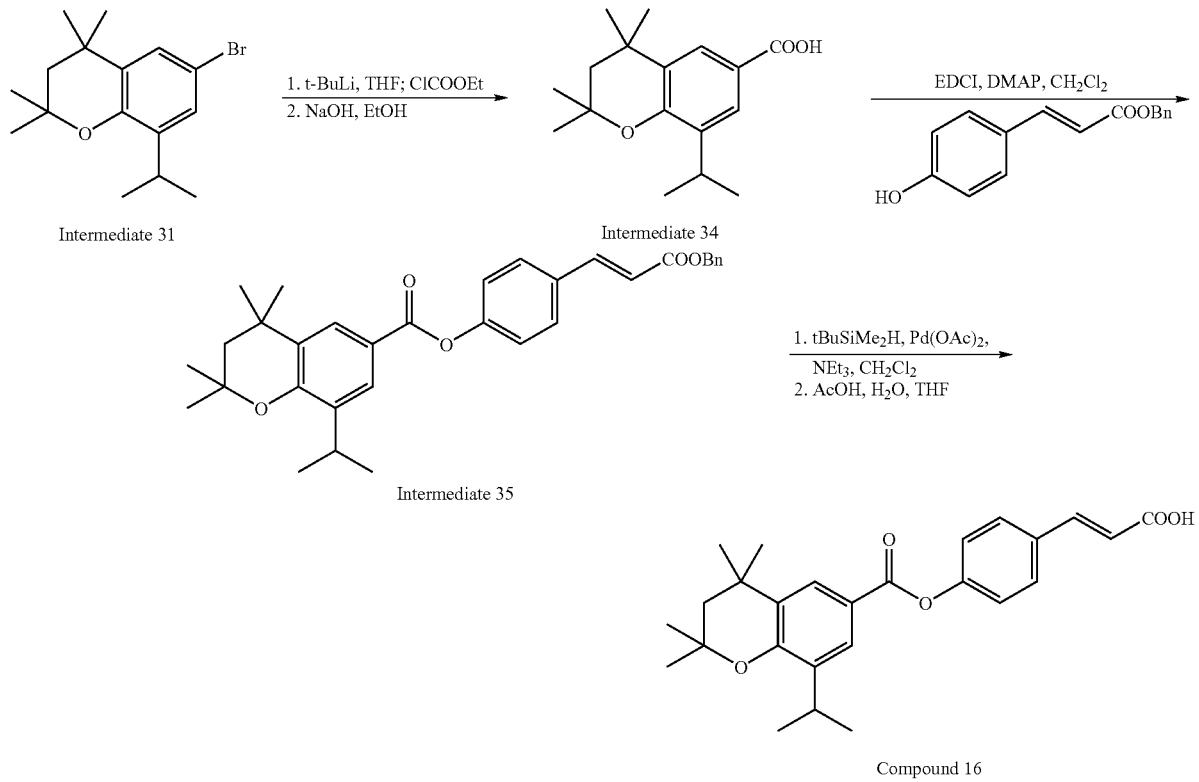

Reaction Scheme 8

8-Isopropyl-2,2,4,4-tetramethyl-chroman-6-carboxylic acid (Intermediate 34)

A stirred, cooled (−78° C.) solution of 6-bromo-8-isopropyl-2,2,4,4-tetramethyl-chroman (Intermediate 31, 0.39 g, 1.26 mmol) in anhydrous diethyl ether (10 mL) was treated with a 1.7M solution of t-butyl lithium in pentane (1.48 mL, 2.516 mmol) and the reaction mixture was stirred for 20 minutes. Carbon dioxide (generated from dry ice) was bubbled into the reaction mixture. The reaction mixture was then quenched with 10% aqueous hydrochloric acid and extracted with ethyl acetate. The organic phase was washed with water and brine, dried over anhydrous sodium sulfate, filtered and evaporated to a residue that was subjected to flash column chromatography to afford the title compound (0.3, 86%).

$^1$H NMR (300 MHz, CDCl$_3$): δ 7.87 (d, 1H, J=2 Hz), 7.72 (d, 1H, J=2 Hz), 3.21 (heptet, 1H, J=7.0 Hz), 1.78 (s, 2H), 1.39 (s, 12H), 1.14 (d, 6H, J=7.0 Hz).

8-Isopropyl-2,2,4,4-tetramethyl-chroman-6-carboxylic acid 4-(2-benzyloxycarbonyl-vinyl)-phenyl ester (Intermediate 35)

A solution of 8-isopropyl-2,2,4,4-tetramethyl-chroman-6-carboxylic acid (Intermediate 34, 0.05 g, 0.18 mmol) and 3-(4-hydroxy-phenyl)-acrylic acid benzyl ester (described in Journal of Natural Products, 1990, 53 (4), p 821–824, Bankova V., 0.046 g, 0.18 mmol) in anhydrous dichloromethane (5 mL) was treated with 4-(dimethylamino)pyridine (0.052 g, 0.27 mmol) and 1-(3-dimethylaminopropyl)-3-ethylcarbodiimide hydrochloride (0.044 g, 0.36 mmol) and the resulting reaction mixture was stirred at ambient temperature overnight. The reaction mixture was then subjected to flash column chromatography using 20% ethyl acetate in hexane as the eluent to afford the title compound as a white solid (0.076 g, 83%).

$^1$H NMR (300 MHz, CDCl$_3$): δ 7.93 (d, 1H, J=2 Hz), 7.78 (d, 1H, J=2 Hz), 7.66 (d, 1H, J=16.1 Hz), 7.49 (d, 2H, J=8.5 Hz), 7.35–7.25 (m, 5H), 7.15 (d, 2H, J=8.5 Hz), 6.39 (d, 1H, J=16.1 Hz), 5.18 (s, 2H), 3.24 (heptet, 1H, J=7.1 Hz), 1.80 (s, 2H), 1.31 (s, 12H), 1.16 (d, 6H, J=7.1 Hz).

8-Isopropyl-2,2,4,4-tetramethyl-chroman-6-carboxylic acid 4-(2-carboxy-vinyl)-phenyl ester (Compound 16)

A suspension of t-butyldimethyl silane (0.3 mL, 1.85 mmol), palladium(II)acetate (0.013 g, 0.06 mmol) and triethyl amine (0.03 mL, 0.2 mmol) in anhydrous dichloromethane (2 mL) under argon was treated with a solution of 8-isopropyl-2,2,4,4-tetramethyl-chroman-6-carboxylic acid 4 (2-benzyloxycarbonyl-vinyl)-phenyl ester (Intermediate 35, 0.063 g, 0.123 mmol) in dichloromethane (2 mL) and the resulting reaction mixture was stirred overnight at ambient temperature. The reaction mixture was quenched with water and extracted with diethyl ether. The organic extract was dried over anhydrous sodium sulfate, filtered and evaporated to a residue that was subjected to flash column chromatography to yield an intermediate that was treated with acetic acid (1 mL) in water (0.3 mL) and tetrahydrofuran (0.3 mL) at ambient temperature for 1 h. The reaction mixture was diluted with water and extracted with ethyl acetate. The organic extract was dried over anhydrous sodium sulfate, filtered and evaporated to a residue that was subjected to preparative reverse phase HPLC using 10% water in acetonitrile as the mobile phase to afford the title compound (0.007 g).

¹H NMR (300 MHz, CDCl₃): δ 7.89 (d, 1H, J=2 Hz), 7.74 (d, 1H, J=2 Hz), 7.67 (d, 1H, J=15.8 Hz), 7.49 (d, 2H, J=8.8 Hz), 7.15 (d, 2H, J=8.8 Hz), 6.32 (d, 1H, J=15.8 Hz), 3.20 (heptet, 1H, J=6.8 Hz), 1.77 (s, 2H), 1.29 (s, 6H), 1.28 (s, 6H), 1.12 (d, 6H, J=6.8 Hz).

Reaction Scheme 9

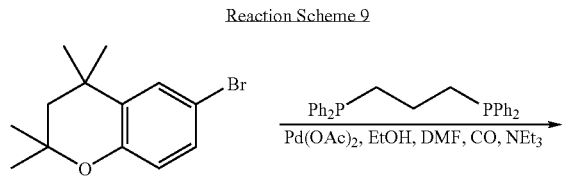

U. S. Pat. No. 6,252,090

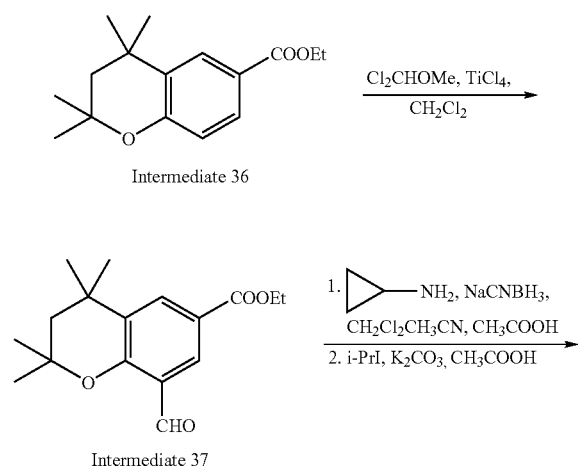

Intermediate 36

Intermediate 37

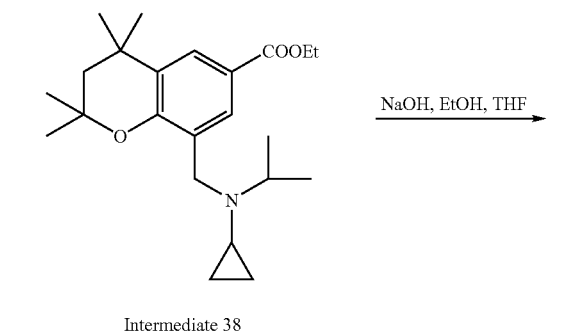

Intermediate 38

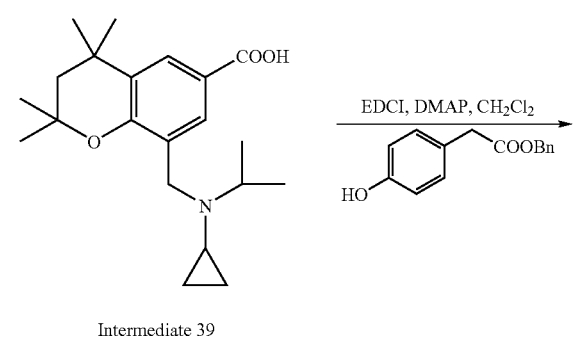

Intermediate 39

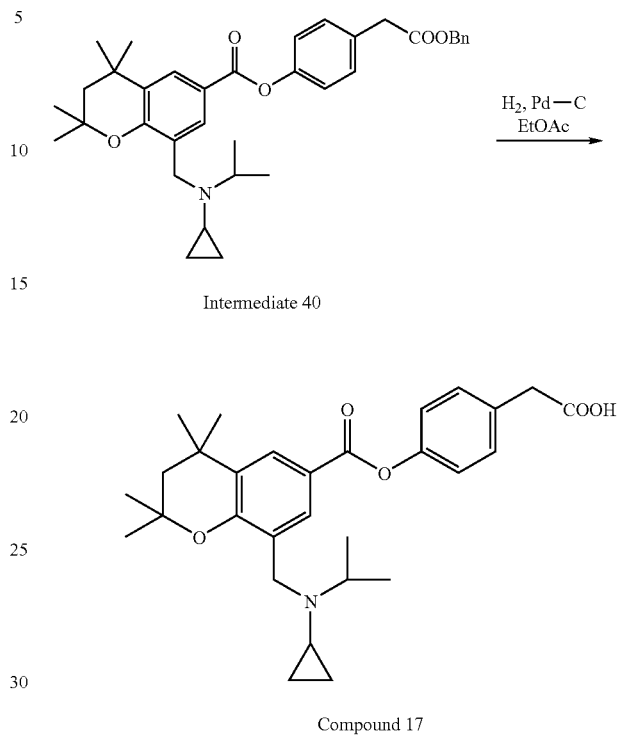

Intermediate 40

Compound 17

Ethyl-2,2,4,4-tetramethyl chroman-6-carboxylate (Intermediate 36)

A solution of 6-bromo-2,2,4,4-tetramethylchroman (U.S. Pat. No. 6,252,090, 2.2 g, 8.08 mmol), palladium acetate (0.145 g, 0.65 mmol) and 1,3-bis(diphenylphosphino)propane (0.267 g, 0.65 mmol) in a mixture of N,N-dimethylformamide (25 mL), ethanol (20 mL) and triethyl amine (7 mL) was heated at 90° C. under an atmosphere of carbon monoxide overnight. The volatiles were distilled off in vacuo and the residue was diluted with water and extracted with ethyl acetate. The combined organic extract was washed with brine (×1), dried over anhydrous magnesium sulfate, filtered and evaporated in vacuo to an oil which was subjected to flash column chromatography over silica gel (230–400 mesh) using 5–10% ethyl acetate in hexane as the eluent to afford the title compound (1.9 g, 90%).

¹H NMR (300 MHz, CDCl₃): δ8.00 (d, 1H, J=2.3 Hz), 7.76 (dd, 1H, J=2.1, 8.5 Hz), 6.79 (d, 1H, J=8.5 Hz), 4.33 (q, 2H, J=7.1 Hz), 1.85 (s, 2H), 1.36 (s, 6H), 1.37 (s, 6H), 1.39–1.33 (m, 3H).

8-Formyl-2,2,4,4-tetramethyl-chroman-6-carboxylic acid ethyl ester (Intermediate 37)

A stirred, cooled (ice bath) solution of of 2,2,4,4-tetramethyl-chroman-6-carboxylic acid ethyl ester (Intermediate 36, 0.5 g, 1.92 mmol) in anhydrous dichloromethane (10 mL) was treated with titanium tetrachloride (0.4 mL, 3.26 mmol) followed by α,α-dichloromethyl ether (0.17 mL, 1.92 mmol). The reaction was allowed to warm to ambient temperature over 2 days, quenched cautiously with ice and water and extracted with dichloromethane. The organic extract was washed with water and brine, dried over sodium sulfate, filtered and evaporated in vacuo to a residue that was subjected to flash column chromatography to afford the title compound (0.11 g, 20%).

$^1$H NMR (300 MHz, CDCl$_3$): δ 10.46 (s, 1H), 8.33 (d, 1H, J=2 Hz), 8.20 (d, 1H, J=2 Hz), 4.36 (q, 2H, J=6.7 Hz), 1.93 (s, 2H), 1.45 (s, 6H), 1.42 (s, 6H), 1.39 (t, 3H, J=6.7 Hz).

(8-[(Cyclopropyl-isopropyl-amino)-methyl]-2,2,4,4-tetramethyl-chroman-6-carboxylic acid ethyl ester (Intermediate 38)

Following General Procedure C and using 8-formyl-2,2,4,4-tetramethyl-chroman-6-carboxylic acid ethyl ester (Intermediate 37, 0.11 g, 0.23 mmol) in dichloromethane (4 mL) and acetonitrile (2 mL), cyclopropyl amine (0.08 mL, 1.1 mmol), acetic acid (0.8 mL) and sodium cyanoborohydride (0.072 g, 1.1 mmol) followed by work up and flash column chromatography afforded an intermediate. The intermediate (0.122 g, 0.22 mmol) was dissolved in acetone (10 mL) and treated with potassium carbonate (0.153 g, 1.1 mmol) and isopropyl iodide (0.04 mL). The resulting reaction mixture was at 60° C. for 4 h. The volatiles were evaporated in vacuo, the residue was diluted with water and extracted with ethyl acetate. The combined organic phase was dried over anhydrous magnesium sulfate, filtered and evaporated to an oil. Flash column chromatography over silica gel (230–400 mesh) using 15–20% ethyl acetate in hexane as the eluent afforded the title compound (0.09 g, 71%) as a clear oil.

$^1$H NMR (300 MHz, CDCl$_3$): δ 7.87 (d, 1H, J=2.1 Hz), 7.85 (d, 1H, J=2.1 Hz), 4.35 (q, 2H, J=7.0 Hz), 3.72 (s, 2H), 2.97 (heptet, 1H, J=6.7 Hz), 1.97 (m, 1H), 1.83 (s, 2H), 1.37 (t, 3H, J=7.0 Hz), 1.37 (s, 6H), 1.35 (s, 6H), 1.08 (d, 6H, J=6.7 Hz), 0.38–0.30 (m, 4H).

8-[(Cyclopropyl-isopropyl-amino)-methyl]-2,2,4,4-tetramethyl-chroman-6-carboxylic acid (Intermediate 39)

A solution of 8-[(cyclopropyl-isopropyl-amino)-methyl]-2,2,4,4-tetramethyl-chroman-6-carboxylic acid ethyl ester (Intermediate 38, 0.09 g, 0.26 mmol) in ethanol (3 mL) and tetrahydrofuran (1 mL) was treated with a 1M solution of sodium hydroxide (3 mL, 3 mmol) and the resulting reaction mixture was stirred at ambient temperature overnight. The volatiles were evaporated in vacuo, the residue was neutralized with dilute hydrochloric acid and extracted with ethyl acetate. The organic extract was washed with water and brine and dried over anhydrous sodium sulfate, filtered and evaporated to afford the title compound (0.079 g, 96%). It was used as such for the next step.

8-[(Cyclopropyl-isopropyl-amino)-methyl]-2,2,4,4-tetramethyl-chroman-6-carboxylic acid 4-benzyloxycarbonylmethyl-phenyl ester (Intermediate 40)

A solution of 8-[(cyclopropyl-isopropyl-amino)-methyl]-2,2,4,4-tetramethyl-chroman-6-carboxylic acid (Intermediate 39, 0.079 g, 0.25 mmol) and benzyl-4-hydroxy-phenyl acetate (APIN, 0.06 g, 0.25 mmol) in anhydrous dichloromethane (5 mL) was treated with 4-(dimethylamino)pyridine (0.06 g, 0.5 mmol) and 1-(3-dimethylaminopropyl)-3-ethylcarbodiimide hydrochloride (0.072 g, 0.37 mmol) and the resulting reaction mixture was stirred at ambient temperature overnight. The reaction mixture was then subjected to flash column chromatography using 20% ethyl acetate in hexane as the eluent to afford the title compound as an oil (0.093 g, 69%).

$^1$H NMR (300 MHz, CDCl$_3$): δ 7.98 (s, 2H), 7.32–7.21 (m, 7H), 7.13 (d, 2H, J=8.5 Hz), 5.11 (s, 2H), 3.73 (s, 2H), 3.66 (s, 2H), 2.93 Septet, 1H, J=6.5 Hz), 1.93 (m, 1H), 1.84 (s, 2H), 1.07 (s, 12H), 1.07 (d, 6H, J=6.5 Hz).

8-[(Cyclopropyl-isopropyl-amino)-methyl]-2,2,4,4-tetramethyl-chroman-6-carboxylic acid 4-carboxymethyl-phenyl ester (Compound 17)

A solution of 8-[(cyclopropyl-isopropyl-amino)-methyl]-2,2,4,4-tetramethyl-chroman-6-carboxylic acid 4-benzyloxycarbonylmethyl-phenyl ester (Intermediate 40, 0.093 g–0.17 mmol) in ethyl acetate (3 mL) was treated with a slurry of 10% palladium on carbon (20 mg) in ethyl acetate and the resulting reaction mixture was stirred under an atmosphere of hydrogen at ambient temperature for 2 h. The reaction mixture was filtered over a bed of celite and the filtrate was evaporated to a residue that was purified by flash column chromatography over silica gel to afford the title compound.

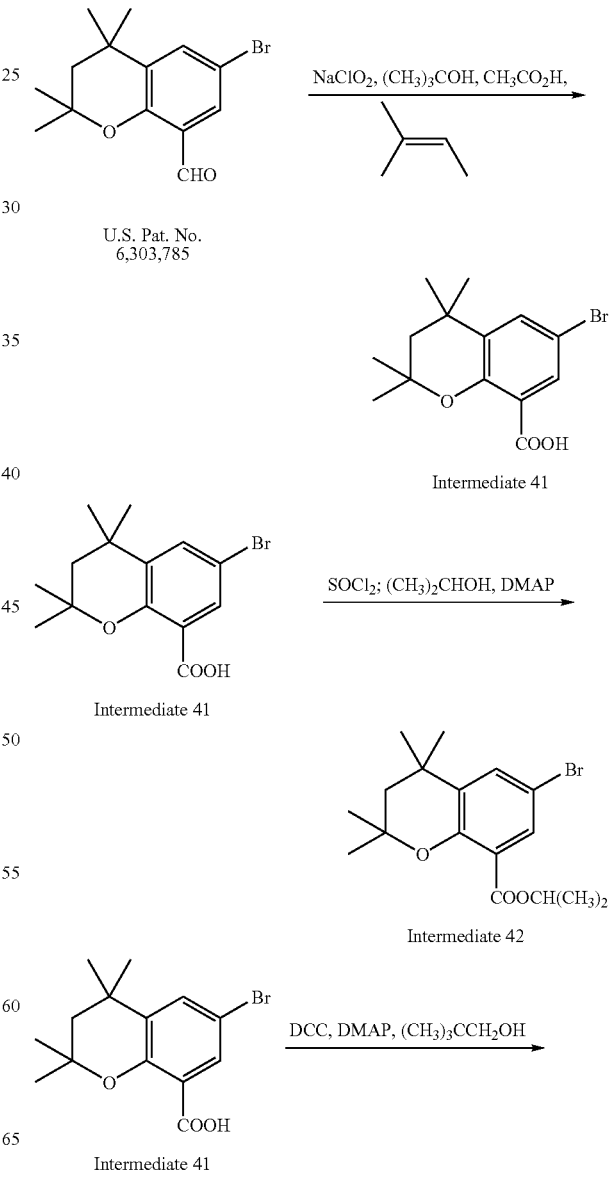

Reaction Scheme 10

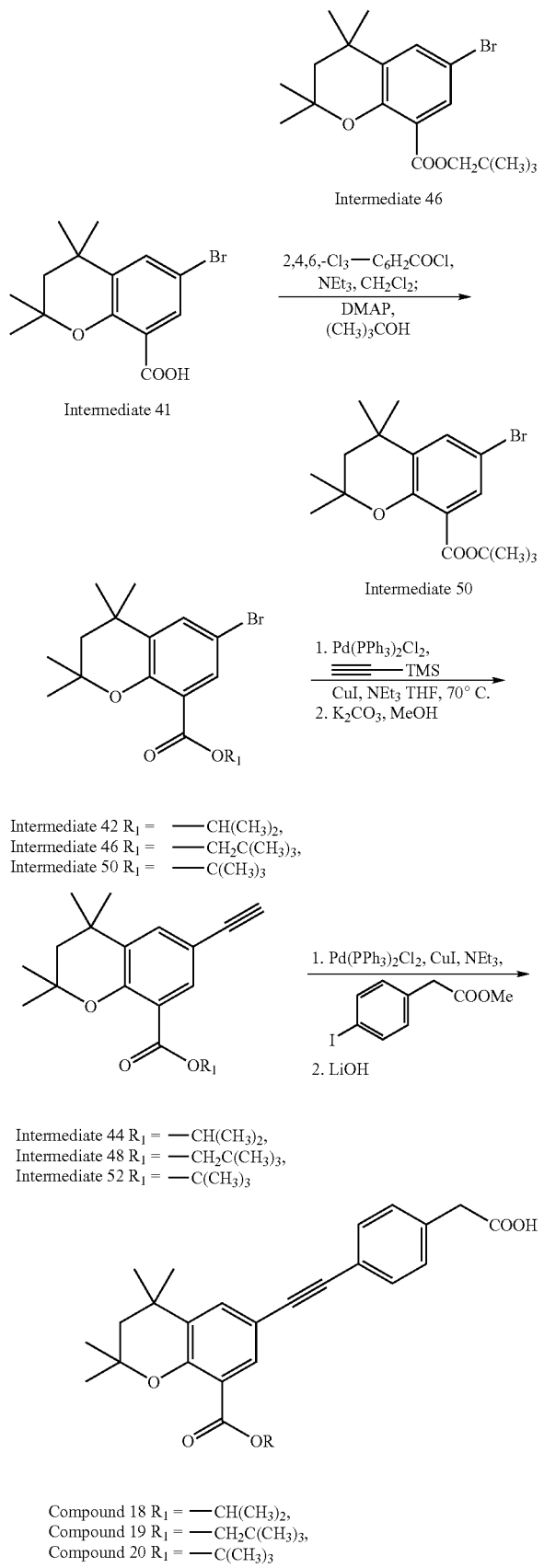

6-Bromo-2,2,4,4-tetramethylchroman-8-carboxylic acid (Intermediate 41)

A stirred, cooled (ice bath) solution of 6-bromo-2,2,4,4-tetramethylchroman-6-carbaldehyde (U.S. Pat. No. 6,303,785 incorporated herein by reference; 3.31 g, 11.15 mmol) in 2-methyl-2-propanol (30 mL) was treated with glacial acetic acid (30 mL) followed by 2-methyl-2-butene (12 mL, 1111.5 mmol). A solution of sodium chlorite (2.15 g, 18.95 mmol) in water (15 mL) was added dropwise to the reaction mixture. The reaction mixture was then allowed to gradually warm up to ambient temperature and stirred for 4 h at the end of which it was made basic 2N sodium hydroxide solution and then acidified with 2N hydrochloric acid and extracted with ethyl acetate. The organic phase was washed with brine, dried over anhydrous magnesium sulfate, filtered and evaporated in vacuo to afford the title product as a yellow solid (3.23 g, 93%).

$^1$H NMR (300 MHz, CDCl$_3$): δ 8.14 (d, 1H, J=2.7 Hz), 7.60 (d, 1H, J=2.7 Hz), 1.95 (s, 2H), 1.50 (s, 6H), 1.39 (s, 6H).

6-Bromo-2,2,4,4-tetramethylchroman-8-carboxylic acid isopropyl ester (Intermediate 42)

A solution of 6-bromo-2,2,4,4-tetramethylchroman-8-carboxylic acid (Intermediate 41, 0.3 g, 0.96 mmol) in anhydrous dichloromethane (15 mL) was treated with thionyl chloride (0.7 mL, 9.6 mmol) and the reaction mixture was refluxed for 18 h. It was then cooled to ambient temperature, the volatiles were distilled off in vacuo and the residue was dissolved in isopropanol (15 mL). 4-(Dimethylamino)pyridine (0.35 g, 9.6 mmol) was added and the reaction mixture was stirred at ambient temperature for 5 h. It was diluted with ethyl acetate and washed with 2N hydrochloric acid (×2), 2N sodium hydroxide (×2), and brine, dried over anhydrous magnesium sulfate, filtered- and evaporated in vacuo to afford the title product as a brown oil (0.32 g, 93%).

$^1$H NMR (300 MHz, CDCl$_3$): δ 7.60 (d, 1H, J=2.4 Hz), 7.45 (d, 1H, J=2.4 Hz), 5.23 (heptet, 1H, J=6.0 Hz), 1.84 (s, 2H), 1.37 (s, 6H), 1.36 (s, 6H), 1.33 (d, 6H, J=6.0 Hz).

2,2,4,4-Tetramethyl-6-trimethylsilanylethynylchroman-8-carboxylic acid isopropyl ester (Intermediate 43)

Following General Procedure D and using 6-bromo-2,2,4,4-tetramethylchroman-8-carboxylic acid isopropyl ester (Intermediate 42, 0.32 g, 0.89 mmol), triethyl amine (2 mL), copper(I)iodide (0.060 g, 0.33 mmol), trimethylsilyl acetylene (0.5 mL, 3.56 mmol) and dichlorobis(triphenylphosphine)palladium(II) (0.16 g, 0.22 mmol) followed by flash column chromatography over silica gel (230–400 mesh) using 20% ethyl acetate in hexane as the eluent, the title compound (0.23 g, 69%) was obtained as a yellow oil.

$^1$H NMR (300 MHz, CDCl$_3$): δ 7.58 (d, 1H, J=2.4 Hz), 7.44 (d, 1H, J=2.4 Hz), 5.18 (heptet, 1H, J=6.3 Hz), 1.80 (s, 2H), 1.32 (s, 6H), 1.31 (s, 6H), 1.29 (d, 6H, J=6.3 Hz), 0.00 (s, 9H).

6-Ethynyl-2,2,4,4-tetramethylchroman-8-carboxylic acid isopropyl ester (Intermediate 44)

A solution of 2,2,4,4-tetramethyl-6-trimethylsilanylethynylchroman-8-carboxylic acid isopropyl ester (Intermediate 43, 0.23 g, 0.62 mmol) in methanol (5 mL) was treated with potassium carbonate (0.85 g, 6.2 mmol) and the resulting reaction mixture was stirred at ambient temperature overnight. The solvent was evaporated in vacuo, the residue was diluted with water and extracted with diethyl ether. The organic phase was washed with brine, dried over anhydrous magnesium sulfate, filtered and evaporated in vacuo to a brown oil that was subjected to flash column chromatography over silica gel (230–400 mesh) using 20% ethyl acetate in hexane as the eluent to afford the title compound (0.0246 g, 13%).

$^1$H NMR (300 MHz, CDCl$_3$): δ 7.66 (d, 1H, J=2.1 Hz), 7.53 (d, 1H, J=2.1 Hz), 5.25 (heptet, 1H, J=6.3 Hz), 3.02 (s, 1H), 1.88 (s, 2H), 1.40 (s, 6H), 1.37 (d, 6H, J=6.3 Hz), 1.36 (s, 6H).

6-(4-Methoxycarbonylmethyl-phenylethynyl)-2,2,4,4-tetramethyl-chroman-8-carboxylic acid isopropyl ester (Intermediate 45)

Following General Procedure B and using 6-ethynyl-2,2,4,4-tetramethylchroman-8-carboxylic acid isopropyl ester (Intermediate 44 0.025 g, 0.08 mmol), 4-iodo phenyl acetic acid methyl ester (0.027 g, 0.1 mmol), triethyl amine (2 mL), copper(I)iodide (0.008 g, 0.04 mmol) and dichlorobis(triphenylphosphine)palladium(II) (0.017 g, 0.024 mmol) followed by flash column chromatography over silica gel (230–400 mesh) using 40% ethyl acetate in hexane as the eluent, the title compound was obtained as a yellow oil (0.019 g, 53%).

$^1$H NMR (300 MHz, CDCl$_3$): δ 7.68 (d, 1H, J=2.1 Hz), 7.55 (d, 1H, J=2.1 Hz), 7.49–7.24 (m, 4H), 5.25 (m, 1H), 3.70 (s, 3H), 3.64 (s, 2H), 1.88 (s, 2H), 1.39 (s, 6H), 1.37 (s, 6H), 1.39–1.35 (d, 6H).

6-(4-Carboxymethyl-phenylethynyl)-2,2,4,4-tetramethyl-chroman-8-carboxylic acid isopropyl ester (Compound 18)

A solution of 6-(4-methoxycarbonylmethyl-phenylethynyl)-2,2,4,4-tetramethyl-chroman-8-carboxylic acid isopropyl ester (Intermediate 45, 0.019 g, 0.043 mmol) in ethanol (0.3 mL), tetrahydrofuran (0.3 mL) and water (0.3 mL) was treated with 1N lithium hydroxide (0.086 mL, 0.086 mmol) and the resulting reaction mixture was stirred at ambient temperature for 30 minutes. The volatiles were evaporated in vacuo to a residue that was washed with hexane:ethyl acetate (3:1) neutralized with 2N hydrochloric acid and extracted with ethyl acetate. The organic phase was washed with water and brine, and dried over anhydrous magnesium sulfate, filtered and evaporated in vacuo to afford the title product as a brown oil (0.015 g, 80%).

$^1$H NMR (300 MHz, CDCl$_3$): δ 7.69 (d, 1H, J=2.4 Hz), 7.55 (d, 1H, J=2.4 Hz), 7.50–7.26 (m, 4H), 5.25 (heptet, 1H), 3.67 (s, 2H), 1.88 (s, 2H), 1.39 (s, 6H), 1.37 (s, 6H), 1.39–1.35 (d, 6H).

6-Bromo-2,2,4,4-tetramethylchroman-8-carboxylic acid 2,2-dimethylpropyl ester (Intermediate 46)

A stirred cooled (ice bath) solution of 6-bromo-2,2,4,4-tetramethylchroman-8-carboxylic acid (Intermediate 41, 0.5 g, 1.6 mmol), neopentylalcohol (0.35 mL, 3.2 mmol) and 4-(dimethylamino)pyridine (0.03 g, 0.24 mmol) in anhydrous dichloromethane (5 mL) was treated with 1,3-dicyclohexylcarbodiimide (0.36 g, 1.76 mmol) and the reaction mixture was allowed to warm to ambient temperature. After 2 h, the reaction mixture was filtered, the filtrate was diluted with ethyl acetate and washed with 2N hydrochloric acid, 2N sodium hydroxide, and brine, dried over anhydrous magnesium sulfate, filtered and evaporated in vacuo to afford the title product as a yellow solid (0.537 g, 88%).

$^1$H NMR (300 MHz, CDCl$_3$): δ 7.60 (d, 1H, J=2.4 Hz), 7.41 (d, 1H, J=2.4 Hz), 3.91 (S, 2H), 1.78 (s, 2H), 1.30 (s, 6H), 1.27 (s, 6H), 0.95 (s; 9H).

2,2,4,4-Tetramethyl-6-trimethylsilanylethynylchroman-8-carboxylic acid 2,2-dimethylpropyl ester (Intermediate 47)

Following General Procedure D and using 6-bromo-2,2,4,4-tetramethylchroman-8-carboxylic acid 2,2dimethylpropyl ester (Intermediate 46, 0.54 g, 1.4 mmol), triethyl amine (3 mL), copper(I)iodide (0.10 g, 0.52 mmol), trimethylsilyl acetylene (0.8 mL, 5.6 mmol) and dichlorobis(triphenylphosphine)palladium(II)(0.25 g, 0.35 mmol) followed by flash column chromatography over silica gel (230–400 mesh) using 10% ethyl acetate in hexane as the eluent, the title compound (0.396 g, 71%) was obtained as a yellow oil.

$^1$H NMR (300 MHz, CDCl$_3$): δ 7.64 (d, 1H, J=1.8 Hz), 7.46 (d, 1H, J=1.8 Hz), 3.94 (s, 2H), 1.81 (s, 2H), 1.33 (s, 6H), 1.30 (s, 6H), 0.98 (s, 9H), 0.002 (s, 9H).

6-Ethynyl-2,2,4,4-tetramethylchroman-8-carboxylic acid 2,2-dimethylpropyl ester (Intermediate 48)

A solution of 2,2,4,4-tetramethyl-6-trimethylsilanylethynylchroman-8-carboxylic acid 2,2-dimethylpropyl ester (Intermediate 47, 0.396 g, 1 mmol) in methanol (5 mL) was treated with potassium carbonate (1.4 g, 10 mmol) and the resulting reaction mixture was stirred at ambient temperature for 30 minutes. The solvent was evaporated in vacuo, the residue was diluted with water and extracted with ethyl acetate. The organic phase was washed with brine, dried over anhydrous magnesium sulfate, filtered and evaporated in vacuo to afford the title compound as a brown oil (0.227 g, 70%).

$^1$H NMR (300 MHz, CDCl$_3$): δ 7.72 (d, 1H, J=1.5 Hz), 7.55 (d, 1H, J=1.5 Hz), 4.00 (s, 2H), 3.02 (s, 1H), 1.88 (s, 2H), 1.40 (s, 6H), 1.36 (s, 6H), 1.04 (s, 9H).

6-(4-Methoxycarbonylmethyl-phenylethynyl)-2,2,4,4-tetramethyl-chroman-8-carboxylic acid 2,2-dimethylpropyl ester (Intermediate 49)

Following General Procedure B and using 6-ethynyl-2,2,4,4-tetramethylchroman-8-carboxylic acid 2,2-dimethylpropyl ester (Intermediate 48, 0.227 g, 0.70 mmol), 4-iodo phenyl acetic acid methyl ester (0.23 g, 0.83 mmol), triethyl amine (3 mL), copper(I)iodide (0.07 g, 0.39 mmol) and dichlorobis(triphenylphosphine)palladium(II) (0.15 g, 0.21 mmol) followed by flash column chromatography over silica gel (230–400 mesh) using 20% ethyl acetate in hexane as the eluent, the title compound was obtained as a yellow oil (0.198 g, 60%).

$^1$H NMR (300 MHz, CDCl$_3$): δ 7.76 (d, 1H, J=2.4 Hz), 7.58 (d, 1H, J=2.4 Hz), 7.49 (d, 2H, J=8.1 Hz), 7.26 (d, 2H, J=8.1 Hz), 4.01 (s, 2H), 3.70 (s, 3H), 3.64 (s, 2H), 1.88 (s, 2H), 1.40 (s, 6H), 1.38 (s, 6H), 1.05 (s, 9H).

6-(4-Carboxymethyl-phenylethynyl)-2,2,4,4-tetramethyl-chroman-8-carboxylic acid 2,2-dimethylpropyl ester (Compound 19)

A solution of 6-(4-methoxycarbonylmethyl-phenylethynyl)-2,2,4,4-tetramethyl-chroman-8-carboxylic acid 2,2-dimethylpropyl ester (Intermediate 49, 0.198 g, 0.42 mmol) in ethanol (1 mL), tetrahydrofuran (1 mL) and water (1 mL) was treated with 1N lithium hydroxide (1.5 mL, 1.5 mmol) and the resulting reaction mixture was stirred at ambient temperature for 30 minutes. The reaction mixture was neutralized with 2N hydrochloric acid and extracted with ethyl acetate. The organic phase was washed with water and brine, and dried over anhydrous magnesium sulfate, filtered and evaporated in vacuo to afford the title product as a greenish-yellow solid (0.16 g, 84%).

$^1$H NMR (300 MHz, CDCl$_3$): δ 7.76 (d, 1H, J=2.1 Hz), 7.59 (d, 1H, J=2.1 Hz), 7.50 (d, 2H, J=8.1 Hz), 7.28 (d, 2H, J=2.1 Hz), 4.02 (s, 2H), 3.67 (s, 2H), 1.89 (s, 2H), 1.41 (s, 6H), 1.39 (s, 6H), 1.06 (s, 9H).

6-Bromo-2,2,4,4-tetramethylchroman-8-carboxylic acid tert-butyl ester (Intermediate 50)

A solution of 6-bromo-2,2,4,4-tetramethylchroman-8-carboxylic acid (Intermediate 41, 0.3 g, 0.96 mmol) and triethyl amine (0.1 g, 0.96 mmol) in anhydrous tetrahydrofuran (3 mL) was treated with 2,4,6-trichlorobenzoyl chloride (0.23 g, 0.96 mmol) and the reaction mixture was allowed to stir for 20 minutes. The precipitated solid was filtered off and the filtrate was evaporated in vacuo to afford a residue that was dissolved in benzene (3 mL) under argon and treated with 4-(dimethylamino)pyridine (0.47 g, 3.84 mmol) and 2-methyl-2-propanol (0.14 g, 1.92 mmol). After 18 h, the reaction mixture was diluted with ethyl acetate and washed with 2N hydrochloric acid, 2N sodium hydroxide and brine, dried over anhydrous magnesium sulfate, filtered and evaporated in vacuo to afford a residue that was subjected to flash column chromatography over silica gel (230–400 mesh) using 10% ethyl acetate in hexane as the eluent to afford the title product as a white solid (0.14 g, 40%).

$^1$H NMR (300 MHz, CDCl$_3$): δ 7.54 (d, 1H, J=2.4 Hz), 7.43 (d, 1H, J=2.4 Hz), 1.84 (s, 2H), 1.58 (s, 9H), 1.37 (s, 6H), 1.33 (s, 6H).

2,2,4,4-Tetramethyl-6-trimethylsilanylethynylchroman-8-carboxylic acid tert-butyl ester (Intermediate 51)

Following General Procedure D and using 6-bromo-2,2,4,4-tetramethylchroman-8-carboxylic acid tert-butyl ester (Intermediate 50, 0.195 g, 0.53 mmol), triethyl amine (2 mL), copper(I)iodide (0.040 g, 0.2 mmol), trimethylsilyl acetylene (0.3 mL, 2.1 mmol) and dichlorobis(triphenylphosphine)palladium(II) (0.09 g, 0.13 mmol) followed by flash column chromatography over silica gel (230–400 mesh) using 10% ethyl acetate in hexane as the eluent, the title compound (0.064 g, 32%) was obtained as a brown oil.

$^1$H NMR (300 MHz, CDCl$_3$): δ 7.57 (d, 1H, J=2.1 Hz), 7.46 (d, 1H, J=2.1 Hz), 1.84 (s, 2H), 1.57 (s, 9H), 1.37 (s, 6H), 1.34 (s, 6H), 0.045 (s, 9H).

6-Ethynyl-2,2,4,4-tetramethylchroman-8-carboxylic acid tert-butyl-ester (Intermediate 52)

A solution of 2,2,4,4-tetramethyl-6-trimethylsilanylethynylchroman-8-carboxylic acid tert-butyl ester (Intermediate 51, 0.064 g, 0.17 mmol) in methanol (5 mL) was treated with potassium carbonate (0.23 g, 1.7 mmol) and the resulting reaction mixture was stirred at ambient temperature for 30 minutes. The solvent was evaporated in vacuo, the residue was diluted with water and extracted with ethyl acetate. The organic phase was washed with brine, dried over anhydrous magnesium sulfate, filtered and evaporated in vacuo to afford the title compound as a brown oil (0.051 g, 97%).

$^1$H NMR (300 MHz, CDCl$_3$): δ 7.52 (d, 1H, J=2.1 Hz), 7.42 (d, 1H, J=1.5 Hz), 2.93 (s, 1H), 1.79 (s, 2H), 1.51 (s, 9H), 1.31 (s, 6H), 1.27 (s, 6H).

6-(4-Methoxycarbonylmethyl-phenylethynyl)-2,2,4,4-tetramethyl-chroman-8-carboxylic acid tert-butyl ester (Intermediate 53)

Following General Procedure B and using 6-ethynyl-2,2,4,4-tetramethylchroman-8-carboxylic acid tert-butyl ester (Intermediate 52, 0.051 g, 0.16 mmol), 4-iodo phenyl acetic acid methyl ester (0.053 g, 0.19 mmol), triethyl amine (3 mL), copper(I)iodide (0.02 g, 0.1 mmol) and dichlorobis(triphenylphosphine)palladium(II) (0.03 g, 0.043 mmol) followed by flash column chromatography over silica gel (230–400 mesh) using 20% ethyl acetate in hexane as the eluent, the title compound was obtained as a yellow oil (0.014 g, 19%).

$^1$H NMR (300 MHz, CDCl$_3$): δ 7.63 (d, 1H, J=2.1 Hz), 7.53 (d, 1H, J=2.1 Hz), 7.48 (d, 2H, J=8.2 Hz), 7.26 (d, 2H, J=8.2 Hz), 3.72 (s, 3H), 3.65 (s, 2H), 1.88 (s, 2H), 1.60 (s, 9H), 1.40 (s, 6H), 1.38 (s, 6H).

6-(4-Carboxymethyl-phenylethynyl)-2,2,4,4-tetramethyl-chroman-8-carboxylic acid tert-butyl ester (Compound 20)

A solution of 6-(4-methoxycarbonylmethyl-phenylethynyl)-2,2,4,4-tetramethyl-chroman-8-carboxylic-acid tert-butyl ester (Intermediate 53, 0.014 g, 0.03 mmol) in ethanol (0.3 mL), tetrahydrofuran (0.3 mL) and water (0.3 mL) was treated with 1N lithium hydroxide (0.12 mL, 0.12 mmol) and the resulting reaction mixture was stirred at ambient temperature for 3 h. The reaction mixture was neutralized with 2N hydrochloric acid and extracted with ethyl acetate. The organic phase was washed with water and brine, and dried over anhydrous magnesium sulfate, filtered and evaporated in vacuo to afford the title product as a yellow oil (0.012 g, 88%).

$^1$H NMR (300 MHz, CDCl$_3$): δ 7.63 (d, 1H, J=2.1 Hz), 7.52 (d, 1H, J=2.1 Hz), 7.47 (d, 2H, J=8.2 Hz), 7.26 (d, 2H, J=2.1 Hz), 3.67 (s, 2H), 1.87 (s, 2H), 1.59 (s, 9H), 1.39 (s, 6H), 1.36 (s, 6H).

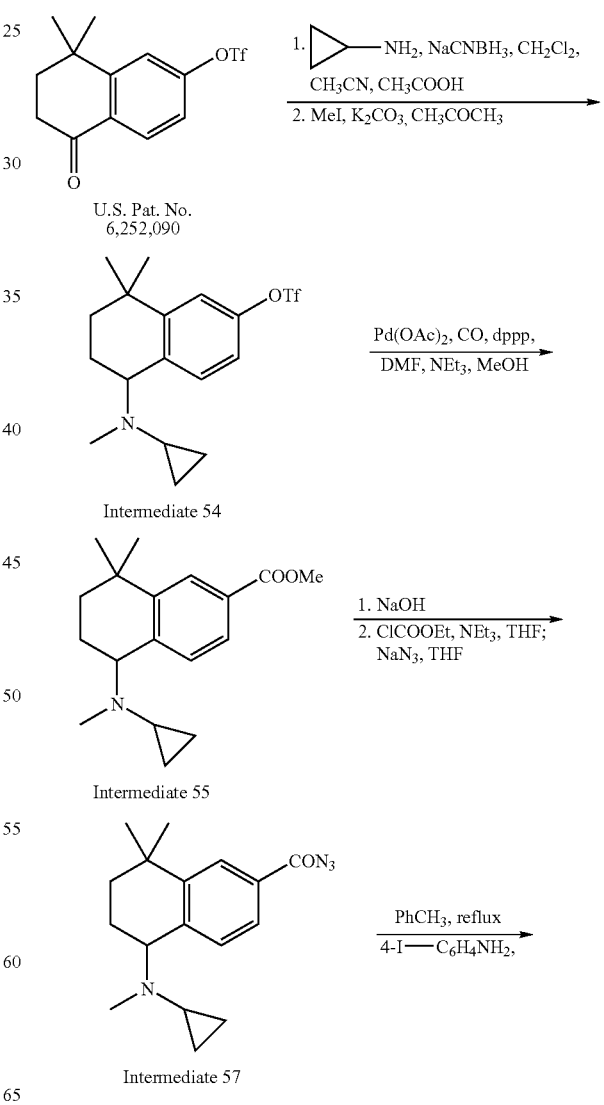

Reaction Scheme 11

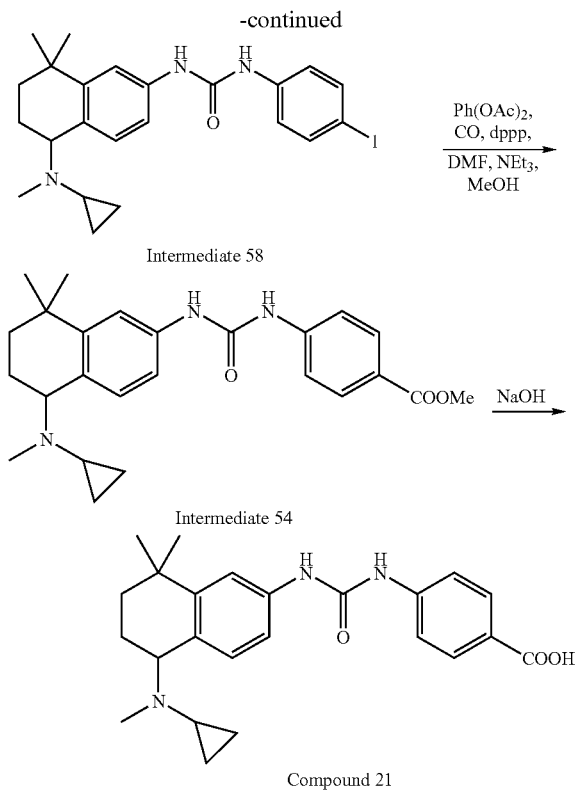

Trifluoro-methanesulfonic acid 5-(cyclopropyl-methyl-amino)-8,8-dimethyl-5,6,7,8-tetrahydro-naphthalen-2-yl ester (Intermediate 54)

A solution of 4,4-dimethyl-6-trifluoromethylsulfonyloxy-1,2,3,4-tetrahydronaphthalene-1-one (U.S. Pat. No. 6,252,090, 0.85 g, 2.64 mmol) in dichloromethane (6 mL) and acetonitrile (3 mL) was treated with cyclopropyl amine (3 mL, 43.4 mmol). After 5 minutes, acetic acid (3 mL) was added followed by sodium cyanoborohydride (0.66 g, 10.55 mmol). The reaction was stirred overnight at ambient temperature. It was then diluted with water and saturated aqueous sodium carbonate solution and extracted with ethyl acetate. The combined organic extract was washed with water and brine, dried over anhydrous sodium sulfate, filtered and evaporated in vacuo to an oil. The oil was dissolved in acetone (20 mL) and treated with potassium carbonate (1.08 g, 7.8 mmol) and methyl iodide (1.6 mL, 26 mmol). The resulting reaction mixture was stirred at ambient temperature overnight. The solids were filtered off, the filtrate was evaporated in vacuo and the residue was subjected to flash column chromatography over silica gel (230–400 mesh) to afford the title compound (0.85 g, 87%) as a colorless oil.

$^1$H NMR (300 MHz, CDCl$_3$): δ 7.61 (d, 1H, J=9.0 Hz), 7.11 (d, 1H, J=2.4 Hz), 6.97 (dd, 1H, J=2.4, 9.0 Hz), 3.92 (t, 1H, J=8.4 Hz), 2.14–2.10 (m, 1H), 2.12 (s, 3H), 1.96–1.89 (m, 2H), 1.79–1.57 (m, 2H), 1.29 (s, 3H), 1.2–5 (s, 3H), 0.52–0.36 (m, 4H).

General Procedure E: 5-(Cyclopropyl-methyl-amino)-8,8-dimethyl-5,6,7,8-tetrahydro-naphthalene-2-carboxylic acid methyl ester (Intermediate 55)

A solution of trifluoro-methanesulfonic acid 5-(cyclopropyl-methyl-amino)-8,8-dimethyl-5,6,7,8-tetrahydro-naphthalen-2-yl ester (Intermediate 54, 0.37 g, 0.98 mmol), palladium acetate (0.05 g, 0.22 mmol) and 1,3-bis(diphenylphosphino)propane (0.096 g, 0.23 mmol) in a mixture of dimethylformamide (4 mL), methanol (4 mL) and triethyl amine (2 mL) was heated at 70° C. under an atmosphere of carbon monoxide overnight. The volatiles were distilled of in vacuo and the residue was diluted with water and extracted with diethyl ether (×3). The combined organic extract was dried over anhydrous magnesium sulfate, filtered a evaporated in vacuo to an oil which was subjected to flash column chromatography over silica gel (230–400 mesh) using 2–5% ethyl acetate in hexane as the eluent, to afford the title compound (0.236 g, 85%).

$^1$H NMR (300 MHz, CDCl$_3$): δ 7.96 (d, 1H, J=1.8 Hz), 7.73 (dd, 1H, J=1.8, 8.1 Hz), 7.59 (d, 1H, J=8.1 Hz), 3.96 (t, 1H, J=7.5 Hz), 3.89 (s, 3H), 2.17–2.10 (m, 1H), 2.12 (s, 3H), 1.98–1.83 (m, 2H), 1.82–1.60 (m, 2H), 1.34 (s, 3H), 1.28 (s, 3H), 0.54–0.39 (m, 4H).

5-(Cyclopropyl-methyl-amino)-8,8-dimethyl-5,6,7,8-tetrahydronaphthalene-2-carboxylic acid (Intermediate 56)

A solution of 5-(cyclopropyl-methyl-amino)-8,8-dimethyl-5,6,7,8-tetrahydro-naphthalene-2-carboxylic acid methyl ester (Intermediate 55, 0.236 g, 0.83 mmol) in methanol (4 mL) and tetrahydrofuran (4 mL) was treated with a 2M solution of sodium hydroxide (4 mL, 8 mmol) and the resulting reaction mixture was stirred at ambient temperature overnight. The volatiles were evaporated in vacuo to a residue that was neutralized with saturated aqueous ammonium chloride solution and extracted with ethyl acetate. The organic phase was dried over anhydrous magnesium sulfate, filtered and evaporated in vacuo to afford the title compound as a solid (0.22 g, 100%).

$^1$H NMR (300 MHz, CDCl$_3$): δ 7.98 (d, 1H, J=1.8 Hz), 7.72 (dd, 1H, J=1.8, 8.2 Hz), 7.51 (d, 1H, J=8.2 Hz), 3.93 (t, 1H, J=7.8 Hz), 2.15–2.04 (m, 1H), 2.10 (s, 3H); 1.94–1.85 (m, 2H), 1.79–1.62 (m, 2H), 1.27 (s, 3H), 1.22 (s, 3H), 0.52–0.40 (m, 4H).

5-(Cyclopropyl-methyl-amino)-8,8-dimethyl-5,6,7,8-tetrahydronaphthalene-2-carboxylic acid azide (Intermediate 57)

A stirred, cooled (ice bath) solution of 5-(cyclopropyl-methyl-amino)-8,8-dimethyl-5,6,7,8-tetrahydronaphthalene-2 carboxylic acid (Intermediate 56, 0.22 g, 0.83 mmol) in anhydrous tetrahydrofuran (4 mL) was treated with triethyl amine (0.16 mL, 1.1 mmol) followed by ethyl chloroformate (0.10 mL, 1.08 mmol). After 5 h, sodium azide (0.081 g, 1.24 mmol) was added and the reaction mixture was allowed to warm to ambient temperature and stirred overnight. The reaction mixture was diluted with water and extracted with ethyl acetate. The organic phase was washed with water and brine, dried over anhydrous sodium sulfate, filtered and evaporated in vacuo to afford the title product that was used as such for the next reaction (0.24 g, 98%).

1-[5-(Cyclopropyl-methyl-amino)-8,8-dimethyl-5,6,7,8-tetrahydro-naphthalen-2-yl]-3-(4-iodo-phenyl)-urea (Intermediate 58)

A solution of 5-(cyclopropyl-methyl-amino)-8,8-dimethyl-5,6,7,8-tetrahydronaphthalene-2-carboxylic acid azide (Intermediate 57, 0.12 g, 0.4 mmol) in anhydrous toluene (14 mL) was refluxed under argon for 2 h. 4-iodoaniline (0.114 g, 0.52 mmol) was added and the solution was cooled to ambient temperature and stirred overnight. The volatiles were evaporated in vacuo and the residue was subjected to flash column chromatography over silica gel (230–400 mesh) using 20–25% ethyl acetate in hexane as the eluent to afford the title compound (0.13 g, 67%).

$^1$H NMR (300 MHz, CDCl$_3$): δ 7.58 (d, 2H, J=8.7 Hz), 7.51 (d, 1H, J=8.1 Hz), 7.23 (d, 1H, J=1.8 Hz), 7.14 (d, 2H, J=8.7 Hz), 6.99 (dd, 1H, J=1.8, 8.1 Hz), 6.99 (br s, 1H), 6.57 (br s, 1H), 3.92 (t, 1H, J=7.2 Hz), 2.13–2.05 (m, 1H), 2.13 (s, 3H), 1.93–1.88 (m, 2H), 1.78–1.62 (m, 2H), 1.29 (s, 3H), 1.26 (s, 3H), 0.52–0.39 (m, 4H).

4-{3-[5-(Cyclopropyl-methyl-amino)-8,8-dimethyl-5,6,7,8-tetrahydro-naphthalen-2-yl]-ureido}-benzoic acid methyl ester (Intermediate 59)

Following General Procedure E and using 1-[5-(cyclopropyl-methyl-amino)-8,8-dimethyl-5,6,7,8-tetrahydro-naphthalen-2-yl]-3-(4-iodo-phenyl)-urea (Intermediate 58, 0.13 g, 0.267 mmol), palladium acetate (0.02 g, 0.09 mmol), 1,3-bis(diphenylphosphino)propane (0.042 g, 0.101 mmol), N,N-dimethylformamide (3 mL), methanol (3 mL) and triethyl amine (1 mL) followed by flash column chromatography over silica gel (230–400 mesh) using 30–40% ethyl acetate in hexane as the eluent the title compound was obtained (0.045 g, 40%).

$^1$H NMR (300 MHz, CDCl$_3$): δ 7.91 (d, 2H, J=8.4 Hz), 7.51 (d, 1H, J=8.1 Hz), 7.42 (s, 1H), 7.37 (d, 2H, J=8.4 Hz), 7.26 (d, 1H, J=1.8 Hz), 7.09 (s, 1H), 6.97 (dd, 1H, J=2.1, 8.1 Hz), 3.89 (s, 3H), 3.90–3.84 (m, 1H), 2.11-2.06 (m, 1H), 2.09 (s, 3H), 1.89–1.80 (m, 2H), 1.80–1.64 (m, 2H), 1.24 (s, 3H), 1.21 (s, 3H), 0.50–0.36 (m, 4H).

4-{3-[5-(Cyclopropyl-methyl-amino)-8,8-dimethyl-5,6,7,8-tetrahydro-naphthalen-2-yl]-ureido}-benzoic acid (Compound 21)

A solution of 4-{3-[5-(cyclopropyl-methyl-amino)-8,8-dimethyl-5,6,7,8-tetrahydro-naphthalen-2-yl]-ureido}-benzoic acid methyl ester (Intermediate 59, 0.045 g, 0.106 mmol) in methanol (2 mL) and tetrahydrofuran (3 mL) was treated with a 2M solution of sodium hydroxide (1 mL, 2 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous magnesium sulfate, filtered and evaporated in vacuo to afford a solid that was recrystallized from hot acetonitrile to afford the title product as a white solid (0.012 g, 28%).

$^1$H NMR (300 MHz, CD$_3$OD): δ 7.95 (d, 2H, J=9.0 Hz), 7.53 (d, 2H, J=9.0 Hz), 7.46 (d, 1H, J=2.1 Hz), 7.40 (d, 1H, J=8.7 Hz), 7.09 (s, 1H), 7.19 (dd, 1H, J=2.1, 8.7 Hz), 4.06 (t, 1H, J=6.0 Hz)), 2.30–2.25 (m, 1H), 2.28 (s, 3H), 2.05–1.98 (m, 2H), 1.82–1.68 (m, 2H), 1.32 (s, 3H), 1.30 (s, 3H), 0.60–0.48 (m, 4H).

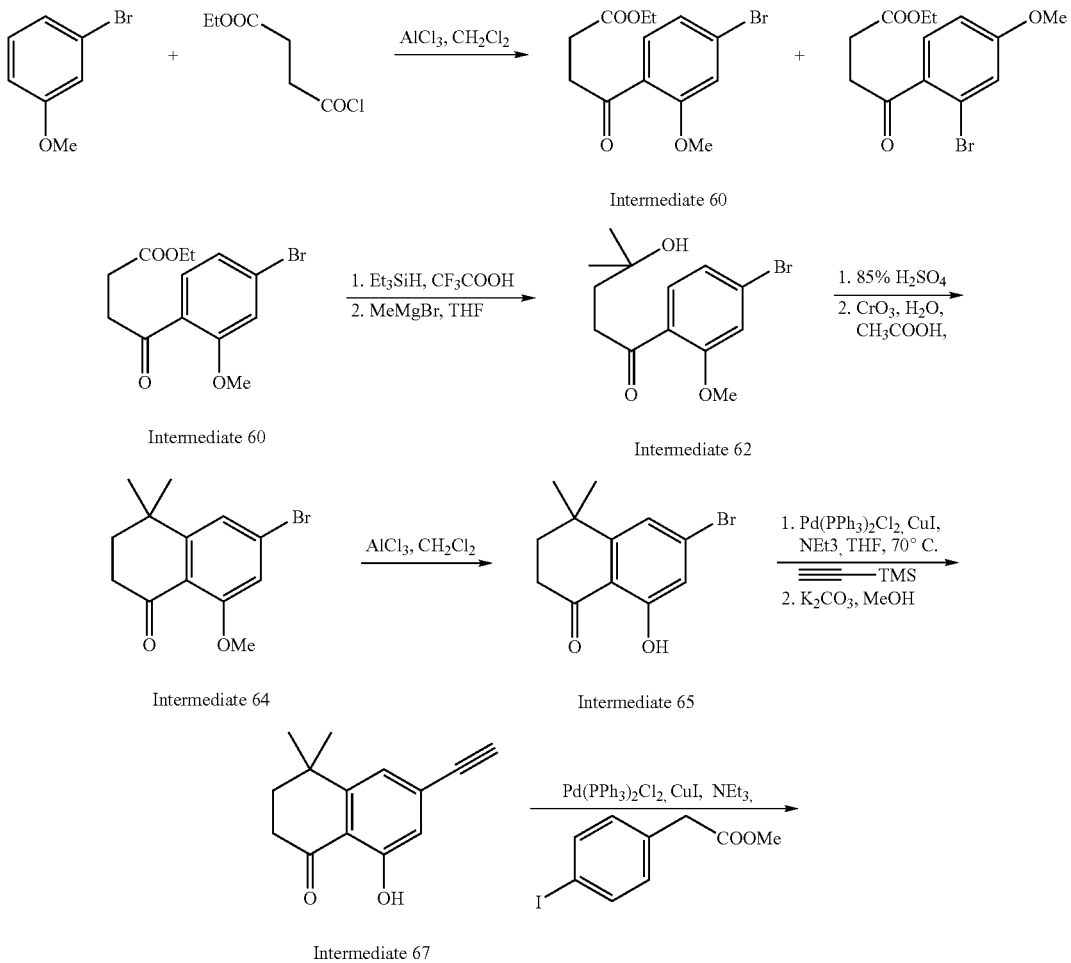

Reaction Scheme 12

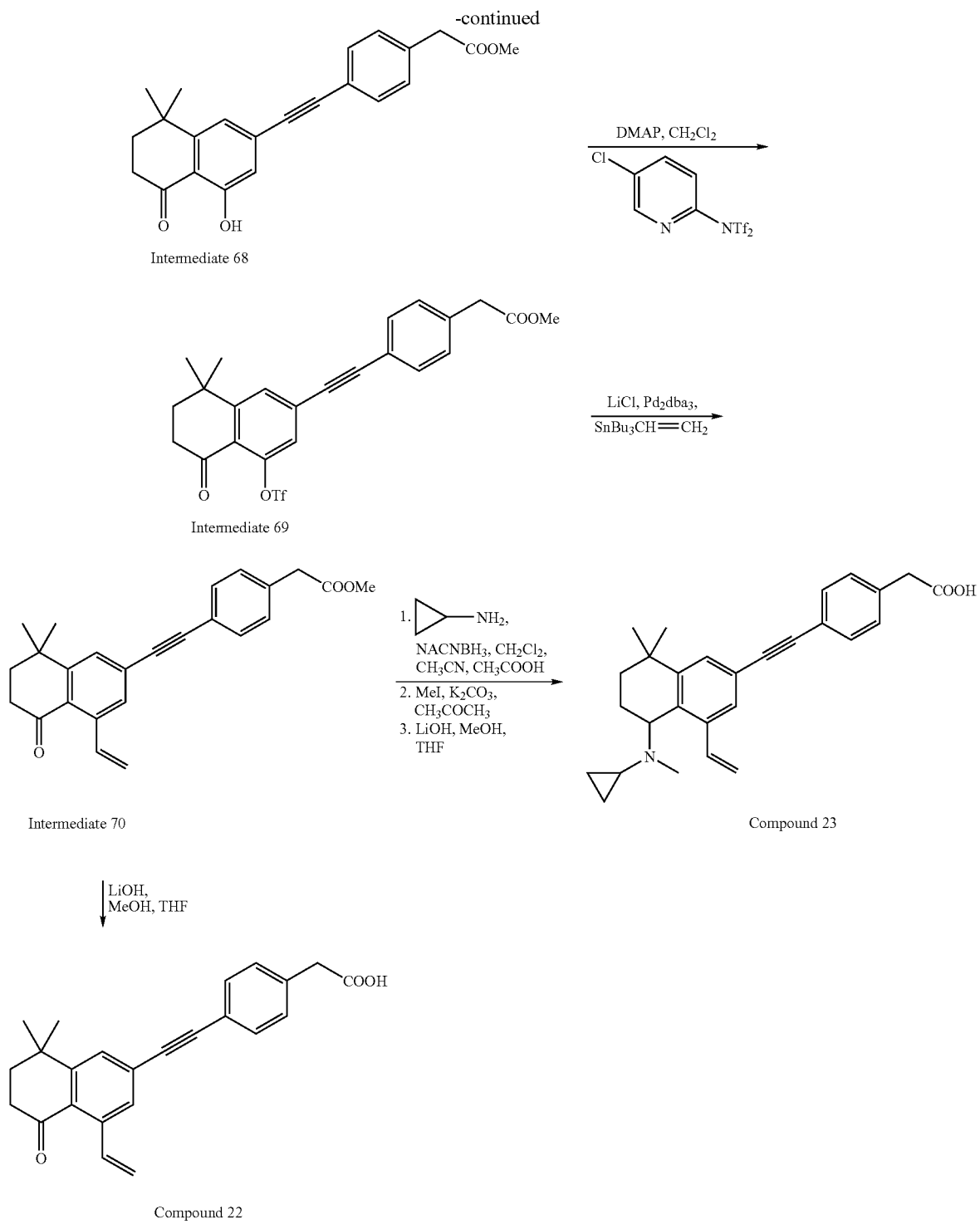

4-(4-Bromo-2-methoxy-phenyl)-4-oxo-butyric acid ethyl ester (Intermediate 60)

A stirred, cooled (−30° C.) solution of 3-bromo anisole (Aldrich, 18.7 g, 100 mmol) and ethyl succinyl chloride (21 mL, 150 mmol) in anhydrous dichloromethane (200 mL) was treated with aluminum chloride (26.6 g, 200 mmol) and the reaction-mixture was allowed to warm to ambient temperature and stirred overnight. The reaction mixture was poured into water and extracted with dichloromethane (×2). The combined organic phase was washed with brine, dried over anhydrous sodium sulfate, filtered and evaporated in vacuo to a brown oil. A solid separated out on standing. The supernatant liquid was decanted and the solid was washed with 1:3 dichloroinethane: hexane and dried to afford the title compound. The combined mother liquor and washings were evaporated to a brown oil that was subjected to flash column chromatography over silica gel (230–400 mesh) using 15% ethyl acetate in hexane as the eluent to afford the title compound (overall 12 g, 38%), and its isomer 4-(2-romo-4-methoxy-phenyl)-4-oxo-butyric acid ethyl ester (11.4 g, 36%) and a 1:1 mixture of both (2 g, 6.3%).

$^1$H NMR (300 MHz, CDCl$_3$): δ 7.56 (d, 1H, J=8.7 Hz), 7.07–7.03 (m, 2H), 4.07 (q, 2H, J=7.2 Hz), 3.84 (s, 3H), 3.20 (t, 2H, J=6.3 Hz), 2.61 (t, 2H, J=6.3 Hz), 1.19 (t, 3H, J=7.2 Hz).

4-(4-Bromo-2-methoxy-phenyl)-butyric acid ethyl ester (Intermediate 61)

A solution of 4-(4-bromo-2-methoxy-phenyl)-4-oxo-butyric acid ethyl ester (Intermediate 60, 14.73 g, 46.8 mmol) in trifluoroacetic acid (72 mL, 935 mmol) was treated with triethylsilane (30 mL, 187 mmol) and the resulting reaction mixture was heated at 55° C. for 4 h. The reaction mixture was then cooled to ambient temperature, neutralized with solid sodium bicarbonate, diluted with water and extracted with diethyl ether. The organic phase was washed with water and brine, dried over anhydrous magnesium sulfate, filtered and evaporated in vacuo to afford a residue that was subjected to flash column chromatography over silica gel (230–400 mesh) using 8% ethyl acetate in hexane as the eluent to afford the title compound (7.4 g, 53%) as a colorless oil.

$^1$H NMR (300 MHz, CDCl$_3$): δ 7.02–6.94 (m, 3H), 4.11 (q, 2H, J=7.2 Hz), 3.79 (s, 3H), 2.60 (t, 2H, J=7.2 Hz), 2.29 (t, 2H, J=7.2 Hz), 1.88 (quintet, 2H, J=7.2 Hz), 1.25 (t, 3H, J=7.2 Hz).

5-(4-Bromo-2-methoxy-phenyl)-2-methyl-pentan-2-ol (Intermediate 62)

A stirred, cooled (−10° C.) solution of 4-(4-bromo-2-methoxy-phenyl)-butyric acid ethyl ester (Intermediate 61, 7.4 g, 24.6 mmol) in anhydrous tetrahydrofuran (50 mL) was treated with a 3M solution of methyl magnesium bromide (20.5 mL, 61.5 mmol) and the resulting reaction mixture was allowed to warm to ambient temperature over 3 h. It was quenched with saturated, aqueous ammonium chloride solution, diluted with water and extracted with diethyl ether. The organic phase was washed with water and brine, dried over anhydrous magnesium sulfate, filtered and evaporated in vacuo to afford the title product (7.3 g, 100%).

$^1$H NMR (300 MHz, CDCl$_3$): δ 6.92–6.87 (m, 3H), 3.71 (s, 3H), 2.48 (t, 2H, J=7.2 Hz), 1.55–1.38 (m, 4H), 1.11 (s, 6H).

7-Bromo-5-methoxy-1,1-dimethyl-1,2,3,4-tetrahydro-naphthalene (Intermediate 63)

5-(4-Bromo-2-methoxy-phenyl)-2-methyl-pentan-2-ol (Intermediate 62, 7.3 g, 24.6 mmol) was treated with 85% sulfuric acid (25 mL) at ambient temperature. After 30 minutes, the reaction mixture Was diluted with cold water and extracted with diethyl ether. The organic phase was washed with water and brine, dried over anhydrous magnesium sulfate, filtered and evaporated in vacuo to afford the title product (5.6 g, 83%).

$^1$H NMR (300 MHz, CDCl$_3$): δ 7.01 (d, 1H, J=1.8 Hz), 6.68 (d, 1H, J=1.8 Hz), 3.71 (s, 3H), 2.49 (t, 2H, J=6.3 Hz), 1.71–1.65 (m, 2H), 1.55–1.51 (in, 2H), 1.18 (s, 6H).

6-Bromo-8-methoxy-4,4-dimethyl-3,4-dihydro-2H-naphthalen-1-one (Intermediate 64)

A solution of 7-bromo-5-methoxy-1,1-dimethyl-1,2,3,4-tetrahydro-naphthalene (Intermediate 63, 5.6 g, 20.81 mmol) in glacial acetic acid (20 mL) was cooled to 0° C. and treated with a solution of chromium trioxide (6.16 g, 61.6 mmol) in acetic acid and water (25 mL). The reaction mixture was then allowed to warm to ambient temperature and stirred for 48 h. It was diluted with water and extracted with diethyl ether (×2). The combined organic phase was washed with water (×3), saturated aqueous sodium bicarbonate (×1) and brine (×1), dried over anhydrous magnesium sulfate, filtered and evaporated in vacuo to afford an oil. Flash column chromatography over silica gel (230–400 mesh) using 10–20–100% ethyl acetate in hexane as the eluent afforded the title compound (2 g, 33%) as a yellow oil and recovered starting material (2.2 g, 39%).

$^1$H NMR (300 MHz, CDCl$_3$): δ 7.12 (d, 1H, J=1.8 Hz), 6.97 (d, 1H, J=1.8 Hz), 3.87 (s, 3H), 2.66 (t, 2H, J=6.6 Hz), 1.92 (t, 2H, J=6.6 Hz), 1.33 (s, 6H).

6-Bromo-8-hydroxy-4,4-dimethyl-3,4-dihydro-2H-naphthalen-1-one (Intermediate 65)

A stirred, cooled (ice bath) solution of 6-bromo-8-methoxy-4,4-dimethyl-3,4-dihydro-2H-naphthalen-1-one (Intermediate-64, 0.24 g, 0.83 mmol) in anhydrous-dichloromethane (4 mL) was treated with aluminum chloride (0.4 g, 3 mmol). The reaction mixture was allowed to warm to ambient temperature and stirred overnight. It was poured into water and extracted with dichloromethane and ethyl acetate. The combined organic phase was dried over anhydrous magnesium sulfate, filtered and evaporated in vacuo to a brown oil that was subjected to flash column chromatography over silica gel (230–400 mesh) using 10% ethyl acetate in hexane as the eluent to afford the title product as a pale yellow solid (0.13 g, 56%).

$^1$H NMR (300 MHz, CDCl$_3$): δ 12.85 (s, 1H), 7.00 (d, 1H, J=1.5 Hz), 6.98 (d, 1H, J=1.5 Hz), 2.74 (t, 2H, J=6.9 Hz), 1.96 (t, 2H, J=6.9 Hz), 1.36 (s, 6H).

8-Hydroxy-4,4-dimethyl-6-trimethylsilanylethynyl-3,4-dihydro-2H-naphthalen-1-one (Intermediate 66)

Following General Procedure D and using 6-bromo-8-hydroxy-4,4-dimethyl-3,4-dihydro-2H-naphthalen-1-one (Intermediate 65, 1.56 g, 5.8 mmol), triethyl amine (20 mL), copper(I)iodide (0.088 g, 0.46 mmol), trimethylsilyl acetylene (3 mL, 21.22 mmol) and dichlorobis(triphenylphosphine)palladium(II) (0.325 g, 0.46 mmol) followed by flash column chromatography over silica gel (230–400 mesh) using hexane to 2–5% ethyl acetate in hexane as the eluent, the title compound (1.67 g, 100%) was obtained as an orange solid.

$^1$H NMR (300 MHz, CDCl$_3$): δ 12.72 (s, 1H), 6.93 (d, 1H, J=1.5 Hz), 6.88 (d, 1H, J=1.5 Hz), 2.74 (t, 2H, J=6.6 Hz), 1.96 (t, 2H, J=6.6 Hz), 1.36 (s, 6H), 0.27 (s, 9H).

6-Ethynyl-8-hydroxy-4,4-dimethyl-3,4-dihydro-2H-naphthalen-1-one (Intermediate 67)

A solution of 8-hydroxy-4,4-dimethyl-6-trimethylsilanyl-ethynyl-3,4-dihydro-2H-naphthalen-1-one (Intermediate 66, 2.2 g, 7.4 mmol) in methanol (20 mL) was treated with potassium carbonate (2.04 g, 14.8 mmol) and the resulting reaction mixture was stirred at ambient temperature for 5 h. The solvent was evaporated in vacuo, the residue was diluted with water and extracted with diethyl ether. The organic phase was dried over anhydrous magnesium sulfate, filtered and evaporated in vacuo to afford the title compound as an oil (1.58 g,~100%).

$^1$H NMR (300 MHz, CDCl$_3$): δ 12.76 (s, 1H), 6.97 (d, 1H J=1.5 Hz), 6.88 (d, 1H, J=1.5 Hz), 3.28 (s, 1H), 2.73 (t, 2H, J=6.6 Hz), 1.94 (t, 2H, J=6.6 Hz), 1.34 (s, 6H).

{4-[8,8-Dimethyl-4-hydroxy-5-oxo-5,6,7,8-tetrahydro-naphthalen-2-ylethynyl]-phenyl}-acetic acid methyl ester (Intermediate 68)

Following General Procedure B and using 6-ethynyl-8-hydroxy-4,4-dimethyl-3,4-dihydro-2H-naphthalen-1-one (Intermediate 67, 1.58 g, 7.4 mmol), 4-iodo phenyl acetic acid methyl ester (2.2 g, 7.94 mmol), triethyl amine (12 mL), copper(I)iodide (0.38 g, 1.99 mmol) and dichlorobis(triphenylphosphine)palladium(II) (1.2 g, 1.71 mmol) followed by flash column chromatography over silica gel (230–400 mesh) using 16% ethyl acetate in hexane as the eluent, the title compound was obtained as a yellow oil (2.1 g, 78%).

$^1$H NMR (300 MHz, CDCl$_3$): δ 12.79 (s, 1H), 7.52 (d, 2H, J=8.7 Hz), 7.29 (d, 2H, J=8.7 Hz), 7.01 (d, 1H, J=1.5 Hz), 6.94 (d, 1H, J=1.5 Hz), 3.71 (m, 3H), 3.65 (s, 2H), 2.76 (t, 2H, J=6.6 Hz), 1.97 (t, 2H, J=6.6 Hz), 1.38 (s, 6H).

{4-[8,8-Dimethyl-5-oxo-4-trifluoromethanesulfonyloxy-5,6,7,8-tetrahydro-naphthalen-2-ylethynyl]-phenyl}-acetic acid methyl ester (Intermediate 69)

A stirred, cooled (0° C.) solution of {4-[8,8-dimethyl-4-hydroxy-5-oxo-5,6,7,8-tetrahydro-naphthalen-2-ylethynyl]-phenyl}-acetic acid methyl ester (Intermediate 68, 2.1 g, 5.8 mmol) in anhydrous dichloromethane (20 mL) was treated with 4-(dimethylamino)pyridine (1.21 g, 9.9 mmol) followed by N-phenyltrifluoromethanesulfonimide (2.2 g, 6.16 mmol). After stirring at ambient temperature overnight, the reaction mixture was subjected to flash column chromatography over silica gel (230–400 mesh) using 20% ethyl acetate in hexane as the eluent to afford the title compound (2.6 g, 91%).

$^1$H NMR (300 MHz, CDCl$_3$): δ 7.57 (d, 1H, J=1.2 Hz), 7.49 (d, 2H, J=8.4 Hz), 7.27 (d, 2H, J=8.4 Hz), 7.19 (d, 1H, J=1.2 Hz), 3.66 (in, 3H), 3.62 (s, 2H), 2.72 (t, 2H, J=6.9 Hz), 1.99 (t, 2H, J=6.9 Hz), 1.38 (s, 6H).

[4-(8,8-Dimethyl-5-oxo-4-vinyl-5,6,78-tetrahydro-naphthalen-2-ylethynyl)-phenyl]-acetic acid methyl ester (Intermediate 70)

A solution of {4-[8,8-dimethyl-5-oxo-4-trifluoromethanesulfonyloxy-5,6,7,8-tetrahydro-naphthalen-2-ylethynyl]-phenyl}-acetic acid methyl ester (Intermediate 69, 0.233 g, 0.47 mmol) in anhydrous 1-methyl 2-pyrrolidinone (3 mL) was sparged with argon, and treated with lithium chloride (0.061 g, 1.45 mmol), tri-2-furylphosphine (0.0071 g, 0.031 mmol) and tris(dibenzylideneacetone)dipalladium(0) (0.007 g, 0.015 mmol). After 5 minutes, tributyl(vinyl)tin (0.175 g, 0.55 mmol) was added and the resulting reaction mixture was stirred at ambient temperature for 2.5 h. The reaction mixture was diluted with water and extracted with ethyl acetate. The organic phase was washed with brine and water, dried over anhydrous sodium sulfate, filtered and evaporated in vacuo to a residue that was subjected to flash column chromatography over silica gel (230–400 mesh) using 10–15% ethyl acetate in hexane as the eluent to afford the title compound (0.15 g, 86%) as a white solid.

$^1$H NMR (300 MHz, CDCl$_3$): δ 7.53 (d, 2H, J=7.8 Hz), 7.51 (d, 1H, J=1.8 Hz), 7.50 (d, 1H, J=1.8 Hz), 7.43 (dd, 1H, J=10.5, 17.1 Hz), 7.29 (d, 2H, J=7.8 Hz), 5.57 (dd, 1H, J=1.5, 17.1 Hz), 5.33 (dd, 1H, J=1.5, 10.5 Hz), 3.71 (s, 3H), 3.66 (s, 2H), 2.74 (t, 2H, J=6.9 Hz), 2.00 (t, 2H, J=6.9 Hz), 1.40 (s, 6H).

[4-(8,8-Dimethyl-5-oxo-4-vinyl-5,6,7,8-tetrahydro-naphthalen-2-ylethynyl)-phenyl]-acetic acid (Compound 22)

A solution of [4-(8,8-dimethyl-5-oxo-4-vinyl-5,6,7,8-tetrahydro-naphthalen-2-ylethynyl)-phenyl]-acetic acid methyl ester (Intermediate 70, 0.082 g, 0.22 mmol) in methanol (3 mL) and tetrahydrofuran (3 mL) was treated with a 2M solution of lithium hydroxide (1.5 mL, 3 mmol) and the resulting reaction mixture was stirred at ambient temperature for 1.5 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to afford the title product as a yellow solid (0.065 g, 82%).

$^1$H NMR (300 MHz, CDCl$_3$): δ 7.53 (d, 2H, J=8.1 Hz), 7.50 (s, 2H), 7.43 (dd, 1H, J=10.8, 17.4 Hz), 7.31 (d, 2H, J=8.1 Hz), 5.57 (dd, 1H, J=1.5, 17.4 Hz), 5.33 (dd, 1H, J=1.5, 10.8 Hz), 3.68 (s, 2H), 2.74 (t, 2H, J=6.3 Hz), 1.99 (t, 2H, J=6.3 Hz), 1.39 (s, 6H).

{4-[5-(Cyclopropyl-methyl-amino)-8,8-dimethyl-4-vinyl-5,6,7,8-tetrahydro-naphthalen-2-ylethynyl]-phenyl}-acetic acid Methyl ester (Intermediate 71)

A solution of [4-(8,8-dimethyl-5-oxo-4-vinyl-5,6,7,8-tetrahydro-naphthalen-2-ylethynyl)-phenyl]-acetic acid methyl ester (Intermediate 70, 0.205 g, 0.55 mmol) in dichloromethane (4 mL) and acetonitrile (2 mL) was treated with cyclopropyl amine (1 mL, 14.45 mmol). After 5 minutes, acetic acid (1 mL) was added followed by sodium cyanoborohydride (0.138 g, 2.2 mmol). The reaction mixture was stirred overnight at ambient temperature. It was then diluted with water and saturated aqueous sodium bicarbonate solution and extracted with ethyl acetate. The combined organic extract was dried over anhydrous sodium sulfate, filtered and evaporated in vacuo to an oil. The oil was dissolved in acetone (0 mL) and treated with potassium carbonate (0.227 g, 1.65 mmol) followed by methyl iodide (0.54 mL, 8.7 mmol) and the resulting reaction mixture was stirred overnight at ambient temperature. Diethyl ether was added to the reaction mixture and the precipitated solids were filtered off, the filtrate was evaporated in vacuo to a residue. Flash column chromatography over silica gel (230–400 mesh) using 4–5% ethyl acetate in hexane as the eluent afforded the title compound (0.14 g, 60%).

$^1$H NMR (300 MHz, CDCl$_3$): δ 7.50 (d, 2H, J=8.4 Hz), 7.47 (s, 1H), 7.45 (s, 1H), 7.26 (d, 2H, J=8.4 Hz), 7.13 (dd, 1H, J=10.8, 17.7 Hz), 5.47 (dd, 1H, J=1.5, 17.7 Hz), 5.11 (dd, 1H, J=1.5, 10.8 Hz), 4.04 (t, 1H, J=5.4 Hz), 3.69 (s, 3H), 3.63 (s, 2H), 2.18 (s, 3H), 2.18–2.14 (m, 1H), 2.02 (m, 1H), 1.90–1.75 (m, 2H), 1.58–1.51 (m, 1H), 1.35 (s, 3H), 1.24 (s, 3H), 0.39–0.31 (m, 3H), 0.21–0.17 (m, 1H).

{4-[5-(Cyclopropyl-methyl-amino)-8,8-dimethyl-4-vinyl-5,6,7,8-tetrahydro-naphthalen-2-ylethynyl]-phenyl}-acetic acid (Compound 23)

A solution of {4-[5-(cyclopropyl-methyl-amino)-8,8-dimethyl-4-vinyl-5,6,7,8-tetrahydro-naphthalen-2-ylethynyl]-phenyl}-acetic acid methyl ester (Intermediate 71, 0.14 g, 0.327 mmol) in methanol (3 mL) and tetrahydrofuran (3 mL) was treated with a 2M solution of lithium hydroxide (1.5 mL, 3 mmol) and the resulting reaction mixture was stirred at ambient temperature for 2 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to afford the title product as a white solid (0.135 g, 96%).

$^1$H NMR (300 MHz, CDCl$_3$): δ 9.99 (br s, 1H), 7.47 (d, 2H, J=8.1 Hz), 7.44 (s, 1H), 7.43 (s, 1H), 7.22 (d, 2H, J=8.1 Hz), 7.11 (dd, 1H, J=10.8, 17.1 Hz), 5.47 (dd, 1H, J=0.9, 17.1 Hz), 5.11 (dd, 1H, J=0.9, 10.8 Hz), 4.06 (t, 1H, J=6.0 Hz), 3.55 (s, 2H), 2.18 (s, 3H), 2.18–2.15 (m, 1H), 2.04 (m, 1H), 1.91–1.77 (m, 2H), 1.56–1.50 (m, 1H), 1.34 (s, 3H), 1.22 (s, 3H), 0.42–0.29 (m, 3H), 0.28–0.21 (m, 1H).

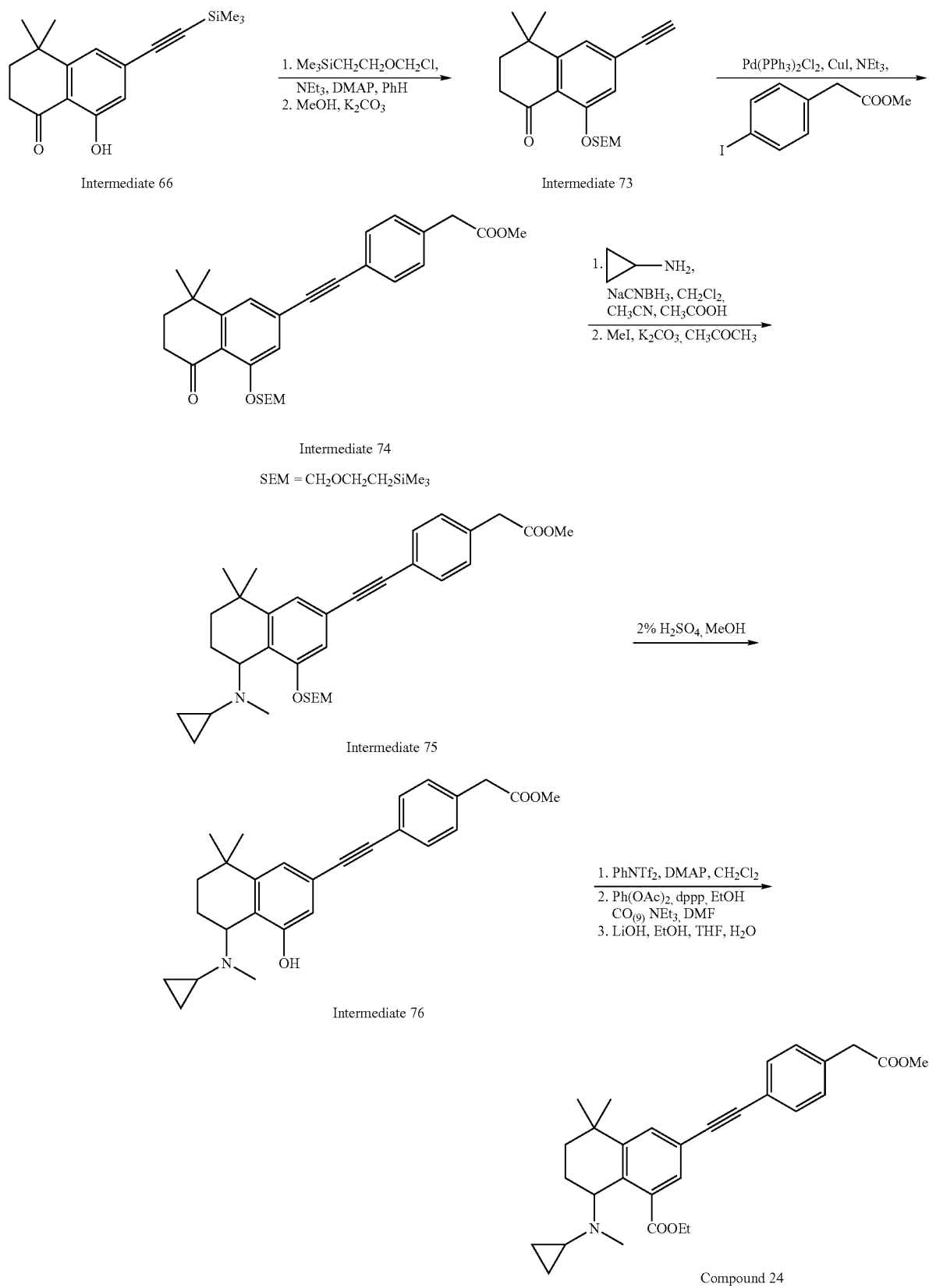
Reaction Scheme 13

4,4-Dimethyl-8-(2-timethylsilanyl-ethoxymethoxy)-6-trimethylsilanylethynyl-3,4-dihydro-2H-naphthalen-1-one (Intermediate 72)

A solution of 8-hydroxy-4,4-dimethyl-6-trimethylsilanyl-ethynyl-3,4-dihydro-2H-naphthalen-1-one (Intermediate 66, 1.67 g; 5.8 mmol) in anhydrous benzene was treated with triethyl amine (1.41 g, 11.6 mmol) and catalytic amount of 4-(dimethylamino)pyridine followed by 2-(trimethylsilyl)ethoxymethyl chloride (1.93 g, 11.6 mmol) and the resulting reaction mixture was refluxed for 3 days. It was cooled to ambient temperature, diluted with water and extracted with ethyl acetate. The organic phase was washed with water and brine, dried over anhydrous magnesium sulfate, filtered and evaporated in vacuo to an oil that was subjected to flash column chromatography over silica gel (230–400 mesh) using 2–6% ethyl acetate in hexane as the eluent to afford the title product as a yellow oil (1.58 g, 66%).

$^1$H NMR (300 MHz, CDCl$_3$): δ 7.16 (d, 1H, J=1.2 Hz), 7.12 (d, 1H, J=1.2 Hz), 5.28 (s, 2H), 3.81 (m, 2H), 2.68 (t, 2H, J=6.9 Hz), 1.94 (t, 2H, J=6.9 Hz), 1.34 (s, 6H), 0.96 (m, 2H), 0.27 (s, 9H), 0.00 (s, 9H).

6-Ethynyl-4,4-dimethyl-8-(2-trimethylsilanyl-ethoxymethoxy)-3,4-dihydro-2H-naphthalen-1-one (Intermediate 73)

A solution 4,4-dimethyl-8-(2-trimethylsilanyl-ethoxymethoxy)-6-trimethylsilanylethynyl-3,4-dihydro-2H-naphthalen-1-one (Intermediate 72, 1.58 g, 3.79 mmol) in methanol (20 mL) was treated with potassium carbonate (0.43 g, 3.11 mmol) and the resulting reaction mixture was stirred at ambient temperature overnight. The solvent was evaporated in vacuo, the residue was diluted with water and extracted with ethyl acetate. The organic phase was washed with brine, dried over anhydrous magnesium sulfate, filtered and evaporated in vacuo to afford the title compound (1.28 g, 98%).

$^1$H NMR (300 MHz, CDCl$_3$): δ 7.19 (d, 1H, J=1.2 Hz), 7.15 (d, 1H, J=1.2 Hz), 5.26 (s, 2H), 3.79 (m, 2H), 3.19 (s, 1H), 2.67 (t, 2H, J=6.6 Hz), 1.94 (t, 2H, J=6.6 Hz), 1.33 (s, 6H), 0.95 (m, 2H), –0.016 (s, 9H).

{4-[8,8-Dimethyl-5-oxo-4-(2-trimethylsilanyl-ethoxymethoxy)-5,6,7,8-tetrahydro-naphthalen-2-ylethynyl]-phenyl}-acetic acid methyl ester (Intermediate 74)

Following General Procedure B and using 6-ethynyl-4,4-dimethyl-8-(2-trimethylsilanyl-ethoxymethoxy)-3,4-dihydro-2H-naphthalen-1-one (Intermediate 73, 1.28 g, 3.7 mmol), 4-iodo phenyl acetic acid methyl ester (1.02 g, 3.7 mmol), triethyl amine (30 mL), copper(I)iodide (0.095 g, 0.5 mmol) and dichlorobis(triphenylphosphine)palladium(II) (0.35 g, 0.5 mmol) followed by flash column chromatography over silica gel (230–400 mesh) using 5–15% ethyl acetate in hexane as the eluent, the title compound was obtained as a yellow oil (1.61 g, 88%).

$^1$H NMR (300 MHz, CDCl$_3$): δ 7.51 (d, 2H, J=8.1 Hz), 7.28 (d, 2H, J=8.1 Hz), 7.24 (d, 1H, J=1.5 Hz), 7.19 (d, 1H, J=1.5 Hz), 5.31 (s, 2H), 3.82 (m, 2H), 3.70 (s, 3H), 3.65 (s, 2H), 2.69 (t, 2H, J=6.6 Hz), 1.96 (t, 2H, J=6.6 Hz), 1.37 (s, 6H), 0.97 (m, 2H), 0.00 (s, 9H).

{4-[5-(Cyclopropyl-methyl-amino)-8,8-dimethyl-4-(2-trimethylsilanyl-ethoxymethoxy)-5,6,7,8-tetrahydro-naphthalen-2-ylethynyl]-phenyl}-acetic acid methyl ester (Intermediate 75)

A solution of {4-[8,8-dimethyl-5-oxo-4-(2-trimethylsilanyl-ethoxymethoxy)-5,6,7,8-tetrahydro-naphthalen-2-ylethynyl]-phenyl}-acetic acid methyl ester (Intermediate 74, 0.905 g, 1.84 mmol) in dichloromethane (8 mL) and acetonitrile (4 mL) was treated with cyclopropyl amine (4 mL, 57.8 mmol). After 5 minutes, acetic acid (4 mL) was added followed by sodium cyanoborohydride (0.46 g, 7.32 mmol). The reaction mixture was stirred overnight at ambient temperature. It was then diluted with water and saturated aqueous sodium carbonate solution and extracted with dichloromethane (×2). The combined organic extract was dried over anhydrous sodium sulfate, filtered and evaporated in vacuo to an oil. The oil was dissolved in acetone (15 mL) and treated with potassium carbonate (0.745 g, 5.4 mmol) followed by methyl iodide (1.2 mL, 19 mmol) and the resulting reaction mixture was stirred overnight at ambient temperature. The precipitated solids were filtered off, the filtrate was evaporated in vacuo to a residue. Flash column chromatography over silica gel (230–400 mesh) using 2–20% ethyl acetate in hexane as the eluent afforded the title compound (0.6 g, 63%).

$^1$H NMR (300 MHz, CDCl$_3$): δ 7.49 (d, 2H, J=8.4 Hz), 7.23 (d, 2H, J=8.4 Hz), 7.18 (d, 1H, J=1.5 Hz), 7.06 (d, 1H, J=1.5 Hz), 5.21 (s, 2H), 4.03 (m, 1H), 3.76 (m, 2H), 3.68 (s, 3H), 3.62 (s, 2H), 2.30 (s, 3H), 2.04–1.40 (m, 5H), 1.33 (s, 3H), 1.18 (s, 3H), 0.97 (m, 2H), 0.26–0.01 (m, 4H), 0.00 (s, 9H).

4-[5-(Cyclopropyl-methyl-amino)-4-hydroxy-8,8-dimethyl-5,6,7,8-tetrahydro-naphthalen-2-ylethynyl]-phenyl}-acetic acid methyl ester (Intermediate 76)

A solution of {4-[5-(cyclopropyl-methyl-amino)-8,8-dimethyl-4-(2-trimethylsilanyl-ethoxymethoxy)-5,6,7,8-tetrahydro-naphthalen-2-ylethynyl]-phenyl}-acetic acid methyl ester (Intermediate 75, 0.37 g, 0.73 mmol) in tetrahydrofuran (12 mL) was treated with 2% sulfuric acid in methanol (14 mL) and the resulting reaction mixture was stirred at ambient temperature overnight. It was neutralized with saturated sodium bicarbonate solution and extracted with ethyl acetate. The organic phase was dried over anhydrous magnesium sulfate, filtered and evaporated in vacuo to a residue that after flash column chromatography over silica gel (230–400 mesh) using 5–20% ethyl acetate in hexane as the eluent afford the title product as a white solid (0.295 g, 87%).

$^1$H NMR (300 MHz, CDCl$_3$): δ 12.26 (s, 1H), 7.45 (d, 2H, J=8.4 Hz), 7.22 (d, 2H, J=8.4 Hz), 6.96 (d, 1H, J=1.5 Hz), 6.69 (d, 1H, J=1.5 Hz), 4.31 (m, 1H), 3.67 (s, 3H), 3.61 (s, 2H), 2.23 (s, 3H), 2.23–2.17 (m, 1H), 2.05–1.97 (m, 2H), 1.71–1.65 (m, 2H), 1.28 (s, 3H), 1.24 (s, 3H), 0.80–0.45 (m, 4H).

4-[5-(Cyclopropyl-methyl-amino)-8,8-dimethyl-4-trifluoromethanesulfonyloxy-5,6,7,8-tetrahydro-naphthalen-2-ylethynyl]-phenyl}-acetic acid methyl ester (Intermediate 77)

A stirred, cooled (0° C.) solution of 4-[5-(cyclopropyl-methyl-amino)-4-hydroxy-8,8-dimethyl-5,6,7,8-tetrahydro-naphthalen-2-ylethynyl]-phenyl}-acetic acid methyl ester (Intermediate 76, 0.15 g, 0.275 mmol) in anhydrous dichloromethane was treated with 4-(dimethylamino)pyridine (0.067 g, 0.55 mmol) followed by N-phenyltrifluoromethanesulfonimide (0.147 g, 0.413 mmol). After stirring at ambient temperature overnight, the reaction mixture was subjected to flash column chromatography over silica gel (230–400 mesh) using 5–10% ethyl acetate in hexane as the eluent to afford the title compound (0.14 g, 93%).

$^1$H NMR (300 MHz, CDCl$_3$): δ 7.51 (d, 2H, J=8.4 Hz), 7.30–7.26 (m, 3H), 7.17 (d, 1H, J=1.5 Hz), 4.04 (m, 1H), 3.72 (s, 3H), 3.66 (s, 2H), 2.37 (s, 3H), 2.25–2.17 (m, 1H), 2.09–1.74 (m, 3H), 1.59–1.52 (m, 1H), 1.40 (s, 3H), 1.23 (s, 3H), 0.28–0.10 (m, 3H), 0.09–0.005 (m, 1H).

8-(Cyclopropyl-methyl-amino)-3-(4-methoxycarbonylmethyl-phenylethynyl)-5,5-dimethyl-5,6,7,8-tetrahydro-naphthalene-1-carboxylic acid ethyl ester (Intermediate 78)

Following General Procedure E and using 4-[5-(cyclopropyl-methyl-amino)-8,8-dimethyl-4-trifluoromethanesulfonyloxy-5,6,7,8-tetrahydro-naphthalen-2-ylethynyl]-phenyl}-acetic acid methyl ester (Intermediate 77, 0.14 g, 0.26 mmol), palladium acetate (0.013 g, 0.06 mmol), 1,3-bis(diphenylphosphino)propane (0.025 g, 0.061 mmol), N,N-dimethylformamide (4 mL), ethanol (1.5 mL) and triethyl amine (1.5 mL) followed by flash column chromatography over silica gel (230–400 mesh) using 7–10% ethyl acetate in hexane as the eluent, the title compound was obtained (0.09 g, 75%).

$^1$H NMR (300 MHz, CDCl$_3$): δ 7.49 (d, 1H, J=1.8 Hz), 7.47 (d, 2H, J=8.1 Hz), 7.30 (d, 1H, J=1.8 Hz), 7.25 (d, 2H, J=8.1 Hz), 4.33 (m, 1H), 4.28–4.13 (m, 2H), 3.70 (s, 3H), 3.63 (s, 2H), 2.06–1.93 (2m, 6H), 1.72–1.66 (m, 2H), 1.36 (t, 3H, J=7.2 Hz), 1.31 (s, 3H), 1.29 (s, 3H), 0.60–0.40 (m, 1H), 0.40–0.25 (m, 2H), 0.15–0.00 (m, 1H).

3-(4-Carboxymethyl-phenylethynyl)-8-(cyclopropyl-methyl-amino)-5,5-dimethyl-5,6,7,8-tetrahydro-naphthalene-1-carboxylic acid ethyl ester (Compound 24)

A solution of 8-(cyclopropyl-methyl-amino)-3-(4-methoxycarbonylmethyl-phenylethynyl)-5,5-dimethyl-5,6,7,8-tetrahydro-naphthalene-1-carboxylic acid ethyl ester (Intermediate 78, 0.09 g, 0.19 mmol) in ethanol (2 mL), tetrahydrofuran (3 mL) and water (1.5 mL) was treated with lithium hydroxide (0.11 g, 2.62 mmol) and the resulting reaction mixture was stirred at ambient temperature for 2 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product as a white solid (0.085 g, 94%).

$^1$H NMR (300 MHz, CDCl$_3$): δ 7.49 (d, 1H, J=1.8 Hz), 7.46 (d, 2H, J=8.1 Hz), 7.30 (d, 1H, J=1.8 Hz), 7.22 (d, 2H, J=8.1 Hz), 4.32 (m, 1H), 4.30–4.10 (m, 2H), 3.58 (s, 2H), 2.06–1.93 (2m, 6H), 1.72–1.65 (m, 2H), 1.35 (t, 3H, J=7.0 Hz), 1.34 (s, 3H), 1.29 (s, 3H), 0.60–0.40 (m, 1H), 0.40–0.25 (m, 2H), 0.15–0.00 (m, 1H).

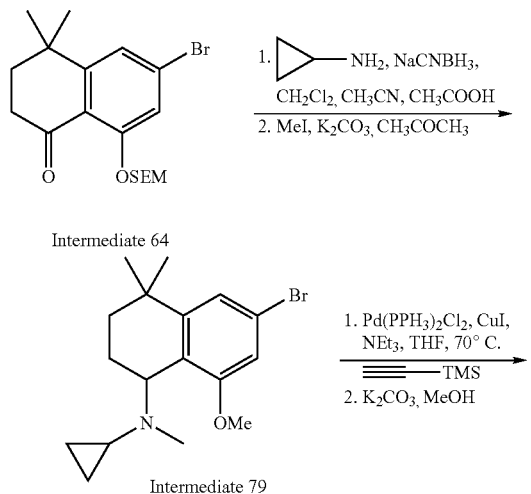

Reaction Scheme 14

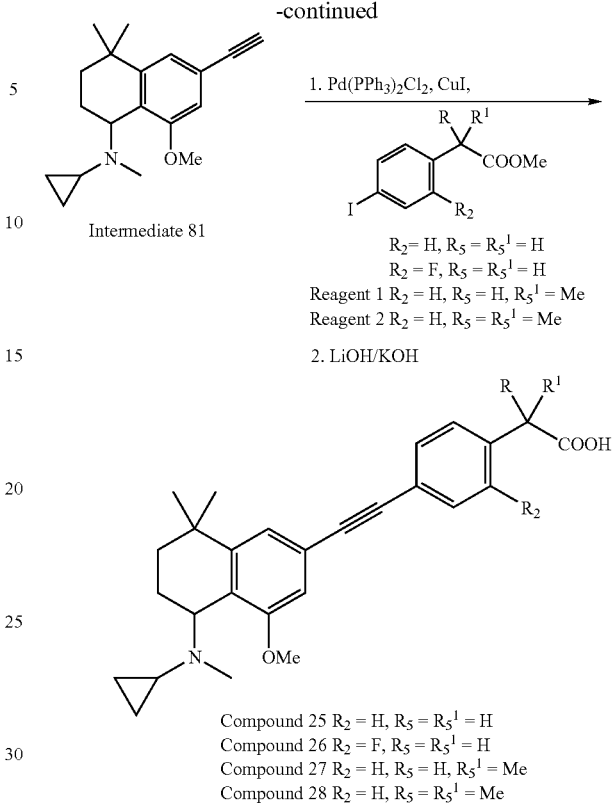

2-Bromo-5-(cyclopropyl-methyl-amino)-8,8-dimethyl-4-methoxy-5,6,7,8-tetrahydro-naphthalene (Intermediate 79)

A solution of 6-bromo-8-methoxy-4,4-dimethyl-3,4-dihydro-2H-naphthalen-1-one (Intermediate 64, 1.08 g, 3.81 mmol) in dichloromethane (8 mL) and acetonitrile (4 mL) was treated with cyclopropyl amine (5 mL, 72.3 mmol). After 5 minutes, acetic acid (5 mL) was added followed by sodium cyanoborohydride (0.96 g, 15.26 mmol). The reaction mixture was stirred for 2 days at ambient temperature. It was then diluted with water and saturated aqueous sodium carbonate solution and extracted with ethyl acetate. The combined organic extract was dried over anhydrous sodium sulfate, filtered and evaporated in vacuo to an oil. The oil was dissolved in acetone (20 mL) and treated with potassium carbonate (1.58 g, 11.43 mmol) followed by methyl iodide (2.1 mL, 33 mmol) and the resulting reaction mixture was stirred overnight at ambient temperature. Diethyl ether was added and the precipitated solids were filtered off, the filtrate was evaporated in vacuo to a residue. Flash column chromatography over silica gel (230–400 mesh) using 2.5–10% ethyl acetate in hexane as the eluent afforded the title compound (1.08 g, 84%).

$^1$H NMR (300 MHz, CDCl$_3$): δ 7.08 (d, 1H, J=1.8 Hz), 6.78 (d, 1H, J=1.8 Hz), 3.97 (m, 1H), 3.79 (s, 3H), 2.30 (s, 3H), 2.04–1.82 (m, 3H), 1.65–1.27 (m, 2H), 1.30 (s, 3H), 1.16 (s, 3H), 0.30–0.22 (m, 2H), 0.07–0.00 (m, 2H).

5-(Cyclopropyl-methyl-amino)-8,8-dimethyl-4-methoxy-2-trimethylsilanylethynyl-5,6,7,8-tetrahydro-naphthalene (Intermediate 80)

Following General Procedure D and using 2-bromo-5-(cyclopropyl-methyl-amino)-8,8-dimethyl-4-methoxy-5,6,7,8-tetrahydro-naphthalene (Intermediate 79, 1.08 g, 3.2 mmol), triethyl amine (5 mL), copper(I)iodide (0.061 g, 0.32 mmol), trimethylsilyl acetylene (3 mL, 21.1 mmol) and dichlorobis(triphenylphosphine)palladium(II) (225 g, 0.32 mmol) followed by flash column chromatography over silica gel (230–400 mesh) using hexane-10% ethyl acetate in hexane as the eluent, the title compound (0.87 g, 80%) was obtained.

$^1$H NMR (300 MHz, CDCl$_3$): δ 7.09 (d, 1H, J=1.5 Hz), 6.73 (d, 1H, J=1.5 Hz), 3.99 (m, 1H), 3.79 (s, 3H), 2.28 (s, 3H), 2.02–1.80 (m, 3H), 1.65–1.26 (2m, 2H), 1.31 (s, 3H), 1.16 (s, 3H), 0.26 (s, 9H), 0.26–0.00 (m, 2H), 0.00–0.01 (m, 2H).

5-(Cyclopropyl-methyl-amino)-2-ethynyl-8,8-dimethyl-4-methoxy-5,6,7,8-tetrahydro-naphthalene (Intermediate 81)

A solution of 5-(cyclopropyl-methyl-amino)-8,8-dimethyl-4-methoxy-2-trimethylsilanylethynyl-5,6,7,8-tetrahydro-naphthalene (Intermediate 80, 0.87 g, 2.45 mmol) in methanol (20 mL) was treated with potassium carbonate (0.4 g, 2.89 mmol) and the resulting reaction mixture was stirred at ambient temperature overnight. The solvent was evaporated in vacuo, the residue was diluted with water and extracted with diethyl ether. The organic phase was washed with brine, dried over anhydrous magnesium sulfate, filtered and evaporated in vacuo to afford the title compound (0.635 g, 92%).

$^1$H NMR (300 MHz, CDCl$_3$): δ 7.16 (d, 1H, J=1.4 Hz), 6.79 (d, 1H, J=1.4 Hz), 4.04 (m, 1H), 3.82 (s, 3H), 2.32 (s, 3H), 2.03–1.95 (m, 2H), 1.90–1.80 (r, H), 1.70–1.55 (m, 1H), 1.45–1.35 (m, 1H), 1.34 (s, 3H), 1.19 (s, 3H), 0.40–0.20 (m, 2H), 0.07–0.00 (m, 2H).

{4-[5-(Cyclopropyl-methyl-amino)-4-methoxy-8,8-dimethyl-5,6,7,8-tetrahydro-naphthalen-2-ylethynyl]-phenyl}-acetic acid methyl ester (Intermediate 82)

Following General Procedure B and using 5-(cyclopropyl-methyl-amino)-2-ethynyl-8,8-dimethyl-methoxy-5,6,7,8-tetrahydro-naphthalene (Intermediate 81, 0.065 g, 0.23 mmol), methyl-4-iodophenylacetate (0.063 g, 0.23 mmol), triethyl amine (8 mL), copper(I)iodide (0.018 g, 0.093 mmol) and dichlorobis(triphenylphosphine)palladium(II) (0.065 g, 0.093 mmol) followed by flash column chromatography over silica gel (230–400 mesh) using 5–20% ethyl acetate in hexane as the eluent, the title compound was obtained as a yellow solid (0.09 g, 90%).

$^1$H NMR (300 MHz, CDCl$_3$): δ 7.50 (d, J=8.2 Hz, 2H), 7.26 (d, J=8.2 Hz, 2H), 7.17 (d, J=1.2 Hz, 1H), 6.81 (d, J=1.2 Hz, 1H), 4.04 (bs, 1H), 3.82 (s, 3H), 3.70 (s, 3H), 3.64 (s, 2H), 2.32 (s, 3H), 2.05–1.94 (m, 2H), 1.90–1.80 (m 1H), 1.70–1.58 (m, 1H), 1.45–1.35 (m, 1H), 1.38 (s, 3H), 1.20 (s, 3H), 0.38–0.20 (m, 2H), 0.18–0.02 (m, 2H).

{4-[5-(Cyclopropyl-methyl-amino)-4-methoxy-8,8-dimethyl-5,6,7,8-tetrahydro-naphthalen-2-ylethynyl]-phenyl}-acetic acid (Compound 25)

A solution of {4-[5-(cyclopropyl-methyl-amino)-4-methoxy-8,8-dimethyl-[5,6,7,8-tetrahydro-naphthalen-2-ylethynyl]-phenyl}-acetic acid methyl ester (Intermediate 82, 0.090 g, 0.208 mmol) in methanol (3 mL) and tetrahydrofuran (2 mL) was treated with a 1.9 M solution of lithium hydroxide (1.5 mL, 2.8 mmol) and the resulting reaction mixture was stirred at ambient temperature for 2 h. The reaction mixture was concentrated, neutralized with ammonium chloride and extracted with ethyl acetate. The organic phase was washed with water and brine, and dried over anhydrous magnesium sulfate, filtered and evaporated in vacuo to a residue that was subjected to flash column chromatography over silica gel (230–400 mesh) using 5–10% methanol in ethyl acetate as the eluent to afford the title product as a white amorphous solid (0.062 g, 60%).

$^1$H NMR (300 MHz, CDCl$_3$): 7.46 (d, J=8.2 Hz, 2H), 7.28 (d, J=8.2 Hz, 2H), 7.18 (d, J=1.2 Hz, 1H), 6.81 (d, J=1.2 Hz, 1H), 4.27 (bs, 1H), 3.81 (s, 3H), 3.58 (s, 2H), 2.42 (s, 3H), 2.28–2.18 (m, 1H), 2.15–1.88 (m 2H), 1.75–1.65 (m, 1H), 1.45–1.38 (m, 1H), 1.32 (s, 3H), 1.17 (s, 3H), 0.75–0.65 (m, 1H), 0.55–0.42 (m, 2H), 0.25–0.15 (m, 1H).

{4-[5-(Cyclopropyl-methyl-amino)-4-methoxy-8,8-dimethyl-5,6,7,8-tetrahydro-naphthalen-2-ylethynyl]-2-fluoro-phenyl}-acetic acid methyl ester (Intermediate 83)

Following General Procedure B and using 5-(cyclopropyl-methyl-amino)-2-ethynyl-8,8-dimethyl-4-methoxy-5,6,7,8-tetrahydro-naphthalene (Intermediate 81, 0.085 g, 0.3 mmol), methyl-2-fluoro-4-iodophenylacetate (0.088 g, 0.3 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230–400 mesh) using 5–20% ethyl acetate in hexane as the eluent, the title compound was obtained as a yellow solid (0.12 g, 89%).

$^1$H NMR (300 MHz, CDCl$_3$): δ 7.36–7.17 (m, 4H), 6.81 (d, J=1.2 Hz, 1H), 4.12 (bs, 1H), 3.83 (s, 3H), 3.72 (s, 3H), 3.69 (s, 2H), 2.33 (s, 3H), 2.08–1.98 (m 2H), 1.98–1.88 (m, 1H), 1.75–1.60 (m, 1H), 1.45–1.35 (m, 1H), 1.35 (s, 3H), 1.19 (s, 3H), 0.35–0.25 (m, 2H), 0.15–0.05 (m, 1H).

{4-[5-(Cyclopropyl-methyl-amino)-4-methoxy-8,8-dimethyl-5,6,7,8-tetrahydro-naphthalen-2-ylethynyl]-2-fluoro-phenyl}-acetic acid (Compound 26)

A solution of {4-[5-(cyclopropyl-methyl-amino)-4-methoxy-8,8-dimethyl-5,6,7,8-tetrahydro-naphthalen-2-ylethynyl]-2-fluoro-phenyl}-acetic acid methyl ester (Intermediate 83, 0.12 g, 0.27 mmol) in methanol (4 mL) and tetrahydrofuran (4 mL) was treated with a 2 M solution of lithium hydroxide (2 mL, 4 mmol) and the resulting reaction mixture was stirred at ambient temperature-for-2 h. The reaction mixture was concentrated, neutralized with ammonium chloride and extracted with ethyl acetate. The organic phase was washed with water and brine, and dried over anhydrous magnesium sulfate, filtered and evaporated in vacuo to a residue that was subjected to flash column chromatography over silica gel (230–400 mesh) using 5–8% methanol in ethyl acetate as the eluent to afford the title product as a white amorphous solid (0.041 g, 35%).

$^1$H NMR (300 MHz, CDCl$_3$): δ 7.35–7.15 (m, 4H), 6.81 (d, J=1.2 Hz, 1H), 4.31 (bs, 1H), 3.82 (s, 3H), 3.64 (s, 2H), 2.46 (s, 3H), 2.32–2.22 (m, 1H), 2.18–1.88 (m 2H), 1.78–1.65 (m, H), 1.50–1.40 (m, 1H), 1.32 (s, 3H), 1.17 (s, 3H), 0.80–0.70 (m, 1H), 0.58–0.40 (m, 2H), 0.28–0.18 (m, 1H).

2-{4-[5-(Cyclopropyl-methyl-amino)-4-methoxy-8,8-dimethyl-5,6,7,8-tetrahydro-naphthalen-2-ylethynyl]-phenyl}-propionic acid methyl ester (Intermediate 84)

Following General Procedure B and using 5-(cyclopropyl-methyl-amino)-2-ethynyl-8,8-dimethyl-4-methoxy-5,6,7,8-tetrahydro-naphthalene (Intermediate 81, 0.085 g, 0.30 mmol), methyl-2-(4-iodophenyl)propionate (Reagent 1, 0.087 g, 0.3 mmol), triethyl amine (8 mL), copper(I)iodide (0.019 g, 0.1 mmol) and dichlorobis(triphenylphosphine) palladium(II) (0.07 g, 0.1 mmol) followed by flash column chromatography over silica gel (230–400 mesh) using 5–20% ethyl acetate in hexane as the eluent, the title compound was obtained as a yellow solid (0.115 g, 86%).

$^1$H NMR (300 MHz, CDCl$_3$): δ 7.50 (d, 2H, J=8.1 Hz), 7.28 (d, 2H, J=8.1 Hz), 7.16 (d, 1H, J=1.2 Hz), 6.81 (d, 1H,

J=1.2 Hz), 4.04 (m, 1H), 3.83 (s, 3H), 3.74 (q, 1H, J=6.9 Hz), 3.67 (s, 3H), 2.31 (s, 3H), 2.03–1.98 (m, 2H), 1.89–1.83 (m, 1H), 1.68–1.59 (m, 1H), 1.51 (d, 3H, J=6.9 Hz), 1.42–1.27 (m, 1H), 1.35 (s, 3H), 1.20 (s, 3H), 0.31–0.23 (m, 2H), 0.07–0.008 (m, 2H).

2-{4-[5-(Cyclopropyl-methyl-amino)-4-methoxy-8,8-dimethyl-5,6,7,8-tetrahydro-naphthalen-2-ylethynyl]-phenyl}-propionic acid (Compound 27)

A solution of 2-{4-[5-(cyclopropyl-methyl-amino)-4-methoxy-8,8-dimethyl-5,6,7,8-tetrahydro-naphthalen-2-ylethynyl]-phenyl}-propionic acid methyl ester (Intermediate 84, 0.115 g, 0.26 mmol) in methanol (3 mL) and tetrahydrofuran (2 mL) was treated with a 3M solution of potassium hydroxide (1 mL, 3 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous magnesium sulfate, filtered and evaporated in vacuo to a residue that was subjected to flash column chromatography over silica gel (230400 mesh) using 8% methanol in ethyl acetate as the eluent to afford the title product as a yellow solid (0.062 g, 56%).

$^1$H NMR (300 MHz, CDCl$_3$): δ 7.50 (d, 2H, J=8.1 Hz), 7.32 (d, 2H, J=8.1 Hz), 7.17 (s, 1H), 6.80 (s, 1H), 4.23 (m, 1H), 3.80 (s, 3H), 3.68 (q, 1H, J=7.2 Hz), 2.38 (s, 3H), 2.22–2.18 (m, 1H), 2.07–1.87 (m, 2H), 1.70–1.57 (m, 1H), 1.47 (d, 3H, J=7.2 Hz), 1.38–1.27 (m, 1H), 1.31 (s, 3H), 1.16 (s, 3H), 0.65–0.62 (m, 1H), 0.41–0.35 (m, 2H), 0.17–0.00 (m, 1H).

2-{4-[5-(Cyclopropyl-methyl-amino)-4-methoxy-8,8-dimethyl-5,6,7,8-tetrahydro-naphthalen-2-ylethynyl]-phenyl}-2-methyl-propionic acid methyl ester (Intermediate 85)

Following General Procedure B and using 5-(cyclopropyl-methyl-amino)-2-ethynyl-8,8-dimethyl-4-methoxy-5,6,7,8-tetrahydro-naphthalene (Intermediate 81, 0.090 g, 0.32 mmol), methyl-2-(4-iodophenyl)-2-methyl-propionate (Reagent-2, 0.097 g, 0.3 mmol), triethyl amine (8 mL) copper (I)iodide (0.019 g, 0.1 mmol) and dichlorobis(triphenylphosphine)palladium(II) (0.07 g, 0.1 mmol) followed by flash column chromatography over silica gel (230–400 mesh) using 5–20% ethyl acetate in hexane as the eluent, the title compound was obtained as a solid (0.09 g, 78%).

$^1$H NMR (300 MHz, CDCl$_3$): δ 7.50 (d, 2H, J=8.1 Hz), 7.31 (d, 2H, J=8.1 Hz), 7.16 (d, 1H, J=1.2 Hz), 6.80 (d, 1H, J=1.2 Hz), 4.03 (m, 1H), 3.83 (s, 3H), 3.66 (s, 3H), 2.31 (s, 3H), 2.01–1.97 (m, 2H), 1.89–1.83 (m, 1H), 1.68–1.59 (m, 1H), 1.59 (s, 6H), 1.42–1.27 (m, 1H), 1.34 (s, 3H), 1.20 (s, 3H), 0.31–0.22 (m, 2H), 0.07–0.00 (m, 2H).

2-{4-[5-(Cyclopropyl-methyl-amino)-4-methoxy-8,8-dimethyl-5,6,7,8-tetrahydro-naphthalen-2-ylethynyl]-phenyl}-2-methyl-propionic acid (Compound 28)

A solution of 2-{4-[5-(cyclopropyl-methyl-amino)-4-methoxy-8,8-dimethyl-5,6,7,8-tetrahydro-naphthalen-2-ylethynyl]-phenyl}-2-methyl-propionic acid methyl ester (Intermediate 85, 0.09 g, 0.196 mmol) in methanol (3 mL) and tetrahydrofuran (2 mL) was treated with a 3M solution of potassium hydroxide (1.5 mL, 4.5 mmol) and the resulting reaction mixture was stirred at ambient temperature for 3 days. The reaction mixture was neutralized with 5% aqueous hydrochloric acid and extracted with ethyl acetate. The organic phase was washed with water and brine, and dried over anhydrous sodium sulfate, filtered and evaporated in vacuo to a residue that was subjected to flash column chromatography over silica gel (230–400 mesh) using 5% methanol in ethyl acetate as the eluent to afford the title product as a yellow solid (0.057 g, 65%).

$^1$H NMR (300 MHz, CDCl$_3$): δ 7.46 (d, 2H, J=8.4 Hz), 7.37 (d, 2H, J=8.4 Hz), 7.18 (d, 1H, J=1.2 Hz), 6.81 (d, H, J=1.2 Hz), 4.22 (m, 1H), 3.83 (s, 3H), 2.38 (s, 3H), 2.19–1.90 (m, 3H), 1.71–1.56 (m, 1H), 1.56 (s, 6H), 1.45–1.33 (m, 1H), 1.33 (s, 3H), 1.17 (s, 3H), 0.70–0.50 (m, 1H), 0.38–0.25 (m, 2H), 0.16–0.00 (m, 1H).

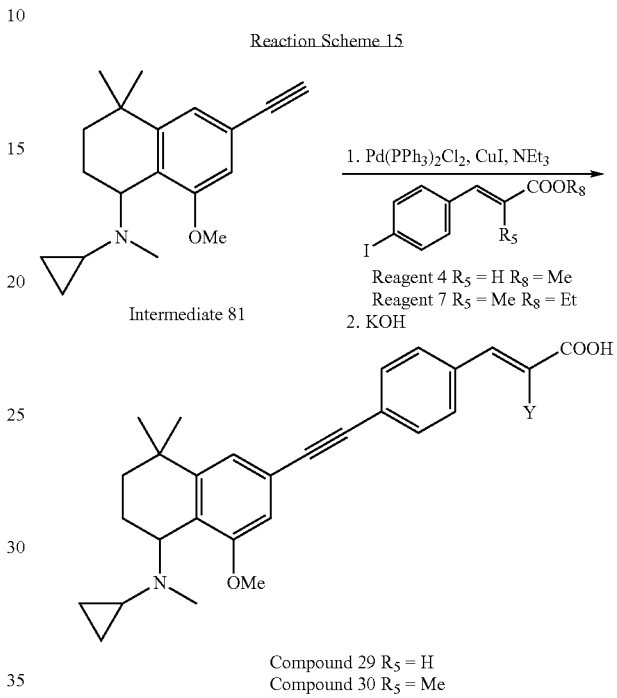

Reaction Scheme 15

Compound 29 R$_5$ = H
Compound 30 R$_5$ = Me (E)-3-{4-[5-(Cyclopropyl-methyl-amino)-4-methoxy-8,8-dimethyl-5,6,7,8-tetrahydro-naphthalen-2-ylethynyl]-phenyl}-acrylic acid methyl ester (Intermediate 86)

Following General Procedure B and using 5-(cyclopropyl-methyl-amino)-2-ethynyl-8,8-dimethyl-4-methoxy-5,6,7,8-tetrahydro-naphthalene (Intermediate 81, 0.095 g, 0.336 mmol), methyl-4-iodocinnamate (Reagent 4, 0.097 g, 0.336 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230–400 mesh) using 5–15% ethyl acetate in hexane as the eluent, the title compound was obtained as a white solid (0.12 g, 80%).

$^1$H NMR (300 MHz, CDCl$_3$): δ 7.68 (d, 1H, J=15.9 Hz), 7.53 (Abq, 4H, J=8.4 Hz), 7.19 (s, 1H), 6.83 (s, 1H), 7.46 (d, 1H, J=15.9 Hz), 4.04 (m, 1H), 3.84 (s, 3H), 3.82 (s, 3H), 2.32 (s, 3H), 2.04–1.97 (m, 2H) 1.90–1.83 (m, 1H), 1.68–1.60 (m, 1H), 1.43–1.27 (m, 1H), 1.36 (s, 3H), 1.21 (s, 3H), 0.32–0.23 (m, 2H), 0.08–0.00 (m, 2H).

(E)-3-{4-[5-(Cyclopropyl-methyl-amino)-4-methoxy-8,8-dimethyl-5,6,7,8-tetrahydro-naphthalen-2-ylethynyl]-phenyl}-acrylic acid (Compound 29)

A solution of (E)-3-{4-[5-(cyclopropyl-methyl-amino)-4-methoxy-8,8-dimethyl-5,6,7,8-tetrahydro-naphthalen-2-ylethynyl]-phenyl}-acrylic acid methyl ester (Intermediate 86, 0.12 g, 0.27 mmol) in methanol (4 mL) and tetrahydrofuran (3 mL) was treated with a 3M solution of potassium hydroxide (1 mL, 3 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous magnesium sulfate, filtered and evaporated in vacuo to a residue that was subjected to flash column chromatography over silica gel (230–400 mesh) using 5% methanol in ethyl acetate as the eluent to afford the title product as a white solid (0.041 g, 35%).

$^1$H NMR (300 MHz, CDCl$_3$): δ 7.58 (d, 1H, J=16.2 Hz), 7.44 (Abq, 4H), 7.13 (s, 1H), 6.77 (s, 1H), 7.45 (d, 1H, J=16.2 Hz), 4.05 (m, 1H), 3.79 (s, 3H), 2.42 (s, 3H), 2.19–1.97 (m, 2H), 1.67–1.45 (m, 1H), 1.45–1.37 (m, 1H), 1.37–1.20 (m, 1H), 1.30 (s, 3H), 1.12 (s, 3H), 0.80–0.60 (m, 1H), 0.50–0.30 (m, 2H), 0.20–0.00 (m, 1H).

(E)-3-{4-[5-(Cyclopropyl-methyl-amino)-4-methoxy-8,8-dimethyl-5,6,7,8-tetrahydro-naphthalen-2-ylethynyl]-cyclohexa-2,4-dienyl}-2-methyl-acrylic acid ethyl ester (Intermediate 87)

Following General Procedure B and using 5-(cyclopropyl-methyl-amino)-2-ethynyl-8,8-dimethyl-4-methoxy-5,6,7,8-tetrahydro-naphthalene (Intermediate 81 0.08 g, 0.28 mmol), (E)-3-(4-iodo-phenyl)-2-methyl-acrylic acid ethyl ester (Reagent 7, 0.09 g, 0.28 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230–400 mesh) using 5–10% ethyl acetate in hexane as the eluent, the title compound was obtained as a white solid (0.12 g, 90%).

$^1$H NMR (300 MHz, CDCl$_3$): δ 7.67 (d, 1H, J=1.2 Hz), 7.57 (d, 2H, J=8.4 Hz), 7.40 (d, 2H, J=8.4 Hz), 7.19 (d, 1H, J=1.5 Hz), 6.83 (d, 1H, J=1.5 Hz), 4.28 (q, 2H, J=7.2 Hz), 4.04 (m, 1H), 3.84 (s, 3H), 2.32 (s, 3H), 2.15 (d, 3H, J=1.2 Hz), 2.03–1.83 (m, 3H), 1.68–1.50 (m, 1H), 1.45–1.20 (m, 1H), 1.36 (s, 3H), 1.35 (t, 3H, J=7.2 Hz), 1.20 (s, 3H), 0.32–0.23 (m, 2H), 0.08–0.00 (m, 2H).

(E)-3-{4-[5-(Cyclopropyl-methyl-amino)-4-methoxy-8,8-dimethyl-5,6,7,8-tetrahydro-naphthalen-2-ylethynyl]-cyclohexa-2,4-dienyl}-2-methyl-acrylic acid (Compound 30)

A solution of (E)-3-{4-[5-(cyclopropyl-methyl-amino)-4-methoxy-8,8-dimethyl-5,6,7,8-tetrahydro-naphthalen-2-ylethynyl]-cyclohexa-2,4-dienyl}-2-methyl-acrylic acid methyl ester (Intermediate 87, 0.12 g, 0.25 mmol) in methanol (3 mL) and tetrahydrofuran (2 mL) was treated with a 3M solution of potassium hydroxide (1 mL, 3 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous magnesium sulfate, filtered and evaporated in vacuo to a residue that was recrystallized from hot acetonitrile to afford the title product as a white solid (0.055 g, 49%).

$^1$H NMR (300 MHz, CDCl$_3$): δ 7.78 (d, 1H, J=1.2 Hz), 7.57 (d, 2H, J=8.1 Hz), 7.43 (d, 2H, J=8.1 Hz), 7.29 (d, 1H, J=1.5 Hz), 6.93 (d, 1H, J=1.5 Hz), 4.93 and 4.70 (2m, 1H), 3.97 (s, 3H), 2.54 (s, 3H), 2.40–1.60 (m, 4H), 2.16 (d, 3H, J=1.2 Hz), 1.46–1.23 (m, 1H), 1.46 (s, 3H), 1.23 (s, 3H), 0.90–0.20 (m, 4H).

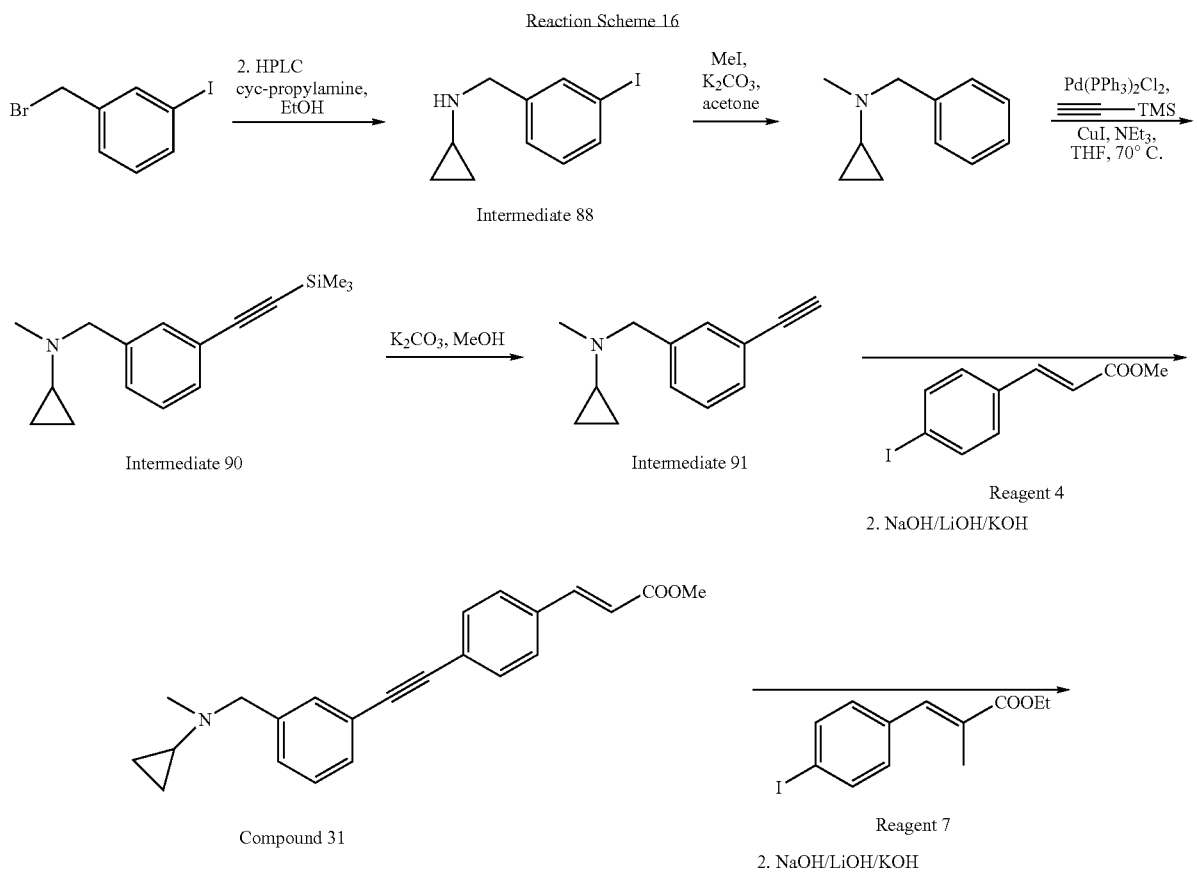

Reaction Scheme 16

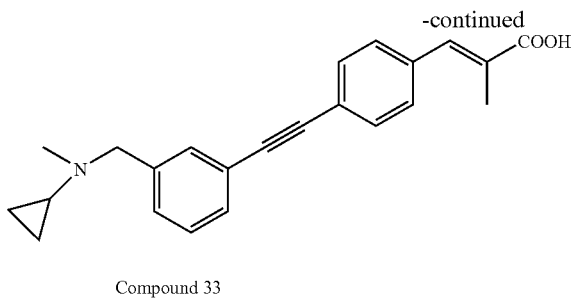

Compound 33

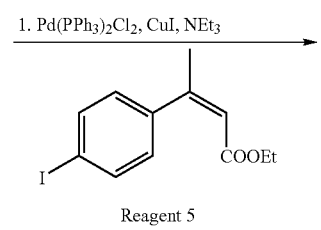

Reagent 5

2. NaOH/LiOH/KOH

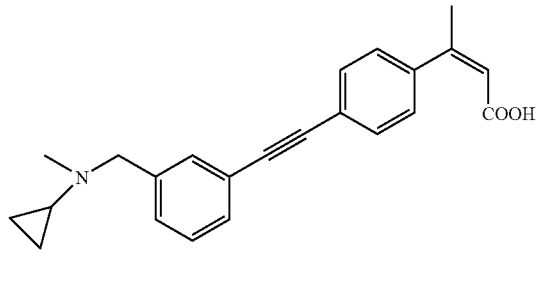

Compound 32

Cyclopropyl-(3-iodo-benzyl)-amine (Intermediate 88)

A solution of 3-iodobenzyl bromide (Aldrich, 3.2 g, 10.77 mmol) in ethanol (20 mL) was treated with cyclopropyl amine (7 mL, 101.5 mmol) and the resulting reaction mixture was stirred over 3 days at ambient temperature. The volatiles were evaporated in vacuo, the residue was diluted with ethyl acetate and washed with saturated, aqueous sodium bicarbonate solution, water and brine, dried over anhydrous sodium sulfate, filtered and evaporated in vacuo to an oil that was subjected to flash column chromatography over silica gel (230–400 mesh) using 10–20% ethyl acetate in hexane as the eluent afford the title product (2.4 g, 81%).

$^1$H NMR (300 MHz, CDCl$_3$): δ 7.67 (s, 1H), 7.58 (d, 1H, J=9.0 Hz), 7.27 (d, 1H, J=6.0 Hz), 7.05 (dd, 1H, J=6.0, 9.0 Hz), 3.78 (s, 2H), 2.13 (I, 1H), 1.76 (br s, 1H), 0.50–0.35 (m, 4H).

Cyclopropyl-(3-iodo-benzyl)-methyl-amine (Intermediate 89)

A solution of cyclopropyl-(3-iodo-benzyl)-amine (Intermediate 88, 4.1 g, 15 mmol) in acetone (20 mL) was treated with potassium carbonate (2.07 g, 15 mmol) and methyl iodide (1.4 mL, 22.5 mmol) and the resulting reaction mixture was stirred at ambient temperature for 1 h. Diethyl ether was added, the solids were filtered off and filtrate was evaporated to a residue that was subjected to flash column chromatography over silica gel (230–400 mesh) using 10% ethyl acetate in hexane as the eluent to afford the title compound (3.3 g, 77%).

$^1$H NMR (300 MHz, CDCl$_3$): δ 7.62 (d, 1H, J=1.5 Hz), 7.55 (dd, 1H, J=1.5, 7.8 Hz), 7.21 (dd, 1H, J=1.5, 7.8 Hz), 7.01 (t, 1H, J=7.8 Hz), 3.61 (s, 2H), 2.22 (s, 3H), 1.69 (m, 1H), 0.50–0.38 (m, 4H).

Cyclopropyl-methyl-(3-trimethylsilanylethynyl-benzyl)-amine (Intermediate 96)

Following General Procedure D and using cyclopropyl-(3-iodo-benzyl)-methyl-amine (Intermediate 89, 0.97 g, 3.4 mmol), triethyl amine (10 mL), copper(I)iodide (0.051 g, 0.27 mmol), trimethylsilyl acetylene (2 mL, 14 mmol) and dichlorobis(triphenylphosphine)palladium(II) (0.19 g, 0.27 mmol) followed by flash column chromatography over silica gel (230–400 mesh) using hexane-5% ethyl acetate in hexane as the eluent, the title compound (0.695 g, 80%) was obtained.

$^1$H NMR (300 MHz, CDCl$_3$): δ 7.37–7.31 (m, 2H), 7.25–7.20 (m, 2H), 3.61 (s, 2H), 2.22 (s, 3H), 1.69 (m, 1H), 0.50–0.32 (m, 4H), 0.25 (s, 9H).

Cyclopropyl-(3-ethynyl-benzyl)-methyl-amine (Intermediate 91)

A solution cyclopropyl-methyl-(3-trimethylsilanylethynyl-benzyl)-amine (Intermediate 90, 0.355 g, 1.38 mmol) in methanol (10 mL) was treated with potassium carbonate (0.13 g, 0.95 mmol) and the resulting reaction mixture was stirred at ambient temperature overnight. The solvent was evaporated in vacuo, the residue was diluted with water and extracted with diethyl ether. The organic phase was washed with brine, dried over anhydrous magnesium sulfate, filtered and evaporated in vacuo to afford the title compound (0.22 g, 86%).

$^1$H NMR (300 MHz, CDCl$_3$): δ 7.41–7.35 (m, 2H), 7.26–7.23 (m, 2H), 3.63 (s, 2H), 3.05 (s, 1H), 2.23 (s, 3H), 1.70 (m, 1H), 0.48–0.40 (m, 4H).

(E)-3-(4-{3-[(Cyclopropyl-methyl-amino)-methyl]-phenylethynyl}phenyl)-acrylic acid methyl ester (Intermediate 92)

Following General Procedure B and using cyclopropyl-(3-ethynyl-benzyl)-methyl-amine (Intermediate 91, 0.060 g, 0.32 mmol), methyl-4-iodo-cinnamate (Reagent 4, 0.093 g, 0.32 mmol), triethyl amine (8 mL), copper(I)iodide (0.015 g, 0.08 mmol) and dichlorobis(triphenylphosphine)palladium (II) (0.056 g, 0.08 mmol) followed by flash column chromatography over silica gel (230–400 mesh) using 5–15% ethyl acetate in hexane as the eluent, the title compound was obtained (0.11 g, 100%).

$^1$H NMR (300 MHz, CDCl$_3$): δ 7.66 (d, 2H, J=16.2 Hz), 7.54–7.39 (m, 2H), 7.31–7.25 (m, 2H), 6.43 (d, 2H, J=16.2 Hz), 3.80 (s, 3H), 3.65 (s, 2H), 2.25 (s, 3H), 1.72 (m, 1H), 0.49–0.42 (m, 4H).

(E)-3-(4-{3-[(Cyclopropyl-methyl-amino)-methyl]-phenylethynyl}-phenyl)-acrylic acid (Compound 31)

A solution of (E)-3-(4-{3-[(cyclopropyl-methyl-amino)-methyl]-phenylethynyl}-phenyl)-acrylic acid methyl ester (Intermediate 92, 0.11 g, 0.32 mmol) in methanol (3 mL) and tetrahydrofuran (2 mL) was treated with a 3M solution of potassium hydroxide (1 mL, 3 mmol) and the resulting reaction mixture was stirred at ambient temperature for 2 days. The reaction mixture was neutralized with 5% aqueous hydrochloric acid and extracted with ethyl acetate. The organic phase was washed with water and brine, and dried over anhydrous sodium sulfate, filtered and evaporated in vacuo to a residue that was subjected to flash column chromatography over silica gel (230–400 mesh) using 10% methanol in ethyl acetate as the eluent to afford the title product as a yellow solid (0.038 g, 36%).

$^1$H NMR (300 MHz, CD$_3$OD): δ 7.61–7.38 (m, 9H), 6.53 (d, 1H, J=15.9 Hz), 3.93 (s, 2H), 2.48 (s, 3H), 2.09 (m, 1H), 0.64–0.61 (m, 4H).

3-(4-{3-[(Cyclopropyl-methyl-amino)-methyl]-phenylethynyl}-phenyl)-but-2-enoic acid ethyl ester (Intermediate 93)

Following General Procedure B and using cyclopropyl-(3-ethynyl-benzyl)-methyl-amine (Intermediate 91, 0.12 g, 0.64 mmol), 3-(4-iodo-phenyl)-but-2Z-enoic acid ethyl ester (Reagent 5, 0.2 g, 0.64 mmol), triethyl amine (8 mL), copper(I)iodide (0.012 g, 0.063 mmol) and dichlorobis(triphenylphosphine)palladium(II) (0.045 g, 0.064 mmol) followed by flash column chromatography over silica gel (230–400 mesh), the title compound was obtained (0.17 g, 70%).

$^1$H NMR (300 MHz, CDCl$_3$): δ 7.52–7.40 (m, 4H), 7.31–7.18 (m, 4H), 5.91 (s, 1H), 4.01 (q, J=7.1 Hz, 2H), 3.66 (s, 2H), 2.26 (s, 3H), 2.17 (s, 3H), 1.74–1.70 (m, 1H), 1.10 (t, J=7.1 Hz, 3H), 0.50–0.43 (m, 4H).

3-(4-{3-[(Cyclopropyl-methyl-amino)-methyl]-phenylethynyl}-phenyl)-but-2-enoic acid (Compound 32)

A solution of 3-(4-{3-[(cyclopropyl-methyl-amino)-methyl]-phenylethynyl}-phenyl)-but-2-enoic acid ethyl ester (Intermediate 93, 0.17 g, 0.46 mmol) in ethanol (3 mL) and tetrahydrofuran (3 mL) was treated with a 3.4M solution of potassium hydroxide (1 mL, 3.4 mmol) and the resulting reaction mixture was stirred at ambient temperature for 36 h. The reaction mixture was extracted with diethyl ether, and the aqueous phase was neutralized with 10% aqueous hydrochloric acid and evaporated to a solid. The solid was subjected to flash column chromatography using ethyl acetate as the eluent to afford the title product as a white solid (0.05 g, 32%).

$^1$H NMR (300 MHz, CDCl$_3$): δ 7.49–7.43 (m, 4H), 7.32–7.20 (m, 4H), 5.93 (s, 1H), 3.70 (s, 2H), 2.29 (s, 3H), 2.17 (s, 3H), 1.76–1.73 (m, 1H), 0.50–0.48 (m, 4H).

3-(4-{3-[(Cyclopropyl-methyl-amino)-methyl]-phenylethynyl}-phenyl)-2-methyl-acrylic acid ethyl ester (Intermediate 94)

Following General Procedure B and using cyclopropyl-(3-ethynyl-benzyl)-methyl-amine (Intermediate 91, 0.1 g, 0.54 mmol), (E)-3-(4-iodo-phenyl)-2-methyl-acrylic acid ethyl ester (Reagent 7, 0.17 g, 0.54 mmol), triethyl amine (10 mL), copper(I)iodide (0.019 g, 0.1 mmol) and dichlorobis(triphenylphosphine)palladium(II)—(0.71 g, 0.1 mmol) followed by flash column chromatography over silica gel (230–400 mesh) using 2–10% ethyl acetate in hexane as the eluent, the title compound was obtained (0.15 g, 75%).

$^1$H NMR (300 MHz, CDCl$_3$): δ 7.66–7.25 (m, 9H), 4.27 (q, J=7.3 Hz, 2H), 3.65 (s, 2H), 2.25 (s, 3H), 2.13 (d, J=1.2 Hz, 3H), 1.75–1.65 (m, 1H), 1.35 (t, J=7.3 Hz, 3H), 0.50–0.40 (m, 4H).

3-(4-{3-[(Cyclopropyl-methyl-amino)-methyl]-phenylethynyl}-phenyl)-2-methyl-acrylic acid (Compound 33)

A solution of 3-(4-{3-[(cyclopropyl-methyl-amino)-methyl]-phenylethynyl}-phenyl)-2-methyl-acrylic acid ethyl ester (Intermediate 94, 0.15 g, 0.4 mmol) in ethanol (3 mL) and tetrahydrofuran (3 mL) was treated with a 3M solution of potassium hydroxide (1 mL, 3 mmol) and the resulting reaction mixture was stirred at ambient temperature for overnight. The reaction mixture was concentrated, neutralized with 5% aqueous hydrochloric acid and extracted with ethyl acetate. The organic phase was washed with water and brine, dried over anhydrous sodium sulfate, filtered and evaporated to a solid. The solid was subjected to flash column chromatography using 5% methanol in ethyl acetate as the eluent to afford the title product as an amorphous solid (0.115 g, 83%).

$^1$H NMR (300 MHz, CDCl$_3$): δ 7.71–7.25 (m, 9H), 3.81 (s, 2H), 2.44 (s, 3H), 2.13 (d, J=1.2 Hz, 3H), 1.92–1.80 (m, 1H), 0.76–0.66 (m, 2H), 0.58–0.48 (m, 2H).

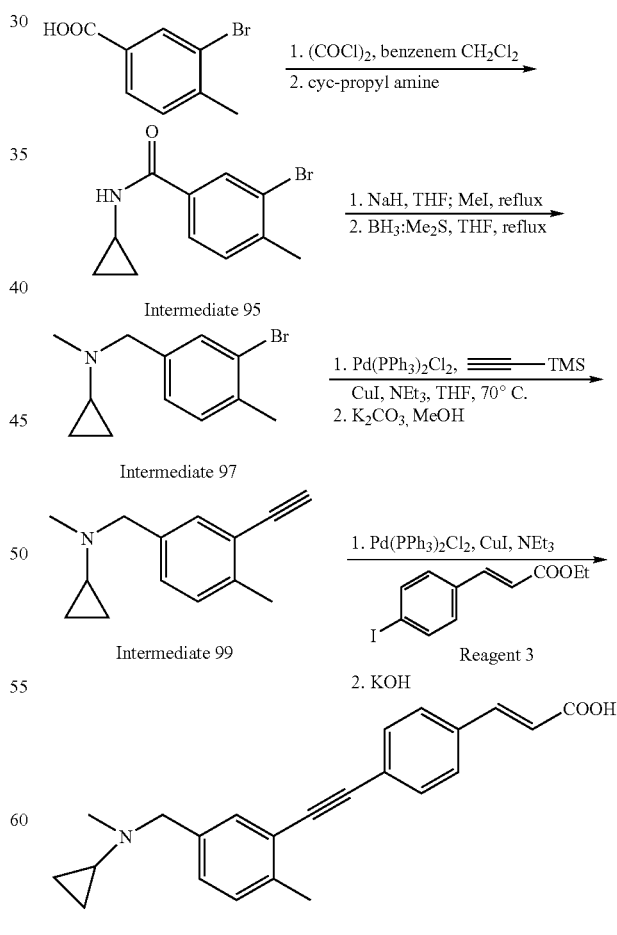

Reaction Scheme 17

Compound 34

3-Bromo-N-cyclopropyl-4-methyl-benzamide (Intermediate 95)

A stirred, cooled (ice bath) solution of 3-bromo-4-methyl-benzoic acid (Aldrich, 5 g, 23.25 mmol) in benzene (50 mL), dichloromethane (10 mL) and N,N-dimethylformamide (0.5 mL) was treated with oxalyl chloride (4 mL, 46.5 mmol). The reaction mixture was allowed to warm to ambient temperature over 3 h. The volatiles were then distilled off in vacuo, the residue was diluted with anhydrous dichloromethane (50 mL) under argon, cooled (ice bath) and treated with 4-(dimethylamino)pyridine (5.67 g, 46.5 mmol) followed by cyclopropyl amine (1.93 mL, 27.9 mmol). After 3 h, the reaction mixture was diluted with dichloromethane and washed with water. The organic phase was dried-over anhydrous sodium sulfate, filtered and evaporated in vacuo to afford the title product that was used as such for the next step (6.0 g,~100%).

3-Bromo-N-cyclopropyl-4,N-dimethyl-benzamide (Intermediate 96)

A stirred, cooled (ice bath) solution of 3-bromo-N-cyclopropyl-4-methyl-benzamide (Intermediate 95, 6 g, 23.25 mmol) in anhydrous tetrahydrofuran (100 mL) under argon was treated with small portions of sodium hydride (1.6 g, 40 mmol, 60% dispersion in mineral oil). The reaction mixture was allowed to warm to ambient temperature and after 1 h, methyl iodide (3.11 mL, 50 mmol) was added and the reaction mixture was refluxed for 5 h. It was cooled to ambient temperature, poured into cold water and extracted with diethyl ether (×2). The combined organic phase was dried over anhydrous magnesium sulfate, filtered and evaporated in vacuo to afford the title product as a dirty brown solid that was used as such for the next step (6.3 g,~100%).

(3-Bromo-4-methyl-benzyl)-cyclopropyl-methyl-amine (Intermediate 97)

A solution of 3-bromo-N-cyclopropyl-4,N-dimethyl-benzamide (Intermediate 96, 5.3 g, 19.77 mmol) in anhydrous tetrahydrofuran (50 mL) was treated with borane-methyl sulfide complex (10 mL, 100 mmol) and the resulting reaction mixture was refluxed for 2 h. It was cooled to ambient temperature and carefully treated with saturated, aqueous sodium carbonate solution till cessation of effervescence, and extracted with diethyl ether (×2). The combined organic phase was dried over anhydrous magnesium sulfate, filtered and evaporated in vacuo to an oil. Flash column chromatography over silica gel (230–400 mesh) using 10% ethyl acetate in hexane as the eluent afforded the title product as an oil (3.2 g, 63%).

$^1$H NMR (300 MHz, CDCl$_3$): δ 7.47 (s, 1H), 7.17 (d, 1H, J=7.8 Hz), 7.12 (d, 1H, J=7.8 Hz), 3.63 (s, 2H), 2.40 (s, 3H), 2.27 (s, 3H), 1.73 (m, 1H), 0.92–0.43 (m, 4H).

Cyclopropyl-methyl-(4-methyl-3-trimethylsilanylethynyl-benzyl)-amine (Intermediate 98)

Following General Procedure D and using cyclopropyl-(3-bromo-4-methyl-benzyl)-methyl-amine (Intermediate 97, 2.24 g, 8.81 mmol), triethyl amine (10 mL), tetrahydrofuran (5 mL), copper(I)iodide (0.4 g, 2.1 mmol), trimethylsilyl acetylene (5 mL, 35.4 mmol) and dichlorobis(triphenylphosphine)palladium(II) (1.45 g, 2.06 mmol) followed by flash column chromatography over silica gel (230–400 mesh) using 6–10% ethyl acetate in hexane as the eluent, the title compound (2.25 g, 94%) was obtained.

$^1$H NMR (300 MHz, CDCl$_3$): δ 7.08 (s, 1H), 6.84 (2s, 2H), 3.31 (s, 2H), 2.15 (s, 3H), 1.95 (s, 3H), 1.41 (m, 1H), 0.25–0.00 (m, 4H), 0.00 (s, 9H).

Cyclopropyl-(3-ethynyl-4-methyl-benzyl)-methyl-amine (Intermediate 99)

A solution of cyclopropyl-methyl-(4-methyl-3-trimethylsilanylethynyl-benzyl)-amine (Intermediate 98, 0.95 g, 3.5 mmol) in methanol (10 mL) was treated with potassium carbonate (2.3 g, 16.6 mmol) and the resulting reaction mixture was stirred at ambient temperature for 1 h. The solvent was evaporated in vacuo, the residue was diluted with water and extracted with diethyl ether. The organic phase was washed with brine, dried over anhydrous magnesium sulfate, filtered and evaporated in vacuo to afford the title compound (0.67 g, 96%).

$^1$H NMR (300 MHz, CDCl$_3$): δ 7.12 (s, 1H), 6.87 (2s, 2H), 3.33 (s, 2H), 2.98 (s, 1H), 2.16 (s, 3H), 1.96 (s, 3H), 1.42 (m, 1H), 0.24–0.00 (m, 4H).

(E)-3-(4-{5-[(Cyclopropyl-methyl-amino)-methyl]-2-methyl-phenylethynyl}-phenyl)-acrylic acid ethyl ester (Intermediate 100)

Following General Procedure B and using cyclopropyl-(3-ethynyl-4-methyl-benzyl)-methyl-amine (Intermediate 99, 0.095 g, 0.48 mmol), ethyl-4-iodo-cinnamate (Reagent 3, 0.144 g, 0.47 mmol), triethyl amine (13 mL), copper(I) iodide (0.019 g, 0.1 mmol) and dichlorobis(triphenylphosphine)palladium(II) (0.071 g, 0.1 mmol) followed by flash column chromatography over silica gel (230–400 mesh) using 5–20% ethyl acetate in hexane as the eluent, the title compound was obtained (0.14 g, 82%).

$^1$H NMR (300 MHz, CDCl$_3$): δ 7.66 (d, 1H, J=15.9 Hz), 7.53 (Abq, 4H, J=6.3 Hz), 7.41 (s, 1H), 7.15 (2s, 2H), 6.44 (d, 1H, J=15.9 Hz), 4.26 (q, 2H, J=7.2 Hz), 3.62 (s, 2H), 2.48 (s, 3H), 2.24 (s, 3H), 1.68 (m, 1H), 1.33 (t, 3H, J=7.2 Hz), 0.49–0.41 (m, 4H).

(E)-3-(4-{5-[(Cyclopropyl-methyl-amino)-methyl]-2-methyl-phenylethynyl}-phenyl)-acrylic acid (Compound 34)

A solution of (E)-3-(4-{5-[(cyclopropyl-methyl-amino)-methyl]-2-methyl-phenylethynyl}-phenyl)-acrylic acid ethyl ester (Intermediate 100, 0.14 g, 0.37 mmol) in ethanol (3 mL) and tetrahydrofuran (3 mL) was treated with a 3M solution of potassium hydroxide (1 mL, 3 mmol) and the resulting reaction mixture was stirred at ambient temperature overnight. The reaction mixture was neutralized with 5% aqueous hydrochloric acid and extracted with ethyl acetate. The organic phase was washed with water and brine, and dried over anhydrous sodium sulfate, filtered and evaporated in vacuo to a residue that was subjected to flash column chromatography over silica gel (230–400 mesh) using 5% methanol in ethyl acetate as the eluent to afford the title product as an amorphous solid (0.071 g, 55%).

$^1$H NMR (300 MHz, CDCl$_3$): δ 7.62 (d, 1H, J=15.9 Hz), 7.61 (s, 1H), 7.38 (s, 4H), 7.19 (s, 2H), 6.56 (d, 1H, J=15.9 Hz), 3.87 (s, 2H), 2.50 (s, 3H), 2.49 (s, 3H), 1.94 (m, 1H), 0.89–0.83 (m, 2H), 0.60–0.57 (m, 2H).

Reaction Scheme 18

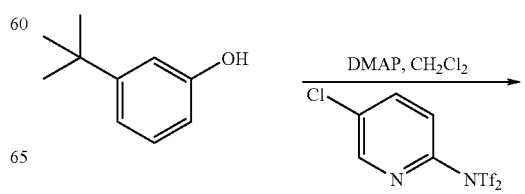

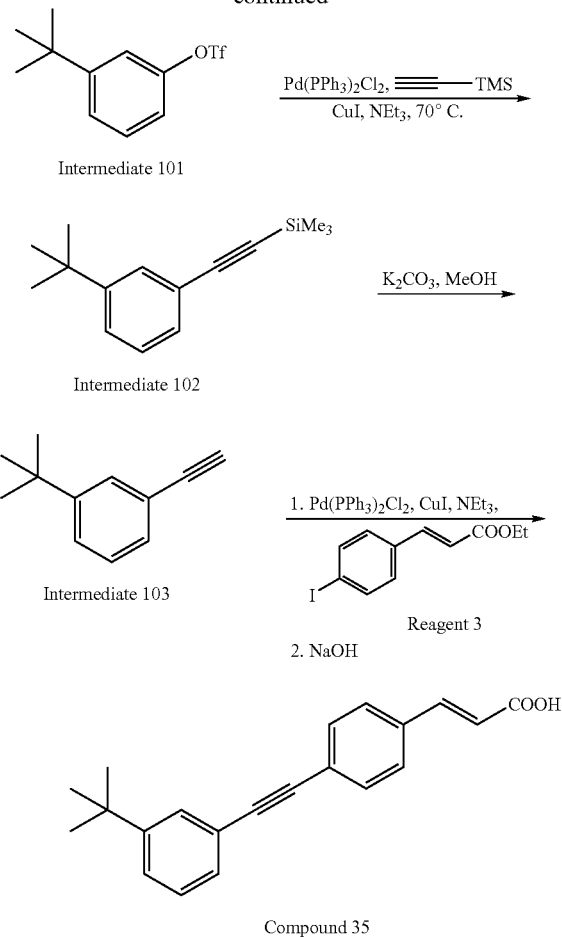

Compound 35

Trifluoro-methanesulfonic acid 3-tert-butyl-phenyl ester (Intermediate 101)

A stirred, cooled (ice bath) solution of 3-tert-butyl phenol (Aldrich, 2 g, 13.3 mmol) in anhydrous dichloromethane (15 mL) was treated with 2-[N,N'-bis(trifluoromethylsulfonyl) amino]-5-chloropyridine (7.8 g, 20 mmol) followed by 4-(dimethylamino)pyridine (3.2 g, 26.6 mmol). The cooling bath was removed and the reaction mixture was stirred at ambient temperature for 18 h. It was diluted with ethyl acetate, washed with 2N hydrochloric acid, 2N sodium hydroxide, and brine, dried over anhydrous magnesium sulfate, filtered and evaporated in vacuo to an oil. Flash column chromatography over silica gel (230–400 mesh) using 10% ethyl acetate in hexane as the eluent afforded the title product as a clear oil (3.06 g, 82%).

$^1$H NMR (300 MHz, CDCl$_3$): δ 7.42–7.32 (m, 2H), 7.24 (d, 1H, J=1.8 Hz), 7.10–1.06 (m, 1H), 1.33 (s, 9H).

(3-tert-Butyl-phenylethynyl)-trimethyl-silane (Intermediate 102)

Following General Procedure D and using trifluoromethanesulfonic acid, 3-tert-butyl-phenyl ester (Intermediate-101, 2.54 g, 0.9.0 mmol), triethyl amine (2 mL), copper(I)iodide (0.63 g, 3.33 mmol), trimethylsilyl acetylene (5 mL, 36 mmol) and, dichlorobis(triphenylphosphine) palladium(II) (1.6 g, 2.25 mmol) followed by flash column chromatography over silica gel (230–400 mesh) using 10% ethyl acetate in hexane as the eluent, the title compound was obtained as a brown oil that was used as such for the next step.

1-tert-Butyl-3-ethynyl-benzene (Intermediate 103)

A solution 3-tert-butyl-trimethylsilanylethynyl benzene (Intermediate 102, 0.47 g, 2.04 mmol) in methanol (20 mL) was treated with potassium carbonate (2.8 g, 20.2 mmol) and the resulting reaction mixture was stirred at ambient temperature for 3 days. The reaction mixture was diluted with ethyl acetate, washed with water and brine, dried over anhydrous magnesium sulfate, filtered and evaporated in vacuo to an oil. Flash column chromatography over silica gel (230–400 mesh) using 10% ethyl acetate in hexane as the eluent afforded the title compound as a light yellow oil (0.125 g, 39%).

$^1$H NMR (300 MHz, CDCl$_3$): δ 7.40 (d, 1H, J=1.5 Hz), 7.39–7.10 (m, 3H), 2.91 (s, 1H), 1.18 (s, 9H).

(E)-3-[4-(3-tert-Butyl-phenylethynyl)-phenyl]-acrylic acid (Compound 35)

A solution of (E)-3-[4-(3-tert-butyl-phenylethynyl)-phenyl]-acrylic acid ethyl ester (Intermediate 103, 0.015 g, 0.047 mmol) in ethanol (2 mL) and tetrahydrofuran (2 mL) was treated with a 2M solution of lithium hydroxide (1 mL, 2 mmol) and the resulting reaction mixture was stirred at ambient temperature overnight. The reaction mixture was neutralized with 10% aqueous hydrochloric acid and evaporated in vacuo to a solid that was washed with water and hexane and dried to afford the title product as a white solid (0.012 g, 85%). $^1$H NMR (300 MHz, CDCl$_3$): δ 7.78 (d, 1H, J=16.2 Hz), 7.59–7.26 (m, 8H), 6.47 (d, 1H, J=16.2 Hz), 1.34 (s, 9H).

Reaction Scheme 19

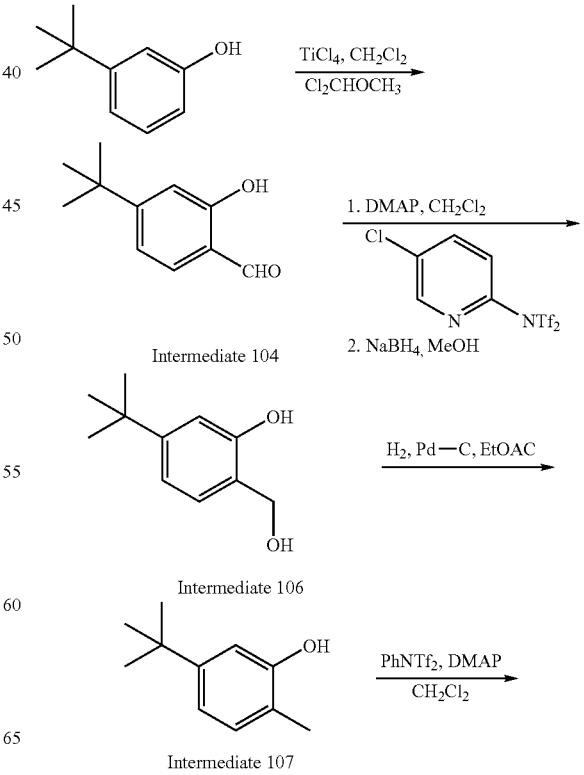

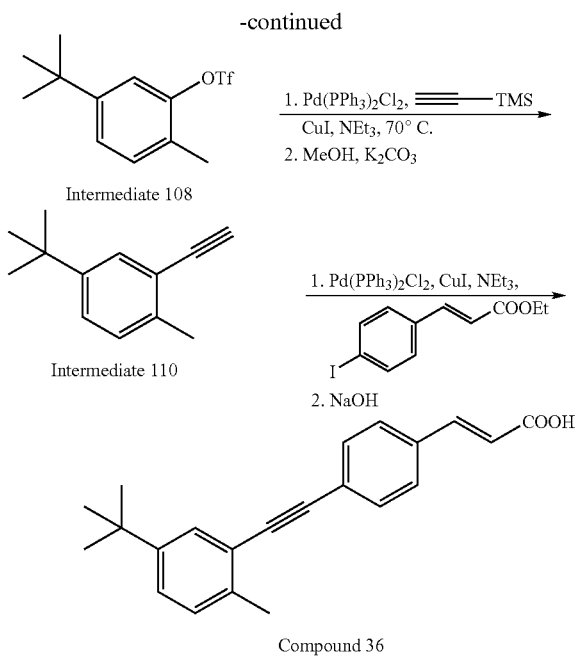

4-tert-Butyl-2-hydroxy-benzaldehyde (Intermediate 104)

A stirred, cooled (ice bath) solution of 3-tert-butyl phenol (1.5 g, 10 mmol) in anhydrous dichloromethane was treated with titanium tetrachloride (1.86 mL, 17 mmol) followed by α,α-dichloromethyl ether (0.9 mL, 20 mmol). The reaction was allowed to warm to ambient temperature over 1 h, quenched cautiously with ice and water and extracted with dichloromethane. The organic extract was washed with water and brine, dried over sodium sulfate, filtered and evaporated in vacuo to a residue that was subjected to flash column chromatography using 2–2.5% ethyl acetate in hexane as the eluent to afford the title compound (1.37 g, 77%).
$^1$H NMR (300 MHz, CDCl$_3$): δ 11.02 (s, 1H), 9.81 (s, 1H), 7.45 (d, J=8.2 Hz, 1H), 7.03 (dd, J=8.2, 1.7 Hz, 1H), 6.99 (d, J=1.7 Hz, 1H), 1.31 (s, 9H).

Trifluoro-methanesulfonic acid 5-tert-butyl-2-formyl-phenyl ester (Intermediate 105)

A stirred, cooled (ice-bath) solution of 4-tert-butyl-2-hydroxy-benzaldehyde (Intermediate 104, 0.75 g, 4.21 mmol) in anhydrous dichloromethane (10 mL) was treated with triethyl amine (1.76 mL, 12.64 mmol) followed by 2-[N,N-bis(trifluoromethylsulfonyl)amino]pyridine (1.81 g, 4.62 mmol). The reaction mixture was allowed to warm to ambient temperature overnight. The volatiles were evaporated and the residue was subjected to flash column chromatography using 2–2.5% ethyl acetate in hexane as the eluent to afford the title compound (0.16 g) and a 1:1 mixture of product and starting material (0.47 g). The title compound was used as such for the next step.

5-tert-Butyl-2-hydroxymethyl-phenol (Intermediate 106)

A stirred, cooled (ice-bath) solution of a 1:1 mixture of trifluoro-methanesulfonic acid 5-tert-butyl-2-formyl-phenyl ester and 4-tert-butyl-2-hydroxy-benzaldehyde (Intermediate 105, 0.47 g) in methanol (8 mL) was treated with sodium borohydride (0.1 g, 2.64 mmol). After 1 h, the reaction mixture was diluted with water and extracted with ethyl acetate. The organic phase was washed with water and brine, dried over anhydrous sodium sulfate, filtered and evaporated in vacuo to a residue that was subjected to flash column chromatography on silica gel (230–400 mesh) to afford the title product (0.3 g).
$^1$H NMR (300 MHz, CDCl$_3$): δ 6.94–6.84 (m, 3H), 4.72 (s, 2H), 1.26 (s, 9H).

5-tert-Butyl-2-methyl-phenol (Intermediate 107)

A solution of 5-tert-butyl-2-hydroxymethyl-phenol (Intermediate 106, 0.215 g, 1.19 mmol) in ethyl acetate was treated with 5% palladium on carbon (0.04 g) and the resulting reaction mixture was stirred under an atmosphere of hydrogen at ambient temperature for 2.5 h. The reaction mixture was then filtered over a bed of celite and the filtrate was evaporated in vacuo to afford the title compound as a white solid (0.19 g, 97%).
$^1$H NMR (300 MHz, CDCl$_3$): δ 7.03 (d, J=7.9 Hz, 1H), 6.86 (dd, J=7.9, 1.7 Hz, 1H), 6.78 (d, J=1.7 Hz, 1H), 5.20 (s, 1H), 2.20 (s, 3H), 1.25 (s, 9H).

Trifluoro-methanesulfonic acid 5-tert-butyl-2-methyl-phenyl ester (Intermediate 108)

A solution of 5-tert-butyl-2-methyl-phenol (Intermediate 107, 0.19 g, 1.15 mmol) and 4-(dimethylamino)pyridine (0.28 g, 2.3 mmol) in anhydrous dichloromethane (8 mL) was treated with N-phenyltrifluoromethanesulfonimide (0.54 g, 1.5 mmol), and the resulting reaction mixture was stirred at ambient temperature overnight. The reaction mixture was concentrated in vacuo and the residue was subjected to flash column chromatography over silica gel (230–400 mesh) to afford the title compound as a colorless oil (0.28 g, 82%).
$^1$H NMR (300 MHz, CDCl$_3$): δ 7.30–7.20 (m, 3H), 2.33 (s, 3H), 1.30 (s, 9H).

(5-tert-Butyl-2-methyl-phenylethynyl)-trimethyl-silane (Intermediate 109)

Following General Procedure D and using trifluoro-methanesulfonic acid 5-tert-butyl-2-methyl-phenyl ester (Intermediate 108, 0.28 g, 0.94 mmol), triethyl amine (3 mL), trimethylsilyl acetylene (1 mL, 7 mmol), N,N-dimethylformamide (6 mL) and dichlorobis(triphenylphosphine)palladium(11) (0.053 g, 0.076 mmol) followed by flash column chromatography over silica gel (230–400 mesh) using hexane as the eluent, the title compound (0.16 g, 69%) was obtained.
$^1$H NMR (300 MHz, CDCl$_3$): δ 7.44 (d, J=1.7 Hz, 1H), 7.22 (dd, J=8.2, 1.7 Hz, 1H), 7.10 (d, J=8.2 Hz, 1H), 2.39 (s, 3H), 1.28 (s, 9H), 0.26 (s, 9H).

4-tert-Butyl-2-ethynyl-1-methyl-benzene (Intermediate 110)

Following general procedure F and using (5-tert-butyl-2-methyl-phenylethynyl)-trimethyl-silane (Intermediate 109, 0.16 g, 0.66 mmol), methanol (5 mL) and potassium carbonate (0.05 g, 0.36 mmol), the title compound was obtained (0.08 g, 67%).
$^1$H NMR (300 MHz, CDCl$_3$): δ 7.49 (d, J=1.7 Hz, 1H), 7.30 (dd, J=8.2, 1.7 Hz, 1H), 7.15 (d, J=8.2 Hz, 1H), 3.16 (s, 1H), 2.42 (s, 3H), 1.32 (s, 9H).

3-[4-(5-tert-Butyl-2-methyl-phenylethynyl)-phenyl]-acrylic acid ethyl ester (Intermediate 111)

Following General Procedure B and using 4-tert-butyl-2-ethynyl-1-methyl-benzene (Intermediate 110, 0.08 g, 0.47 mmol), ethyl-4-iodocinnamate (0.12 g, 0.4 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230–400 mesh) using 2–4% ethyl acetate in hexane as the eluent, the title compound was obtained (0.09 g, 55%).

$^1$H NMR (300 MHz, CDCl$_3$): δ 7.67 (d, J=16.1 Hz, 1H), 7.56–7.48 (m, 5H), 7.28 (dd, J=8.2, 1.7 Hz, 1H), 7.16 (d, J=8.2 Hz, 1H), 6.44 (d, J=16.1 Hz, 1H), 4.27 (q, J=7.1 Hz, 2H), 2.48 (s, 3H), 1.33 (t, J=7.1 Hz, 3H), 1.32 (s, 9H).

3-[4-(5-tert-Butyl-2-methyl-phenylethynyl)-phenyl]-acrylic acid (Compound 36)

A solution of 3-[4-(5-tert-butyl-2-methyl-phenylethynyl)-phenyl]-acrylic acid ethyl ester (Intermediate 111, 0.09 g, 0.26 mmol) in ethanol (3 mL) and tetrahydrofuran (3 mL) was treated with 3M potassium hydroxide solution (1 mL, 3 mmol) and the resulting reaction mixture was stirred overnight at ambient temperature. The reaction mixture was concentrated in vacuo slightly, the residue was neutralized with dilute hydrochloric acid, and the solid that was formed was filtered and washed with water and acetonitrile and dried to afford title product (0.064 g, 77%).

$^1$H NMR (300 MHz, CDCl$_3$): δ 7.78 (d, J=16.1 Hz, 1H), 7.58–7.53 (m, 5H), 7.29 (dd, J=7.9, 1.7 Hz, 1H), 7.17 (d, J=7.9 Hz, 1H), 6.47 (d, J=16.1 Hz, 1H), 2.48 (s, 3H), 1.32 (s, 9H).

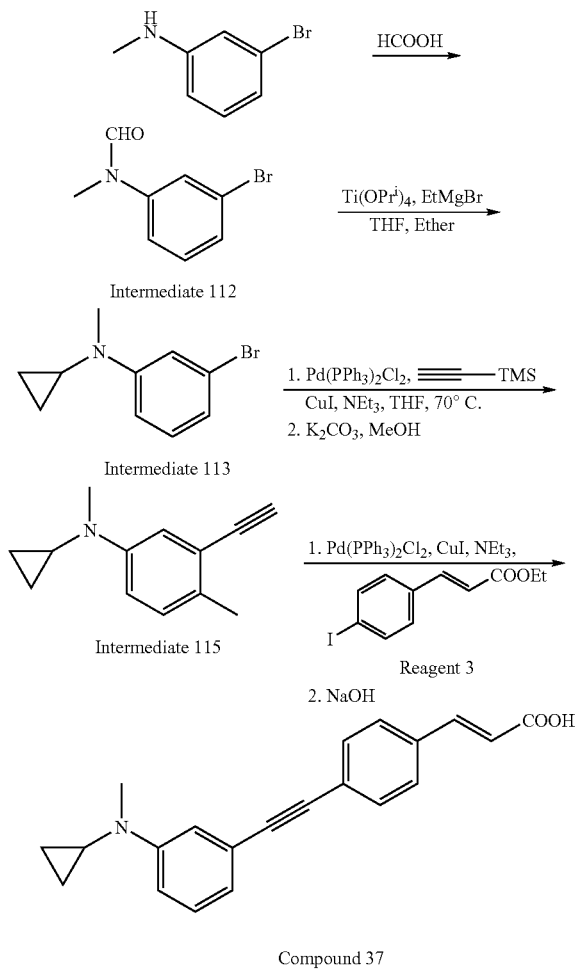

Reaction Scheme 20

Compound 37

N-(3-Bromo-phenyl)-N-methyl-formamide (Intermediate 112)

A solution of 3-bromo-N-methyl aniline (made as described by Lopez et al. in Tet. Lett., 1999, 40, 11, p 2071–2074 incorporated herein by reference; 7.4 g, 39.5 mmol) in formic acid (20 mL) was refluxed for 3 h. The reaction mixture was then cooled to ambient temperature, diluted with water and extracted with diethyl ether. The organic phase was washed with saturated, aqueous sodium bicarbonate solution, water and brine, dried over anhydrous magnesium sulfate, filtered and evaporated in vacuo to afford the title product as a dark brown oil.

(3-Bromo-phenyl)-cyclopropyl-methyl-amine (Intermediate 113)

A stirred, cooled (0° C.) solution of N-(3-bromo-phenyl)-N-methyl-formamide (Intermediate 112, 2.6 g, 9.7 mmol) and titanium tetra-iso-propoxide (3.9 mL, 10.67 mmol) in tetrahydrofuran (40 mL) was treated with a 3M solution of ethyl magnesium bromide in ether (8.08 mL, 24.25 mmol) under argon and the resulting reaction mixture was allowed to warm to ambient temperature gradually and refluxed at 55° C. overnight. It was then cooled in an ice-bath, quenched with saturated aqueous ammonium chloride solution, filtered over celite and the aqueous phase was extracted with diethyl ether. The organic phase was dried over anhydrous magnesium sulfate, filtered and evaporated in vacuo to afford an oil. Flash column chromatography over silica gel (230–400 mesh) using 1.5% ethyl acetate in hexane as the eluent afforded the title compound (0.321 g, 15%).

Cyclopropyl-methyl-(3-trimethylsilanylethynyl-phenyl)-amine (Intermediate 114)

Following General Procedure D and using (3-bromo-phenyl)-cyclopropyl-methyl-amine (Intermediate 113, 0.056 g, 0.25 mmol), triethyl amine (3 mL), copper(I)iodide (0.025 g, 0.13 mmol), trimethylsilyl acetylene (2.5 mL, 17.6 mmol) and dichlorobis(triphenylphosphine)palladium(II) (0.065 g, 0.09 mmol) followed by flash column chromatography over silica gel (230–400 mesh) using 1.5% ethyl acetate in hexane as the eluent, the title compound (0.051 g, 84%) was obtained.

Cyclopropyl-(3-ethynyl-phenyl)-methyl-amine (Intermediate 115)

A solution of cyclopropyl-methyl-(3-trimethylsilanylethynyl-phenyl)-amine (Intermediate 114, 0.05 g, 0.2 mmol) in methanol (5 mL) was treated with potassium carbonate (0.063 g, 0.46 mmol) and the resulting reaction mixture was heated at 80° C. for 3 h. The solvent was evaporated in vacuo, the residue was diluted with water and extracted with diethyl ether. The organic phase was dried over anhydrous magnesium sulfate, filtered and evaporated in vacuo to afford the title compound (0.035 g, 100%).

(E)-3-{4-[3-(Cyclopropyl-methyl-amino)-phenylethynyl]}-acrylic acid ethyl ester (Intermediate 116)

Following General Procedure B and using cyclopropyl-(3-ethynyl-phenyl)-methyl-amine (Intermediate 115, 0.035 g, 0.2 mmol), ethyl-4-iodo-cinnamate (0.082 g, 0.27 mmol), triethyl amine (3 mL), copper(I)iodide (0.025 g, 0.13 mmol) and dichlorobis(triphenylphosphine)palladium(II) (0.033 g, 0.047 mmol) followed by flash column chromatography over silica gel (230–400 mesh), and preparative normal phase HPLC using 10% ethyl acetate in hexane as the mobile phase, the title compound was obtained (0.020 g, 29%).

(E)-3-{4-[3-(Cyclopropyl-methyl-amino)-phenylethynyl]-phenyl}-acrylic acid (Compound 37)

A solution of (E)-3-{4-[3-(cyclopropyl-methyl-amino)-phenylethynyl}-acrylic acid ethyl ester (Intermediate 116, 0.020 g, 0.057 mmol) in ethanol (1 mL) was treated with a 1M solution of sodium hydroxide (1 mL, 1 mmol) and the resulting reaction mixture was heated at 80° C. for 30 minutes. The volatiles were evaporated in vacuo to a residue that was neutralized with saturated aqueous ammonium chloride solution and extracted with ethyl acetate. The organic phase was dried over anhydrous magnesium sulfate, filtered and evaporated in vacuo to afford a residue that on preparative reverse phase HPLC using 10% water in acetonitrile as the mobile phase afforded the title product as a yellow solid (0.006 g, 33%).

Reaction Scheme 21

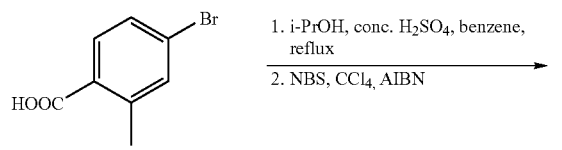

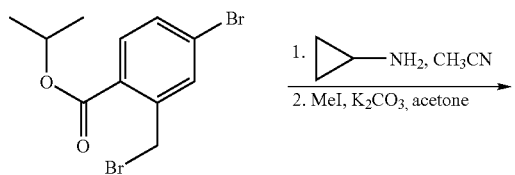

Intermediate 118

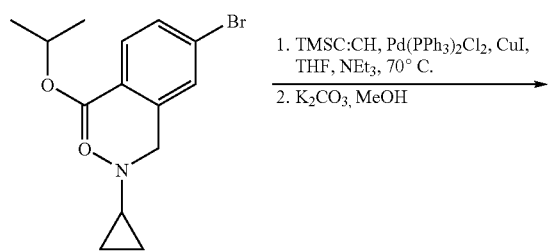

Intermediate 120

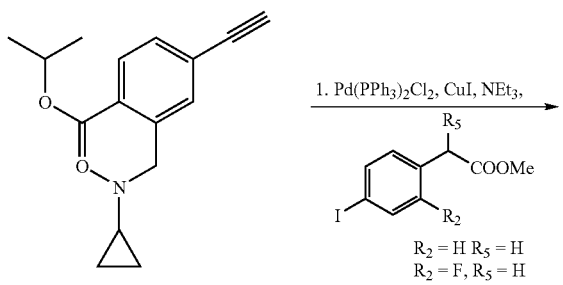

Intermediate 122

Reagent 1 $R_2$ = H, $R_5$ = H
$R_2$ = F, $R_5$ = H
$R_2$ = H, $R_5$ = Me

2. LiOH, MeOH, THF, H$_2$O

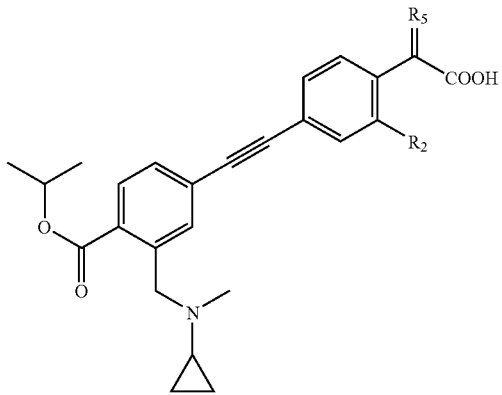

Compound 38 $R_2$ = H $R_5$ = H
Compound 39 $R_2$ = F, $R_5$ = H
Compound 40 $R_2$ = H, $R_5$ = Me

4-Bromo-2-methyl-benzoic acid isopropyl ester (Intermediate 117)

A solution of 4-bromo-2-methyl-benzoic acid (Aldrich, 5.4 g, 25 mmol) in benzene (75 mL) and isopropanol (75 mL) was treated with concentrated sulfuric acid (1.5 mL) and heated to reflux over 4 days using a Dean-Stark water trap. The volatiles were evaporated in vacuo, the residue was diluted with water and extracted with diethyl ether. The organic phase was washed with water and saturated, aqueous sodium bicarbonate solution, dried over anhydrous magnesium sulfate, filtered and evaporated in vacuo to afford the title product as a clear oil that was used as such for the next step (6.12 g, 95%).

4-Bromo-2-bromomethyl-benzoic acid isopropyl ester (Intermediate 118)

A solution of 4-bromo-2-methyl-benzoic acid isopropyl ester (Intermediate 117, 6.12 g, 23.8 mmol) in carbon tetrachloride (120 mL) was treated with N-bromosuccinimide (4.6 g, 26.18 mmol) and 2,2'-azobisisobutyronitrile (0.6 g) and the resulting reaction mixture was refluxed overnight. It was cooled to ambient temperature, the solids were filtered off and washed with 1:1 hexane:diethyl ether, and the filtrate and washings were evaporated in vacuo to afford an oil (5.1 g, 64%) that was used as such for the next step.

4-Bromo-2-cyclopropylaminomethyl-benzoic acid isopropyl ester (Intermediate 119)

A stirred, cooled (ice bath) solution of 4-bromo-2-bromomethyl-benzoic acid isopropyl ester (Intermediate 118, 5.1 g, 15.17 mmol) in acetonitrile (25 mL) was treated with cyclopropyl amine (2 mL, 28.9 mmol). The reaction mixture was allowed to warm to ambient temperature. After 2 h, the volatiles were evaporated in vacuo, the residue was diluted with water and extracted with diethyl ether (×2). The combined organic phase was dried over anhydrous magnesium sulfate, filtered and evaporated in vacuo to an oil. Flash column chromatography over silica gel (230–400 mesh) using 4–20% ethyl acetate in hexane as the eluent to afforded the title product (1.33 g, 28%).

$^1$H NMR (300 MHz, CDCl$_3$): δ 7.73 (d, 1H, J=8.4 Hz), 7.56 (d, 1H, J=2.1 Hz), 7.41 (dd, 1H, J=2.1, 8.4 Hz), 5.21 (heptet, 1H, J=6.3 Hz), 4.00 (s, 2H), 2.39 (br s, 1H), 2.06 (m, 1H), 1.35 (d, 0.6H, J=6.3 Hz), 0.42–0.34 (m, 4H).

4-Bromo-2-[(cyclopropyl-methyl-amino)-methyl]-benzoic acid isopropyl ester (Intermediate 120)

A solution of 4-bromo-2-cyclopropylaminomethyl-benzoic acid isopropyl ester (Intermediate 119, 1.33 g, 4.26 mmol) in acetone (8 mL) was treated with potassium carbonate (2.36 g, 17.05 mmol) and methyl iodide (0.53 mL, 8.52 mmol) and the resulting reaction mixture was stirred at ambient temperature for 3 h. The volatiles were evaporated in vacuo, the residue was diluted with water and extracted with diethyl ether (×2). The combined organic phase was dried over anhydrous magnesium sulfate, filtered over a short bed of silica gel (230–400 mesh) and evaporated in vacuo to afford the title product (1.23 g, 70%).

$^1$H NMR (300 MHz, CDCl$_3$): δ 7.64 (d, 1H, J=2.1 Hz), 7.58 (d, 1H, J=8.4 Hz), 7.39 (dd, 1H, J=2.1, 8.4 Hz), 5.20 (heptet, 1H, J=6.0 Hz), 3.97 (s, 2H), 2.22 (s, 3H), 1.77 (m, 1H), 1.35 (d, 6H, J=6.0 Hz), 0.46–0.38 (m, 4H).

2-[(Cyclopropyl-methyl-amino)-methyl]-4-trimethylsilanylethynyl-benzoic acid isopropyl ester (Intermediate 121)

Following General Procedure D and using 4-bromo-2-[(cyclopropyl-methyl-amino)-methyl]-benzoic acid isopropyl ester (Intermediate 120, 1.23 g, 3.68 mmol), triethyl amine (10 mL), tetrahydrofuran (5 mL), copper(I)iodide (0.21 g, 1.1 mmol), trimethylsilyl acetylene (2.1 mL, 14.7 mmol) and dichlorobis(triphenylphosphine)palladium(II) (0.77 g, 1.1 mmol) followed by flash column chromatography over silica gel (230–400 mesh) using 7% ethyl acetate in hexane as the eluent, the title compound was obtained as an oil (1.2 g,~100%).

$^1$H NMR (300 MHz, CDCl$_3$): δ 7.62 (d, 1H, J=8.1 Hz), 7.53 (s, 1H), 7.35 (d, 1H, J=8.4 Hz), 5.20 (heptet, 1H, J=6.3 Hz), 3.95 (s, 2H), 2.22 (s, 3H), 1.74 (m, 1H), 1.36 (d, 6H, J=6.3 Hz), 0.37–0.28 (m, 4H), 0.27 (s, 9H).

2-[(Cyclopropyl-methyl-amino)-methyl]-4-ethynyl-benzoic acid isopropyl ester (Intermediate 122)

A solution 2-[(cyclopropyl-methyl-amino)-methyl]-4-trimethylsilanylethynyl-benzoic acid isopropyl ester (Intermediate 121, 0.34 g, 1 mmol) in methanol (2 mL) was treated with potassium carbonate (0.207 g, 1.5 mmol) and the resulting reaction mixture was stirred at ambient temperature for 4 h. The volatiles were evaporated in vacuo, the residue was diluted with water and extracted with diethyl ether, dried over anhydrous magnesium sulfate, filtered and evaporated in vacuo to afford the title compound as an oil (0.21 g, 78%).

$^1$H NMR (300 MHz, CDCl$_3$): δ 7.67 (d, 1H, J=7.8 Hz), 7.64 (d, 1H, J=1.8 Hz), 7.38 (dd, 1H, J=1.8, 7.8 Hz), 5.21 (heptet, 1H, J=6.0 Hz), 3.96 (s, 2H), 3.16 (s, 1H), 2.22 (s, 3H), 1.74 (m, 1H), 1.36 (d, 6H, J=6.0 Hz), 0.44–0.33 (m, 4H).

2-[(Cyclopropyl-methyl-amino)-methyl]4-(4-methoxycarbonylmethyl-phenylethynyl)-benzoic acid isopropyl ester (Intermediate 123)

Following General Procedure B and using 2-[(cyclopropyl-methyl-amino)-methyl]-4-ethynyl-benzoic acid isopropyl ester (Intermediate 122, 0.09 g, 0.33 mmol), 4-iodophenyl acetic acid methyl ester (0.09 g, 0.33 mmol), triethyl amine (2 mL), copper(I)iodide (0.04 g, 0.21 mmol) and dichlorobis(triphenylphosphine)palladium(II) (0.1 g, 0.14 mmol) followed by flash-column chromatography over silica gel (230–400 mesh) using 10–15% ethyl acetate in hexane as the eluent, the title compound was obtained as an oil. (0.1 g, 72%).

$^1$H NMR (300 MHz, CDCl$_3$): δ 7.70 (d, 1H, J=7.8 Hz), 7.62 (d, 1H, J=1.8 Hz), 7.52 (d, 2H, J=8.1 Hz), 7.43 (dd, 1H, J=1.8, 7.8 Hz), 7.28 (d, 2H, J=8.1 Hz), 5.25 (heptet, 1H, J=6.0 Hz), 4.00 (s, 2H), 3.71 (s, 3H), 3.65 (s, 2H), 2.26 (s, 3H), 1.78 (m, 1H), 1.38 (d, 6H, J=6.0 Hz), 0.44–0.40 (m, 4H).

4-(4-Carboxymethyl-phenylethynyl)-2-[(cyclopropyl-methyl-amino)-methyl]-benzoic acid isopropyl ester (Compound 38)

A solution of 2-[(cyclopropyl-methyl-amino)-methyl]-4-(4-methoxycarbonylmethyl-phenylethynyl)-benzoic acid isopropyl ester (Intermediate 123, 0.1 g, 0.23 mmol) in a mixture of methanol (2 mL), tetrahydrofuran (2 mL) and water (1 mL) was treated with lithium hydroxide monohydrate (0.042 g, 1 mmol) and the resulting reaction mixture was stirred at ambient temperature for 2 h. The volatiles were evaporated in vacuo, the residue was neutralized with saturated, aqueous ammonium chloride solution and extracted with ethyl acetate. The combined organic extract was dried over anhydrous magnesium sulfate, filtered and evaporated in vacuo to a solid. Preparative reverse phase HPLC using 10% water in acetonitrile as the mobile phase afforded the title product as a white solid (0.068 g, 72%).

$^1$H NMR (300 MHz, CDCl$_3$): δ 9.05 (br s, 1H), 7.73 (d, 1H, J=8.4 Hz), 7.66 (s, 1H), 7.44–7.37 (m, 3H), 7.23–7.21 (m, 2H), 5.20 (heptet, 1H, J=6.0 Hz), 4.21 (s, 2H), 3.52 (s, 2H), 2.36 (s, 3H), 1.94 (m, 1H), 1.36 (d, 6H, J=6.0 Hz), 0.55–0.43 (m, 4H).

2-[(Cyclopropyl-methyl-amino)-methyl]-4-(3-fluoro-4-methoxycarbonylmethyl-phenylethynyl)-benzoic acid isopropyl ester (Intermediate 124)

Following General Procedure B and using 2-[(cyclopropyl-methyl-amino)-methyl]-4-ethynyl-benzoic acid isopropyl ester (Intermediate 122, 0.05 g, 0.18 mmol), 2-fluoro-4-iodo phenylacetic acid methyl ester (0.07 g, 0.24 mmol), triethyl amine (2 mL), copper(I)iodide (0.04 g, 0.21 mmol) and dichlorobis(triphenylphosphine)palladium(II) (0.07 g, 0.11 mmol) followed by flash column chromatography over silica gel (230–400 mesh) using 15–16% ethyl acetate in hexane as the eluent, the title compound was obtained as an oil (0.04 g, 50%).

$^1$H NMR (300 MHz, CDCl$_3$): δ 7.63 (d, 1H, J=7.8 Hz), 7.55 (d, 1H, J=1.2 Hz), 7.35 (dd, 1H, J=1.2, 7.8 Hz), 7.26–7.17 (m, 3H), 5.16 (heptet, 1H, J=6.3 Hz), 3.93 (s, 2H), 3.66 (s, 3H), 3.64 (s, 2H), 2.20 (s, 3H), 1.71 (m, 1H), 1.31 (d, 6H, J=6.3 Hz), 0.40–0.33 (m, 4H).

4-(4-Carboxymethyl-3-fluoro-phenylethynyl)-2-[(cyclopropyl-methyl-amino)-methyl]-benzoic acid isopropyl ester (Compound 39)

A solution of 2-[(cyclopropyl-methyl-amino)-methyl]-4-(3-fluoro-4-methoxycarbonylmethyl-phenylethynyl)-benzoic acid isopropyl ester (Intermediate 124, 0.04 g, 0.09 mmol) in a mixture of methanol (2 mL), tetrahydrofuran (2 mL) and water (1 mL) was treated with lithium hydroxide monohydrate (0.042 g, 1 mmol) and the resulting reaction mixture was stirred at ambient temperature for 2 h. The volatiles were evaporated in vacuo, the residue was neutralized with saturated, aqueous ammonium chloride solution and extracted with ethyl acetate. The combined organic extract was dried over anhydrous magnesium sulfate, filtered and evaporated in vacuo to a solid. Preparative reverse phase HPLC using 10% water in acetonitrile as the mobile phase afforded the title product as a white solid (0.026 g, 54%).

$^1$H NMR (300 MHz, CDCl$_3$): δ 7.71 (d, 1H, J=8.1 Hz), 7.64 (s, 1H), 7.41 (d, 1H, J=8.1 Hz), 7.17–7.09 (m, 3H), 5.20

(heptet, 1H, J=6.3 Hz), 4.16 (s, 2H), 3.54 (s, 2H), 2.34 (s, 3H), 1.91 (m, 1H), 1.36 (d, 6H, J=6.3 Hz), 0.50–0.41 (m, 4H).

2-[(Cyclopropyl-methyl-amino)-methyl]-4-(4-methoxycarbonylmethyl-phenylethynyl)-benzoic acid isopropyl ester (Intermediate 125)

Following General Procedure B and using 2-[(cyclopropyl-methyl-amino)-methyl]-4-ethynyl-benzoic acid isopropyl ester (Intermediate 122, 0.07 g, 0.26 mmol), methyl-2-(4-iodophenyl)-propionate (Reagent 1, 0.081 g, 0.29 mmol), triethyl amine (2 mL), copper(I)iodide (0.03 g, 0.158 mmol) and dichlorobis(triphenylphosphine)palladium(II) (0.07 g, 0.1 mmol) followed by flash column chromatography over silica gel (230–400 mesh) using 10–15% ethyl acetate in hexane as the eluent, the title compound was obtained as an oil (0.09 g, 81%).

$^1$H NMR (300 MHz, CDCl$_3$): δ 7.57 (d, 1H, J=8.1 Hz), 7.49 (d, 1H, J=1.8 Hz), 7.39 (d, 2H, J=8.4 Hz), 7.30 (dd, 1H, J=1.8, 8.1 Hz), 7.18 (d, 2H, J=8.4 Hz), 5.10 (heptet, 1H, J=6.0 Hz), 3.88 (s, 2H), 3.63 (q, 1H, J=7.2 Hz), 3.56 (s, 3H), 2.13 (s, 3H), 1.65 (m, 1H), 1.40 (d, 3H, J=7.2 Hz), 1.25 (d, 6H, J=6.0 Hz), 0.35–0.27 (m, 4H).

4-[4-(1 Carboxy-ethyl)-phenylethynyl]-2-[(cyclopropyl-methyl-amino)-methyl]-benzoic acid isopropyl ester (Compound 40)

A solution of 2-[(cyclopropyl-methyl-amino)-methyl]-4-(4-methoxycarbonylmethyl-phenylethynyl)-benzoic acid isopropyl ester (Intermediate 125, 0.09 g, 0.21 mmol) in a mixture of methanol (2 mL), tetrahydrofuran (2 mL) and water (1 mL) was treated with lithium hydroxide monohydrate (0.042 g, 1 mmol) and the resulting reaction mixture was stirred at ambient temperature for 4 h. The volatiles were evaporated in vacuo, the residue was neutralized with saturated, aqueous ammonium chloride solution and extracted with ethyl acetate. The combined organic extract was dried over anhydrous magnesium sulfate, filtered and evaporated in vacuo to afford the title product as a white solid foam (0.053 g, 61%).

$^1$H NMR (300 MHz, CDCl$_3$): δ 7.68 (d, 1H, J=8.1 Hz), 7.58 (d, 1H, J=1.8 Hz), 7.44–7.25 (m, 5H), 5.13 (heptet, 1H, J=6.0 Hz), 4.18 (s, 2H), 3.79 (m, 1H), 2.32 (s, 3H), 1.89 (m, 1H), 1.39 (d, 3H, J=6.6 Hz), 1.28 (d, 6H, J=6.3 Hz), 0.52–0.21 (m, 4H).

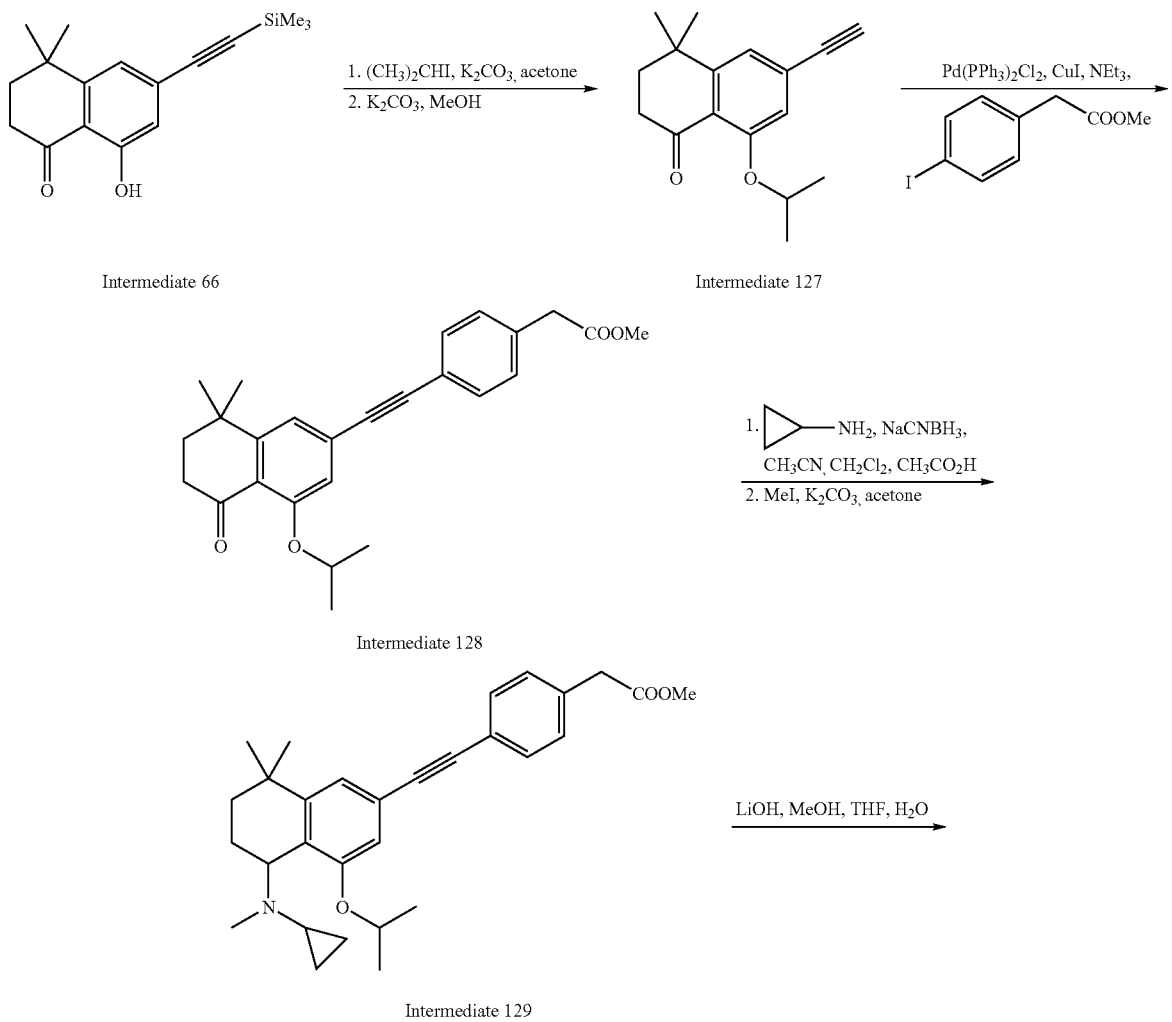

Reaction Scheme 21

-continued

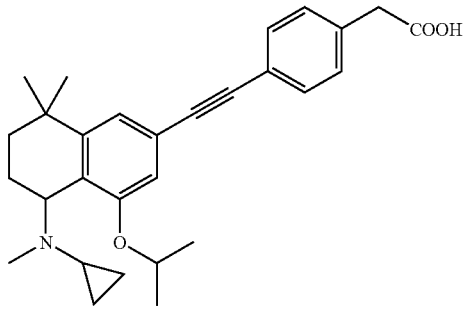

Compound 41

4,4-Dimethyl-8-(2-propoxy)-6-trimethylsilanylethynyl-3,4-dihydro-2H-naphthalen-1-one (Intermediate 126)

A solution of 8-hydroxy-4,4-dimethyl-6-trimethylsilanylethynyl-3,4-dihydro-2H-naphthalen-1-one (Intermediate 66, 0.32 g, 1.12 mmol) in acetone (20 mL) was treated with potassium carbonate (0.773 g, 5.6 mmol) and 2-iodopropane (2 g, 11.76 mmol) and the resulting reaction mixture was refluxed for 3 days. It was cooled to ambient temperature, the solids were filtered off and the filtrate was evaporated in vacuo to an oil that was subjected to flash column chromatography over silica gel (230–400 mesh) using 2–6% ethyl acetate in hexane as the eluent to afford the title product as (0.055 g, 15%).

$^1$H NMR (300 MHz, CDCl$_3$): δ 7.04 (d, 1H, J=1.2 Hz), 6.89 (d, 1H, J=1.2 Hz), 4.57 (heptet, 1H, J=6.3 Hz), 2.66 (t, 2H, J=7.2 Hz), 1.92 (t, 2H, J=7.2 Hz), 1.38 (d, 6H, J=6.3 Hz), 1.33 (s, 6H), 0.27 (s, 9H).

4,4-Dimethyl-6-ethynyl-8-(2-propoxy)-3,4-dihydro-2H-naphthalen-1-one (Intermediate 127)

A solution 4,4-dimethyl-8-(2-propoxy)-6-trimethylsilanylethynyl-3,4-dihydro-2H-naphthalen-1-one (Intermediate 126, 0.055 g, 0.167 mmol) in methanol (5 mL) was treated with potassium carbonate (0.03 g, 0.22 mmol) and the resulting reaction mixture was stirred at ambient temperature overnight. The solvent was evaporated in vacuo, the residue was diluted with water and extracted with ethyl acetate. The organic phase was washed with brine, dried over anhydrous magnesium sulfate, filtered and evaporated in vacuo to afford the title compound (0.042 g, 98%).

$^1$H NMR (300 MHz, CDCl$_3$): δ 7.08 (d, 1H, J=1.2 Hz), 6.93 (d, 1H, J=1.2 Hz), 4.56 (heptet, 1H, J=6.0 Hz), 3.19 (s, 1H), 2.67 (t, 2H, J=6.9 Hz), 1.93 (t, 2H, J=6.9 Hz), 1.39 (d; 6H, J=6.0 Hz), 1.34 (s, 6H).

{4-[8,8-Dimethyl-5-oxo-4-(2-propoxy)-5,6,7,8-tetrahydro-naphthalen-2-ylethynyl]-phenyl}-acetic acid methyl ester (Intermediate 128)

Following General Procedure B and using 4,4-dimethyl-6-ethynyl-8-(2-propoxy)-3,4-dihydro-2H-naphthalen-1-one (Intermediate 127, 0.075 g, 0.29 mmol), 4-iodo phenyl acetic acid methyl ester (0.081 g, 0.29 mmol), triethyl amine (8 mL), tetrahydrofuran (3 mL), copper(I)iodide (0.019 g, 0.1 mmol) and dichlorobis(triphenylphosphine)palladium (II) (0.07 g, 0.1 mmol) followed by flash column chromatography over silica gel (230–400 mesh) using 5–15% ethyl acetate in hexane as the eluent, the title compound was obtained as a yellow oil (0.07 g, 64%).

$^1$H NMR (300 MHz, CDCl$_3$): δ 7.52 (d, 2H, J=8.4 Hz), 7.29 (d, 2H, J=8.4 Hz), 7.12 (d, 1H, J=1.5 Hz), 6.97 (d, 1H, J=1.5 Hz), 4.60 (heptet, 1H, J=5.8 Hz), 3.71 (s, 3H), 3.66 (s, 2H), 2.68 (t, 2H, J=6.6 Hz), 1.95 (t, 2H, J=6.6 Hz), 1.41 (d, 6H, J=5.8 Hz), 1.36 (s, 6H).

{4-[5-(Cyclopropyl-methyl-amino)-4-isopropoxy-8,8-dimethyl-5,6,7,8-tetrahydro-naphthalen-2-ylethynyl]-phenyl}-acetic acid methyl ester (Intermediate 129)

A solution of {4-[8,8-dimethyl-5-oxo-4-(2-propoxy)-5,6,7,8-tetrahydro-naphthalen-2-ylethynyl]-phenyl}-acetic acid methyl ester (Intermediate 128, 0.07 g, 0.187 mmol) in dichloromethane (3 mL) and acetonitrile (1.5 mL) was treated with cyclopropyl amine (1 mL, 14.45 mmol). After 5 minutes, acetic acid (1 mL) was added followed by sodium cyanoborohydride (0.12 g, 1.91 mmol). The reaction mixture was stirred overnight at ambient temperature. It was then diluted with water and saturated aqueous sodium carbonate solution and extracted with dichloromethane (×2). The combined organic extract was dried over anhydrous sodium sulfate, filtered and evaporated in vacuo to an oil. The oil was dissolved in acetone (15 mL) and treated with potassium carbonate (0.2 g, 1.45 mmol)-followed by methyl iodide (1-mL, 15.8 mmol) and the resulting reaction mixture was stirred overnight at ambient temperature. The precipitated solids were filtered off, the filtrate was evaporated in vacuo to a residue. Flash column chromatography over silica gel (230–400 mesh) using 2.5–6% ethyl acetate in hexane as the eluent afforded the title compound (0.045 g, 53%).

$^1$H NMR (300 MHz, CDCl$_3$): δ 7.50 (d, 2H, J=8.4 Hz), 7.26 (d, 2H, J=8.4 Hz), 7.12 (d, 1H, J=1.5 Hz), 6.77 (d, 1H, J=1.5 Hz), 4.58 (heptet, 1H, J=6.3 Hz), 4.04 (m, 1H), 3.70 (s, 3H), 3.64 (s, 2H), 2.32 (s, 3H), 2.10–1.95 (m, 2H), 1.84–1.78 (m, 1H), 1.66–1.60 (m, 1H), 1.40–1.26 (m, 1H), 1.39 and 1.35 (2d, 6H, J=6.3 Hz), 1.34 (s, 3H), 1.19 (s, 3H), 0.29–0.22 (m, 2H), 0.083–0.00 (m, 2H).

{4-[5-(Cyclopropyl-methyl-amino)-4-isopropoxy-8,8-dimethyl-5,6,7,8-tetrahydro-naphthalen-2-ylethynyl]-phenyl}-acetic acid (Compound 41)

A solution of {4-[5-(cyclopropyl-methyl-amino)-4-isopropoxy-8,8-dimethyl-5,6,7,8-tetrahydro-naphthalen-2-ylethynyl]-phenyl}-acetic acid methyl ester (Intermediate 129, 0.045 g, 0.098 mmol) in methanol (2 mL) and tetrahydrofuran (2 mL) was treated with 2M lithium hydroxide (1 mL, 2 mmol) and the resulting reaction mixture was stirred at ambient temperature for 2 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to a residue that was subjected to flash column chromatography over silica gel (230–400 mesh) using 5% methanol in ethyl acetate as the eluent to afford the title product as a white solid (0.027 g, 61%).

¹H NMR (300 MHz, CDCl₃): δ 7.46 (d, 2H, J=8.1 Hz), 7.29 (d, 2H, J=8.1 Hz, 7.14 (d, 1H, J=1.2 Hz) 6.80 (d, 1H, J=1.2 Hz), 4.62 (heptet, 1H, J=6.0 Hz), 4.31 (m, 1H), 3.58 (s, 2H), 2.46 (s, 3H), 2.46–2.39 (m, 1H), 2.14–1.87 (m, 2H), 1.72–1.67 (m, 1H), 1.42–1.23 (m, 1H), 1.40 and 1.34 (2d, 6H, J=6.0 Hz), 1.31 (s, 3H), 1.16 (s, 3H), 0.80–0.70 (m, 1H), 0.53–0.38 (m, 2H), 0.23–0.18 (m, 1H).

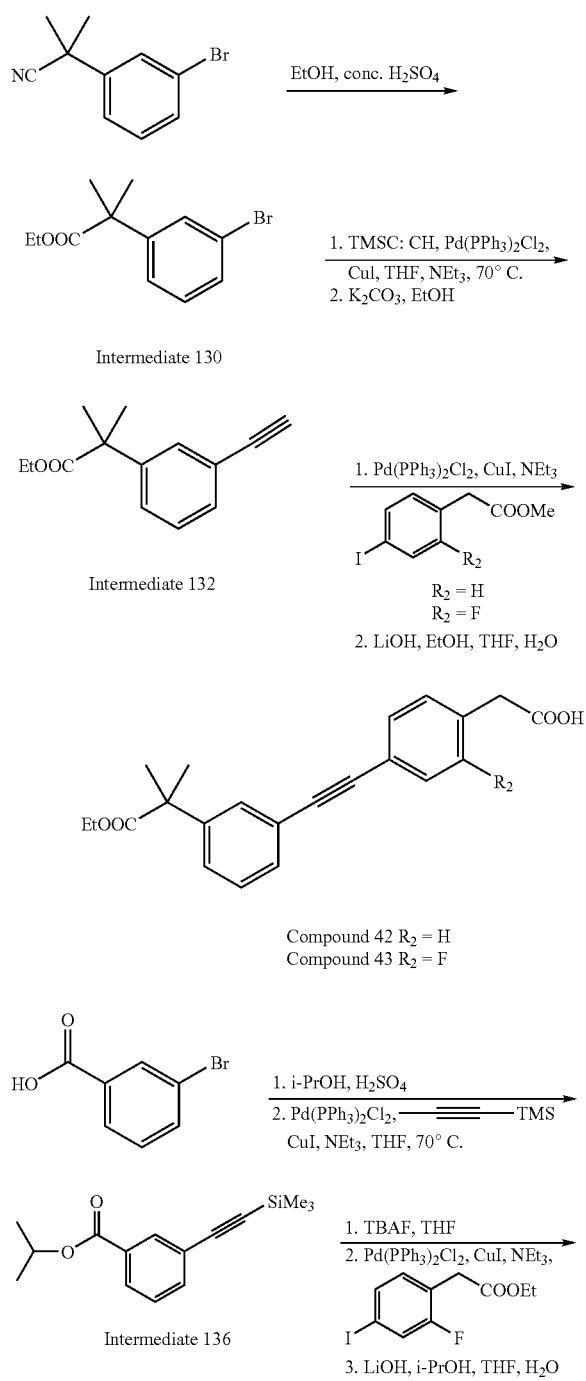

Reaction Scheme 23

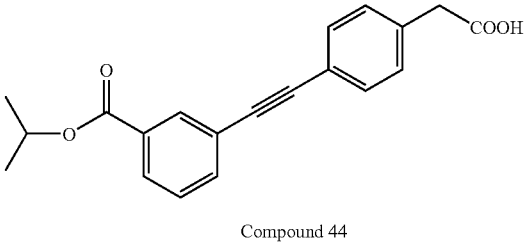

Compound 44

2-(3-Bromo-phenyl)-2-methyl-propionic acid ethyl ester (Intermediate 130)

A solution of 2-(3-bromo-phenyl)-2-methyl-propionitrile (prepared as described by Barlaam et al. *J. Med. Chem.*, 1999, 42, 23, 4890–4908 incorporated herein by reference; 1.4 g, 6.24 mmol) was dissolved in ethanol (40 mL), treated with concentrated sulfuric acid (1 mL) and the resulting reaction mixture was refluxed for 36 h. The reaction mixture was cooled to ambient temperature, diluted with water and extracted with ethyl acetate. The organic phase was washed with water and brine, dried over anhydrous magnesium sulfate, filtered and evaporated in vacuo to a residue that was subjected to flash column chromatography over silica gel (230–400 mesh) using 5% ethyl acetate in hexane as the eluent to afford the title product as an orange oil (0.77 g, 46%).

¹H NMR (300 MHz, CDCl₃): δ 7.48 (s, 1H), 7.36 (dd, 1H, J=2.8, 7.7 Hz), 7.26 (dd, 1H, J=2.8, 8.3 Hz), 7.20 (dd, 1H, J=7.8, 8.3 Hz), 4.12 (q, 2H, J=7.0 Hz), 1.55 (s, 6H), 1.18 (t, 3H, J=7.0 Hz).

2-Methyl-2-(3-trimethylsilanylethynyl-phenyl)-propionic acid ethyl ester (Intermediate 131)

Following General Procedure D and using 2-(3-bromo-phenyl)-2-methyl-propionic acid ethyl ester (Intermediate 130, 0.77 g, 2.84 mmol), triethyl amine (5 mL), copper(I) iodide (0.044 g, 0.23 mmol), trimethylsilyl acetylene (2 mL, 14.1 mmol) and dichlorobis(triphenylphosphine)palladium (II) (0.159 g, 0.23 mmol) followed by flash column chromatography over silica gel (230–400 mesh) using hexane to 5% ethyl acetate in hexane as the eluent, the title compound (0.74 g, 90%) was obtained as an orange oil.

¹H NMR (300 MHz, CDCl₃): δ 7.45 (s, 1H), 7.33–7.24 (m, 3H), 4.12 (q, 2H, J=7.0 Hz), 1.56 (s, 6H), 1.17 (t, 3H, J=7.0 Hz), 0.25 (s, 9H).

2-(3-Ethynyl-phenyl)-2-methyl-propionic acid ethyl ester (Intermediate 132)

A solution of 2-methyl-2-(3-trimethylsilanylethynyl-phenyl)-propionic acid ethyl ester (Intermediate 131, 0.74 g, 2.56 mmol) in ethanol (10 mL) was treated with potassium carbonate (0.2 g, 1.45 mmol). The resulting reaction mixture was stirred at ambient temperature overnight. The volatiles were evaporated in vacuo and the residue was diluted with water and extracted with diethyl ether. The organic phase was washed with water and brine, dried over anhydrous magnesium sulfate, filtered and evaporated in vacuo to a residue that was subjected to flash column chromatography over silica gel (230–400 mesh) using 1–5% ethyl acetate in hexane as the eluent to afford the title product (0.4 g, 72%).

¹H NMR (300 MHz, CDCl₃): δ 7.56 (s, 1H), 7.45–7.33 (m, 3H), 4.18 (q, 2H, J=7.0 Hz), 3.14 (s, 1H), 1.63 (s, 6H), 1.24 (t, 3H, J=7.0 Hz).

2-[3-(4-Methoxycarbonylmethyl-phenylethynyl)-phenyl]-2-methyl-propionic acid ethyl ester (Intermediate 133)

Following General Procedure B and using 2-(3-ethynyl-phenyl)-2-methyl-propionic acid ethyl ester (Intermediate 132, 0.101 g, 0.47 mmol), 4-iodo phenyl acetic acid methyl ester (0.129 g, 0.47 mmol), triethyl amine (8 mL), copper (I)iodide (0.01 g, 0.05 mmol) and dichlorobis(triphenylphosphine)palladium(II) (0.035 g, 0.05 mmol) followed by flash column chromatography over silica gel (230–400 mesh) using 10–15% ethyl acetate in hexane as the eluent, the title compound was obtained as an oil (0.14 g, 82%).

¹H NMR (300 MHz, CDCl₃): δ 7.52–7.25 (m, 8H), 4.13 (q, 2H, J=7.0 Hz), 3.70 (s, 3H), 3.64 (s, 2H), 1.58 (s, 6H), 1.18 (t, 3H, J=7.0 Hz).

2-[3-(4-Methoxycarbonylmethyl-phenylethynyl)-phenyl]-2-methyl-propionic acid (Compound 42)

A solution of 2-[3-(4-methoxycarbonylmethyl-phenylethynyl)-phenyl]-2-methyl-propionic acid ethyl ester (Intermediate 133, 0.12 g, 0.33 mmol) in ethanol (2 mL) and tetrahydrofuran (2 mL) was treated with 2M lithium hydroxide (1 mL, 2 mmol) and the resulting reaction mixture was stirred at ambient temperature for 1 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product as an oil (0.11 g, 95%).

¹H NMR (300 MHz, CDCl₃): δ 7.48 (s, 1H), 7.35–7.04 (m, 7H), 4.11 (q, 2H, J=7.0 Hz), 3.32 (s, 2H), 1.50 (s, 6H), 1.11 (t, 3H, J=7.0 Hz).

2-[3-(3-Fluoro-4-methoxycarbonylmethyl-phenylethynyl)-phenyl]-2-methyl-propionic acid ethyl ester (Intermediate 134)

Following General Procedure B and using 2-(3-ethynyl-phenyl)-2-methyl-propionic acid ethyl ester (Intermediate 132, 0.10 g, 0.46 mmol), 2-fluoro-4-iodo phenyl acetic acid methyl ester (0.136 g, 0.46 mmol), triethyl amine (8 mL), copper(I)iodide (0.01 g, 0.05 mmol) and dichlorobis(triphenylphosphine)palladium(II) (0.035 g, 0.05 mmol) followed by flash column chromatography over silica gel (230–400 mesh) using 10–15% ethyl acetate in hexane as the eluent, the title compound was obtained as an oil (0.15 g, 85%).

¹H NMR (300 MHz, CDCl₃): δ 7.52 (s, 1H) 7.39–7.21 (m, 6H), 4.13 (q, 2H, J=7.0 Hz), 3.71 (s, 3H), 3.68 (s, 2H), 1.58 (s, 6H), 1.18 (t, 3H, J=7.0 Hz).

2-[3-(3-Fluoro-4-methoxycarbonylmethyl-phenylethynyl)-phenyl]-2-methyl-propionic acid (Compound 43)

A solution of 2-[3-(3-fluoro-4-methoxycarbonylmethyl-phenylethynyl)-phenyl]-2-methyl-propionic acid ethyl ester (Intermediate 134, 0.13 g, 0.34 mmol) in ethanol (2 mL) and tetrahydrofuran (2 mL) was treated with 2M lithium hydroxide (1 mL, 2 mmol) and the resulting reaction mixture was stirred at ambient temperature for 45 minutes. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.125 g,~100%).

¹H NMR (300 MHz, CDCl₃): δ 7.48 (s, 1H) 7.34–7.06 (m, 6H), 4.10 (q, 2H, J=7.0 Hz), 3.41 (s, 2H), 1.52 (s, 6H), 1.13 (t, 3H, J=7.0 Hz).

3-Bromo-benzoic acid isopropyl ester (Intermediate 135)

A solution of 3-bromo benzoic acid (Aldrich, 2.4 g, 11.9 mmol) in isopropanol (20 mL) was treated with 1 mL of concentrated sulfuric acid and the resulting reaction mixture was refluxed overnight. The reaction mixture was then cooled to ambient temperature and diluted with water and extracted with diethyl ether. The organic phase was dried over anhydrous sodium sulfate, filtered and evaporated to an oil that was subjected to flash column chromatography over silica gel (230–400 mesh) using 10% ethyl acetate in hexane as the eluent to afford the title compound as an oil (2.54 g, 88%).

¹H NMR (300 MHz, CDCl₃): δ 8.14 (s, 1H), 7.95 (d, J=7.6 Hz, 1H), 7.64 (d, J=7.6 Hz, 1H), 7.29 (t, J=7.6 Hz, 1H), 5.24 (hept, J=6.1 Hz, 1H), 1.35 (d, J=6.1 Hz, 6H).

3-Trimethylsilanylethynyl-benzoic acid isopropyl ester (Intermediate 136)

Following General Procedure D and using 3-bromo-benzoic acid isopropyl ester (Intermediate 135, 1.25 g, 5.14 mmol), triethyl amine (12 mL), copper(I)iodide (0.078 g, 0.41 mmol), trimethylsilyl acetylene (4 mL, 28.16 mmol) and dichlorobis(triphenylphosphine)palladium(II) (0.288 g, 0.41 mmol) followed by flash column chromatography over silica gel (230–400 mesh) using 3% ethyl acetate in hexane as the eluent, the title compound (1.25 g, 94%) was obtained as an orange oil.

¹H NMR (300 MHz, CDCl₃): δ 8.09 (s, 1H), 7.96 (d, J=7.6 Hz, 1H), 7.59 (d, J=7.6 Hz, 1H), 7.35 (t, J=7.6 Hz, 1H), 5.24 (hept, J=6.1 Hz, 1H), 1.35 (d, J=6.1 Hz, 6H), 0.25 (s, 9H).

3-Ethynyl-benzoic acid isopropyl ester (Intermediate 137)

A solution of 3-trimethylsilanylethynyl-benzoic acid isopropyl ester (Intermediate 136, 0.6 g, 2.3 mmol) in anhydrous tetrahydrofuran (3 mL) was treated with a 1M solution of tetra-n-butyl ammonium fluoride in tetrahydrofuran (4.6 mL, 4.6 mmol) and the resulting reaction mixture was stirred in an ice bath for 5 min. Water was added and the reaction mixture was extracted with ethyl acetate. The organic phase was washed with water and brine, dried over anhydrous sodium sulfate, filtered and evaporated to an oil that was purified by flash column chromatography using 5%–30% ethyl acetate in hexane as the eluent to afford the title compound as a solid (0.33 g, 76%).

¹H NMR (300 MHz, CDCl₃): δ 8.15 (s, 1H), 8.01 (d, J=7.6 Hz, 1H), 7.64 (d, J=7.6 Hz, 1H), 7.39 (t, J=7.6 Hz, 1H), 5.25 (hept, J=6.1 Hz, 1H), 3.13 (s, 1H), 1.37 (d, J=6.1 Hz, 6H).

3-(4-Ethoxycarbonylmethyl-3-fluoro-phenylethynyl)-benzoic acid isopropyl ester (Intermediate 138)

Following General Procedure B and using 3-ethynyl-benzoic acid isopropyl ester (Intermediate 137, 0.099 g, 0.53 mmol), 2-fluoro-4-iodo phenyl acetic acid ethyl ester (0.164 g, 0.53 mmol), triethyl amine (3 mL), copper(I)iodide (0.01 g, 0.05 mmol) and dichlorobis(triphenylphosphine)palladium(II) (0.035 g, 0.5 mmol) followed by flash column chromatography over silica gel (230–400 mesh) using 7–10% ethyl acetate in hexane as the eluent, the title compound was obtained as a light orange oil (0.08 g, 92%).

¹H NMR (300 MHz, CDCl₃): δ 8.17 (s, 1H), 8.01 (d, J=7.6 Hz, 1H), 7.67 (d, J=7.6 Hz, 1H), 7.42 (t, J=7.6 Hz,

1H), 7.29–7.22 (m, 3H), 5.21 (hept, J=6.1 Hz, 1H), 4.18 (q, J=7.1 Hz, 2H), 3.68 (s, 2H), 1.38 (d, J=6.1 Hz, 6H), 1.26 (t, J=7.1 Hz, 3H).

3-(4-Carboxymethyl-3-fluoro-phenylethynyl)-benzoic acid isopropyl ester (Compound 44)

A solution of 3-(4-ethoxycarbonylmethyl-3-fluoro-phenylethynyl)-benzoic acid isopropyl ester (Intermediate 138, 0.1 g, 0.27 mmol) in isopropanol (2 mL) and tetrahydrofuran (2 mL) was treated with a 2M solution of lithium hydroxide (1 mL, 2 mmol). After 40 min. at ambient temperature, the reaction mixture was concentrated in vacuo a bit, neutralized with 10% hydrochloric acid and the solid formed was filtered, washed with water and dried to afford the title compound (0.09 g, 97%).

$^1$H NMR (300 MHz, CDCl$_3$): δ 8.18 (s, 1H), 8.02 (d, J=7.6 Hz, 1H), 7.68 (d, J=7.6 Hz, 1H), 7.44 (t, J=7.6 Hz, 1H), 7.31–7.24 (m, 3H), 5.27 (hept, J=6.1 Hz, 1H), 3.74 (s, 2H), 1.39 (d, J=6.1 Hz, 6H).

Reaction Scheme 24

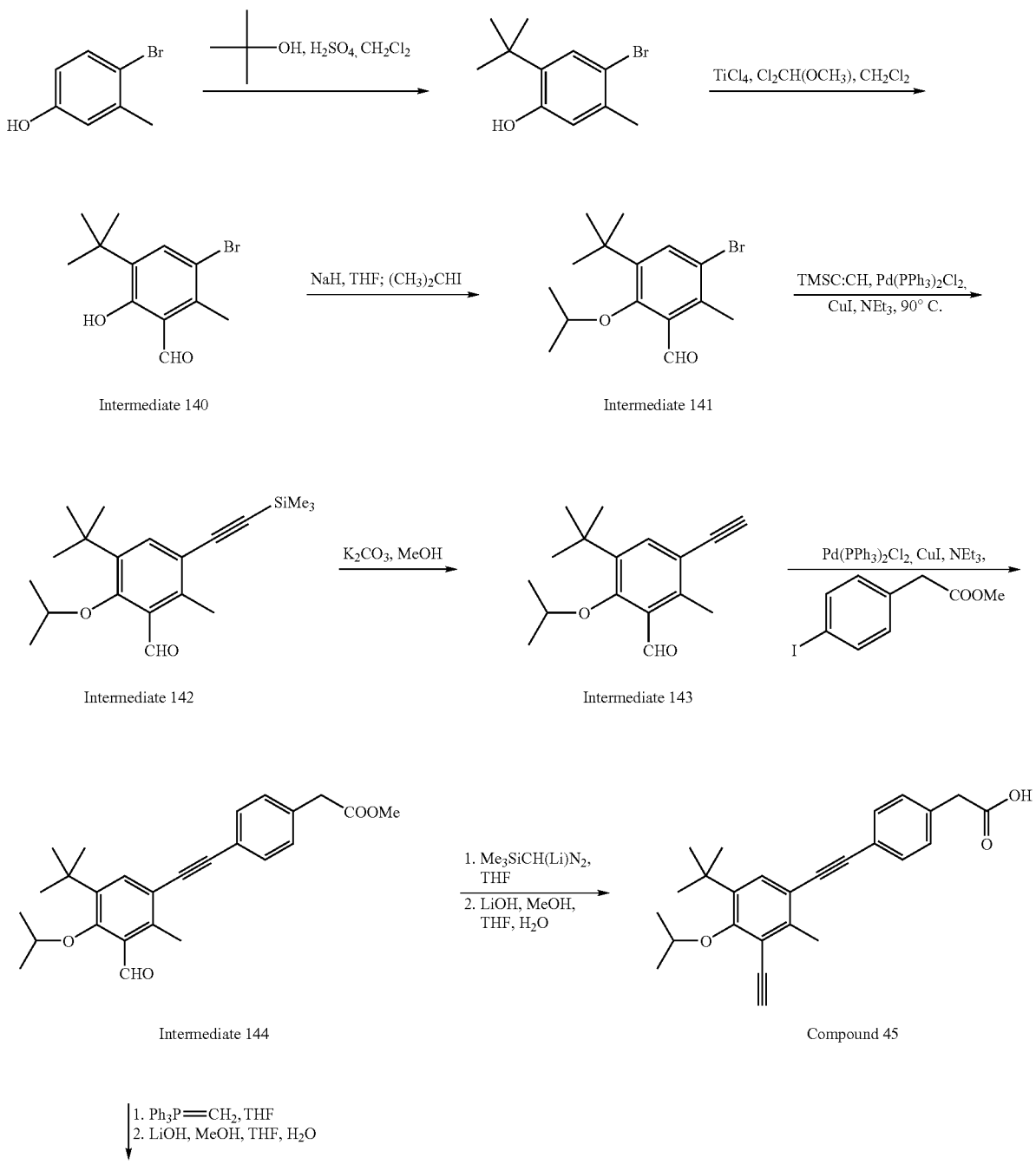

-continued

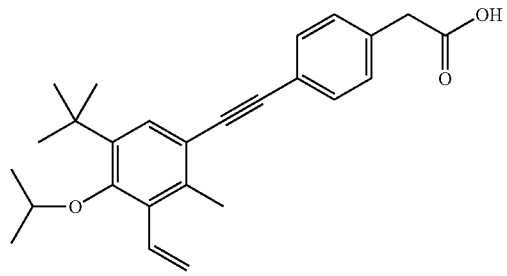

Compound 46

4-Bromo-2-tert-butyl-5-methyl-phenol (Intermediate 139)

A solution of 4-bromo-3-methylphenol (Aldrich, 5.1 g, 27.3 mmol) in anhydrous dichloromethane (50 mL) was treated with 2-methyl-2-propanol (15 mL) and concentrated sulfuric acid (3 mL) and stirred at ambient temperature for 3 months. The volatiles were evaporated in vacuo, the residue was diluted with water and extracted with diethyl ether. The combined organic phase was dried over anhydrous magnesium sulfate, filtered and evaporated in vacuo to an oil. Flash column chromatography using 3–5% ethyl acetate in hexane as the eluent afforded the title compound as a deep yellow oil (3.42 g, 51%). It was used as such for the next step.

$^1$H NMR (300 MHz, CDCl$_3$): δ 7.40 (s, 1H), 6.56 (s, 1H), 5.23 (s, 1H), 2.30 (s, 3H), 1.41 (s, 9H).

3-Bromo-5-tert-butyl-6-hydroxy-2-methyl-benzaldehyde (Intermediate 140)

A stirred, cooled (ice bath) solution of 4-bromo-2-tert-butyl-5-methyl-phenol (Intermediate 139, 0.85 g, 3.5 mmol) in anhydrous dichloromethane (7 mL) was treated with titanium tetrachloride (0.64 mL, 5.8 mmol) followed by α,α-dichloro methyl ether (0.3 g, 3.5 mmol). The reaction mixture was allowed to warm to ambient temperature for 4 h. The reaction mixture was diluted with diethyl ether, washed with brine (×1) and dried over anhydrous sodium sulfate, filtered and evaporated in vacuo to a residue which was subjected to flash column chromatography over silica gel (230–400 mesh) using 1% ethyl acetate in hexane to afford the title compound as a yellow solid (0.58 g, 61%).

$^1$H NMR (300 MHz, CDCl$_3$): δ δ 12.89 (s, 1H), 10.32 (s, 1H), 7.60 (s, 1H), 2.63 (s, 3H), 1.38 (s, 9H).

3-Bromo-5-tert-butyl-6-isopropoxy-2-methyl-benzaldehyde (Intermediate

A stirred, cooled (ice bath) solution of 3-bromo-5-tert-butyl-6-hydroxy-2-methyl-benzaldehyde (Intermediate 140, 0.58 g, 2.14 mmol) in anhydrous N,N-dimethylformamide (10 mL) was treated with sodium hydride (0.34 g of 60% suspension in mineral oil, 8.56 mmol). After 30 minutes, 2-iodopropane (1.3 mL, 12.84 mmol) was added and the reaction mixture was heated at 75° C. overnight. The reaction mixture was then cooled and poured into iced water and extracted with diethyl ether. The organic extract was then washed with water and brine, dried over anhydrous magnesium sulfate, filtered and evaporated in vacuo to an oil. Flash column chromatography using 2–4% ethyl acetate in hexane as the eluent afforded the title product (0.43 g, 64%).

$^1$H NMR (300 MHz, CDCl$_3$): δ 10.23 (s, 1H), 7.68 (s, 1H), 4.34 (heptet, 1H, J=6.2 Hz), 2.57 (s, 3H), 1.40 (s, 9H), 1.28 (d, 6H, J=6.2 Hz).

3-tert-Butyl-2-isopropoxy-6-methyl-5-trimethylsilanylethynyl-benzaldehyde (Intermediate 142)

Following General Procedure D and using 3-bromo-5-tert-butyl-6-isopropoxy-2-methyl-benzaldehyde (Intermediate 141, 0.43 g, 1.37 mmol), triethyl amine, copper(I)iodide (0.021 g, 0.11 mmol), trimethylsilyl acetylene (1 mL), and dichlorobis(triphenylphosphine)palladium(II) (0.077 g, 0.11 mmol) followed by flash column chromatography over silica gel (230–400 mesh) using 2% ethyl acetate in hexane as the eluent, the title compound was obtained (0.45 g,~100%).

$^1$H NMR (300 MHz, CDCl$_3$): δ 10.10 (s, 1H), 7.41 (s, 1H), 4.19 (heptet, 1H, J=6.1 Hz), 2.44 (s, 3H), 1.21 (s, 9H), 1.09 (d, 6H, J=6.1 Hz), 0.08 (s, 9H).

3-tert-Butyl-5-ethynyl-2-isopropoxy-6-methyl-benzaldehyde (Intermediate 143)

A solution of 3-tert-butyl-2-isopropoxy-6-methyl-5-trimethylsilanylethynyl-benzaldehyde (Intermediate 142, 0.45 g, 1.37 mmol) in methanol (5 mL) and tetrahydrofuran was treated with potassium carbonate (0.2 g, 1.45 mmol) and the resulting reaction mixture was stirred at ambient temperature for 3 h. The reaction mixture was evaporated in vacuo and the residue was extracted with diethyl ether and washed with water and brine. The organic phase was dried, filtered and evaporated in vacuo to afford the title compound (0.35 g, 90%).

$^1$H NMR (300 MHz, CDCl$_3$): δ 10.28 (s, 1H), 7.63 (s, 1H), 4.38 (heptet, 1H, J=6.2 Hz), 3.48 (s, 1H), 2.63 (s, 3H), 1.39 (s, 9H), 1.29 (d, 6H, J=6.2 Hz).

[4-(5-tert-Butyl-3-formyl-4-isopropoxy-2-methyl-phenylethynyl)-phenyl]-acetic acid methyl ester (Intermediate 144)

Following General Procedure B and using 3-tert-butyl-5-ethynyl-2-isopropoxy-6-methyl-benzaldehyde (Intermediate 143, 0.35 g, 1.355 mmol), 4-iodo phenyl acetic acid methyl ester (0.374 g, 1.35 mmol), triethyl amine (8 mL), copper(I)iodide (0.02 g, 0.1 mmol) and dichlorobis(triphenylphosphine)palladium(II) (0.072 g, 0.1 mmol) followed by flash column chromatography over silica gel (230–400 mesh) using 3–5% ethyl acetate in hexane as the eluent, the title compound was obtained as a white solid (0.37 g, 75%).

$^1$H NMR (300 MHz, CDCl$_3$): δ 10.29 (s, 1H), 7.65 (s, 1H), 7.48 (d, 2H, J=8.2 Hz), 7.53 (d, 2H, J=8.2 Hz), 4.38 (heptet, 1H, J=6.1 Hz), 3.68 (s, 3H), 3.62 (s, 2H), 2.68 (s, 3H), 1.41 (s, 9H), 1.27 (d, 6H, J=6.1 Hz).

[4-(5-tert-Butyl-3-ethynyl-4-isopropoxy-2-methyl-phenylethynyl)-phenyl]-acetic acid methyl ester (Intermediate 145)

Anhydrous tetrahydrofuran (3 mL) was added to a 2M solution of trimethylsilyl diazomethane in hexanes (0.37 mL, 0.74 mmol) and the resulting reaction mixture was cooled to −78° C. A solution of 1.6M n-butyl lithium in hexanes (0.5 mL, 0.8 mmol) was added followed, after 30 minutes, by a solution of [4-(5-tert-butyl-3-formyl-4-isopropoxy-2-methyl-phenylethynyl)-phenyl]-acetic acid methyl ester (Intermediate 144, 0.2 g, 0.49 mmol) in anhydrous tetrahydrofuran and the resulting reaction mixture was stirred at −78° C. for 1 h and at 0° C. for 40 minutes. The reaction mixture was then quenched with saturated aqueous ammonium chloride solution and extracted with diethyl ether. The organic phase was washed with brine, dried over anhydrous magnesium sulfate, filtered and evaporated in vacuo to a residue that was subjected to flash column chromatography over silica gel (230–400 mesh) using 2.5–4% ethyl acetate in hexane as the eluent followed by preparative normal phase HPLC using 5% ethyl acetate in hexane as the mobile phase to afford the title product as a colorless oil (0.023 g, 11.6%).

$^1$H NMR (300 MHz, CDCl$_3$): δ 7.49 (d, 2H, J=8.0 Hz), 7.44 (s, 1H), 7.26 (d, 2H, J=8.0 Hz), 5.76 (heptet, 1H, J=6.1 Hz), 3.70 (s, 3H), 3.64 (s, 2H), 3.58 (s, 1H), 2.58 (s, 3H), 1.39 (s, 9H), 1.31 (d, 6H, J=6.1 Hz).

[4 (5-tert-Butyl-3-ethynyl-4-isopropoxy-2-methyl-phenylethynyl)-phenyl]-acetic acid (Compound 45)

A solution of [4-(5-tert-butyl-3-ethynyl-4-isopropoxy-2-methyl-phenylethynyl)-phenyl]-acetic acid methyl ester (Intermediate 145, 0.023 g, 0.057 mmol) in methanol (1.5 mL) and tetrahydrofuran (1.5 mL) was treated with 1M lithium hydroxide (0.5 mL, 1 mmol) and the resulting reaction mixture was stirred at ambient temperature for 45 minutes. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.020 g, 91%).

$^1$H NMR (300 MHz, CDCl$_3$): δ 7.47 (d, 2H, J=8.0 Hz), 7.43 (s, 1H), 7.24 (d, 2H, J=8.0 Hz), 5.75 (heptet, 1H, J=6.1 Hz), 3.62 (s, 2H), 3.57 (s, 1H), 2.57 (s, 3H), 1.38 (s, 9H), 1.30 (d, 6H, J=6.1 Hz).

[4-(5-tert-Butyl-4-isopropoxy-2-methyl-3-vinyl-phenylethynyl)-phenyl]-acetic acid methyl ester (Intermediate 146)

A solution of methylidene triphenyl phosphorane [5 mL of 0.1M solution, 0.5 mmol, generated from methyl triphenylphosphonium bromide (2.5 g, 7 mmol) and 1.6M n-butyllithium solution in hexanes (2.9 mL, 4.7 mmol) in 50 mL of tetrahydrofuran] was added to a solution of [4-(5-tert-butyl-3-formyl-4-isopropoxy-2-methyl-phenylethynyl)-phenyl]-acetic acid methyl ester (Intermediate 144, 0.052 g, 0.13 mmol) in tetrahydrofuran (1 mL). After 1 h the reaction mixture was quenched with water and extracted with ethyl acetate. The organic phase was washed with water and brine, dried over anhydrous sodium sulfate, filtered and evaporated in vacuo to a clear oil that after flash column chromatography over silica gel (230–400 mesh) using 5% ethyl acetate in hexane as the eluent afforded the title compound (0.02 g, 39%).

$^1$H NMR (300 MHz, CDCl$_3$): δ 7.48 (d, 2H, J=7.9 Hz), 7.39 (s, 1H), 7.25 (d, 2H, J=7.9 Hz), 6.73 (dd, 1H, J=11.4, 17.9 Hz), 5.49 (dd, 1H, J=2.0, 11.4 Hz), 5.37 (dd, 1H, J=2.1, 17.9 Hz), 4.93 (heptet, 1H, J=6.4 Hz), 3.70 (s, 3H), 3.63 (s, 2H), 2.44 (s, 3H), 1.40 (s, 9H), 1.17 (d, 6H, J=6.4 Hz).

[4-(5-tert-Butyl-4-isopropoxy-2-methyl-3-vinyl-phenylethynyl)-phenyl]-acetic acid (Compound 46)

A solution of [4-(5-tert-butyl-4-isopropoxy-2-methyl-3-vinyl-phenylethynyl)-phenyl]acetic acid methyl ester (Intermediate 146, 0.02 g, 0.049 mmol) in methanol (1.5 mL) and tetrahydrofuran (1.5 mL) was treated with 1M lithium hydroxide (0.5 mL, 1 mmol) and the resulting reaction mixture was stirred at ambient temperature for 45 minutes. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.020 g,~100%).

$^1$H NMR (300 MHz, CDCl$_3$): δ 7.48 (d, 2H, J=8.2 Hz), 7.39 (s, 1H); 7.24 (d, 2H, J=8.2 Hz), 6.72 (dd, 1H, J=11.4, 17.9 Hz), 5.49 (dd, 1H, J=2.0, 11.4 Hz), 5.37 (dd, 1H, J=2.1, 17.9 Hz), 4.92 (heptet, 1H, J=6.2 Hz), 3.64 (s, 2H), 2.43 (s, 3H), 1.40 (s, 9H), 1.17 (d, 6H, J=6.2 Hz).

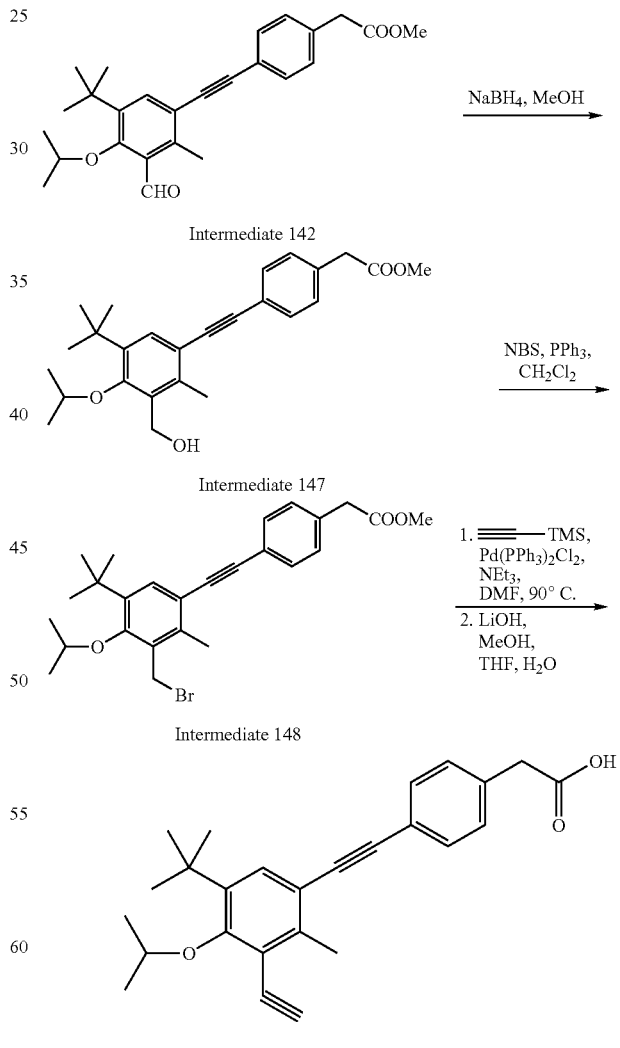

Reaction Scheme 25

[4-(5-tert-Butyl-3-hydroxymethyl-4-isopropoxy-2-methyl-phenylethynyl)-phenyl]-acetic acid methyl ester (Intermediate 147)

A stirred, cooled (ice bath) solution of [4-(5-tert-butyl-3-formyl-4-isopropoxy-2-methyl-phenylethynyl)-phenyl]-acetic acid methyl ester (Intermediate 142, 0.172 g, 0.42 mmol) in methanol (4 mL) was treated with sodium borohydride (0.02 g, 0.51 mmol) and the resulting reaction mixture was stirred for 1.5 h. The reaction mixture was quenched with water and extracted with diethyl ether. The organic phase was washed with water (×1) and brine (×1), dried over anhydrous sodium sulfate, filtered and evaporated in vacuo to a residue that was subjected to flash column chromatography over silica gel (230–400 mesh) using 15–20% ethyl acetate in hexane as the eluent to afford the title product as a white solid (0.15 g, 88%).

$^1$H NMR (300 MHz, CDCl$_3$): δ 7.48 (d, 2H, J=8.5 Hz), 7.47 (s, 1H), 7.25 (d, 2H, J=8.5 Hz), 4.74 (br s, 2H), 4.74–4.60 (m, 1H), 3.69 (s, 3H), 3.63 (s, 2H), 2.60 (s, 3H), 1.40 (s, 9H), 1.27 (d, 6H, J=6.2 Hz).

[4-(3-Bromomethyl-5-tert-butyl-4-isopropoxy-2-methyl-phenylethynyl)-phenyl]-acetic acid methyl ester (Intermediate 148)

A stirred, cooled (ice bath) solution of [4-(5-tert-butyl-3-hydroxymethyl-4-isopropoxy-2-methyl-phenylethynyl)-phenyl]-acetic acid methyl ester (Intermediate 147, 0.15 g, 0.37 mmol) and triphenylphosphine (0.125 g, 0.48 mmol) in anhydrous dichloromethane (5 mL) was treated with N-bromo succinimide (0.085 g, 0.48 mmol) under argon and the resulting reaction mixture was allowed to warm to ambient temperature and stirred overnight. The reaction mixture was quenched with dilute, aqueous sodium bicarbonate solution and extracted with diethyl ether. The organic phase was washed with water (×1) and brine (×1), dried over anhydrous magnesium sulfate, filtered and evaporated in vacuo to a residue that on flash column chromatography over silica gel (230–400 mesh) using 4–5% ethyl acetate in hexane as the eluent afforded the title compound (0.12 g, 69%) as a colorless oil. It was used as such for the next step.

{4-[5-tert-Butyl-4-isopropoxy-2-methyl-3-(3-trimethylsilanyl-prop-2-ynyl)-phenylethynyl phenyl]-acetic acid methyl ester (Intermediate 149)

A solution of [4-(3-bromomethyl-5-tert-butyl-4-isopropoxy-2-methyl-phenylethynyl)-phenyl]-acetic acid methyl ester (Intermediate 148, 0.12 g, 0.25 mmol) in triethyl amine (1 mL) and N,N-dimethylformamide (4 mL) was sparged with argon and treated with trimethylsilylacetylene (0.5 mL, 3.5 mmol) and dichlorobis(triphenylphosphine)palladium (II) (0.025 g, 0.036 mmol). The resulting reaction mixture was heated at 85° C. overnight at the end of which it was cooled to ambient temperature and subjected to flash column chromatography over silica gel (230–400 mesh) using 4% ethyl acetate in hexane as the eluent followed by preparative normal phase HPLC using 3% ethyl acetate in hexane as the mobile phase to afford the title compound as an oil (0.038 g, 31%).

$^1$H NMR (300 MHz, CDCl$_3$): δ 7.50 (d, 2H, J=7.9 Hz), 7.48 (s, 1H), 7.26 (d, 2H, J=7.9 Hz), 4.89 (heptet, 1H, J=6.5 Hz), 3.70 (s, 3H), 3.64 (s, 2H), 3.50 (s, 2H), 2.57 (s, 3H), 1.40 (s, 9H), 1.27 (d, 6H, J=6.5 Hz), 0.12 (s, 9H).

[4-(5-tert-Butyl-4-isopropoxy-2-methyl-3-prop-2-ynyl-phenylethynyl)-phenyl]-acetic acid (Compound 47)

A solution of {4-[5-tert-butyl-4-isopropoxy-2-methyl-3-(3-trimethylsilanyl-prop-2-ynyl)-phenylethynyl]-phenyl}-acetic acid methyl ester (Intermediate, 149, 0.038 g, 0.078 mmol) in methanol (1.5 mL) and tetrahydrofuran (1.5 mL) was treated with 2M lithium hydroxide (1 mL, 2 mmol) and the resulting reaction mixture was stirred at ambient temperature for 1.5 h. The volatiles were evaporated in vacuo to a residue that was neutralized with saturated aqueous ammonium chloride solution and extracted with ethyl acetate. The organic phase was washed with water and brine, and dried over anhydrous magnesium sulfate, filtered and evaporated in vacuo to afford the title product (0.032 g, 98%). $^1$H NMR (300 MHz, CDCl$_3$): δ 7.50 (d, 2H, J=8.1 Hz), 7.43 (s, 1H), 7.27 (d, 2H, J=8.1 Hz), 4.82 (heptet, 1H, J=6.4 Hz), 3.67 (s, 2H), 3.48 (d, 2H, J=2.5 Hz), 2.58 (s, 3H), 1.39 (s, 9H), 1.28 (d, 6H, J=6.4 Hz).

Reaction Scheme 26

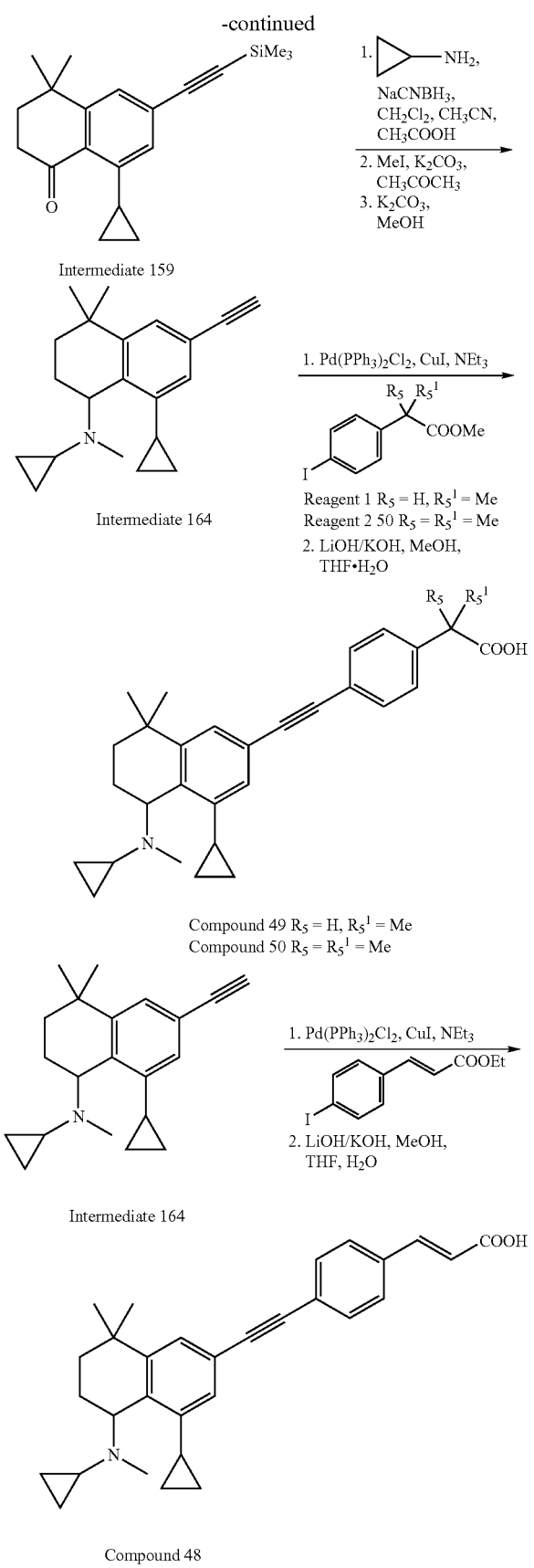

4-(2-Bromo-4-methoxy-phenyl)-4-oxo-butyric acid ethyl ester (Intermediate-150)

A stirred, cooled (−30° C.) solution of 3-bromo anisole (18.7 g, 100 mmol) and ethyl succinyl chloride (21 mL, 150 mmol) in anhydrous dichloromethane (200 mL) was treated with aluminum chloride (26.6 g, 200 mmol) and the reaction mixture was allowed to warm to ambient temperature and stirred overnight. The reaction mixture was poured into water and extracted with dichloromethane (×2). The combined organic phase was washed with brine, dried over anhydrous sodium sulfate, filtered and evaporated in vacuo to a brown oil. A solid separated out on standing. The supernatant liquid was decanted and the solid was washed with 1:3 dichloromethane: hexane and dried to afford the isomer 4-(4-bromo-2-methoxy-phenyl)-4-oxo-butyric acid ethyl ester. The combined mother liquor and washings was evaporated to a brown oil that was subjected to flash column chromatography over silica gel (230–400 mesh) using 15% ethyl acetate in hexane as the eluent to afford the isomer 4-(4-bromo-2-methoxy-phenyl)-4-oxo-butyric acid ethyl ester (overall 12 g, 38%), and the title compound (11.4 g, 36%) and a 1:1 mixture of both (2 g, 6.3%).

$^1$H NMR (300 MHz, CDCl$_3$): δ 7.59 (d, 1H, J=8.8 Hz), 7.14 (d, 1H, J=2.6 Hz), 6.87 (dd, 1H, J=2.6, 8.8 Hz), 4.14 (q, 2H, J=7.0 Hz), 3.83 (s, 3H), 3.23 (t, 2H, J=6.4 Hz), 2.74 (t, 2H, J=6.4 Hz), 1.25 (t, 3H, J=7.0 Hz).

4-(2-Bromo-4-methoxy-phenyl)-butyric acid ethyl ester (Intermediate 151)

A solution of 4-(2-bromo-4-methoxy-phenyl)-4-oxo-butyric acid ethyl ester (Intermediate 150, 6.45 g, 20.5 mmol) in trifluoroacetic acid (32 mL, 409 mmol) was treated with triethylsilane (14.4 mL, 90 mmol) and the resulting reaction mixture was heated at 55° C. for 3 h. The reaction mixture was then cooled to ambient temperature, neutralized with solid sodium bicarbonate, diluted with water and extracted with diethyl ether. The organic phase was washed with water and brine, dried over anhydrous magnesium sulfate, filtered and evaporated in vacuo to afford the title compound (5.4 g, 88%) as a colorless oil.

$^1$H NMR (300 MHz, CDCl$_3$): δ 7.11 (d, 1H, J=8.2 Hz), 7.08 (d, 1H, J=2.6 Hz), 6.79 (dd, 1H, J=2.6, 8.2 Hz), 4.13 (q, 2H, J=7.3 Hz), 3.76 (s, 3H), 2.71 (t, 2H, J=7.6 Hz), 2.34 (t, 2H, J=7.6 Hz), 1.92 (quintet, 2H, J=7.6 Hz), 1.26 (t, 3H, J=7.3 Hz).

5-(2-Bromo-4-methoxy-phenyl)-2-methyl-pentan-2-ol (Intermediate 152)

A stirred, cooled (−10° C.) solution of 4-(2-bromo-4-methoxy-phenyl)-butyric acid ethyl ester (Intermediate 151, 5.4 g, 18 mmol) in anhydrous tetrahydrofuran (100 mL) was treated with a 3M solution of methyl magnesium bromide (16 mL, 48 mmol) and the resulting reaction mixture was allowed to warm to ambient temperature over 3 h. It was quenched with saturated, aqueous ammonium chloride solution, diluted with water and extracted with diethyl ether. The organic phase was washed with water and brine, dried over anhydrous magnesium sulfate, filtered and evaporated in vacuo to afford the title product as a viscous oil (5.16 g,~100%).

$^1$H NMR (300 MHz, CDCl$_3$): δ 7.11 (d, 1H, J=8.5 Hz), 7.08 (d, 1H, J=2.6 Hz), 6.78 (dd, 1H, J=2.6, 8.5 Hz), 3.77 (s, 3H), 2.67 (t, 2H, J=7.3 Hz), 1.69–1.43 (m, 4H), 1.21 (s, 6H).

5-Bromo-2-methoxy-1,1-dimethyl-12,3,4-tetrahydro-naphthalene (Intermediate 153)

5-(2-Bromo-4-methoxy-phenyl)-2-methyl-pentan-2-ol (Intermediate 152, 5.16 g, 17.9 mmol) was treated with 85% sulfuric acid (50 mL) at ambient temperature. After 30 minutes, the reaction mixture was diluted with cold water and extracted with diethyl ether. The organic phase was washed with water and brine, dried over anhydrous magnesium sulfate, filtered and evaporated in vacuo to afford the title product (4.63 g, 96%) as a pale yellow oil.

$^1$H NMR (300 MHz, CDCl$_3$): δ 6.96 (d, 1H, J=2.6 Hz), 6.86 (d, 1H, J=2.6 Hz), 3.76 (s, 3H), 2.68 (t, 2H, J=6.7 Hz), 1.83–1.75 (m, 2H), 1.62–1.58 (m, 2H), 1.26 (s, 6H).

8-Bromo-6-methoxy-4,4-dimethyl-3,4-dihydro-2H-naphthalen-1-one (Intermediate 154)

A solution of 5-bromo-2-methoxy-1,1-dimethyl-1,2,3,4-tetrahydro-naphthalene (Intermediate 153, 4.6 g, 17.1 mmol) in glacial acetic acid (20 mL) was cooled to 0° C. and treated with a solution of chromium trioxide (5.5 g, 55 mmol) in acetic acid and water (20 mL each). The reaction mixture was then allowed to warm to ambient temperature and stirred for 24 h. It was diluted with water and extracted with diethyl ether (×2). The combined organic phase was washed with water (×3), saturated aqueous sodium bicarbonate (×1) and brine (×1), dried over anhydrous magnesium sulfate, filtered and evaporated in vacuo to afford the title compound (3.9 g, 81%) as a yellow oil.

$^1$H NMR (300 MHz, CDCl$_3$): δ 7.09 (d, 1H, J=2.6 Hz), 6.87 (d, 1H, J=2.6 Hz), 3.85 (s, 3H), 2.71 (t, 2H, J=7.0 Hz), 1.96 (t, 2H, J=7.0 Hz), 1.35 (s, 6H).

6-Methoxy-4,4-dimethyl-8-vinyl-3,4-dihydro-2H-naphthalen-1-one (Intermediate 155)

A solution of 8-bromo-6-methoxy-4,4-dimethyl-3,4-dihydro-2H-naphthalen-1-one (Intermediate 154, 2.83 g, 10 mmol) and tributyl(vinyl)tin (3 mL, 10 mmol) in anhydrous N,N-dimethyl formamide (30 mL) was sparged with argon and treated with tetrakis(triphenylphosphine)palladium (0) (0.3 g, 0.26 mmol). The resulting reaction mixture was heated to 91° C. for two days at the end of which it was cooled to ambient temperature, diluted with water and extracted with diethyl ether (×2). The combined organic phase was washed with water (×1), and brine (×1), dried over anhydrous magnesium sulfate, filtered and evaporated to a pale yellow oil. Flash chromatography using 15% ethyl acetate in hexane as the eluent afforded the title product (1.7 g, 73%) as a pale yellow oil.

$^1$H NMR (300 MHz, CDCl$_3$): δ 7.50 (dd, 1H, J=10.8, 17.3 Hz), 6.85 (s, 2H), 5.50 (dd, 1H, J=1.4, 17.3 Hz), 5.28 (dd, 1H, J=1.4, 10.8 Hz), 3.88 (s, 3H), 2.68 (t, 2H, J=6.7 Hz), 1.95 (t, 2H, J=6.7 Hz), 1.35 (s, 6H).

8-Cyclopropyl-6-methoxy-4,4-dimethyl-3,4-dihydro-2H-naphthalen-1-one (Intermediate 156) A stirred, cooled (−40° C.) solution of 6-methoxy-4,4-dimethyl-8-vinyl-3,4-dihydro-2H-naphthalen-1-one (Intermediate 155, 51.7 g, 7.4 mmol) in diethyl ether (10 mL) was treated with a solution of diazomethane in ether (40 mmol in 50 mL of ether) followed by palladium(II)acetate (0.08 g) and the resulting reaction mixture was warmed to −25° C. when effervescence was observed. The reaction mixture was then filtered through a plug of silica and the filtrate was evaporated to afford a dark brown residue that was subjected to flash column chromatography over silica gel (23–400 mesh) using 20% ethyl acetate in hexane as the eluent to afford the title product as a pale yellow solid (1.5 g, 83%).

$^1$H NMR (300 MHz, CDCl$_3$): δ 6.71 (d, 1H. J=2.6 Hz), 6.44 (d, 1H, J=2.6 Hz), 3.82 (s, 3H), 2.98 (m, 1H), 2.69 (t, 2H, J=6.7 Hz), 1.94 (t, 2H, J=6.7 Hz), 1.34 (s, 6H), 1.02–0.88 (m, 2H), 0.65–0.59 (m, 2H).

8-Cyclopropyl-6-hydroxy-3,4-dihydro-2H-naphthalen-1-one (Intermediate 157)

A solution of 8-cyclopropyl-6-methoxy-4,4-dimethyl-3,4-dihydro-2H-naphthalen-1-one (Intermediate 156, 1.5 g, 6.14 mmol) and sodium cyanide (2 g, 40.8 mmol) in anhydrous dimethylsulfoxide (25 mL) was heated at 230° C. overnight under argon. The reaction mixture was then cooled to ambient temperature, poured into ice and acidified (Caution! Hydrogen cyanide evolution!) with dilute hydrochloric acid and extracted with ethyl acetate (×2). The combined organic extract was washed with brine (×1), dried over anhydrous sodium sulfate, filtered and evaporated to afford a dark brown oil. Flash column chromatography on silica gel (230–400 mesh) using 25% ethyl acetate in hexane as the eluent afforded the title compound as a solid (1.1 g, 78%).

$^1$H NMR (300 MHz, CD$_3$COCD$_3$): δ 8.14 (s, 1H), 6.75 (d, 1H, J=2.4 Hz), 6.40 (d, 1H, J=2.4 Hz), 3.02 (m, 1H), 2.62 (t, 2H, J=6.8 Hz), 1.94 (t, 2H, J=6.8 Hz), 1.33 (s, 6H), 0.93–0.89 (m, 2H), 0.59–0.55 (m, 2H).

Trifluoro-methanesulfonic acid 4-cyclopropyl-8,8-dimethyl-5-oxo-5,6,7,8-tetrahydro-naphthalen-2-yl ester (Intermediate 158)

A solution of 8-cyclopropyl-6-hydroxy-4,4-dimethyl-3,4-dihydro-2H-naphthalen-1-one (Intermediate 157, 1.1 g, 4.78 mmol) and 4-dimethylaminopyridine (1.22 g, 10 mmol) in anhydrous dichloromethane (20 mL) was treated 2-[N,N-bis(trifluoromethylsulfonyl)amino]-5-chloro-pyridine (2.07 g, 5.26 mmol) under argon at ambient temperature. After 3.5 h, the reaction mixture was subjected to flash column chromatography on silica gel (230–400 mesh) using 10% ethyl acetate in hexane as the eluent to afford the title compound as solid (1.76 g, 100%).

$^1$H NMR (300 MHz, CDCl$_3$): δ 7.10 (d, 1H, J=2.3 Hz), 6.78 (d, 1H, J=2.3 Hz), 2.90 (m, 1H), 2.78 (t, 2H, J=7.0 Hz), 2.01 (t, 2H, J=7.0 Hz), 1.38 (s, 6H), 1.10–1.04 (m, 2H), 0.67–0.62 (m, 2H).

8-Cyclopropyl-4,4-dimethyl-6-(trimethylsilanyl)ethynyl-3,4-dihydro-2H-naphthalene-1-one (Intermediate 159)

Following General Procedure B and using trifluoro-methanesulfonic acid 4-cyclopropyl-8,8-dimethyl-5-oxo-5,6,7,8-tetrahydro-naphthalen-2yl ester (Intermediate 158, 1.09 g, 3 mmol), triethyl amine (5 mL), tetrahydrofuran (5 mL), copper(I)iodide (0.12 g, 0.6 mmol), dichlorobis(triphenylphosphine)palladium(II) (0.42 g, 0.6 mmol) and (trimethylsilyl)acetylene (2.2 mL, 15 mmol) followed by flash column chromatography over silica gel (230–400 mesh) using 7% ethyl acetate in hexane as the eluent, the title compound was obtained as an orange oil (1.05 g, quantitative).

$^1$H NMR (300 MHz, CDCl$_3$): δ 7.29 (d, 1H, J=1.2 Hz), 6.98 (d, 1H, J=1.2 Hz), 2.81 (m, 1H), 2.72 (t, 2H, J=6.7 Hz), 1.95 (t, 2H, J=6.7 Hz), 1.34 (s, 6H), 1.01–0.95 (m, 2H), 0.66–0.61 (m, 2H), 0.26 (s, 9H).

8-Cyclopropyl-4,4-dimethyl-6-ethynyl-1-tetralone (Intermediate 160)

Following General Procedure F and using 8-cyclopropyl-4,4-dimethyl-6-(trimethylsilanyl)ethynyl-1-tetralone (Intermediate 159, 1.05 g, 3.38 mmol), methanol (20 mL) and potassium carbonate (1 g, 14.5 mmol) followed by flash column chromatography using 7% ethyl acetate in hexane as the eluent, the title compound was obtained (0.57 g, 80%) as a pale yellow solid.

$^1$H NMR (300 MHz, CDCl$_3$): δ 7.34 (d, 1H, J=2.5 Hz), 7.02 (d, 1H, J=2.5 Hz), 3.19 (s, 1H), 2.83 (m, 1H), 2.74 (t,

2H, J=6.7 Hz), 1.97 (t, 2H, J=6.7 Hz), 1.35 (s, 6H), 1.03–0.86 (m, 2H), 0.66–0.61 (m, 2H).

3-[4-(4-Cyclopropyl-8,8-dimethyl-5-oxo-5,6,7,8-tetrahydro-naphthalen-2-ylethynyl)-phenyl]-acrylic acid ethyl ester (Intermediate 161)

Following General Procedure B and using 8-cyclopropyl-4,4-dimethyl-6-ethynyl-1-tetralone (Intermediate 160, 0.1 g, 0.42 mmol), (E)-3 (4-iodo-phenyl) acrylic acid ethyl ester (0.13 g 0.42 mmol), triethyl amine (1 mL), copper(I)iodide (0.02 g, 0.1 mmol) and dichlorobis(triphenylphosphine) palladium(II) (0.070 g, 0.1 mmol) followed by flash column chromatography over silica gel (230–400 mesh), the title compound was obtained (0.12 g, 69%).

$^1$H NMR (300 MHz, CDCl$_3$): δ 7.65 (d, 1H, J=15.8 Hz), 7.52 (ABq, 4H, J=8.1 Hz), 7.37 (d, 2H, J=1.5 Hz), 7.05 (d, 1H, J=1.5 Hz), 6.45 (d, 1H, J=15.8 Hz), 4.26 (q, 2H, J=7.2 Hz), 2.88–2.79 (m, 1H), 2.77–2.71 (m, 2H), 2.00–1.92 (m, 2H), 1.36–1.21 (m, 9H), 1.04–0.97 (m, 2H), 0.69–0.59 (m, 2H).

3-{4-[4-Cyclopropyl-5-(cyclopropyl-methyl-amino)-8,8-dimethyl-5,6,7,8-tetrahydro-naphthalen-2-ylethynyl]-phenyl}-acrylic acid ethyl ester (Intermediate 162)

Following General Procedure C and using 3-[4-(4-cyclopropyl-8,8-dimethyl-5-oxo-5,6,7,8-tetrahydro-naphthalen-2-ylethynyl)-phenyl]-acrylic acid ethyl ester (Intermediate 161, 0.12 g, 0.29 mmol) in dichloromethane (4 mL) and acetonitrile (2 mL), cyclopropyl amine (1 mL, 14.5 mmol), acetic acid (1 mL) and sodium cyanoborohydride (0.16 g, 2.4 mmol) followed by work up afforded an intermediate as an oil, that was used as such for the next step. The residue (crude 0.18 g) was dissolved in acetone (6 mL) and treated with potassium carbonate (0.28 g, 2 mmol) and methyl iodide (1 mL, 16 mmol). The resulting reaction mixture was stirred at ambient temperature overnight. The volatiles were evaporated in vacuo, the residue was diluted with water and extracted with diethyl ether (×2). The combined organic phase was dried over anhydrous magnesium sulfate, filtered and evaporated to an oil. Flash column chromatography over silica gel (230–400 mesh) followed by preparative normal phase HPLC using 5% ethyl acetate in hexane as the mobile phase afforded the title compound (0.08 g) as a clear oil, which was used as such for the next step.

3-{4-[4-Cyclopropyl-5-(cyclopropyl-methyl-amino)-8,8-dimethyl-5,6,7,8-tetrahydro-naphthalen-2-ylethynyl]-phenyl}-acrylic acid (Compound 48)

A solution of 3-{4-[4-cyclopropyl-5-(cyclopropyl-methyl-amino)-8,8-dimethyl-5,6,7,8-tetrahydro-naphthalen-2-ylethynyl]-phenyl}-acrylic acid ethyl ester (Intermediate 164, 0.08 g, 0.17 mmol) in methanol (3 mL) and tetrahydrofuran (3 mL) was treated with 2M sodium hydroxide solution (2 mL, 4 mmol) and the resulting reaction mixture was refluxed overnight. The reaction mixture was cooled to ambient temperature, the volatiles were evaporated in vacuo, the residue was diluted with saturated aqueous ammonium chloride solution, and extracted with ethyl acetate (×2). The combined organic extract was dried over anhydrous sodium sulfate, filtered and evaporated in vacuo to a solid. Preparative reverse phase HPLC using 10% water in acetonitrile as the mobile phase afforded the title product as a solid (0.04 g, 50%).

$^1$H NMR (300 MHz, CDCl$_3$): δ 7.76 (d, 1H, J=15.8 Hz), 7.54 (Abq, 4H, J=8.8 Hz), 7.38 (d, 1H, J=1.5 Hz), 6.96 (d, 1H, J=1.5 Hz), 6.47 (d, 1H, J=15.8 Hz), 4.31 (t, 1H, J=4.7 Hz) 2.27 (s, 3H), 2.40–1.43 (m, 6H), 1.38 (s, 3H), 1.23 (s, 3H), 0.98–0.78 (m, 4H), 0.39–0.13 (m, 4H).

8-Cyclopropyl-5-(cyclopropyl-methyl-amino)-4,4-dimethyl-(2-trimethylsilanyl)ethynyl-1,2,3,4-tetrahydronaphthalene (Intermediate 163)

Following General Procedure C and using 8-cyclopropyl-4,4-dimethyl-6-(trimethylsilanyl)ethynyl-3,4-dihydro-2H-naphthalen-1-one (Intermediate 159, 0.77 g, 2.5 mmol) in dichloromethane (6 mL) and acetonitrile (3 mL), cyclopropyl amine (3 mL, 45 mmol), acetic acid (1 mL) and sodium cyanoborohydride-(0.63 g, 9.5 mmol) followed by work up afforded an intermediate as an oil, that was used as such for the next step. Th residue (crude 2.5 mmol) was dissolved in acetone (20 mL) and treated with potassium carbonate (1.03 g, 7.5 mmol) and methyl iodide (1.55 mL, 25 mmol). The resulting reaction mixture was stirred at ambient temperature over 2 days. The solids were filtered off, thr filtrate and washings were evaporated in vacuo to an oil. Flash column chromatography over silica gel (230–400 mesh) using 2–4% ethyl acetate in hexane as the mobile phase afforded the title compound (0.58 g, 75%).

$^1$H NMR (300 MHz, CDCl$_3$): δ 7.31 (d, J=1.6 Hz, 1H), 6.89 (d, J=1.6 Hz, 1H), 4.27 (br s, 1H), 2.40–2.30 (m, 1H), 2.30–2.20 (m, 1H), 2.24 (s, 3H), 2.10–2.00 (m, 1H), 2.00–1.80 (m, 2H), 1.60–1.50 (m, 1H), 1.35 (s, 3H), 1.20 (s, 3H), 0.90–0.75 (m, 4H), 0.40–0.25 (m, 3H), 0.26 (s, 9H), 0.20–0.10 (m, 1H).

8-Cyclopropyl-5-(cyclopropyl-methyl-amino)-2-ethynyl-4,4-dimethyl-1,2,3,4-tetrahydronaphthalene (Intermediate 164)

A solution of 8-cyclopropyl-5-(cyclopropyl-methyl-amino)-4,4-dimethyl-(2-trimethylsilanyl)ethynyl-1,2,3,4-tetrahydronaphthalene (Intermediate 163, 0.3 g, 0.82 mmol) in methanol (10 mL) was treated with potassium carbonate (0.2 g, 1.44 mmol) and the resulting reaction mixture was stirred at ambient temperature overnight. The solids were filtered off, the residue was diluted with water and extracted with diethyl ether. The organic phase was dried over anhydrous magnesium sulfate, fltered and evaporated to aford the title compound (0.22 g, 92%).

$^1$H NMR (300 MHz, CDCl$_3$): δ 7.44 (d, J=1.6 Hz, 1H), 7.01 (d, J=1.6 Hz, 1H), 4.38 (br s, 1H), 3.11 (s, 1H), 2.48–2.38 (m, 1H), 2.38–2.28 (m, 1H), 2.34 (s, 3H), 2.18–2.08 (m, 1H), 2.05–1.85 (m, 2H), 1.70–1.60 (m, 1H), 1.44 (s, 3H), 1.30 (s, 3H), 1.00–0.85 (m, 4H), 0.50–0.35 (m, 3H), 0.30–0.18 (m, 1H).

2-{4-[4-Cyclopropyl-5-(cyclopropyl-methyl-amino)-8,8-dimethyl-56,7,8-tetrahydro-naphthalen-2-ylethynyl]-phenyl}-propionic acid methyl ester (Intermediate 165)

Following General Procedure B and using 8-cyclopropyl-5-(cyclopropyl-methyl-amino)-2-ethynyl-4,4-dimethyl-1,2,3,4-tetrahydronaphthalene (Intermediate 164, 0.11 g, 0.37 mmol), methyl-2-(4-iodo phenyl)propionate (Reagent 1, 0.108 g, 0.37 mmol), triethyl amine (10 mL), copper(I) iodide (0.019 g, 0.1 mmol) and dichlorobis(triphenylphosphine)palladium(II) (0.07 g, 0.1 mmol) followed by work up and flash column chromatography over silica gel (230–400 mesh) using 1%–4% ethyl acetate in hexane as the eluent, the title compound was obtained as a pale yellow amorphous solid (0.148 g, 87%).

$^1$H NMR (300 MHz, CDCl$_3$): δ 7.51 (d, J=8.5 Hz, 2H), 7.39 (d, J=1.6 Hz, 1H), 7.29 (d, J=8.5 Hz, 2H), 6.97 (d, J=1.6 Hz, 1H), 4.32 (bs, 1H), 3.75 (q, J=7.0 Hz, 1H), 3.70 (s, 3H), 2.40–2.30 (m, 1H), 2.30–2.20 (m, 1H), 2.28 (s, 3H), 2.18–2.08 (m, 1H), 2.02–1.82 (m, 2H), 1.62–1.52 (m, 1H), 1.52 (d, J=7.0 Hz, 3H), 1.39 (s, 3H), 1.25 (s, 3H), 0.98–0.80 (m, 4H), 0.45–0.25 (m, 3H), 0.20–0.15 (m, 1H).

2-{4-[4-Cyclopropyl-5-(cyclopropyl-methyl-amino)-8,8-dimethyl-5,6,7,8-tetrahydro-naphthalen-2-ylethynyl]-phenyl}-propionic acid (Compound 49)

A solution of 2-{4-[4-cyclopropyl-5-(cyclopropyl-methyl-amino)-8,8-dimethyl-5,6,7,8-tetrahydro-naphthalen-2-ylethynyl]-phenyl}-propionic acid methyl ester (Intermediate 165, 0.075 g, 0.16 mmol) in methanol (2 mL) and tetrahydrofuran (2 mL) was treated with 2M lithium hydroxide (1 mL, 2 mmol) and the resulting reaction mixture was stirred at ambient temperature for 5 h. The reaction mixture was neutralized with ammonium chloride and extracted with ethyl acetate. The organic phase was washed with water and brine, and dried over anhydrous sodium sulfate, filtered and evaporated in vacuo to afford the title product as a yellow solid (0.07 g, 96%).

$^1$H NMR (300 MHz, CDCl$_3$): δ 7.50 (d, J=8.5 Hz, 2H), 7.39 (d, J=1.6 Hz, 1H), 7.31 (d, J=8.5 Hz, 2H), 6.97 (d, J=1.6 Hz, 1H), 4.34 (bs, 1H), 3.74 (q, J=7.0 Hz, 1H), 2.40–2.30 (m, 1H), 2.30–2.20 (m, 1H), 2.29 (s, 3H), 2.18–2.08 (m, 1H), 2.02–1.82 (m, 2H), 1.62–1.52 (m, 1H), 1.52 (d, J=7.0 Hz, 3H), 1.39 (s, 3H), 1.24 (s, 3H), 0.98–0.80 (m, 4H), 0.40–0.30 (m, 3H), 0.20–0.15 (m, 1H).

2-{4-[4-Cyclopropyl-5-(cyclopropyl-methyl-amino)-8,8-dimethyl-5,6,7,8-tetrahydro-naphthalen-2-ylethynyl]-phenyl}-2-methyl-propionic acid methyl ester (Intermediate 166)

Following General Procedure B and using 8-cyclopropyl-5-(cyclopropyl-methyl-amino)-2-ethynyl-4,4-dimethyl-1,2,3,4-tetrahydronaphthalene (Intermediate 164, 0.1 g, 0.37 mmol), methyl-2-(4-iodo phenyl)-2-methyl-propionate (Reagent 2, 0.118 g, 0.39 mmol), triethyl amine (10 mL), copper(I)iodide (0.019 g, 0.1 mmol) and dichlorobis(triphenylphosphine)palladium(II) (0.07 g, 0.1 mmol) followed by work up and flash column chromatography over silica gel (230–400 mesh) using 1%–4% ethyl acetate in hexane as the eluent, the title compound was obtained as a pale yellow amorphous solid (0.125 g, 70%).

$^1$H NMR (300 MHz, CDCl$_3$): δ 7.51 (d, J=8.5 Hz, 2H), 7.39 (d, J=1.6 Hz, 1H), 7.33 (d, J=8.5 Hz, 2H), 6.97 (d, J=1.6 Hz, 1H), 4.32 (bs, 1H), 3.68 (s, 3H), 2.40–2.30 (m, 1H), 2.30–2.20 (m, 1H), 2.28 (s, 3H), 2.15–2.05 (m, 1H), 2.00–1.80 (m, 2H), 1.61 (s, 6H), 1.62–1.52 (m, 1H), 1.39 (s, 3H), 1.25 (s, 3H), 0.95–0.80 (r, 4-H), 0.45–0.30 (m, 3H), 0.20–0.10 (m, 1H).

2-{4-[4-Cyclopropyl-methyl-amino)-8,8-dimethyl-5,6,7,8-tetrahydro-naphthalen-2-ylethynyl]-phenyl}-2-methyl-propionic acid (Compound 50)

A solution of 2-{4-[4-cyclopropyl-5-(cyclopropyl-methyl-amino)-8,8-dimethyl-5,6,7,8-tetrahydro-naphthalen-2-ylethynyl]-phenyl}-2-methyl-propionic acid methyl ester (Intermediate 166, 0.125 g, 0.266 mmol) in methanol (2.5 mL) and tetrahydrofuran (2.5 mL) was treated with 3M potassium hydroxide (1 mL, 3 mmol) and the resulting reaction mixture was stirred at ambient temperature overnight. The reaction mixture was neutralized with ammonium chloride and extracted with ethyl acetate. The organic phase was washed with water and brine, and dried over anhydrous sodium sulfate, filtered and evaporated in vacuo to afford the title product as an amorphous pale yellow solid (0.12 g, 98%).

$^1$H NMR (300 MHz, CDCl$_3$): δ 7.51 (d, J=8.5 Hz, 2H), 7.40–7.38 (m, 3H), 6.97 (d, J=1.6 Hz, 1H), 4.33 (bs, 1H), 2.40–2.30 (m, 1H), 2.30–2.20 (m, 1H), 2.28 (s, 3H), 2.10–2.00 (m, 1H), 2.00–1.80 (m, 2H), 1.62 (s, 6H), 1.60–1.50 (m, 1H), 1.39 (s, 3H), 1.24 (s, 3H), 0.95–0.80 (m, 4H), 0.45–0.30 (m, 3H), 0.20–0.10 (m, 1H).

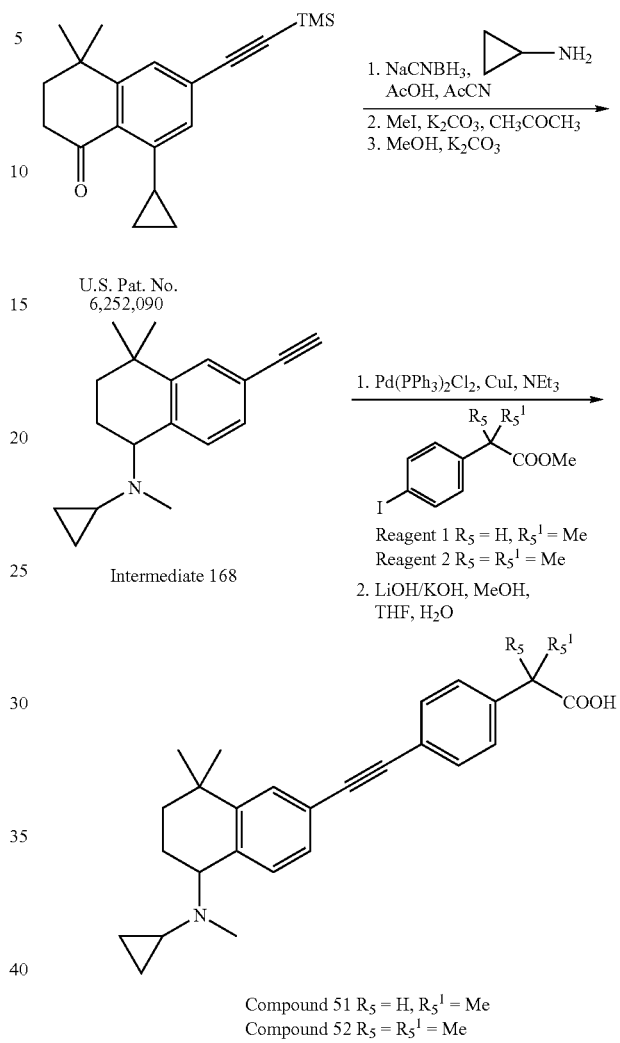

Reaction Scheme 27

Compound 51 R$_5$ = H, R$_5^1$ = Me
Compound 52 R$_5$ = R$_5^1$ = Me

Cyclopropyl-(4,4-dimethyl-6-trimethylsilanylethynyl-1,2,3,4-tetrahydro-naphthalen-1-yl)-methyl-amine (Intermediate 167)

Following General Procedure C and using 4,4-dimethyl-6-trimethylsilanylethynyl-3,4-dihydro-2H-naphthalen-1-one (described in U.S. Pat. No. 6,252,090, 1.23 g, 4.6 mmol) in dichloromethane (7 mL) and acetonitrile (3 mL), cyclopropyl amine (2.5 mL, 36 mmol), acetic acid (2.5 mL) and sodium cyanoborohydride (0.58 g, 8.6 mmol) followed by work up and flash column chromatography over silica gel (230–400 mesh) using 8% ethyl acetate in hexane as the eluent afforded an intermediate as a golden yellow solid (1.07 g, 76%). The intermediate (0.67 g, 2.62 mmol) was dissolved in acetone (10 mL) and treated with potassium carbonate (2.2 g, 16 mmol) and methyl iodide (0.75 mL, 12 mmol). The resulting reaction mixture was stirred at ambient temperature overnight. The volatiles were evaporated in vacuo, the residue was diluted with water and extracted with diethyl ether. The organic phase was dried over anhydrous magnesium sulfate, filtered and evaporated to an oil which was used as such for the next step.

Cyclopropyl-(6-ethynyl-4,4-dimethyl-1,2,3,4-tetrahydro-naphthalen-1-yl)-methyl-amine (Intermediate 168)

A solution of cyclopropyl-(4,4-dimethyl-6-trimethylsilanylethynyl-1,2,3,4-tetrahydro-naphthalen-1-yl)-methyl-amine (Intermediate 167, 0.67 g, 2.62 mmol) in methanol (10 mL) was treated with potassium carbonate (1 g, 7.23 mmol) and the resulting reaction mixture was stirred at ambient temperature overnight. The volatiles were evaporated in vacuo and the residue was diluted with water and extracted with diethyl ether. The organic extract was dried over anhydrous magnesium sulfate, filtered and evaporated in vacuo to afford the title product as a light yellow oil (0.5 g, 75%).

$^1$H NMR (300 MHz, CDCl$_3$): δ 7.47 (d, 1H, J=8.2 Hz), 7.41 (d, 1H, J=1.4 Hz), 6.79 (dd, 1H, J=8.2, 1.4 Hz), 3.92 (t, 1H, J=8.2 Hz), 3.01 (s, 3H), 2.11 (s, 3H), 2.15–2.07 (m, 1H), 1.95–1.57 (m, 4H), 1.29 (s, 3H), 1.24 (s, 3H), 0.53–0.37 (m, 4H).

2-{4-[5-(Cyclopropyl-methyl-amino)-8,8-dimethyl-5,6,7,8-tetrahydro-naphthalen-2-ylethynyl]-phenyl}-propionic acid methyl ester (Intermediate 169)

Following General Procedure B and using 5-(cyclopropyl-methyl-amino)-2-ethynyl-8,8-dimethyl-5,6,7,8-tetrahydro-naphthalene (Intermediate 168, 0.116 g, 0.46 mmol), methyl-2-(4-iodophenyl)propionate (Reagent 1, 0.17 g, 0.59 mmol), triethyl amine (0.75 mL), copper(I)iodide (0.07 g, 0.37 mmol) and tetrakis(triphenylphosphine)palladium(0) (0.022 g, 0.019 mmol) followed by flash column chromatography over silica gel (230–400 mesh) and preparative normal phase HPLC using 5% ethyl acetate in hexane as the eluent, the title compound was obtained (0.08 g, 42%).

$^1$H NMR (300 MHz, CDCl$_3$): δ 7.51–7.43 (m, 3H), 7.29–7.22 (m, 4H), 3.94 (t, 1H, J=7.9 Hz), 3.76–3.62 (m, 1H), 3.65 (s, 3H), 2.12 (s, 3H), 2.15–2.08 (m, 1H), 2.00–1.54 (2 m, 4H), 1.52–1.46 (2d, 3H, J=7.4 Hz), 1.31 (s, 3H), 1.27 (s, 3H), 0.53–0.38 (m, 4H).

2-[4-[5-(Cyclopropyl-methyl-amino)-8,8-dimethyl-5,6,7,8-tetrahydro-naphthalen-2-ylethynyl]-phenyl}-propionic acid (Compound 51)

A solution of 2-{4-[5-(cyclopropyl-methyl-amino)-8,8-dimethyl-5,6,7,8-tetrahydro-naphthalen-2-ylethynyl]-phenyl}-propionic acid methyl ester (Intermediate 169, 0.022 g, 0.05 mmol) in methanol (2 mL) and tetrahydrofuran (2 mL) was treated with a 2M solution of sodium hydroxide (1 mL, 2 mmol) and the resulting reaction mixture was stirred at ambient temperature overnight. The reaction mixture was neutralized with saturated aqueous ammonium chloride solution and extracted with ethyl acetate. The organic phase was washed with water and brine, and dried over anhydrous magnesium sulfate, filtered and evaporated in vacuo to a residue that was subjected to preparative reverse phase HPLC using 10% water in acetonitrile as the mobile phase to afford the title product (0.008 g, 40%).

$^1$H NMR (300 MHz, CDCl$_3$): δ 7.50–7.44 (m, 3H), 7.31–7.27 (m, 3H), 7.20 (dd, 1H, J=8.2, 1.5 Hz), 4.00 (t, 1H, J=8.2 Hz), 3.74 (q, 1H, J=7.1 Hz), 1H), 2.15 (s, 3H), 2.15–2.10 (m, 1H), 1.98–1.81 (m, 2H), 1.80–1.63 (m, 2H), 11.51 (d, 3H, J=0.7.1 Hz), 1.31 (s, 3H), 1.27 (s, 3H), 0.52–0.49 (m, 4H).

2-{4-[5-(Cyclopropyl-methyl-amino)-8,8-dimethyl-5,6,7,8-tetrahydro-naphthalen-2-ylethynyl]-phenyl}-2-methyl-propionic acid methyl ester (Intermediate 170)

Following General Procedure B and using 5-(cyclopropyl-methyl-amino)-2-ethynyl-8,8-dimethyl-5,6,7,8-tetrahydro-naphthalene (Intermediate 168, 0.16 g, 0.63 mmol), methyl-2-(4-iodophenyl)-2-methyl-propionate (Reagent 2, 0.18 g, 0.58 mmol), triethyl amine (3 mL), copper(I)iodide (0.048 g, 0.25 mmol) and tetrakis(triphenylphosphine)palladium(0) (0.032 g, 0.027 mmol) followed by flash column chromatography over silica gel (230–400 mesh) and preparative normal phase HPLC using 6% ethyl acetate in hexane as the mobile phase, the title compound was obtained (0.14 g, 56%).

$^1$H NMR (300 MHz, CDCl$_3$): δ 7.54–7.47 (m, 4H), 7.34–7.26 (m, 3H), 3.97 (t, 1H, J=7.9 Hz), 3.68 (s, 3H), 2.16 (s, 3H), 2.16–2.00 (m, 1H), 2.00–1.61 (2m, 4H), 1.61 (s, 6H), 1.35 (s, 3H), 1.30 (s, 3H), 0.56–0.44 (m, 4H).

2-{4-[5-(Cyclopropyl-methyl-amino)-8,8-dimethyl-5,6,7,8-tetrahydro-naphthalen-2-ylethynyl]-phenyl}-2-methyl-propionic acid (Compound 52)

A solution of 2-{4-[5-(cyclopropyl-methyl-amino)-8,8-dimethyl-5,6,7,8-tetrahydro-naphthalen-2-ylethynyl]-phenyl}-2-methyl-propionic acid methyl ester (Intermediate 170, 0.08 g, 0.19 mmol) in methanol (3 mL) and tetrahydrofuran (3 mL) was treated with a 2M solution of sodium hydroxide (2 mL, 4 mmol) and the resulting reaction mixture was refluxed overnight. The volatiles were evaporated in vacuo and the residue was diluted with saturated aqueous ammonium chloride solution and extracted with ethyl acetate. The organic phase was dried over anhydrous magnesium sulfate, filtered and evaporated in vacuo to afford the title product (0.07 g,~100%).

$^1$H NMR (300 MHz, CDCl$_3$): δ 9.47 (br s, 1H), 7.53–7.49 (m, 4H), 7.39 (d, 2H, J=8.5 Hz), 7.26 (dd, 1H, J=7.9, 1.5 Hz), 3.97 (t, 1H, J=7.9 Hz), 2.16 (s, 3H), 2.16–2.00 (m, 1H), 2.00–1.61 (2m, 4H), 1.61 (s, 6H), 1.35 (s, 3H), 1.30 (s, 3H), 0.56–0.44 (m, 4H).

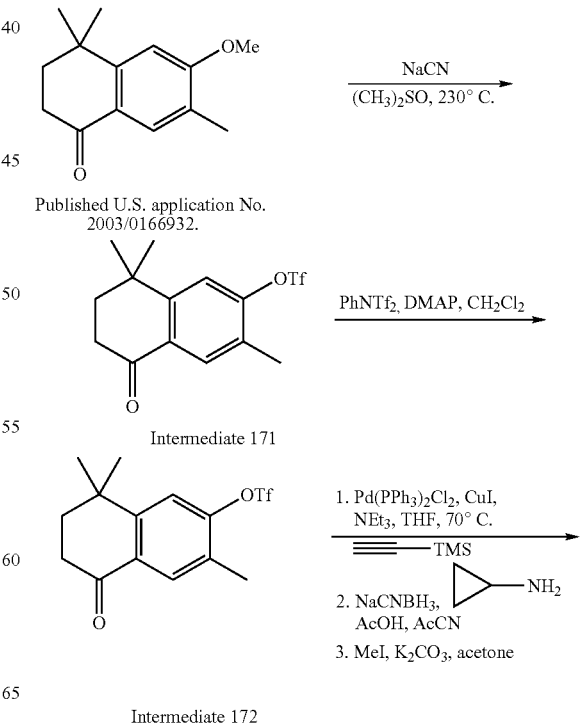

Reaction Scheme 28

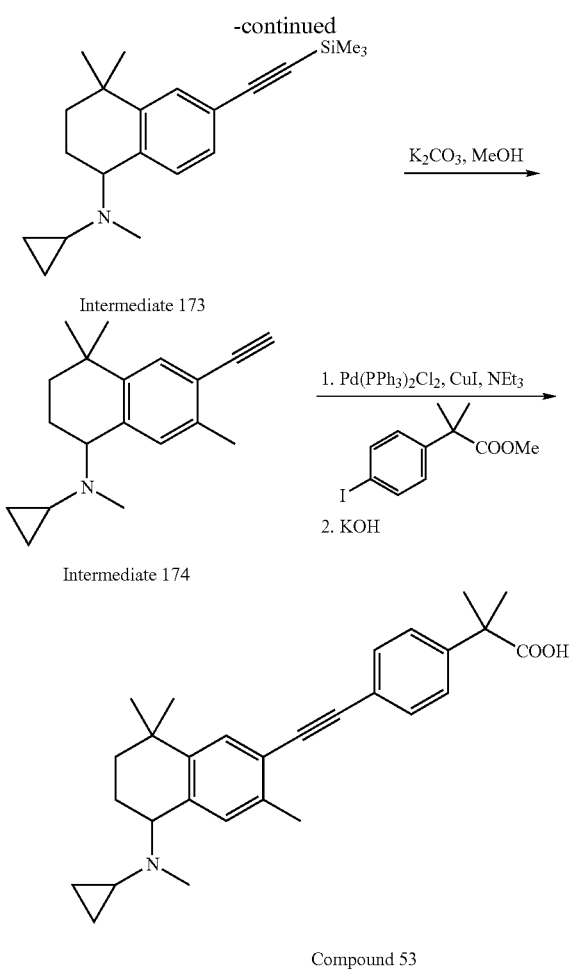

Intermediate 173

Intermediate 174

Compound 53

6-Hydroxy-4,47-trimethyl-3,4-dihydro-2H-naphthalen-1-one (Intermediate 171)

A solution of 6-methoxy-4,4,7-trimethyl-3,4-dihydro-2H-naphthalen-1-one (described in U.S. 2003/0166932, published Sep. 4, 2003, incorporated herein by reference; 5.5 g, 25.6 mmol) and sodium cyanide (6.25 g, 127 mmol) in anhydrous dimethylsulfoxide (100 mL) was heated at 230° C. for 48 h under argon. The reaction mixture was then cooled to ambient temperature, poured into ice and acidified (Caution! Hydrogen cyanide evolution!) with dilute hydrochloric acid and extracted with ethyl acetate (×2). The combined organic extract was washed with brine (×1), dried over anhydrous sodium sulfate, filtered and evaporated to afford the title compound, which was used as such for the next step (5.2 g,~100%).

$^1$H NMR (300 MHz, CDCl$_3$): δ 7.86 (s, 1H), 6.87 (s, 1H), 2.70 (t, 2H, J=7.0 Hz), 2.24 (s, 3H), 1.97 (t, 2H, J=7.0 Hz), 1.32 (s, 6H).

Trifluoro-methanesulfonic acid 3,8,8-trimethyl-5-oxo-5,6,7,8-tetrahydro-naphthalen-2-yl ester (Intermediate 172)

A solution of 6-hydroxy-4,4,7-trimethyl-3,4-dihydro-2H-naphthalen-1-one (Intermediate 171, 5.2 g, 25.6 mmol) and 4-dimethylaminopyridine (6.1 g, 50 mmol) in anhydrous dichloromethane (50 mL) was treated with N-phenyltrifluoromethanesulfonimide (9.54 g, 26.7 mmol) under argon and stirred at ambient temperature for 1 h. The reaction mixture was subjected to flash column chromatography on silica gel (230–400 mesh) using 6–7% ethyl acetate in hexane as the eluent to afford the title compound (6.4 g, 75%).

$^1$H NMR (300 MHz, CDCl$_3$): δ 7.96 (s, 1H), 7.28 (s, 1H), 2.74 (t, 2H, J=7.0 Hz), 2.37 (s, 3H), 2.04 (t, 2H, J=7.0 Hz), 1.39 (s, 6H).

4,4,7-Trimethyl-6-trimethylsilanylethynyl-3,4-dihydro-2H-naphthalen-1-one (Intermediate 173)

Following General Procedure D and using trifluoro-methanesulfonic acid 3,8,8-trimethyl-5-oxo-5,6,7,8-tetrahydro-naphthalen-2-yl ester (Intermediate 172, 5.04 g, 15 mmol), triethyl amine (20 mL), copper(I)iodide (0.6 g, 3 mmol), trimethylsilyl acetylene (5.3 mL, 37.5 mmol) and dichlorobis(triphenylphosphine)palladium(II) (2.2 g, 3 mmol) followed by flash column chromatography over silica gel (230–400 mesh) using 6% ethyl acetate in hexane as the eluent, the title compound (4 g, 93%) was obtained as a pale yellow solid.

$^1$H NMR (300 MHz, CDCl$_3$): δ 7.54 (s, 1H), 7.19 (s, 1H), 2.42 (t, 2H, J=7.0 Hz), 2.14 (s, 3H), 1.70 (t, 2H, J=7.0 Hz), 1.08 (s, 6H), 0.00 (s, 9H).

Cyclopropyl-(6-ethynyl-4,4,7-trimethyl-1,2,3,4-tetrahydro-naphthalen-1-yl)-methyl-amine (Intermediate 174)

Following General Procedure C and using 4,4,7-trimethyl-6-trimethylsilanylethynyl-3,4-dihydro-2H-naphthalen-1-one (Intermediate 173, 4 g, 14 mmol) in dichloromethane (30 mL) and acetonitrile (10 mL), cyclopropyl amine (3.11 mL, 45 mmol), acetic acid (3.2 mL) and sodium cyanoborohydride (2 g, 30 mmol) followed by work up and flash column chromatography over silica gel (230–400 mesh) using 10% ethyl acetate in hexane as the eluent afforded an intermediate as a pale yellow solid, that was used as such for the next step (4.1 g, 90%). The intermediate (4.1 g, 13 mmol) was dissolved in acetone (40 mL) and treated with potassium carbonate (10 g, 72 mmol) and methyl iodide (2.5 mL, 40 mmol). The resulting reaction mixture was stirred at ambient temperature overnight. The volatiles were evaporated in vacuo, the residue was dissolved in methanol (100 mL) and treated with potassium carbonate (10 g, 72 mmol) and the resulting reaction mixture was stirred at ambient temperature for 1.5 h. The volatiles were evaporated in vacuo, the residue was diluted with water and extracted with diethyl ether (×2). The combined organic phase was dried over anhydrous magnesium sulfate, filtered and evaporated to an oil that was filtered over a short plug of silica gel (230–400 mesh) to afford the title compound (3.2 g, 92%) as a clear oil.

$^1$H NMR (300 MHz, CDCl$_3$): δ 7.42 (s, 1H), 7.38 (s, 1H), 3.49 (t, 1H, J=7.0 Hz), 3.23 (s, 1H), 2.40 (s, 3H), 2.15 (s, 3H), 2.15–2.10 (m, 1H), 1.97–1.62 (2m, 4H), 1.30 (s, 3H), 1.26 (s, 3H), 0.56–0.28 (m, 4H).

2-{4-[5-(Cyclopropyl-methyl-amino)-3,8,8-trimethyl-5,6,7,8-tetrahydro-naphthalen-2-ylethynyl]-phenyl}-2-methyl-propionic acid methyl ester (Intermediate 175)

Following General Procedure B and using cyclopropyl-(6-ethynyl-4,4,7-trimethyl-1,2,3,4-tetrahydro-naphthalen-1-yl)-methyl-amine (Intermediate 174, 0.1 g, 0.29 mmol), methyl-2-(4-iodophenyl)-2-methyl-propionate (Reagent 2, 0.09 g, 0.29 mmol), triethyl amine (8 mL), copper(I)iodide (0.019 g, 0.11 mmol) and dichlorobis(triphenylphosphine) palladium(II) (0.07 g, 0.1 mmol) followed by flash column chromatography over silica gel (230–400 mesh) using 1–2% ethyl acetate in hexane as the eluent, the title compound was obtained (0.035 g, 26%).

$^1$H NMR (300 MHz, CDCl$_3$): δ 7.49 (d, J=8.5 Hz, 2H), 7.41 (s, 1H), 7.38 (d, J=8.5 Hz, 2H), 7.32 (s, 1H), 3.92 (m,

1H), 3.67 (s, 3H), 2.43 (s, 3H), 2.18–2.10 (m, 1H), 2.14 (s, 3H), 1.98–1.85 (m, 2H), 1.80–1.64 (m, 2H), 1.60 (s, 6H), 1.31 (s, 3H), 1.26 (s, 3H), 0.58–0.42 (m, 4H).

2-{4-[5-(Cyclopropyl-methyl-amino)-3,8,8-trimethyl-5,6,7,8-tetrahydro-naphthalen-2-ylethynyl]-phenyl}-2-methyl-propionic acid (Compound 53)

A solution of 2-{4-[5-(cyclopropyl-methyl-amino)-3,8,8-trimethyl-5,6,7,8-tetrahydro-naphthalen-2-ylethynyl]-phenyl}-2-methyl-propionic acid methyl ester (Intermediate 175, 0.035 g, 0.08 mmol) in methanol (2 mL) and tetrahydrofuran (2 mL) was treated with a 2M solution of sodium hydroxide (2 mL, 4 mmol) and the resulting reaction mixture was refluxed for 2 days. The volatiles were evaporated in vacuo and the residue was neutralized with 5% aqueous hydrochloric acid and extracted with ethyl acetate. The organic phase was washed with water and brine, dried over anhydrous sodium sulfate, filtered and evaporated in vacuo to a residue that was purified by preparative reverse phase HPLC using 10% water in acetonitrile as the mobile phase to afford the title product (0.022 g, 64%).

$^1$H NMR (300 MHz, CDCl$_3$): δ 7.48 (d, J=8.5 Hz, 2H), 7.41 (s, 1H), 7.37–7.34 (m, 3H), 3.95 (m, 1H), 2.40 (s, 3H), 2.18–2.10 (m, 1H), 2.14 (s, 3H), 1.98–1.85 (m, 2H), 1.80–1.64 (m, 2H), 1.57 (s, 6H), 1.29 (s, 3H), 1.25 (s, 3H), 0.56–0.42 (m, 4H).

Reaction Scheme 29

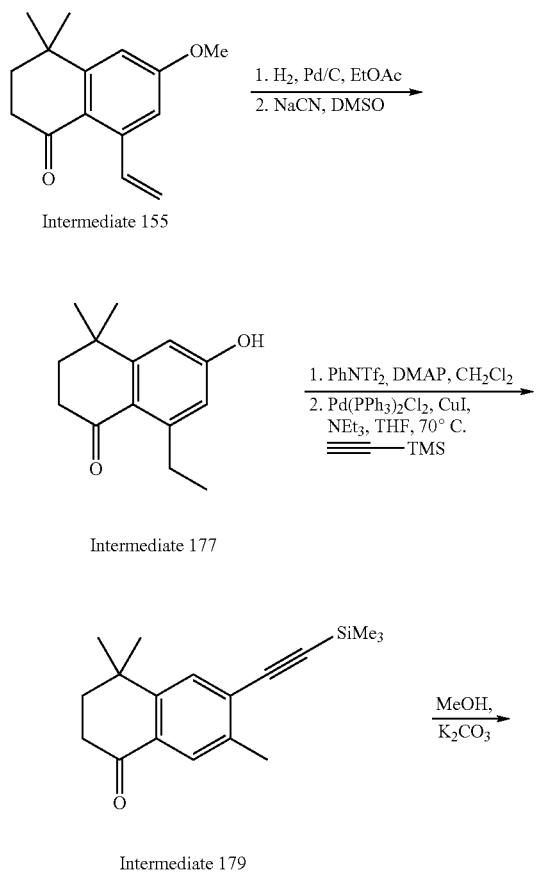

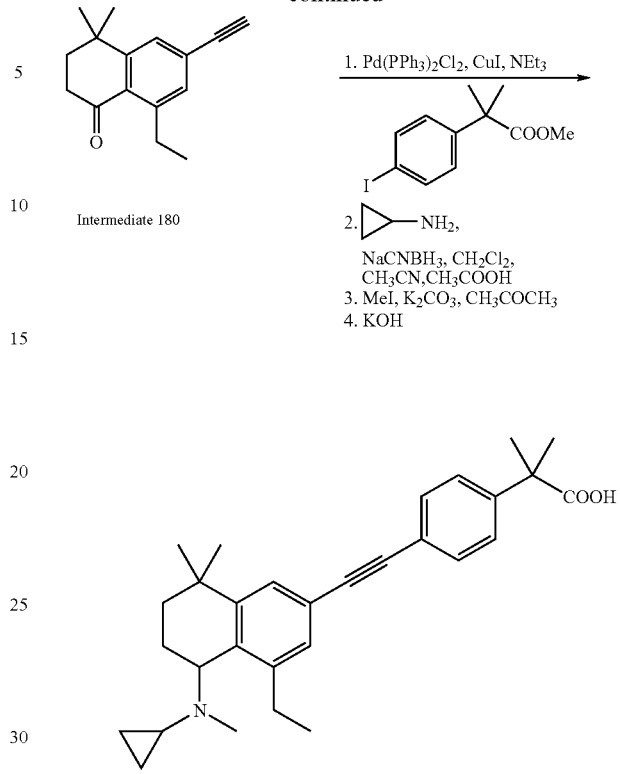

Compound 54

8-Ethyl-4,4-dimethyl-6-methoxy-3,4-dihydro-2H-naphthalen-1-one (Intermediate 176)

A solution of 8-vinyl-6-methoxy-4,4-dimethyl-3,4-dihydro-2H-naphthalen-1-one (Intermediate 155, 1.12 g, 4.86 mmol) in ethyl acetate (10 mL) was treated with 10% palladium on carbon (100 mg) and the resulting reaction mixture was stirred under an atmosphere of hydrogen overnight. The reaction mixture was filtered over a bed of celite and the filtrate was evaporated to afford the title product (1.1 g, 98%).

$^1$H NMR (300 MHz, CDCl$_3$): δ 6.77 (d, 1H, J=2.6 Hz), 6.54 (d, 1H, J=2.6 Hz), 3.87 (s, 3H), 3.05 (q, 2H, J=7.3 Hz), 2.67 (t, 2H, J=6.7 Hz), 1.95 (t, 2H, J=6.7 Hz), 1.36 (s, 6H), 1.23 (t, 3H, J=7.3 Hz).

8-Ethyl-6-hydroxy-4,4-dimethyl-3,4-dihydro-2H-naphthalen-1-one (Intermediate 177)

A solution of 8-ethyl-4,4-dimethyl-6-methoxy-3,4-dihydro-2H-naphthalen-1-one (Intermediate 176, 1.1 g, 4.73 mmol) and sodium cyanide (1.6 g, 33 mmol) in anhydrous dimethylsulfoxide (20 mL) was heated at 210° C. overnight under argon. The reaction mixture was then cooled to ambient temperature, poured into ice and acidified (Caution! Hydrogen cyanide evolution!) using 10% hydrochloric acid and extracted with ethyl acetate. The combined organic extract was washed with brine (×1), dried over anhydrous sodium sulfate, filtered and evaporated to afford a dark orange solid. Flash column chromatography on silica gel (230–400 mesh) using 10–20% ethyl acetate in hexane as the eluent afforded the title compound as a yellow solid (0.82 g, 82%).

¹H NMR (300 MHz, CD₃COCD₃): δ 8.99 (s, 1H), 6.81 (d, 1H, J=2.6 Hz), 6.64 (d, 1H, J=2.6 Hz), 2.99 (q, 2H, J=7.3 Hz), 2.60 (t, 2H, J=6.7 Hz), 1.93 (t, 2H, J=6.7 Hz), 1.34 (s, 6H), 1.17 (t, 3H, J=7.3 Hz).

Trifluoro-methanesulfonic acid 4-ethyl-8,8-dimethyl-5-oxo-5,6,7,8-tetrahydro-naphthalen-2yl ester (Intermediate 178)

A solution of 8-ethyl-6-hydroxy-4,4-dimethyl-3,4-dihydro-2H-naphthalen-1-one (Intermediate 177, 0.27 g, 1.24 mmol) and 4-dimethylaminopyridine (0.242 g, 1.98 mmol) in anhydrous dichloromethane (10 mL) was treated with 2-[N,N-bis(trifluoromethylsulfonyl)amino]-5-chloro-pyridine (0.58 g, 1.48 mmol) under argon at ambient temperature for 5 h. The reaction mixture was subjected to flash column chromatography on silica gel (230–400 mesh) using 5% ethyl acetate in hexane as the eluent to afford the title compound (0.43 g, 98%).

¹H NMR (300 MHz, CDCl₃): δ 7.15 (d, 1H, J=2.6 Hz), 7.04 (d, 1H, J=2.6 Hz), 3.05 (q, 2H, J=7.3 Hz), 2.74 (t, 2H, J=6.7 Hz), 2.00 (t, 2H, J=6.7 Hz), 1.38 (s, 6H), 1.24 (t, 3H, J=7.3 Hz).

8-Ethyl-4,4-dimethyl-6-(trimethylsilanyl)ethynyl-3,4-dihydro-2H-naphthalen-1-one (Intermediate 179)

Following General Procedure D and using trifluoro-methanesulfonic acid 4-ethyl-8,8-dimethyl-5-oxo-5,6,7,8-tetrahydro-naphthalen-2yl ester (Intermediate 178, 0.9 g, 2.57 mmol), triethyl amine (6 mL), anhydrous N,N-dimethylformamide (5 mL), dichlorobis(triphenylphosphine)palladium (II) (0.144 g, 0.2 mmol) and (trimethylsilyl)acetylene (2 mL, 13.64 mmol), the reaction was conducted overnight in a sealed tube at 90° C. Work-up followed by flash column chromatography over silica gel (230–400 mesh) using 2–3% ethyl acetate in hexane as the eluent to afforded the title compound as an orange oil (0.82 g, quantitative).

¹H NMR (300 MHz, CDCl₃): δ 7.34 (d, 1H, J=1.5 Hz), 7.21 (d, 1H, J=1.5 Hz), 2.97 (q, 2H, J=7.6 Hz), 2.69 (t, 2H, J=6.7 Hz), 1.95 (t, 2H, J=6.7 Hz), 1.35 (s, 6H), 1.20 (t, 3H, J=7.6 Hz), 0.27 (s, 9H).

8-Ethyl-6-ethynyl-4,4-dimethyl-3,4-dihydro-2H-naphthalen-1-one (Intermediate 180)

Following General Procedure F and using 8-ethyl-4,4-dimethyl-6-(trimethylsilanyl)ethynyl-3,4-dihydro-2H-naphthalen-1-one (Intermediate 179, 0.66 g, 2.2 mmol), methanol (10 mL) and potassium carbonate (0.4 g, 2.9 mmol) the title compound was obtained as an orange oil (0.59 g, 100%).

¹H NMR (300 MHz, CDCl₃): δ 7.51 (d, 1H, J=1.5 Hz), 7.37 (d, 1H, J=1.5 Hz), 3.32 (s, 1H), 3.10 (q, 2H, J=7.3 Hz), 2.84 (t, 2H, J=6.7 Hz), 2.08 (t, 2H, J=6.7 Hz), 1.48 (s, 6H), 1.33 (t, 3H, J=7.3 Hz).

2-[4-(4-Ethyl-8,8-dimethyl-5-oxo-5,6,7,8-tetrahydro-naphthalen-2-ylethynyl)-phenyl]-2-methyl-propionic acid methyl ester (Intermediate 181)

Following General Procedure B and using 8-ethyl-6-ethynyl-4,4-dimethyl-3,4-dihydro-2H-naphthalen-1-one (Intermediate 180, 0.09 g, 0.39 mmol), methyl-2-(4-iodo phenyl)-2-methyl-propionate (Reagent 2, 0.152 g, 0.5 mmol), triethyl amine (8 mL), copper(I)iodide (0.024 g, 0.12 mmol) and dichlorobis(triphenylphosphine)palladium(II) (0.087 g, 0.12 mmol) followed by flash column chromatography over silica gel (230–400 mesh) using 2–10% ethyl acetate in hexane as the eluent, the title compound was obtained as an oil (0.095 g, 59%).

¹H NMR (300 MHz, CDCl₃): δ 7.53 (d, 2H, J=8.8 Hz), 7.43 (d, 1H, J=1.8 Hz), 7.35 (d, 2H, J=8.8 Hz), 7.30 (d, J=1.8 Hz, 1H), 3.68 (s, 3H), 3.03 (q, J=7.3 Hz, 2H), 2.73 (t, J=6.9 Hz, 2H), 1.99 (t, J=6.9 Hz, 2H), 1.61 (s, 6H), 1.40 (s, 6H), 1.25 (t, J=7.3 Hz, 3H).

2-{4-[5-(Cyclopropyl-methyl-amino)-4-ethyl-8,8-dimethyl-5,6,7,8-tetrahydro-naphthalen-2-ylethynyl]-phenyl}-2-methyl-propionic acid methyl ester (Intermediate 182)

Following General Procedure C and using 2-[4-(4-ethyl-8,8-dimethyl-5-oxo-5,6,7,8-tetrahydro-naphthalen-2-yl-ethynyl)-phenyl]-2-methyl-propionic acid methyl ester (Intermediate 181, 0.095 g, 0.23 mmol) in dichloromethane (3 mL) and acetonitrile (1.5 mL), cyclopropyl amine (1 mL, 14.5 mmol), acetic acid (1 mL) and sodium cyanoborohydride (0.12 g, 1.91 mmol) followed by work up afforded an intermediate as an oil, that was used as such for the next step. The intermediate (crude 0.23 mmol, 0.13 g) was dissolved in acetone (6 mL) and treated with potassium carbonate (0.23 g, 1.66 mmol) and methyl iodide (1.5 mL, 25 mmol). The resulting reaction mixture was stirred at ambient temperature overnight. The solids were filtered off, the filtrate and washings were evaporated in vacuo to an oil. Flash column chromatography over silica gel (230–400 mesh) using 5–10% ethyl acetate in hexane as the eluent afforded the title compound (0.07, 65%).

¹H NMR (300 MHz, CDCl₃): δ 7.55 (d, J=8.8 Hz, 2H), 7.43 (d, J=1.7 Hz, 1H), 7.37 (d, J=8.8 Hz, 2H), 7.22 (d, J=1.7 Hz, 1H), 4.13 (m, 1H), 3.72 (s, 3H), 2.78–2.68 (m, 2H), 2.32–2.24 (m, 1H), 2.25 (s, 3H), 2.18–2.08 (m, 1H), 1.99–1.79 (m, 2H), 1.65 (s, 6H), 1.63–1.53 (m, 1H), 1.42 (s, 3H), 1.29 (s, 3H), 1.23 (t, J=7.3 Hz, 3H), 0.50–0.40 (m, 3H), 0.30–0.20 (m, 1H).

2-{4-[5-(Cyclopropyl-methyl-amino)-4-ethyl, 8,8-dimethyl-5,6,7,8-tetrahydro-naphthalen-2-ylethynyl]-phenyl}-2-methyl-propionic acid (Compound 54)

A solution of 2-{4-[5-(cyclopropyl-methyl-amino)-4-ethyl-8,8-dimethyl-5,6,7,8-tetrahydro-naphthalen-2-ylethynyl]-phenyl}-2-methyl-propionic acid methyl ester (Intermediate 182, 0.035 g, 0.076 mmol) in methanol (3 mL) and tetrahydrofuran (2 mL) was treated with 3M potassium hydroxide (2 mL, 4 mmol) and the resulting reaction mixture was heated at 80° C. for 2 days. The reaction mixture was neutralized with ammonium chloride and extracted with ethyl acetate. The organic phase was washed with water and brine, and dried over anhydrous sodium sulfate, filtered and evaporated in vacuo to afford a residue that was purified by preparative reverse phase HPLC to afford the title product (0.023 g, 69%).

¹H NMR (300 MHz, CDCl₃): δ 7.49 (d, J=8.4 Hz, 2H), 7.36–7.26 (m, 3H), 7.16 (d, J=1.7 Hz, 1H), 4.06 (m, 1H), 2.71–2.63 (m, 2H), 2.25–2.17 (m, 1H), 2.18 (s, 3H), 2.05–2.00 (m, 1H), 1.95–1.78 (m, 2H), 1.60–1.50 (m, 1H), 1.58 (s, 6H), 1.35 (s, 3H), 1.22 (s, 3H), 1.16 (t, J=7.3 Hz, 3H), 0.4–0.3 (m, 3H), 0.2–0.1 (m, 1H).

Reaction Scheme 30

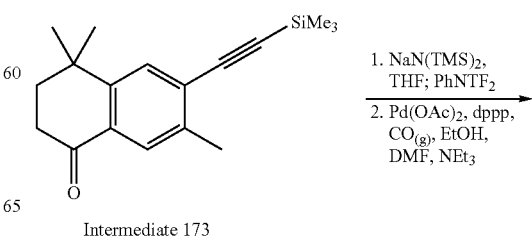

Intermediate 173

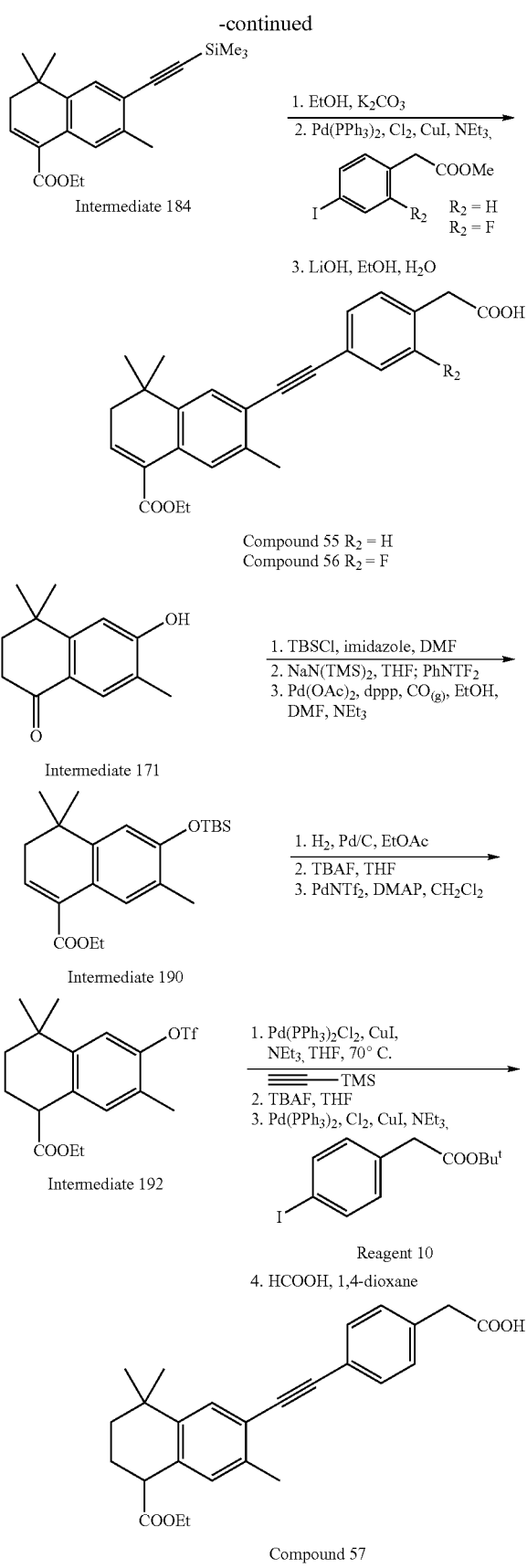

Trifluoro-methanesulfonic acid 4,4,7-trimethyl-6-trimethylsilanylethynyl-3,4-dihydro-naphthalen-1-yl ester (Intermediate 183)

A stirred, cooled (−78° C.) solution of 4,4,7-trimethyl-6-trimethylsilanylethynyl-3,4-dihydro-2H-naphthalen-1-one (Intermediate 173, 0.95 g, 3.33 mmol) in anhydrous tetrahydrofuran (10 mL) under argon was treated with a 1M solution of sodium bis(trimethylsilyl)amide in tetrahydrofuran (5 mL, 5 mmol). After 1 h, N-phenyltrifluoromethanesulfonimide (1.08 g, 3.33 mmol) was added and the reaction mixture was stirred at ambient temperature for 1 h. The reaction was quenched with saturated aqueous ammonium chloride solution, diluted with water and extracted with diethyl ether (×2). The combined organic extract was dried over anhydrous magnesium sulfate, filtered and evaporated in vacuo to a residue that was subjected to flash column chromatography on silica gel using 2–4% ethyl acetate in hexane as the eluent to afford the title compound (0.73 g, 52%).

$^1$H NMR (300 MHz, CDCl$_3$): δ 7.08 (s, 1H), 6.92 (s, 1H), 5.67 (t, 2H, J=5.0 Hz), 2.15 (s, 3H), 2.08 (d, 2H, J=5.0 Hz), 1.00 (s, 6H), 0.00 (s, 9H).

4,4,7-Trimethyl-6-trimethylsilanylethynyl-3,4-dihydro-naphthalene-1-carboxylic acid ethyl ester (Intermediate 184)

Following General Procedure E and using trifluoro-methanesulfonic acid 4,4,7-trimethyl-6-trimethylsilanylethynyl-3,4-dihydro-naphthalen-1-yl ester (Intermediate 183, 0.73 g, 1.75 mmol), palladium acetate (6.1 g, 0.45 mmol), 1,3-bis(diphenylphosphino)propane (0.1 g, 0.24 mmol), N,N-dimethylformamide (3.5 mL), ethanol (3.5 mL) and triethyl amine (3.5 mL) followed by flash column chromatography over silica gel (230–400 mesh) using 5–10% ethyl acetate in hexane as the eluent the title compound was obtained (0.435 g, 73%).

$^1$H NMR (300 MHz, CDCl$_3$): δ 7.42 (s, 1H), 7.10 (s, 1H), 6.76 (t, 2H, J=5.0 Hz), 4.04 (q, 2H, J=7.0 Hz), 2.15 (s, 3H), 2.02 (d, 2H, J=5.0 Hz), 1.09 (t, 3H, J=7.0 Hz), 0.97 (s, 6H), 0.00 (s, 9H).

6-Ethynyl-4,4,7-trimethyl-3,4-dihydro-naphthalene-1-carboxylic acid ethyl ester (Intermediate 185)

Following General Procedure F and using 4,4,7-trimethyl-6-trimethylsilanylethynyl-3,4-dihydro-naphthalene-1-carboxylic acid ethyl ester (Intermediate 184, 0.43 g, 1.3 mmol), ethanol (4 mL) and potassium carbonate (0.84 g, 6.06 mmol), the title compound was obtained (0.33 g, 95%).

$^1$H NMR (300 MHz, CDCl$_3$): δ 7.70 (s, 1H), 7.40 (s, 1H), 7.05 (t, 2H, J=5.0 Hz), 4.30 (q, 2H, J=7.0 Hz), 2.43 (s, 3H), 2.30 (d, 2H, J=5.0 Hz), 1.36 (t, 3H, J=7.0 Hz), 1.23 (s, 6H).

6-(4-Methoxycarbonylmethyl-phenylethynyl)-4,4,7-trimethyl-3,4-dihydro-naphthalene-1-carboxylic acid ethyl ester (Intermediate 186)

Following General Procedure B and using 6-ethynyl-4,4,7-trimethyl-3,4-dihydro-naphthalene-1-carboxylic acid ethyl ester (Intermediate 185, 0.126 g, 0.47 mmol), 4-iodo phenyl acetic acid methyl ester (0.13 g, 0.47 mmol), triethyl amine (2 mL), copper(I)iodide (0.029 g, 0.15 mmol) and dichlorobis(triphenylphosphine)palladium(II) (0.07 g, 0.1 mmol) followed by flash column chromatography over silica gel (230–400 mesh) using 10–12% ethyl acetate in hexane as the eluent, the title compound was obtained as a viscous oil (0.144 g, 74%).

$^1$H NMR (300 MHz, CDCl$_3$): δ 7.72 (s, 1H), 7.47 (d, 2H, J=8.1 Hz), 7.35 (s, 1H), 7.27 (d, 2H, J=8.1 Hz), 7.05 (t, 2H, J=5.0 Hz), 4.34 (q, 2H, J=7.0 Hz), 3.70 (s, 3H), 3.64 (s, 2H), 2.48 (s, 3H), 2.32 (d, 2H, J=5.0 Hz), 1.38 (t, 3H, J=7.0 Hz), 1.27 (s, 6H).

6-(4-Carboxymethyl-phenylethynyl)-4,4,7-trimethyl-3,4-dihydro-naphthalene-1-carboxylic acid ethyl ester (Compound 55)

A solution of 6-(4-carboxymethyl-phenylethynyl)-4,4,7-trimethyl-3,4-dihydro-naphthalene-1-carboxylic acid ethyl ester (Intermediate 186, 0.144 g, 0.35 mmol) in ethanol (2 mL) was treated with a 1M solution of lithium hydroxide (1 mL, 1 mmol) and the resulting reaction mixture was stirred at ambient temperature for 3 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to a residue that was purified by preparative reverse phase HPLC using 10% water in acetonitrile as the mobile phase to afford the title product (0.071 g, 50%).

$^1$H NMR (300 MHz, CDCl$_3$): δ 7.68 (s, 1H), 7.47 (br d, 2H, J=8.1 Hz), 7.41 (s, 1H), 7.21 (br d, 214), 7.04 (t, 2H, J=5.0 Hz), 4.31 (q, 2H, J=7.0 Hz), 3.65 (br s, 2H), 2.46 (s, 3H), 2.30 (d, 2H, J=5.9 Hz), 1.37 (t, 3H, J=7.0 Hz), 1.24 (s, 6H).

6-(3-Fluoro-4-methoxycarbonylmethyl-phenylethynyl)-4,4,7-trimethyl-3,4-dihydro-naphthalene-1-carboxylic acid ethyl ester (Intermediate 187)

Following General Procedure B and using 6-ethynyl-4,4,7-trimethyl-3,4-dihydro-naphthalene-1-carboxylic acid ethyl ester (Intermediate 185, 0.2 g, 0.75 mmol), 2-fluoro-4-iodo phenyl acetic acid methyl ester (0.22 g, 0.75 mmol), triethyl amine (2 mL), copper(I)iodide (0.03 g, 0.16 mmol) and dichlorobis(triphenylphosphine)palladium(II) (0.1 g, 0.14 mmol) followed by flash column chromatography over silica gel (230–400 mesh) using 10–12% ethyl acetate in hexane as the eluent, the title compound was obtained as a viscous oil (0.23 g, 73%)

$^1$H NMR (300 MHz, CDCl$_3$): δ 7.73 (s, 1H), 7.42 (s, 1H), 7.30–7.20 (m, 3H), 7.06 (t, 2H, J=5.0 Hz), 4.32 (q, 2H, J=7.0 Hz), 3.71 (s, 3H), 3.68 (s, 2H), 2.47 (s, 3H), 2.32 (d, 2H, J=5.0 Hz), 1.37 (t, 3H, J=7.0 Hz), 1.26 (s, 6H).

6-(4-Carboxymethyl-3-fluoro-phenylethynyl)-4,4,7-trimethyl-3,4-dihydro-naphthalene-1-carboxylic acid ethyl ester (Compound 56)

A solution of 6-(4-carboxymethyl-3-fluoro-phenylethynyl)-4,4,7-trimethyl-3,4-dihydro-naphthalene-1-carboxylic acid ethyl ester (Intermediate 187, 0.24 g, 0.54 mmol) in ethanol (2 mL) was treated with a 2M solution of lithium hydroxide (mL, 2 mmol) and the resulting reaction mixture was stirred at ambient temperature for 3 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to a residue that was purified by preparative reverse phase HPLC using 10% water in acetonitrile as the mobile phase to afford the title product (0.05 g, 22%).

$^1$H NMR (300 MHz, CDCl$_3$): δ 7.69 (s, 1H), 7.41 (s, 1H), 7.27–7.19 (m, 3H), 7.05 (t, 2H, J=4.7 Hz), 4.32 (q, 2H, J=7.0 Hz), 3.64 (br s, 2H), 2.45 (s, 3H), 2.31 (d, 2H, J=4.7 Hz), 1.37 (t, 3H, J=7.0 Hz), 1.25 (s, 6H).

6-(tert-Butyl-dimethyl-silanyloxy)-4,4,7-trimethyl-3,4-dihydro-2H-naphthalen-1-one (Intermediate 188)

A solution of 6-hydroxy-4,4,7-trimethyl-3,4-dihydro-2H-naphthalen-1-one (Intermediate 171, 2.04 g, 10 mmol) in anhydrous N,N-dimethyl formamide (10 mL) under argon was treated with imidazole (1 g, 14.7 mmol) followed by tert-butyldimethylsilyl chloride (1.5 g, 10 mmol). After stirring the reaction mixture at ambient temperature overnight, it was poured into water and extracted with diethyl ether (×2). The combined organic phase was dried over anhydrous sodium sulfate, filtered and evaporated to a residue that was purified by flash column chromatography on silica gel (230–400 mesh) usng 8–14% ethyl acetate in hexane as the eluent to afford the title compound (2.5 g, 79%).

$^1$H NMR (300 MHz, CDCl$_3$): δ 7.74 (s, 1H), 6.65 (s, 1H), 2.56 (t, 2H, J=6.8 Hz), 2.09 (s, 3H), 1.88 (t, 2H, J=6.8 Hz), 1.24 (s, 6H), 0.93 (s, 9H), 0.17 (s, 6H).

Trifluoro-methanesulfonic acid 6-(tert-butyl-dimethyl-silanyloxy)-4,4,7-trimethyl-3,4-dihydro-naphthalen-1-yl ester (Intermediate 189)

A stirred, cooled (−78° C.) solution of trifluoro-methanesulfonic acid 6-(tert-butyl-dimethyl-silanyloxy)-4,4,7-trimethyl-3,4-dihydro-naphthalen-1-yl ester (Intermediate 188, 2.53 g, 8 mmol) in anhydrous tetrahydrofuran (25 mL) under argon was treated with a 1M solution of sodium bis(trimethylsilyl)amide in tetrahydrofuran (12 mL, 12 mmol). After 1 h, N-phenyltrifluoromethanesulfonimide (4.28 g, 12 mmol) was added and the reaction mixture was stirred at ambient temperature for 1 h. The reaction was quenched with saturated aqueous ammonium chloride solution, diluted with water and extracted with diethyl ether (×2). The combined organic extract was dried over anhydrous magnesium sulfate, filtered and evaporated in vacuo to a residue that was subjected to flash column chromatography on silica gel using 4% ethyl acetate in hexane as the eluent to afford the title compound (1.4 g, 39%).

$^1$H NMR (300 MHz, CDCl$_3$): δ 6.90 (s, 1H), 6.4.9 (s, 1H), 5.53 (t, 2H, J=5.0 Hz), 2.09 (d, 2H, J=5.0 Hz), 1.95 (s, 3H), 1.01 (s, 6H), 0.78 (s, 9H), 0.00 (s, 6H).

6-(tert-Butyl-dimethyl-silanyloxy)-4,4,7-trimethyl-3,4-dihydro-naphthalene-1-carboxylic acid ethyl ester (Intermediate 190)

Following General Procedure E and using trifluoro-methanesulfonic acid 6-(tert-butyl-dimethyl-silanyloxy)-4,4,7-trimethyl-3,4-dihydro-naphthalen-1-yl ester (Intermediate 189, 3.4 g, 7.55 mmol), palladium acetate (0.36 g, 1.62 mmol), 1,3-bis(diphenylphosphino)propane (0.36 g, 0.86 mmol), N,N-dimethylformamide (7 mL), ethanol (7 mL) and triethyl amine (7 mL) followed by flash column chromatography over silica gel (230–400 mesh) using 7% ethyl acetate in hexane as the eluent the title compound was obtained (1.35 g, 48%).

$^1$H NMR (300 MHz, CDCl$_3$): δ 7.40 (s, 1H), 6.65 (t, 2H, J=5.0 Hz), 6.65 (s, 1H), 4.08 (q, 2H, J=7.0 Hz), 2.04 (d, 2H, J=5.0 Hz), 1.96 (s, 3H), 1.13 (t, 3H, J=7.0 Hz), 0.99 (s, 6H), 0.79 (s, 9H), 0.00 (s, 6H).

6-(tert-Butyl-dimethyl-silanyloxy)-4,4,7-trimethyl-1,2,3,4-tetrahydro-naphthalene-1-carboxylic acid ethyl ester (Intermediate 191)

A solution of 6-(tert-butyl-dimethyl-silanyloxy)-4,4,7-trimethyl-3,4-dihydro-naphthalene-1-carboxylic acid ethyl ester (Intermediate 190, 0.95 g, 2.54 mmol) in ethanol was treated with a slurry of 5% palladium on carbon (0.3 g) in ethyl acetate (0.5 mL) and the resulting reaction mixture was stirred under an atmosphere of hydrogen overnight. The solids were filtered over a bed of celite and the filtrate was evaporated in vacuo to aford the title compound as a viscous oil (0.95 g,~100%).

$^1$H NMR (300 MHz, CDCl$_3$): δ 6.66 (s, 1H), 6.51 (s, 1H), 3.95 (q, 2H, J=7.0 Hz), 3.46 (m, 1H), 1.92 (s, 3H), 1.93–1.75

(m, 2H), 1.64–1.55 (m, 1H), 1.38–1.30 (m, 1H), 1.06 (s, 3H), 1.01 (t, 3H, J=7.0 Hz), 1.01 (s, 3H), 0.80 (s, 9H), 0.00 (s, 6H).

4,4,7-Trimethyl-6-trifluoromethanesulfonyloxy-1,2,3,4-tetrahydro-naphthalene-1-carboxylic acid ethyl ester (Intermediate 192)

6-(Tert-butyl-dimethyl-silanyloxy)-4,4,7-trimethyl-1,2,3,4-tetrahydro-naphthalene-1-carboxylic acid ethyl ester (Intermediate 191, 0.95 g, 2.54 mmol) was treated with a 1M solution of tetra-n-butyl ammonium fluoride in tetrahydrofuran (4 mL, 2 mmol) under argon and the resulting reaction mixture was stirred at ambient temperature for 45 min. Water was added and the reaction mixture was extracted with 110% ethyl acetate in diethyl ether. The organic phase was washed with water and brine, dried over anhydrous sodium sulfate, filtered and evaporated to an oil that was used for the next step. The oil was dissolved in anhydrous dichloromethane under argon and treated with 4-(dimethylamino)pyridine (0.62 g, 5.11 mmol) and N-phenyltrifluoromethanesulfonimide (0.91 g, 2.54 mmol). After 1 h at ambient temperature, the reaction mixture was subjected to flash column chromatography using 8% ethyl acetate in hexane as the eluent to afford the title compound as an oil (0.86 g, 86%).

$^1$H NMR (300 MHz, CDCl$_3$): δ 7.19 (s, 1H), 7.07 (s, 1H), 4.17 (q, 2H, J=7.0 Hz), 3.73 (t, 1H, J=5.9 Hz), 2.30 (s, 3H), 2.18–1.97 (m, 2H), 1.87–1.78 (m, 1H), 1.70–1.56 (m, 1H), 1.31–1.25 (2s, 3H and 1t, 3H, overlapping).

4,4,7-Trimethyl-6-trimethylsilanylethynyl-1,2,3,4-tetrahydro-naphthalene-1-carboxylic acid ethyl ester (Intermediate 193)

Following General Procedure D in a sealed tube and using 4,4,7-trimethyl-6-trifluoromethanesulfonyloxy-1,2,3,4-tetrahydro-naphthalene-1-carboxylic acid ethyl ester (Intermediate 192, 0.86 g, 2.2 mmol), triethyl amine (2 mL), copper (I)iodide (0.083 g, 0.44 mmol), trimethylsilyl acetylene (2 mL, 14 mmol) and dichlorobis(triphenylphosphine)palladium(II) (0.306 g, 0.44 mmol) followed by flash column chromatography over silica gel (230–400 mesh) using 5% ethyl acetate in hexane as the eluent, and preaprative normal phase HPLC using 5% ethyl acetate in hexane as the mobile phase in order to separate recovered starting material from the product, the title compound (0.26 g) was obtained.

$^1$H NMR (300 MHz, CDCl$_3$): δ 7.21 (s, 1H), 6.72 (s, 1H), 3.95 (q, 2H, J=7.0 Hz), 3.49 (t, 1H, J=5.8 Hz), 2.13 (s, 3H), 1.95–1.62 (m, 2H), 1.60–1.48 (m, 1H), 1.42–1.31 (m, 1H), 1.10–1.00 (2s, 3H and 1t, 3H, overlapping), 0.04 (s, 9H).

6-(4-tert-Butoxycarbonylmethyl-phenylethynyl)-4,4,7-trimethyl-1,2,3,4-tetrahydro-naphthalene-1-carboxylic acid ethyl ester (Intermediate 194)

4,4,7-Trimethyl-6-trimethylsilanylethynyl-1,2,3,4-tetrahydro-naphthalene-1-carboxylic acid ethyl ester (Intermediate 193, 0.26 g, 0.76 mmol) was treated with a 1M solution of tetra-n-butyl ammonium fluoride in tetrahydrofuran (3 mL, 3 mmol) under argon and the resulting reaction mixture was stirred at ambient temperature for 1 h. Water was added and the reaction mixture was extracted with diethyl ether. The organic phase was washed with water and brine, dried over anhydrous sodium sulfate, filtered and evaporated to an oil that was used as such for the next step. Following General Procedure B and using the oil (0.76 mmol), 4-iodo-tert-butyl phenyl acetate (Reagent 10, 0.23 g, 0.72 mmol), triethyl amine (2 mL), copper(I)iodide (0.06 g, 0.32 mmol) and dichlorobis(triphenylphosphine)palladium(II) (0.14 g, 0.2 mmol) followed by flash column chromatography over silica gel (230–400 mesh) using 12% ethyl acetate in hexane as the eluent, the title compound was obtained as a viscous, pale yellow oil (0.23 g, 66%).

$^1$H NMR (300 MHz, CDCl$_3$): δ 7.50 (s, 1H), 7.48 (d, 2H, J=8.5 Hz), 7.24 (d, 2H, J=8.5 Hz), 6.98 (s, 1H), 4.17 (q, 2H, J=7.0 Hz), 3.74 (t, 1H, J=5.8 Hz), 3.52 (s, 2H), 2.42 (s, 3H), 2.27–1.99 (m, 2H), 1.87–1.78 (m, 1H), 1.63–1.44 (m, 1H), 1.43 (s, 9H), 1.32 (s, 3H), 1.26 (s, 3H), 1.23 (t, 3H, buried).

6-(4-Carboxymethyl-phenylethynyl)-4,4,7-trimethyl-1,2,3,4-tetrahydro-naphthalene-1-carboxylic acid ethyl ester (Compound 57)

A solution of 6-(4-tert-butoxycarbonylmethyl-phenylethynyl)-4,4,7-trimethyl-1,2,3,4-tetrahydro-naphthalene-1-carboxylic acid ethyl ester (Intermediate 194, 0.23 g, 0.5 mmol) in 1,4-dioxane (1 mL) was treated with formic acid (3 mL) and the resulting reaction mixture was stirred at ambient temperature for 6 h. Water was added and the reaction mixture was extracted with ethyl acetate(×2). The combined organic phase was washed with water, dried over anhydrous magnesium sulfate, filtered and evaporated to an oil. Preparative reverse phase HPLC using 10% water in acetonitrile as the mobile phase afforded the title compound (0.15 g, 74%).

$^1$H NMR (300 MHz, CDCl$_3$): δ 7.48 (s, 1H), 7.46 (br d, 2H), 7.23 (br d, 2H), 6.96 (s, 1H), 4.17 (q, 2H, J=7.0 Hz), 3.73 (t, 1H, J=5.8 Hz), 3.54 (br s, 2H), 2.40 (s, 3H), 2.29–1.95 (m, 2H), 1.85–1.77 (m, H), 1.62–1.44 (m, 1H), 1.31 (s, 3H), 1.26 (s, 3H), 1.25 (t, 3H, buried).

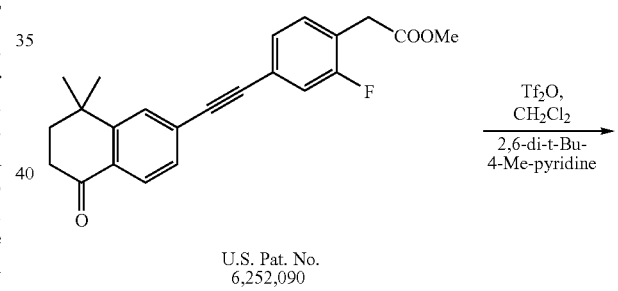

U.S. Pat. No. 6,252,090

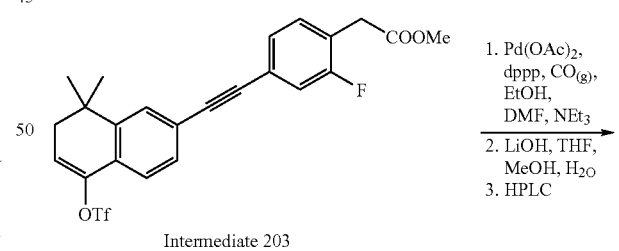

Intermediate 203

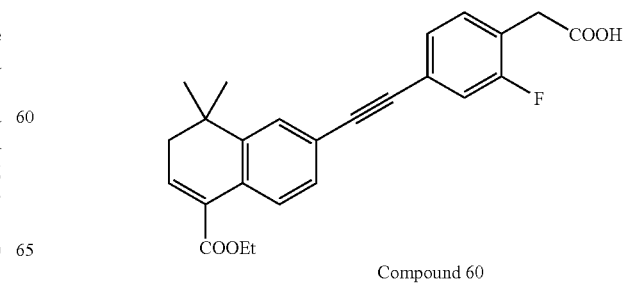

Compound 60

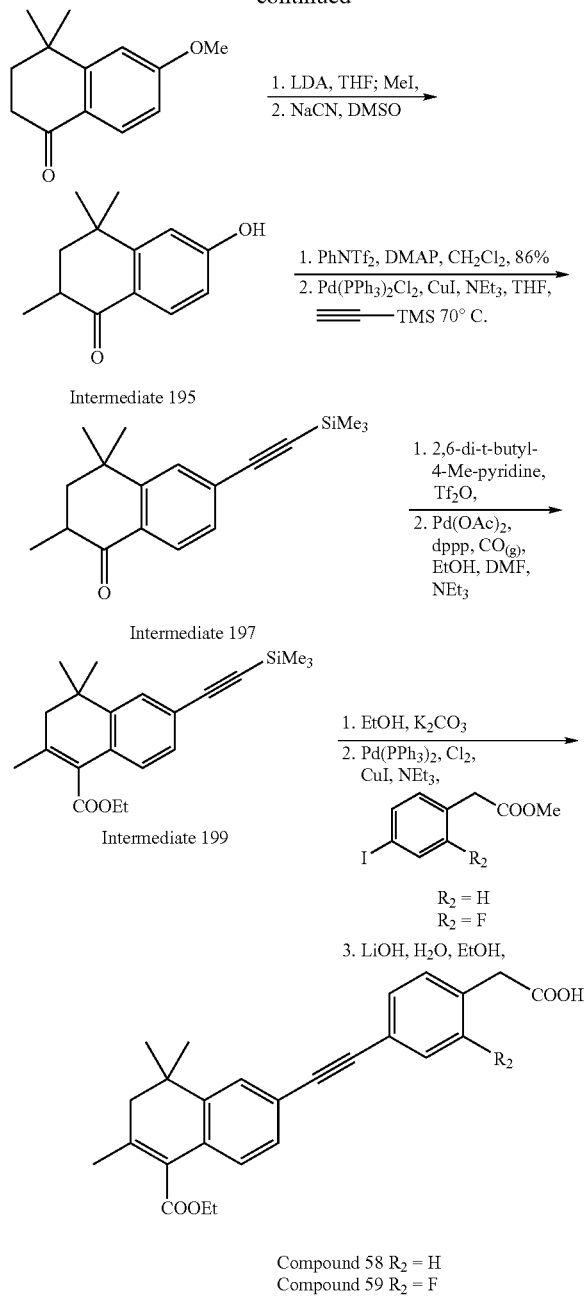

6-Hydroxy-2,4,4-trimethyl-3,4-dihydro-2H-naphthalen-1-one (Intermediate 195)

A solution 6-methoxy-2,4,4-trimethyl-3,4-dihydro-2H-naphthalen-1-one (described in Journal of Pharmaceutival Sciences, 1970, 59 (6), p 869–870, Floyd et al. incorporated herein by reference; 1.2 g, 5.5 mmol) and sodium cyanide (2 g, 41 mmol) in anhydrous dimethylsulfoxide (15 mL) was heated at 230° C. for 24 h under argon. The reaction mixture was then cooled to ambient temperature, poured into ice and acidified (Caution! Hydrogen cyanide evolution!) with dilute hydrochloric acid and extracted with ethyl acetate (×2). The combined organic extract was washed with brine (×1), dried over anhydrous sodium sulfate, filtered and evaporated to afford the title compound, which was used as such for the next step (1 g, 89%).

Trifluoro-methanesulfonic acid 6,8,8-trimethyl-5-oxo-5,6,7,8-tetrahydro-naphthalen-2-yl ester (Intermediate 196)

A solution of 6-hydroxy-2,4,4-trimethyl-3,4-dihydro-2H-naphthalen-1-one (Intermediate 195, 1 g, 5 mmol) and 4-(dimethylamino)pyridine (1.22 g, 10 mmol) in anhydrous dichloromethane (10 mL) was treated with N-phenyltrifluoromethanesulfonimide (1.78 g, 10 mmol), and the resulting reaction mixture was stirred at ambient temperature for 2 h. Flash column chromatography of the reaction mixture over silica gel (230–400 mesh) using 5% ethyl acetate in hexane as the eluent afforded the title compound as a white solid (1.45 g, 86%).

$^1$H NMR (300 MHz, CDCl$_3$): δ 8.06 (d, 1H, J=8.5 Hz), 7.25 (d, 1H, J=2.0 Hz), 6.79 (dd, 1H, J=8.5, 2.0 Hz), 2.79 (m, 1H), 1.94 (m, 2H), 1.41 (s, 3H), 1.37 (s, 3H), 1.22 (d, 3H, J=6.7 Hz).

2,4,4-Trimethyl-6-trimethylsilanylethynyl-3,4-dihydro-2H-naphthalen-1-one (Intermediate 197)

Following General Procedure D and using trifluoro-methanesulfonic acid 6,8,8-trimethyl-5-oxo-5,6,7,8-tetrahydro-naphthalen-2-yl ester (Intermediate 196, 1.45 g, 4.3 mmol), triethyl amine (5 mL), copper(I)iodide (0.21 g, 0.26 mmol), trimethylsilyl acetylene (3 mL, 21 mmol) and dichlorobis(triphenylphosphine)palladium(II) (0.75 g, 1.07 mmol) followed by flash column chromatography over silica gel (230–400 mesh) using 5% ethyl acetate in hexane as the eluent, the title compound (1.28 g, 100%) was obtained.

$^1$H NMR (300 MHz, CDCl$_3$): δ 7.64 (d, 1H, J=7.9 Hz), 7.22 (d, 1H, J=2.0 Hz), 7.08 (dd, 1H, J=7.9, 2.0 Hz), 2.50 (m, 1H), 1.94 (d, 2H, J=8.8 Hz)), 1.13 (s, 3H), 1.08 (s, 3H), 0.96 (d, 3H, J=6.8 Hz), 0.00 (s, 9H).

Trifluoro-methanesulfonic acid 2,4,4-trimethyl-6-trimethylsilanylethynyl-3,4-dihydro-naphthalen-1-yl ester (Intermediate 198)

A stirred, cooled (ice bath) solution of 2,4,4-trimethyl-6-trimethylsilanylethynyl-3,4-dihydro-2H-naphthalen-1]-one (Intermediate 0.197, 1.28 g, 4.5 mmol) in anhydrous dichloromethane (10 mL) was treated with 2,6-di-t-butyl-4-methyl pyridine (2.04 g, 9.91 mmol) and trifluoromethanesulfonic anhydride (1.52 mL, 9 mmol) and the resulting reaction mixture was stirrred at ambient temperature for 5 days at the end of which it was subjected to flash column chromatography on silica gel (230–400 mesh) using 5% ethyl acetate in hexane as the eluent to afford the title compound as an oil (1.59 g, 85%).

$^1$H NMR (300 MHz, CDCl$_3$): δ 7.09 (d, 1H, J=7.9 Hz), 7.07 (d, 1H, J=1.5 Hz), 6.98 (dd, 1H, J=7.9, 1.5 Hz), 2.04 (s, 2H), 1.72 (s, 3H), 1.03 (s, 6H), 0.00 (s, 9H).

2,4,4-Trimethyl-6-trimethylsilanylethynyl-3,4-dihydro-naphthalene-1-carboxylic acid ethyl ester-(Intermediate 199)

Following General Procedure E and using trifluoro-methanesulfonic acid 2,4,4-trimethyl-6-trimethylsilanylethynyl-3,4-dihydro-naphthalen-1-yl ester (Intermediate 198, 1.59 g, 3.8 mmol), palladium acetate (0.1 g, 0.45 mmol), 1,3-bis(diphenylphosphino)propane (0.1 g, 0.24 mmol), N,N-dimethylformamide (2.4 mL), ethanol (2.4 mL) and triethyl amine (2.4 mL) followed by flash column chromatography over silica gel (230–400 mesh) using 5% ethyl acetate in hexane as the eluent the title compound was obtained (0.31 g, 24%) as a yellow oil.

$^1$H NMR (300 MHz, CDCl$_3$): δ 7.12 (d, 1H, J=1.5 Hz), 7.01 (dd, 1H, J=8.2, 1.8 Hz), 6.77 (d, 1H, J=8.2 Hz), 4.10 (q,

2H, J=7.0 Hz), 1.93 (s, 2H), 1.73 (s, 3H), 1.08 (t, 3H, J=7.0 Hz), 0.99 (s, 6H), 0.00 (s, 9H).

6-Ethynyl-2,4,4-trimethyl-3,4-dihydro-naphthalene-1-carboxylic acid ethyl ester (Intermediate 200)

Following general procedure F and using 2,4,4-trimethyl-6-trimethylsilanylethynyl-3,4-dihydro-naphthalene-1-carboxylic acid ethyl ester (Intermediate 199, 0.31 g, 0.92 mmol), ethanol (2 mL) and potassium carbonate (0.3 g, 2.2 mmol), the title compound was obtained (0.26 g, >100%).

$^1$H NMR (300 MHz, CDCl$_3$): δ 7.32 (d, 1H, J=1.5 Hz), 7.20 (dd, 1H, J=8.2, 1.5 Hz), 6.96 (d, 1H, J=8.2 Hz), 4.27 (q, 2H, J=7.0 Hz), 3.00 (s, 1H), 2.10 (s, 2H), 1.90 (s, 3H), 1.27 (t, 3H, J=7.0 Hz), 1.16 (s, 6H).

6-(4-Methoxycarbonylmethyl-phenylethynyl)-2,4,4-trimethyl-3,4-dihydro-naphthalene-1-carboxylic acid ethyl ester (Intermediate 201)

Following General Procedure B and using 6-ethynyl-2,4,4-trimethyl-3,4-dihydro-naphthalene-1-carboxylic acid ethyl ester (Intermediate 200, 0.106 g, 0.38 mmol), 4-iodo phenyl acetic acid methyl ester (0.106 g, 0.38 mmol), triethyl amine (2 mL), copper(I)iodide (0.02 g, 6.105 mmol) and dichlorobis(triphenylphosphine)palladium(II) (0.07 g, 0.1 mmol) followed by flash column chromatography over silica gel (230–400 mesh) using 12–15% ethyl acetate in hexane as the eluent, the title compound was obtained as a pale yellow oil (0.075 g, 47%).

$^1$H NMR (300 MHz, CDCl$_3$): δ 7.49 (d, 2H, J=7.9 Hz), 7.45 (d, 1H, J=1.5 Hz), 7.32 (dd, 1H, J=7.9, 1.5 Hz), 7.26 (d, 2H, J=7.9 Hz), 7.07 (d, 1H, J=7.9 Hz), 4.37 (q, 2H, J=7.0 Hz), 3.70 (s, 3H), 3.63 (s, 2H), 2.22 (s, 2H), 2.00 (s, 3H), 1.38 (t, 3H, J=7.0 Hz), 1.27 (s, 6H).

6-(4-Carboxymethyl-phenylethynyl)-2,4,4-trimethyl-3,4-dihydro-naphthalene-1-carboxylic acid ethyl ester (Compound 58)

A solution of 6-(4-carboxymethyl-phenylethynyl)-2,4,4-trimethyl-3,4-dihydro-naphthalene-1-carboxylic acid ethyl ester (0.075 g, 0.18 mmol) in ethanol (2 mL) was treated with a 1M solution of lithium hydroxide (1 mL, 1 mmol) and the resulting reaction mixture was stirred at ambient temperature for 0.5 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to afford the title product (0.055 g, 76%).

$^1$H NMR (300 MHz, CDCl$_3$): δ 7.48 (d, 2H, J=7.9 Hz), 7.44 (d, 1H, J=1.5 Hz), 7.31 (dd, 1H, J=7.9, 1.7 Hz), 7.23 (br d, 2H, J=7.7 Hz), 7.06 (d, 1H, J=7.9 Hz), 4.36 (q, 2H, J=7.0 Hz), 3.60 (br s, 2H), 2.20 (s, 2H), 1.99 (s, 3H), 1.37 (t, 3H, J=7.0 Hz), 1.26 (s, 6H).

6-(3-Fluoro-4-methoxycarbonylmethyl-phenylethynyl)-2,4,4-triethyl-3,4-dihydro-naphthalene-1-carboxylic acid ethyl ester (Intermediate 202)

Following General Procedure B and using 6-ethynyl-2,4,4-trimethyl-3,4-dihydro-naphthalene-1-carboxylic acid ethyl ester (0.16 g, 0.59 mmol), 2-fluoro-4-iodo phenyl acetic acid methyl ester (Intermediate 200, 0.16 g, 0.56 mmol), triethyl amine (2 mL), copper(I)iodide (0.07 g, 0.37 mmol) and dichlorobis(triphenylphosphine)palladium(II) (0.11 g, 0.116 mmol) followed by flash column chromatography over silica gel (230–400 mesh) using 12–15% ethyl acetate in hexane as the eluent, the title compound was obtained as a viscous oil (0.15 g, 58%).

$^1$H NMR (300 MHz, CDCl$_3$): δ 7.44 (d, 1H, J=1.5 Hz), 7.32 (dd, 1H, J=7.9, 1.5 Hz), 7.30–7.19 (m, 3H), 7.08 (d, 1H, J=7.9 Hz), 4.37 (q, 2H, J=7.0 Hz), 3.71 (s, 3H), 3.68 (s 2H), 2.21 (s, 2H), 2.00 (s, 3H), 1.37 (t, 3H, J=7.0 Hz), 1.27 (s, 6H).

6-(4-Carboxymethyl-3-fluoro-phenylethynyl)-2,4,4-trimethyl-3,4-dihydro-naphthalene-1-carboxylic acid ethyl ester (Compound 59)

A solution of 6-(4-carboxymethyl-3-fluoro-phenylethynyl)-2,4,4-trimethyl-3,4-dihydro-naphthalene-1-carboxylic acid ethyl ester (Intermediate 202, 0.15 g, 0.35 mmol) in ethanol (2 mL) was treated with a 1M solution of lithium hydroxide (1 mL, 1 mmol) and the resulting reaction mixture was stirred at ambient temperature for 0.5 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to afford the title product (0.1 g, 67%).

$^1$H NMR (300 MHz, CDCl$_3$): δ 7.44 (d, 1H, J=1.5 Hz), 7.32 (dd, 1H, J=8.2, 1.5 Hz), 7.22–7.18 (m, 3H), 7.07 (d, 1H, J=7.9 Hz), 4.36 (q, 2H, J=7.0 Hz), 3.66 (br s, 2H), 2.20 (s, 2H), 1.99 (s, 3H), 1.37 (t, 3H, J=7.0 Hz), 1.26 (s, 6H).

[4-(8,8-Dimethyl-5-trifluoromethanesulfonyloxy-7,8-dihydro-naphthalen-2-ylethynyl)-2-fluoro-phenyl]-acetic acid methyl ester (Intermediate-203)

A solution of [4-(8,8-dimethyl-5-oxo-5,6,7,8-tetrahydro-naphthalen-2-ylethynyl)-2-fluoro-phenyl]-acetic acid methyl ester (U.S. Pat. No. 6,252,090; 0.28 g, 0.77 mmol) in anhydrous dichloro methane (5 mL) was treated with 2,6-di-t-butyl-4-methyl pyridine (0.189 g, 0.92 mmol) and trifluoromethanesulfonic anhydride (0.136 mL, 0.81 mmol) and the resulting reaction mixture was stirrred at ambient temperature for 4 h at the end of which it was diluted with water and extracted with ethyl acetate. The organic extract was washed with water and brine, dried over anhydrous sodium sulfate, filtered and evaporated in vacuo to a residue that was subjected to flash column chromatography on silica gel (230–400 mesh) using 5% ethyl acetate in hexane as the eluent to afford the title compound as a pale orange oil (0.32 g, 84%).

$^1$H NMR (300 MHz, CDCl$_3$): δ 7.46–7.22 (m, 6H), 6.00 (t, J=4.8 Hz, 1H), 3.72 (s, 3H), 3.70 (s, 2H), 2.41 (d, J=4.8 Hz, 2H), 1.33 (s, 6H).

6-(3-Fluoro-4-methoxycarbonylmethyl-phenylethynyl)-4,4-dimethyl-3,4-dihydro-naphthalene-1-carboxylic acid ethyl ester (Intermediate 204)

Following General Procedure E and using [4-(8,8-dimethyl-5-trifluoromethanesulfonyloxy-7,8-dihydro-naphthalen-2-ylethynyl)-2-fluoro-phenyl]-acetic acid methyl ester (Intermediate 203, 0.32 g, 0.65 mmol), palladium acetate (0.015 g, 0.064 mmol), 1,3-bis(diphenylphosphino)propane (0.027 g, 0.064 mmol), N,N-dimethylformamide (55 mL), ethanol (2 mL) and triethyl amine (2 mL) followed by flash column chromatography over silica gel (230–400 mesh) using 5–15% ethyl acetate in hexane as the eluent the title compound was obtained (0.15 g, 55%) as a yellow oil.

$^1$H NMR (300 MHz, CDCl$_3$): δ 7.84 (d, J=8.2 Hz, 1H), 7.47 (d, J=1.7 Hz, 1H), 7.37 (dd, J=8.2, 1.7 Hz, 1H), 7.30–7.15 (m, 3H), 7.08 (t, J=4.8 Hz, 1H), 4.31 (q, J=7.0 Hz, 2H), 3.71 (s, 3H), 3.68 (s, 2H), 2.34 (d, J=4.8 Hz, 2H), 1.37 (t, J=7.0 Hz, 3H), 1.28 (s, 6H).

6-(4-Carboxymethyl-3-fluoro-phenylethynyl)-4,4-dimethyl-3,4-dihydro-naphthalene-1-carboxylic acid ethyl ester (Compound 60)

A solution of 6-(3-fluoro-4-methoxycarbonylmethyl-phenylethynyl)-4,4-dimethyl-3,4-dihydro-naphthalene-1-carboxylic acid ethyl ester (Intermediate 204, 0.15 g, 0.36 mmol) in ethanol (3 mL) and tetrahydrofuran (3 mL) was treated with a 2M solution of lithium hydroxide (1.5 mL, 0.3 mmol) and the resulting reaction mixture was stirred at ambient temperature for 1.5 h. The volatiles were evaporated in vacuo, the residue was neutralized with saturated aqueous ammonium chloride solution and extracted with diethyl ether and ethyl acetate. The organic phase was dried over anhydrous magnesium sulfate, filtered and evaporated in vacuo to a residue that was purified by preparative reverse phase HPLC using 5% water in acetonitrile as the mobile phase to afford the title product (0.04 g, 27%). $^1$H NMR (300 MHz, CDCl$_3$): δ 7.81 (d, J=8.2 Hz, 1H), 7.46 (d, J=1.7 Hz, 1H), 7.37 (dd, J=8.2 & 1.7 Hz, 1H), 7.27–7.09 (m, 3H), 7.07 (t, J=4.8 Hz, 1H), 4.31 (q, J=7.0 Hz, 2H), 3.66 (s, 2H), 2.33 (d, J=4.8 Hz, 2H), 1.37 (t, J=7.0 Hz, 3H), 1.27 (s, 6H).

3,5-Dibromo-benzoic acid isopropyl ester (Intermediate 205)

A solution of 3,5-dibromobenzoic Acid (Aldrich, 2.4 g, 8.6 mmol) in benzene (150 mL) and isopropanol (50 mL) was treated with concentrated sulfuric acid (2 mL) and heated to reflux overnight using a Dean-Stark water trap. The volatiles were evaporated in vacuo, the residue was diluted with water and extracted with diethyl ether. The organic phase was washed with water and saturated, aqueous sodium bicarbonate solution, dried over anhydrous magnesium sulfate, filtered and evaporated in vacuo to afford the title product as a clear oil that was used as such for the next step (2.7 g, ~100%).

3,5-Diethynyl-benzoic acid isopropyl ester (Intermediate 206)

Following General Procedure D and using 3,5-dibromo-benzoic acid isopropyl ester (Intermediate 205, 2.7 g, 8.6 mmol), triethyl amine (30 mL), copper(I)iodide (0.45 g, 2.4 mmol), trimethylsilyl acetylene (6.8 mL, 48 mmol) and dichlorobis(triphenylphosphine)palladium(II) (1.75 g, 2.4

Reaction Scheme 32

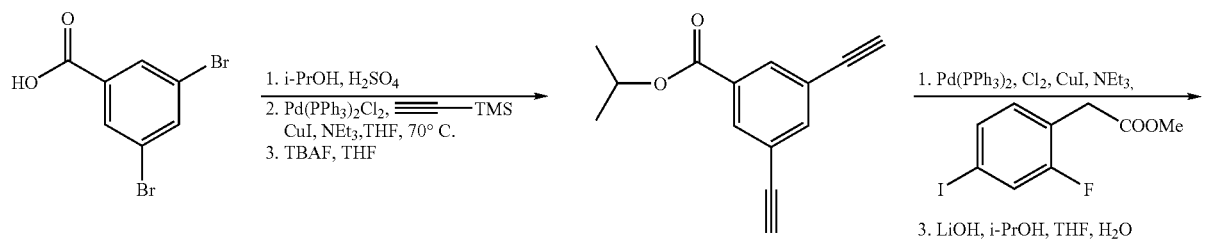

Intermediate 205

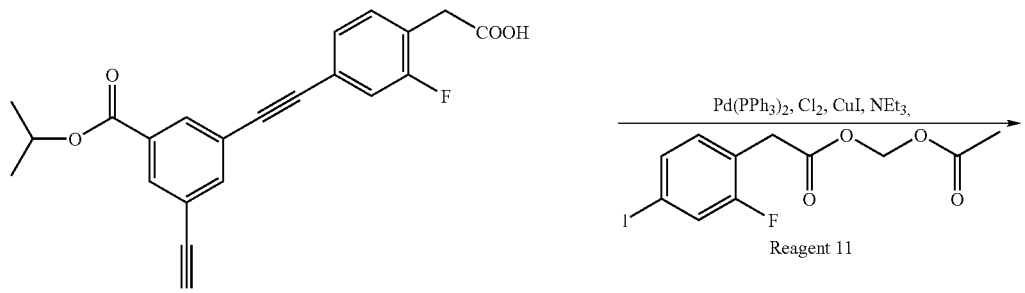

Compound 61

Reagent 11

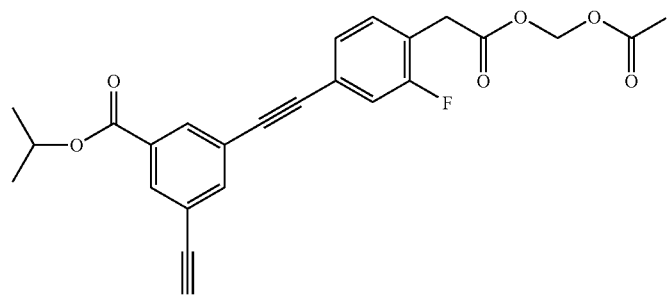

Compound 62 mmol) followed by flash column chromatography over silica gel (230–400 mesh) using 3% ethyl acetate in hexane as the eluent, the intermediate 3,5-bis-trimethylsilanylethynyl-benzoic acid isopropyl ester was obtained. The intermediate (2.8 g, 7.85 mmol) was treated with a 1M solution of tetra-n-butyl ammonium fluoride in tetrahydrofuran (25 mL, 25 mmol) and the resulting reaction mixture was stirred in an ice bath for 1 h. Water was added and the reaction mixture was extracted with diethyl ether. The organic phase was washed with water and brine, dried over anhydrous sodium sulfate, filtered and evaporated to an oil that was redissolved in diethyl ether (10 mL) and treated with hexane (150 mL). The solid that precipitated out was filtered and dried to afford the title compound (1.3 g, 78%).

$^1$H NMR (300 MHz, CDCl$_3$): δ 8.08 (d, 1H, J=1.4 Hz), 7.73 (d, 1H, J=1.4 Hz), 5.23 (heptet, 1H, J=6.3 Hz), 3.13 (s, 2H), 1.35 (d, 6H, J=6.1 Hz).

3-Ethynyl-5-[3-fluoro-4-(3-trimethylsilanyl-propoxycarbonylmethyl)-phenylethynyl]-benzoic acid isopropyl ester (Intermediate 207)

Following General Procedure B and using 3,5-diethynyl-benzoic acid isopropyl ester (Intermediate 206, 0.36 g, 1.12 mmol), (2-fluoro-4-iodo-phenyl)-acetic acid 2-trimethylsilanyl-ethyl ester (0.132 g, 0.86 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230–400 mesh) using 5–10% ethyl acetate in hexane as the eluent, the title compound was obtained as a colorless oil (0.15 g, 37%).

$^1$H NMR (300 MHz, CDCl$_3$): δ 8.10 (m, 1H), 8.07 (m, 1H), 7.75 (m, 1H), 7.19–7.25 (m, 3H), 5.24 (hept, J=6.2 Hz, 1H), 4.19 (t, J=8.5 Hz, 2H), 3.64 (s, 2H), 3.14 (s, 1H), 1.35 (d, J=6.2 Hz, 6H), 0.97 (t, J=8.5 Hz, 2H), 0.00 (s, 9H).

3-(4-Carboxymethyl-3-fluoro-phenylethynyl)-5-ethynyl-benzoic acid isopropyl ester (Compound 61)

A solution of 3-ethynyl-5-[3-fluoro-4-(3-trimethylsilanyl-propoxycarbonylmethyl)-phenylethynyl]-benzoic acid isopropyl ester (Intermediate 207, 0.15 g, 0.32 mmol) in anhydrous dimethysulfoxide (4 mL) was treated with tetra-n-ethyl ammonium fluoride (0.19 mL, 1.3 mmol) and the resulting reaction mixture was stirred at ambient temperature for 5 min. Water was added and the reaction mixture was extracted with ethyl acetate. The organic phase was washed with water and brine, dried over anhydrous sodium sulfate, filtered and evaporated to an oil that was purified by recrystallization from ethyl acetate/hexane to afford the title compound as a white solid (0.045 g, 38%).

$^1$H NMR (300 MHz, CDCl$_3$): δ 8&13 (m, 1H), 8.10 (m, 1H), 7.78 (m, 1H), 7.23–7.30 (m, 3H), 5.29 (hept, J=6.4 Hz, 1H), 3.74 (s, 2H), 3.15 (s, 1H), 1.38 (d, J=6.4 Hz, 6H).

3-(4-Acetoxymethoxycarbonylmethyl-3-fluoro-phenylethynyl)-5-ethynyl-benzoic acid isopropyl ester (Compound 62)

Following General Procedure B and using 3,5-diethynyl-benzoic acid isopropyl ester (Intermediate 2.06, 0.27 g, 1–0.27 mmol), (2-fluoro-4-iodo phenyl)-acetic acid acetoxymethyl ester (0.224 g, 0.64 mmol), triethyl amine (8 mL), copper(I)iodide (0.019 g, 0.1 mmol) and dichlorobis(triphenylphosphine)palladium(II) (0.07 g, 0.1 mmol) followed by flash column chromatography over silica gel (230–400 mesh) using 2.5–20% ethyl acetate in hexane as the eluent, the title compound was obtained as an orange solid (0.09 g, 32%).

$^1$H NMR (300 MHz, CDCl$_3$): δ 8.13 (m, 1H), 8.10 (m, 1H), 7.79 (m, 1H), 7.23–7.32 (m, 3H), 5.78 (s, 2H), 5.27 (hept, J=6.4 Hz, 1H), 3.75 (s, 2H), 3.15 (s, 1H), 2.12 (s, 3H), 1.38 (d, J=6.4 Hz, 6H).

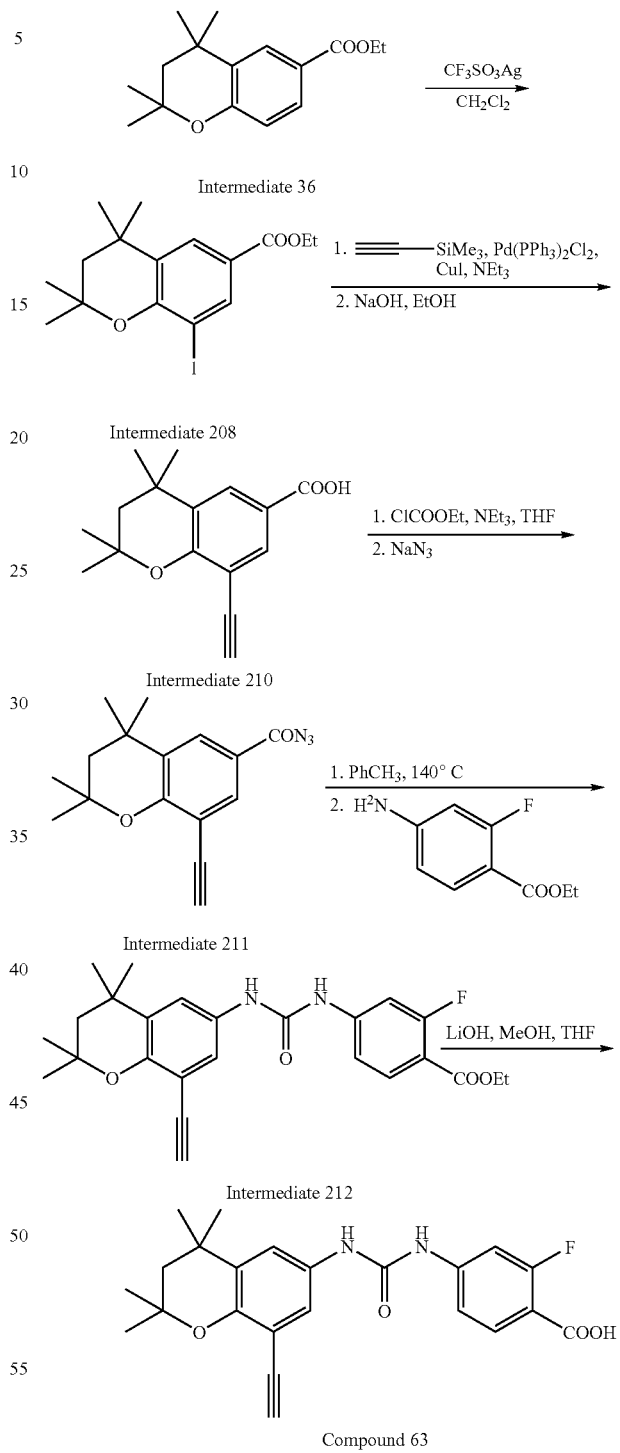

Ethyl-8-iodo-2,2,4,4-tetramethyl chroman-6-carboxylate (Intermediate 208)

A solution of ethyl-2,2,4,4-tetramethyl chroman-6-carboxylate (Intermediate 36, 0.733 g, 2.8 mmol) in anhydrous dichloromethane (10 mL) was treated with silver(I)trifluoromethanesulfonate (0.719 g, 2.8 mmol) and iodine (0.71 g, 2.8 mmol) and the resulting solution was stirred at ambient temperature for 4 h. The reaction mixture was treated with saturated, aqueous sodium thiosulfate solution and extracted with ethyl acetate. The organic phase was dried over anhydrous magnesium sulfate, filtered and evaporated in vacuo to a residue which was subjected to flash column chromatography over silica gel (230–400 mesh) using 5–10% ethyl acetate in hexane as the eluent to afford the title compound (0.88 g, 81%) as a pale yellow oil.

$^1$H NMR (300 MHz, CDCl$_3$): δ 8.26 (d, 1H, J=2.0 Hz), 7.96 (d, 1H, J=2.0 Hz), 4.34 (q, 2H, J=7.1 Hz), 1.87 (s, 2H), 1.40 (s, 6H), 1.37 (s, 6H), 1.41–1.35 (m, 3H).

Ethyl-8-trimethylsilanylethynyl-2,2,4,4-tetramethyl chroman-6-carboxylate (Intermediate 209)

A solution of ethyl-8-iodo-2,2,4,4-tetramethyl chroman-6-carboxylate (Intermediate 208, 0.88 g, 2.26 mmol) in triethyl amine (10 mL) was treated with copper(I)iodide (0.043 g, 0.226 mmol) and sparged with argon for 5 minutes. Trimethylsilyl acetylene (3 mL, 21.22 mmol) was then added followed by dichlorobis(triphenylphosphine)palladium(II) (0.159 g, 0.226 mmol). The resulting reaction mixture was heated at 70° C. overnight in a sealed tube. It was then cooled to ambient temperature, diluted with diethyl ether and filtered over a bed of celite. The filtrate was evaporated vacuo to an oil which was subjected to flash column chromatography over silica gel (230–400 mesh) using 10% ethyl acetate in hexane as the eluent to afford the title compound (0.83 g, 99%).

$^1$H NMR (300 MHz, CDCl$_3$): δ 7.93 (s, 1H), 7.92 (s, 1H), 4.32 (q, 2H, J=7.0 Hz), 1.86 (s, 2H), 1.38 (s, 6H), 1.34 (s, 6H), 1.38–1.34 (m, 3H), 0.24 (s, 9H).

8-Ethynyl-2,2,4,4-tetramethyl chroman-6-carboxylic acid (Intermediate 210)

A solution of ethyl-8-trimethylsilanylethynyl-2,2,4,4-tetramethyl-chroman-6-carboxylate (Intermediate 209, 0.525 g, 1.47 mmol) in ethanol (5 mL) was treated with 2N aqueous sodium hydroxide solution (5 mL, 10 mmol) and the resulting solution was adjusted to pH 5 with 10% aqueous hydrochloric acid and extracted with ethyl acetate. The organic phase was dried over anhydrous magnesium sulfate, filtered and evaporated in vacuo to afford the title product as a brown solid (0.316 g, 84%).

$^1$H NMR (300 MHz, CDCl$_3$): δ 8.02 (s, 2H), 3.23 (s, 1H), 1.89 (s, 2H), 1.42 (s, 6H), 1.38 (s, 6H).

8-Ethynyl-2,2,4,4-tetramethyl-chroman-6-carboxylic acid azide (Intermediate 211)

A stirred, cooled (ice bath) solution of 8-ethynyl-2,2,4,4-tetramethyl-chroman-6-carboxylic acid (Intermediate 210, 0.52 g, 2 mmol) in anhydrous tetrahydrofuran (10 mL) under argon, was treated with triethyl amine (0.86 mL, 6 mmol) follwed by ethyl chloroformate (0.25 mL, 2.6 mmol) and the resulting reaction mixture was allowed to warm to ambient temperature and stirred for 2 h. Sodium azide 0.19 g, 3 mmol) was added and the reaction mixture was stirred overnight. The reaction mixture was then diluted with water and extracted with diethyl ether. The organic extract was dried over anhydrous magnesium sulfate, filtered and evaporated to a residue that was purified by flash column chromatography over silica gel (230–400 mesh) to afford the title compound as a yellow solid (0.32 g, 56%).

$^1$H NMR (300 MHz, CDCl$_3$): δ 7.96 (ABq, 2H, J=2.1 Hz), 3.24 (s, 1H), 1.89 (s, 2H), 1.42 (s, 6H), 1.37 (s, 6H).

4-[3-(8-Ethynyl-2,2,4,4-tetramethyl-chroman-6-yl)-ureido]-2-fluoro-benzoic acid ethyl ester (Intermediate 212)

A solution of 8-ethynyl-2,2,4,4-tetramethyl-chroman-6-carboxylic acid azide (Intermediate 211, 0.104 g, 0.37 mmol) in anhydrous toluene was refluxed under argon overnight. Ethyl-4-amino-2-fluoro-benzoate (described in Teng et al, Journal of Medicinal Chemistry, 1996, 39, p 3035–3038, 0.114 g, 0.622 mmol) was added and the reaction mixture was refluxed for 5.5 h. The reaction mixture was cooled to ambient temperature and subjected to flash column chromatography over silica gel (230–400 mesh) using 20–33% ethyl acetate in hexane as the eluent to afford the title compound contaminated with some ethyl-4-amino-2-fluoro-benzoate. It was used as such for the next step.

4-[3-(8-Ethynyl-2,2,4,4-tetramethyl-chroman-6-yl)-ureido]-2-fluoro-benzoic acid (Compound 63)

A solution of 4-[3-(8-ethynyl-2,2,4,4-tetramethyl-chroman-6-yl)-ureido]-2-fluoro-benzoic acid ethyl ester (Intermediate 212, 0.12 g) in methanol (2 mL), tetrahydrofuran (2 mL) and water (1 mL) was treated with lithium hydroxide (0.177 g, 4.2 mmol) and the resulting reaction mixture was stirred at ambient temperature overnight. The volatiles were evaporated in vacuo, the residue was diluted with water and neutralized with dilute hydrochloric acid and extracted with ethyl acetate. The organic phase was dried over anhydrous magnesium sulfate, filtered and evaporated to afford the title compound as a solid (0.07 g, 46% for two steps).

$^1$H NMR (300 MHz, CD$_3$OD): δ 7.86 (dd, 1H, J=8.8, 8.5 Hz), 7.53 (dd, 1H, J=13.7, 2.0 Hz), 7.42 (d, 1H, J=2.3 Hz), 7.28 (d, 1H, J=2.3 Hz), 7.14 (dd, 1H, J=2.0, 8.8 Hz), 3.50 (s, 1H), 1.86 (s, 2H), 1.35 (s, 12H).

What is claimed is:

1. A compound of the formula

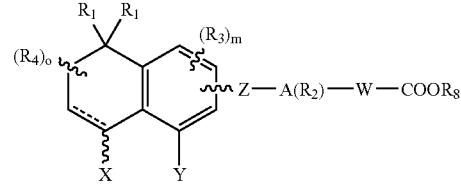

wherein A is a phenyl or naphthyl group, said phenyl and naphthyl groups being optionally substituted with one or two R$_2$ groups;

X is NRR$_7$ where R is H, alkyl of 1 to 6 carbons or benzyl;

Y is H, alkyl of 1 to 10 carbons, benzyl, C$_{1-6}$ alkyl or halogen substituted benzyl, fluoro-substituted alkyl of 1 to 10 carbons, cycloalkyl of 3 to 6 carbons, C$_{1-6}$ alkyl substituted cycloalkyl of 3 to 6 carbons, alkenyl of 2 to 6 carbons and having 1 or 2 double bonds, alkynyl of 2 to 6 carbons, alkenyl-alkynyl of 4 to 6 carbons, alkynyl-alkenyl of 4 to 6 carbons, Cl, Br, I, or —COOR$_1$;

Z is —C≡C

R$_1$ is independently H or alkyl of 1 to 6 carbons;

R$_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

R$_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

W is CR$_5$=CR$_5$—;

$R_5$ is independently H, halogen, or alkyl of 1 to 3 carbons;

$R_7$ is H, alkyl of 1 to 6 carbons, cycloalkyl of 3 to 6 carbons or $C_{1-6}$ alkyl substituted cycloalkyl of 1 to 6 carbons, and $R_8$ is H, alkyl of 1 to 6 carbons, —$CH_2O(C_{1-6}$-alkyl), $CH_2OCO(C_{1-6}$-alkyl) or a cation of a pharmaceutically acceptable base.

2. A compound in accordance with claim 1 where Y is H or $COOR_1$, $R_7$ is cyclopropyl and $R_8$ is H, lower alkyl of 1 to 3 carbons, —$CH_2O(C_{1-3}$-alkyl) or —$CH_2OCO(C_{1-3}$-alkyl) or a cation of a pharmaceutically acceptable base.

3. A compound in accordance with claim 2 where the compound has the formula

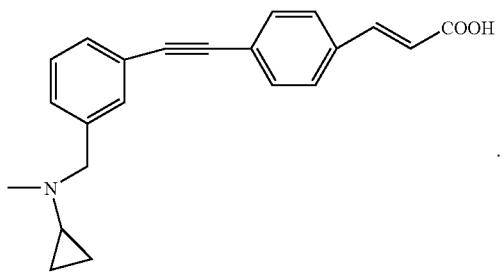

4. A compound of the formula

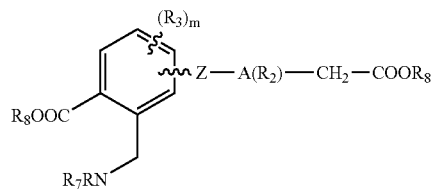

wherein A is a phenyl or naphthyl group, said phenyl and naphthyl groups being optionally substituted with one or two $R_2$ groups;

Z is —C≡C—;

R is H or alkyl of 1 to 6 carbons;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_7$ is H, alkyl of 1 to 6 carbons, cycloalkyl of 3 to 6 carbons or $C_{1-6}$ alkyl substituted cycloalkyl of 1 to 6 carbons, and $R_8$ independently is H, alkyl of 1 to 6 carbons, —$CH_2O$ ($C_{1-6}$-alkyl), $CH_2OCO(C_{1-6}$-alkyl) or a cation of a pharmaceutically acceptable base.

* * * * *

UNITED STATES PATENT AND TRADEMARK OFFICE
CERTIFICATE OF CORRECTION

PATENT NO.        : 7,226,951 B2                                    Page 1 of 1
APPLICATION NO.   : 11/014460
DATED             : June 5, 2007
INVENTOR(S)       : Jayasree Vasudevan et al.

It is certified that error appears in the above-identified patent and that said Letters Patent is hereby corrected as shown below:

Col. 178, Line 35
In Claim 1, line 2, delete

"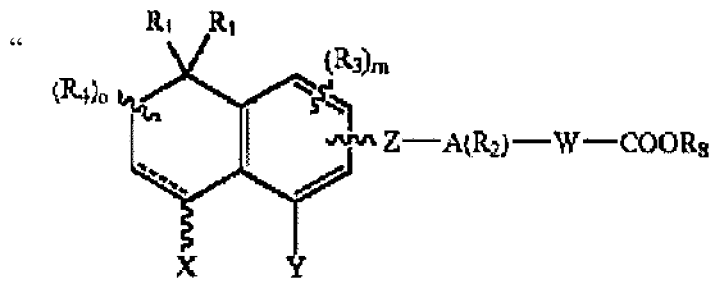"

and insert therefor

--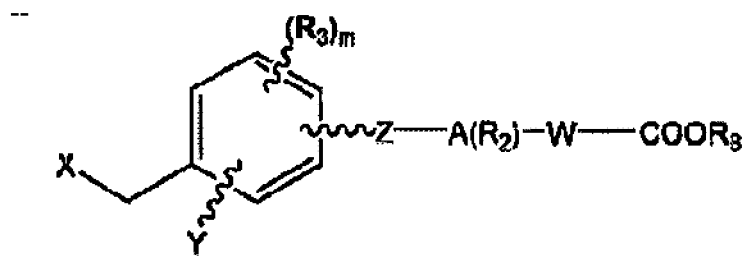--; and

Col. 178, Line 57
In Claim 1, line 22, delete
" Z is —C≡C " and insert therefor --Z is -C≡C-; --.

Signed and Sealed this

Seventh Day of August, 2007

JON W. DUDAS
*Director of the United States Patent and Trademark Office*

Disclaimer

7,226,951—Jayasree Vasudevan, Anaheim CA (US); Liming Wang, Irvine, CA (US); Xiaoxia Liu, Tustin, CA (US); Kwork Yin Tsang; Irvine, CA (US); Ling Li, Irvine, CA (US); Janet A. Takeuchi, Anaheim, CA (US); Thong Vu, Garden Grove, CA (US); Richard Beard, Newport Beach, CA (US); Smita Bhat, Irvine, CA (US); Vidyasagar Vuligonda, Irvine, CA (US); Roshantha A. Chandraratna, Laguna Hills, CA (US); COMPOUND HAVING SELECTIVE CYTOCHROME P450RAI-2 INHIBITORY ACTIVITY AND METHODS OF OBTAINING THE SAME, Patent dated June 5, 2007. Disclaimer filed Aug. 8, 2011, by the Assignee, Allergan, Inc.
  Hereby enters this disclaimer to claims 1-4, of said patent.

(*Official Gazette January 24, 2012*)